US012679881B2

(12) United States Patent
Gray-Rupp et al.

(10) Patent No.: US 12,679,881 B2
(45) Date of Patent: Jul. 14, 2026

(54) SYNTHETIC PATHWAY ACTIVATORS

(71) Applicant: Arsenal Biosciences, Inc., South San Francisco, CA (US)

(72) Inventors: Levi Gray-Rupp, Philadelphia, PA (US); Thomas Gardner, South San Francisco, CA (US); Anzhi Yao, South San Francisco, CA (US)

(73) Assignee: Arsenal Biosciences, Inc.

( * ) Notice: Subject to any disclaimer, the term of this patent is extended or adjusted under 35 U.S.C. 154(b) by 0 days.

(21) Appl. No.: 19/201,822

(22) Filed: May 7, 2025

(65) Prior Publication Data

US 2025/0270288 A1 Aug. 28, 2025

Related U.S. Application Data

(63) Continuation of application No. PCT/US2024/019690, filed on Mar. 13, 2024.

(60) Provisional application No. 63/613,713, filed on Dec. 21, 2023, provisional application No. 63/495,865, filed on Apr. 13, 2023, provisional application No. 63/489,842, filed on Mar. 13, 2023.

(51) Int. Cl.

| | |
|---|---|
| *C07K 14/715* | (2006.01) |
| *A61K 40/11* | (2025.01) |
| *A61K 40/31* | (2025.01) |
| *A61K 40/42* | (2025.01) |
| *C07K 14/705* | (2006.01) |
| *C07K 14/71* | (2006.01) |

(52) U.S. Cl.
CPC .......... *C07K 14/7155* (2013.01); *A61K 40/11* (2025.01); *A61K 40/31* (2025.01); *A61K 40/4204* (2025.01); *A61K 40/4217* (2025.01); *A61K 40/4224* (2025.01); *C07K 14/70596* (2013.01); *C07K 14/71* (2013.01); *A61K 2239/15* (2023.05); *A61K 2239/21* (2023.05); *A61K 2239/22* (2023.05); *C07K 2319/03* (2013.01); *C07K 2319/033* (2013.01); *C07K 2319/70* (2013.01)

(58) Field of Classification Search
None
See application file for complete search history.

(56) References Cited

U.S. PATENT DOCUMENTS

| | | |
|---|---|---|
| 10,548,921 B2 | 2/2020 | Leen et al. |
| 10,800,854 B2 | 10/2020 | Pulé et al. |
| 10,858,443 B2 | 12/2020 | Ngo |
| 11,202,801 B2 | 12/2021 | Roybal et al. |
| 11,230,698 B2 | 1/2022 | Rubinstein et al. |
| 11,717,538 B2 | 8/2023 | Leen et al. |
| 11,993,652 B2 | 5/2024 | Riddell et al. |
| 2007/0128197 A1* | 6/2007 | Nash ...................... A61P 35/00 |
| | | 435/336 |
| 2018/0127786 A1 | 5/2018 | Bouchon et al. |
| 2019/0183936 A1 | 6/2019 | Shum, Shum et al. |
| 2019/0284288 A1 | 9/2019 | Bonifant |
| 2019/0292533 A1 | 9/2019 | Nager et al. |
| 2020/0002402 A1 | 1/2020 | Emtage et al. |
| 2020/0197437 A1 | 6/2020 | Leen et al. |
| 2020/0216514 A1 | 7/2020 | Fussenegger et al. |
| 2020/0239545 A1 | 7/2020 | Peddareddigari et al. |
| 2020/0360432 A1 | 11/2020 | Pulé et al. |
| 2020/0392204 A1 | 12/2020 | Leung |
| 2021/0040227 A1 | 2/2021 | Pulé et al. |
| 2021/0161961 A1 | 6/2021 | Xiao et al. |
| 2021/0163574 A1 | 6/2021 | Schneider et al. |
| 2021/0238258 A1 | 8/2021 | Garcia et al. |
| 2022/0185858 A1 | 6/2022 | Li et al. |
| 2022/0289826 A1 | 9/2022 | Song et al. |
| 2023/0183709 A1 | 6/2023 | Roybal et al. |
| 2024/0182526 A1 | 6/2024 | Evseenko et al. |

FOREIGN PATENT DOCUMENTS

| | | |
|---|---|---|
| EP | 3305890 A1 | 4/2018 |
| EP | 4293041 A1 | 12/2023 |
| WO | WO-2018038945 A1 | 3/2018 |
| WO | WO-2020097582 A1 | 5/2020 |
| WO | WO-2020180664 A1 | 9/2020 |
| WO | WO-2020180694 A1 | 9/2020 |
| WO | WO-2020200325 A1 | 10/2020 |
| WO | WO-2021016174 A1 | 1/2021 |
| WO | WO-2021044439 A1 | 3/2021 |
| WO | WO-2021050752 | 3/2021 |
| WO | WO-2021060926 | 4/2021 |
| WO | WO-2021061862 | 4/2021 |
| WO | WO-2021061872 A1 | 4/2021 |
| WO | WO-2021068068 | 4/2021 |
| WO | WO-2021170666 A1 | 9/2021 |
| WO | WO-2021/207526 A1 | 10/2021 |
| WO | WO-2022047237 A1 | 3/2022 |
| WO | WO-2022171179 A9 | 8/2022 |
| WO | WO-2023192948 A1 | 10/2023 |

(Continued)

OTHER PUBLICATIONS

Nicholson, S. et al., 2000, PNAS, vol. 97: pp. 6493-6498.*
NovoPro labs, pEF-BOS plasmid data sheet, one page, printed 2025.*
Fraietta, J. A. et al., Determinants of response and resistance to CD19 chimeric antigen receptor (CAR) T cell therapy of chronic lymphocytic leukemia, Nat Med. May 2018; 24(5): 563-571, doi: 10.1038/s41591-081-0010-1.
Kagoya, Y. et al., A novel chimeric antigen receptor containing a JAK-STAT signaling domain mediates superior antitumor effects, Nat Med. Mar. 2018; 24(3); 352-359, doi: 10.1038/nm.4478.

(Continued)

*Primary Examiner* — Michael D Burkhart
(74) *Attorney, Agent, or Firm* — Goodwin Procter LLP

(57) ABSTRACT

Provided herein are novel synthetic pathway activators comprising multimerization regions, transmembrane domains, and intracellular signaling domains.

30 Claims, 26 Drawing Sheets

Specification includes a Sequence Listing.

(56)            References Cited

FOREIGN PATENT DOCUMENTS

WO      WO-2023205724 A2      10/2023
WO      WO-2024186656 A1       9/2024

OTHER PUBLICATIONS

Garbers, C., et al., The IL-6/gp130/STAT3 signaling axis: recent advances towards specific inhibition. Curr Opin Immunol. Jun. 2015; 34:75-82.

Jiang Z., et al. IL-6 trans-signaling promotes the expansion and anti-tumor activity of CAR T cells. Leukemia. May 2021; 35(5):1380-1391.

Dechow, T., et al., GP130 Activation induces myeloma and collaborates with MYC, J. Clin Invest. 124(12), pp. 5263-5274, (2014).

Pellenz, S. et al., New Human Chromosomal Sites with "Safe Harbor" Potential for Targeted Transgene Insertion, Human Gene Therapy, vol. 30(7), pp. 814-828 (2019).

Sadelain, M. et al., Safe harbours for the integration of new DNA in the human genome, Nature Reviews Cancer, 12(1), pp. 51-58.

Schaper, F. et al., Activation of the Protein Tyrosine Phosphatase SHP2 Via the Interleukin-6 Signal Transducing Receptor Protein GP130 Requires Tyrosine Kinase JAK1 and Limits Acute-Phase Protein Expression, Journal of Biochemistry, Oxford Universtiy Press, GB, vol. 335, Jan. 1, 1998 (Jan. 1, 1998), pp. 557-565, XP002948400, ISSN: 0021-924X.

Stuhlmann-Laeisz, C., et al., Forced Dimerization of gp130 Leads to Constitutive STAT3 Activation, Cytokine-independent Growth, and Blockade of Differentiation of Embryonic Stem Cells, Molecular Biology of the Cell, vol. 17, Jul. 1, 2006 (Jun. 1, 2006), pp. 2986-2995, XP093035289, DOI: 10.1091/mbc.E05-12-1129).

Zhu, I. et al., Modular design of synthetic receptors for programmed gene regulation in cell therapies, Cell 185, pp. 1431-1443, Apr. 14, 2022 (Apr. 14, 2022), retrieved from https://doi.org/10.1016/j.cell.2022.03.023.

PCT/US2024/019690 International Search Report and Written Opinion dated Aug. 14, 2024, 14 pages.

\* cited by examiner

Total T cells

Total Receptor + cells

SEQUENCE LISTING

Sequence total quantity: 243
SEQ ID NO: 1               moltype = AA   length = 386
FEATURE                    Location/Qualifiers
source                     1..386
                           mol_type = protein
                           organism = synthetic construct
SEQUENCE: 1
MALPVTALLL PLALLLHAAR PELPTQGTFS NVSTNVSELC GGRIARLEEK VKTLKAQNSE   60
LASTANMLRE QVAQLKQKVM NAQGEIEAIV VPVCLAFLLT TLLGVLFCFN KRDLIKKHIW  120
PNVPDPSKSH IAQWSPHTPP RHNFNSKDQM YSDGNFTDVS VVEIEANDKK PFPEDLKSLD  180
LFKKEKINTE GHSSGIGGSS CMSSSRPSIS SSDENESSQN TSSTVQFSTV VHSGYRHQVP  240
SVQVFSRSES TQPLLDSEER PEDLQLVDHV DGGDGILPRQ QYFKQNCSQH ESSPDISHFE  300
RSKQVSSVNE EDFVRLKQQI SDHISQSCGS GQMKMFQEVS AADAFGPGTE GQVERFETVG  360
MEAATDEGMP KSYLPQTVRQ GGYMPQ                                       386

SEQ ID NO: 2               moltype = AA   length = 345
FEATURE                    Location/Qualifiers
source                     1..345
                           mol_type = protein
                           organism = synthetic construct
SEQUENCE: 2
MALPVTALLL PLALLLHAAR PELPTQGTFS NVSTNVSELC GGRIARLEEK VKTLKAQNSE   60
LASTANMLRE QVAQLKQKVM NAQGEIEAIV VPVCLAFLLT TLLGVLFCFN KRDLIKKHIW  120
PNVPDPSKSH IAQWSPHTPP RHNFNSKDQM YSDGNFTDVS VVEIEANDKK PFPEDLKSLD  180
LFKKEKINTE GHSSGIGGSS CMSSSRPSIS SSDENESSQN TSSTVQFSTV VHSGYRHQQQ  240
YFKQNCSQHE SSPDISHFER SKQVSSVNEE DFVRLKQQIS DHISQSCGSG QMKMFQEVSA  300
ADAFGPGTEG QVERFETVGM EAATDEGMPK SYLPQTVRQG GYMPQ                  345

SEQ ID NO: 3               moltype = AA   length = 345
FEATURE                    Location/Qualifiers
source                     1..345
                           mol_type = protein
                           organism = synthetic construct
SEQUENCE: 3
MALPVTALLL PLALLLHAAR PELPTQGTFS NVSTNVSELC GGRIARLEEK VKTLKAQNSE   60
LASTANMLRE QVAQLKQKVM NAQGEIEAIV VPVCLAFLLT TLLGVLFCFN KRDLIKKHIW  120
PNVPDPSKSH IAQWSPHTPP RHNFNSKDQM YSDGNFTDVS VVEIEANDKK PFPEDLKSLD  180
LFKKEKINTE GHSSGIGGSS CMSSSRPSIS SSDENESSQN TSSTVQYSTV VHSGYRHQQQ  240
YFKQNCSQHE SSPDISHFER SKQVSSVNEE DFVRLKQQIS DHISQSCGSG QMKMFQEVSA  300
ADAFGPGTEG QVERFETVGM EAATDEGMPK SYLPQTVRQG GYMPQ                  345

SEQ ID NO: 4               moltype = AA   length = 381
FEATURE                    Location/Qualifiers
source                     1..381
                           mol_type = protein
                           organism = synthetic construct
SEQUENCE: 4
MALPVTALLL PLALLLHAAR PELPTQGTFS NVSTNVSRIA RLEEKVKTLK AQNSELASTA   60
NMLREQVAQL KQKVMNAQGE IEAIVVPVCL AFLLTTLLGV LFCFNKRDLI KKHIWPNVPD  120
PSKSHIAQWS PHTPPRHNFN SKDQMYSDGN FTDVSVVEIE ANDKKPFPED LKSLDLFKKE  180
KINTEGHSSG IGGSSCMSSS RPSISSSDEN ESSQNTSSTV QYSTVVHSGY RHQVPSVQVF  240

```
SRSESTQPLL DSEERPEDLQ LVDHVDGGDG ILPRQQYFKQ NCSQHESSPD ISHFERSKQV   300
SSVNEEDFVR LKQQISDHIS QSCGSGQMKM FQEVSAADAF GPGTEGQVER FETVGMEAAT   360
DEGMPKSYLP QTVRQGGYMP Q                                            381

SEQ ID NO: 5              moltype = AA   length = 381
FEATURE                   Location/Qualifiers
source                    1..381
                          mol_type = protein
                          organism = synthetic construct
SEQUENCE: 5
MALPVTALLL PLALLLHAAR PELPTQGTFS NVSTNVSRIA RLEEKVKTLK AQNSELASTA   60
NMLREQVAQL KQKVMNAQGE IEAIVVPVCL AFLLTTLLGV LFCFNKRDLI KKHIWPNVPD   120
PSKSHIAQWS PHTPPRHNFN SKDQMYSDGN FTDVSVVEIE ANDKKPFPED LKSLDLFKKE   180
KINTEGHSSG IGGSSCMSSS RPSISSSDEN ESSQNTSSTV QFSTVVHSGY RHQVPSVQVF   240
SRSESTQPLL DSEERPEDLQ LVDHVDGGDG ILPRQQYFKQ NCSQHESSPD ISHFERSKQV   300
SSVNEEDFVR LKQQISDHIS QSCGSGQMKM FQEVSAADAF GPGTEGQVER FETVGMEAAT   360
DEGMPKSYLP QTVRQGGYMP Q                                            381

SEQ ID NO: 6              moltype = AA   length = 340
FEATURE                   Location/Qualifiers
source                    1..340
                          mol_type = protein
                          organism = synthetic construct
SEQUENCE: 6
MALPVTALLL PLALLLHAAR PELPTQGTFS NVSTNVSRIA RLEEKVKTLK AQNSELASTA   60
NMLREQVAQL KQKVMNAQGE IEAIVVPVCL AFLLTTLLGV LFCFNKRDLI KKHIWPNVPD   120
PSKSHIAQWS PHTPPRHNFN SKDQMYSDGN FTDVSVVEIE ANDKKPFPED LKSLDLFKKE   180
KINTEGHSSG IGGSSCMSSS RPSISSSDEN ESSQNTSSTV QFSTVVHSGY RHQQQYFKQN   240
CSQHESSPDI SHFERSKQVS SVNEEDFVRL KQQISDHISQ SCGSGQMKMF QEVSAADAFG   300
PGTEGQVERF ETVGMEAATD EGMPKSYLPQ TVRQGGYMPQ                        340

SEQ ID NO: 7              moltype = AA   length = 340
FEATURE                   Location/Qualifiers
source                    1..340
                          mol_type = protein
                          organism = synthetic construct
SEQUENCE: 7
MALPVTALLL PLALLLHAAR PELPTQGTFS NVSTNVSRIA RLEEKVKTLK AQNSELASTA   60
NMLREQVAQL KQKVMNAQGE IEAIVVPVCL AFLLTTLLGV LFCFNKRDLI KKHIWPNVPD   120
PSKSHIAQWS PHTPPRHNFN SKDQMYSDGN FTDVSVVEIE ANDKKPFPED LKSLDLFKKE   180
KINTEGHSSG IGGSSCMSSS RPSISSSDEN ESSQNTSSTV QYSTVVHSGY RHQQQYFKQN   240
CSQHESSPDI SHFERSKQVS SVNEEDFVRL KQQISDHISQ SCGSGQMKMF QEVSAADAFG   300
PGTEGQVERF ETVGMEAATD EGMPKSYLPQ TVRQGGYMPQ                        340

SEQ ID NO: 8              moltype = AA   length = 386
FEATURE                   Location/Qualifiers
source                    1..386
                          mol_type = protein
                          organism = synthetic construct
SEQUENCE: 8
MALPVTALLL PLALLLHAAR PELPTQGTFS NVSTNVSELC GGRIARLEEK VKTLKAQNSE   60
LASTANMLRE QVAQLKQKVM NAQGEIEAIV VPVCLAFLLT TLLGVLFCFN KRDLIKKHIW   120
PNVPDPSKSH IAQWSPHTPP RHNFNSKDQM YSDGNFTDVS VVEIEANDKK PFPEDLKSLD   180
LFKKEKINTE GHSSGIGGSS CMSSSRPSIS SSDENESSQN TSSTVQYSTV VHSGYRHQVP   240
SVQVFSRSES TQPLLDSEER PEDLQLVDHV DGGDGILPRQ QYFKQNCSQH ESSPDISHFE   300
RSKQVSSVNE EDFVRLKQQI SDHISQSCGS GQMKMFQEVS AADAFGPGTE GQVERFETVG   360
MEAATDEGMP KSYLPQTVRQ GGYMPQ                                       386

SEQ ID NO: 9              moltype = AA   length = 336
FEATURE                   Location/Qualifiers
source                    1..336
                          mol_type = protein
                          organism = synthetic construct
SEQUENCE: 9
MRIARLEEKV KTLKAQNSEL ASTANMLREQ VAQLKQKVMN NKRDLIKKHI WPNVPDPSKS   60
HIAQWSPHTP PRHNFNSKDQ MYSDGNFTDV SVVEIEANDK KPFPEDLKSL DLFKKEKINT   120
EGHSSGIGGS SCMSSSRPSI SSSDENESSQ NTSSTVQYST VVHSGYRHQV PSVQVFSRSE   180
STQPLLDSEE RPEDLQLVDH VDGGDGILPR QQYFKQNCSQ HESSPDISHF ERSKQVSSVN   240
EEDFVRLKQQ ISDHISQSCG SGQMKMFQEV SAADAFGPGT EGQVERFETV GMEAATDEGM   300
PKSYLPQTVR QGGYMPQMSK DGKKKKKKSK TKCVIM                           336

SEQ ID NO: 10             moltype = AA   length = 337
FEATURE                   Location/Qualifiers
source                    1..337
                          mol_type = protein
                          organism = synthetic construct
SEQUENCE: 10
MALPVTALLL PLALLLHAAR PELPTQGTFS NVSTNVSELC GGRIARLEEK VKTLKAQNSE   60
LASTANMLRE QVAQLKQKVM NAQGEIEAIV VPVCLAFLLT TLLGVLFCFN KRDLIKKHIW   120
```

```
PNVPDPSKSH IAQWSPHTPP RHNFNSKDQM YSDGNFTDVS VVEIEANDKK PFPETVQYST    180
VVHSGYRHQV PSVQVFSRSE STQPLLDSEE RPEDLQLVDH VDGGDGILPR QQYFKQNCSQ    240
HESSPDISHF ERSKQVSSVN EEDFVRLKQQ ISDHISQSCG SGQMKMFQEV SAADAFGPGT    300
EGQVERFETV GMEAATDEGM PKSYLPQTVR QGGYMPQ                             337

SEQ ID NO: 11              moltype = AA   length = 345
FEATURE                    Location/Qualifiers
source                     1..345
                           mol_type = protein
                           organism = synthetic construct
SEQUENCE: 11
MALPVTALLL PLALLLHAAR PELPTQGTFS NVSTNVSELC GGRIARLEEK VKTLKAQNSE    60
LASTANMLRE QVAQLKQKVM NAQGEIEAIV VPVCLAFLLT TLLGVLFCFN KRDLIKKHIW    120
PNVPDPSKSH IAQWSPHTPP RHNFNSKDQM YSDGNFTDVS VVEIEANDKK PFPEDLKSLD    180
LFKKEKINTE GHSSGIGGSS CMSSSRPSIS SSDENESSQN TSSTVQYSTV VHSGYRHQQQ    240
YFKQNCSQHE SSPDISHFER SKQVSSVNEE DFVRLKQQIS DHISQSCGSG QMKMFQEVSA    300
ADAFGPGTEG QVERFETVGM EAATDEGMPK SYLPQTVRQG GYMPQ                    345

SEQ ID NO: 12              moltype = AA   length = 302
FEATURE                    Location/Qualifiers
source                     1..302
                           mol_type = protein
                           organism = synthetic construct
SEQUENCE: 12
MALPVTALLL PLALLLHAAR PELPTQGTFS NVSTNVSELC GGRIARLEEK VKTLKAQNSE    60
LASTANMLRE QVAQLKQKVM NAQGEIEAIV VPVCLAFLLT TLLGVLFCFN KRDLIKKHIW    120
PNVPDPSKSH IAQWSPHTPP RHNFNSKDQM YSDGNFTDVS VVEIEANDKK PFPEDLKSLD    180
LFKKEKINTE GHSSGIGGSS CMSSSRPSIS SSDENESSQN TSSTVQYSTV VHSGYRHQVP    240
SVQVFSRSES TQPLLDSEER PEDLQLVDHV DGGDGILPRQ QYFKQPKSYL PQTVRQGGYM    300
PQ                                                                  302

SEQ ID NO: 13              moltype = AA   length = 296
FEATURE                    Location/Qualifiers
source                     1..296
                           mol_type = protein
                           organism = synthetic construct
SEQUENCE: 13
MALPVTALLL PLALLLHAAR PELPTQGTFS NVSTNVSELC GGRIARLEEK VKTLKAQNSE    60
LASTANMLRE QVAQLKQKVM NAQGEIEAIV VPVCLAFLLT TLLGVLFCFN KRDLIKKHIW    120
PNVPDPSKSH IAQWSPHTPP RHNFNSKDQM YSDGNFTDVS VVEIEANDKK PFPETVQYST    180
VVHSGYRHQQ QYFKQNCSQH ESSPDISHFE RSKQVSSVNE EDFVRLKQQI SDHISQSCGS    240
GQMKMFQEVS AADAFGPGTE GQVERFETVG MEAATDEGMP KSYLPQTVRQ GGYMPQ        296

SEQ ID NO: 14              moltype = AA   length = 261
FEATURE                    Location/Qualifiers
source                     1..261
                           mol_type = protein
                           organism = synthetic construct
SEQUENCE: 14
MALPVTALLL PLALLLHAAR PELPTQGTFS NVSTNVSELC GGRIARLEEK VKTLKAQNSE    60
LASTANMLRE QVAQLKQKVM NAQGEIEAIV VPVCLAFLLT TLLGVLFCFN KRDLIKKHIW    120
PNVPDPSKSH IAQWSPHTPP RHNFNSKDQM YSDGNFTDVS VVEIEANDKK PFPEDLKSLD    180
LFKKEKINTE GHSSGIGGSS CMSSSRPSIS SSDENESSQN TSSTVQYSTV VHSGYRHQQQ    240
YFKQPKSYLP QTVRQGGYMP Q                                              261

SEQ ID NO: 15              moltype = AA   length = 253
FEATURE                    Location/Qualifiers
source                     1..253
                           mol_type = protein
                           organism = synthetic construct
SEQUENCE: 15
MALPVTALLL PLALLLHAAR PELPTQGTFS NVSTNVSELC GGRIARLEEK VKTLKAQNSE    60
LASTANMLRE QVAQLKQKVM NAQGEIEAIV VPVCLAFLLT TLLGVLFCFN KRDLIKKHIW    120
PNVPDPSKSH IAQWSPHTPP RHNFNSKDQM YSDGNFTDVS VVEIEANDKK PFPETVQYST    180
VVHSGYRHQV PSVQVFSRSE STQPLLDSEE RPEDLQLVDH VDGGDGILPR QQYFKQPKSY    240
LPQTVRQGGY MPQ                                                       253

SEQ ID NO: 16              moltype = AA   length = 212
FEATURE                    Location/Qualifiers
source                     1..212
                           mol_type = protein
                           organism = synthetic construct
SEQUENCE: 16
MALPVTALLL PLALLLHAAR PELPTQGTFS NVSTNVSELC GGRIARLEEK VKTLKAQNSE    60
LASTANMLRE QVAQLKQKVM NAQGEIEAIV VPVCLAFLLT TLLGVLFCFN KRDLIKKHIW    120
PNVPDPSKSH IAQWSPHTPP RHNFNSKDQM YSDGNFTDVS VVEIEANDKK PFPETVQYST    180
VVHSGYRHQQ QYFKQPKSYL PQTVRQGGYM PQ                                  212

SEQ ID NO: 17              moltype = AA   length = 381
```

```
FEATURE               Location/Qualifiers
source                1..381
                      mol_type = protein
                      organism = synthetic construct
SEQUENCE: 17
MALPVTALLL PLALLLHAAR PELPTQGTFS NVSTNVSRIA RLEEKVKTLK AQNSELASTA    60
NMLREQVAQL KQKVMNAQGE IEAIVVPVCL AFLLTTLLGV LFCFNKRDLI KKHIWPNVPD   120
PSKSHIAQWS PHTPPRHNFN SKDQMYSDGN FTDVSVVEIE ANDKKPFPED LKSLDLFKKE   180
KINTEGHSSG IGGSSCMSSS RPSISSSDEN ESSQNTSSTV QYSTVVHSGY RHQVPSVQVF   240
SRSESTQPLL DSEERPEDLQ LVDHVDGGDG ILPRQQYFKQ NCSQHESSPD ISHFERSKQV   300
SSVNEEDFVR LKQQISDHIS QSCGSGQMKM FQEVSAADAF GPGTEGQVER FETVGMEAAT   360
DEGMPKSYLP QTVRQGGYMP Q                                             381

SEQ ID NO: 18        moltype = AA   length = 402
FEATURE               Location/Qualifiers
source                1..402
                      mol_type = protein
                      organism = synthetic construct
SEQUENCE: 18
MALPVTALLL PLALLLHAAR PELPTQGTFS NVSTNVSMVD PVGFAEAWKA QFPDSEPPRM    60
ELRSVGDIEQ ELERCKASIR RLEQEVNQER FRMIYLQTLL AKEAIVVPVC LAFLLTTLLG   120
VLFCFNKRDL IKKHIWPNVP DPSKSHIAQW SPHTPPRHNF NSKDQMYSDG NFTDVSVVEI   180
EANDKKPFPE DLKSLDLFKK EKINTEGHSS GIGGSSCMSS SRPSISSSDE NESSQNTSST   240
VQYSTVVHSG YRHQVPSVQV FSRSESTQPL LDSEERPEDL QLVDHVDGGD GILPRQQYFK   300
QNCSQHESSP DISHFERSKQ VSSVNEEDFV RLKQQISDHI SQSCGSGQMK MFQEVSAADA   360
FGPGTEGQVE RFETVGMEAA TDEGMPKSYL PQTVRQGGYM PQ                      402

SEQ ID NO: 19        moltype = AA   length = 347
FEATURE               Location/Qualifiers
source                1..347
                      mol_type = protein
                      organism = synthetic construct
SEQUENCE: 19
MALPVTALLL PLALLLHAAR PELPTQGTFS NVSTNVSELC GGAQGEIEAI VVPVCLAFLL    60
TTLLGVLFCF NKRDLIKKHI WPNVPDPSKS HIAQWSPHTP PRHNFNSKDQ MYSDGNFTDV   120
SVVEIEANDK KPFPEDLKSL DLFKKEKINT EGHSSGIGGS SCMSSSRPSI SSSDENESSQ   180
NTSSTVQYST VVHSGYRHQV PSVQVFSRSE STQPLLDSEE RPEDLQLVDH VDGGDGILPR   240
QQYFKQNCSQ HESSPDISHF ERSKQVSSVN EEDFVRLKQQ ISDHISQSCG SGQMKMFQEV   300
SAADAFGPGT EGQVERFETV GMEAATDEGM PKSYLPQTVR QGGYMPQ                 347

SEQ ID NO: 20        moltype = AA   length = 341
FEATURE               Location/Qualifiers
source                1..341
                      mol_type = protein
                      organism = synthetic construct
SEQUENCE: 20
MALPVTALLL PLALLLHAAR PELPTQGTFS NVSTNVSELC GGAIVVPVCL AFLLTTLLGV    60
LFCFNKRDLI KKHIWPNVPD PSKSHIAQWS PHTPPRHNFN SKDQMYSDGN FTDVSVVEIE   120
ANDKKPFPED LKSLDLFKKE KINTEGHSSG IGGSSCMSSS RPSISSSDEN ESSQNTSSTV   180
QYSTVVHSGY RHQVPSVQVF SRSESTQPLL DSEERPEDLQ LVDHVDGGDG ILPRQQYFKQ   240
NCSQHESSPD ISHFERSKQV SSVNEEDFVR LKQQISDHIS QSCGSGQMKM FQEVSAADAF   300
GPGTEGQVER FETVGMEAAT DEGMPKSYLP QTVRQGGYMP Q                       341

SEQ ID NO: 21        moltype = AA   length = 386
FEATURE               Location/Qualifiers
source                1..386
                      mol_type = protein
                      organism = synthetic construct
SEQUENCE: 21
MALPVTALLL PLALLLHAAR PELPTQGTFS NVSTNVSELC GGAQGEIEAI VVPVCLAFLL    60
TTLLGVLFCF NKRDLIKKHI WPNVPDPSKS HIAQWSPHTP PRHNFNSKDQ MYSDGNFTDV   120
SVVEIEANDK KPFPEDLKSL DLFKKEKINT EGHSSGIGGS SCMSSSRPSI SSSDENESSQ   180
NTSSTVQYST VVHSGYRHQV PSVQVFSRSE STQPLLDSEE RPEDLQLVDH VDGGDGILPR   240
QQYFKQNCSQ HESSPDISHF ERSKQVSSVN EEDFVRLKQQ ISDHISQSCG SGQMKMFQEV   300
SAADAFGPGT EGQVERFETV GMEAATDEGM PKSYLPQTVR QGGYMPQRIA RLEEKVKTLK   360
AQNSELASTA NMLREQVAQL KQKVMN                                        386

SEQ ID NO: 22        moltype = AA   length = 380
FEATURE               Location/Qualifiers
source                1..380
                      mol_type = protein
                      organism = synthetic construct
SEQUENCE: 22
MALPVTALLL PLALLLHAAR PELPTQGTFS NVSTNVSELC GGAIVVPVCL AFLLTTLLGV    60
LFCFNKRDLI KKHIWPNVPD PSKSHIAQWS PHTPPRHNFN SKDQMYSDGN FTDVSVVEIE   120
ANDKKPFPED LKSLDLFKKE KINTEGHSSG IGGSSCMSSS RPSISSSDEN ESSQNTSSTV   180
QYSTVVHSGY RHQVPSVQVF SRSESTQPLL DSEERPEDLQ LVDHVDGGDG ILPRQQYFKQ   240
NCSQHESSPD ISHFERSKQV SSVNEEDFVR LKQQISDHIS QSCGSGQMKM FQEVSAADAF   300
GPGTEGQVER FETVGMEAAT DEGMPKSYLP QTVRQGGYMP QRIARLEEKV KTLKAQNSEL   360
```

```
ASTANMLREQ VAQLKQKVMN                                                            380

SEQ ID NO: 23                moltype = AA   length = 386
FEATURE                      Location/Qualifiers
source                       1..386
                             mol_type = protein
                             organism = synthetic construct
SEQUENCE: 23
MALPVTALLL PLALLLHAAR PELPTQGTFS NVSTNVSELC GGAQGEIEAI VVPVCLAFLL    60
TTLLGVLFCF NKRDLIKKHR IARLEEKVKT LKAQNSELAS TANMLREQVA QLKQKVMNIW    120
PNVPDPSKSH IAQWSPHTPP RHNFNSKDQM YSDGNFTDVS VVEIEANDKK PFPEDLKSLD    180
LFKKEKINTE GHSSGIGGSS CMSSSRPSIS SSDENESSQN TSSTVQYSTV VHSGYRHQVP    240
SVQVFSRSES TQPLLDSEER PEDLQLVDHV DGGDGILPRQ QYFKQNCSQH ESSPDISHFE    300
RSKQVSSVNE EDFVRLKQQI SDHISQSCGS GQMKMFQEVS AADAFGPGTE GQVERFETVG    360
MEAATDEGMP KSYLPQTVRQ GGYMPQ                                         386

SEQ ID NO: 24                moltype = AA   length = 380
FEATURE                      Location/Qualifiers
source                       1..380
                             mol_type = protein
                             organism = synthetic construct
SEQUENCE: 24
MALPVTALLL PLALLLHAAR PELPTQGTFS NVSTNVSELC GGAIVVPVCL AFLLTTLLGV    60
LFCFNKRDLI KKHRIARLEE KVKTLKAQNS ELASTANMLR EQVAQLKQKV MNIWPNVPDP    120
SKSHIAQWSP HTPPRHNFNS KDQMYSDGNF TDVSVVEIEA NDKKPFPEDL KSLDLFKKEK    180
INTEGHSSGI GGSSCMSSSR PSISSSDENE SSQNTSSTVQ YSTVVHSGYR HQVPSVQVFS    240
RSESTQPLLD SEERPEDLQL VDHVDGGDGI LPRQQYFKQN CSQHESSPDI SHFERSKQVS    300
SVNEEDFVRL KQQISDHISQ SCGSGQMKMF QEVSAADAFG PGTEGQVERF ETVGMEAATD    360
EGMPKSYLPQ TVRQGGYMPQ                                                380

SEQ ID NO: 25                moltype = AA   length = 342
FEATURE                      Location/Qualifiers
source                       1..342
                             mol_type = protein
                             organism = synthetic construct
SEQUENCE: 25
MALPVTALLL PLALLLHAAR PELPTQGTFS NVSTNVSFAC DIYIWAPLAG TCGVLLLSLV    60
ITLYCNKRDL IKKHIWPNVP DPSKSHIAQW SPHTPPRHNF NSKDQMYSDG NFTDVSVVEI    120
EANDKKPFPE DLKSLDLFKK EKINTEGHSS GIGGSSCMSS SRPSISSSDE NESSQNTSST    180
VQYSTVVHSG YRHQVPSVQV FSRSESTQPL LDSEERPEDL QLVDHVDGGD GILPRQQYFK    240
QNCSQHESSP DISHFERSKQ VSSVNEEDFV RLKQQISDHI SQSCGSGQMK MFQEVSAADA    300
FGPGTEGQVE RFETVGMEAA TDEGMPKSYL PQTVRQGGYM PQ                       342

SEQ ID NO: 26                moltype = AA   length = 383
FEATURE                      Location/Qualifiers
source                       1..383
                             mol_type = protein
                             organism = synthetic construct
SEQUENCE: 26
MALPVTALLL PLALLLHAAR PELPTQGTFS NVSTNVSTTT PAPRPPTPAP TIASQPLSLR    60
PEACRPAAGG AVHTRGLDFA CDIYIWAPLA GTCGVLLLSL VITLYCNKRD LIKKHIWPNV    120
PDPSKSHIAQ WSPHTPPRHN FNSKDQMYSD GNFTDVSVVE IEANDKKPFP EDLKSLDLFK    180
KEKINTEGHS SGIGGSSCMS SSRPSISSSD ENESSQNTSS TVQYSTVVHS GYRHQVPSVQ    240
VFSRSESTQP LLDSEERPED LQLVDHVDGG DGILPRQQYF KQNCSQHESS PDISHFERSK    300
QVSSVNEEDF VRLKQQISDH ISQSCGSGQM KMFQEVSAAD AFGPGTEGQV ERFETVGMEA    360
ATDEGMPKSY LPQTVRQGGY MPQ                                            383

SEQ ID NO: 27                moltype = AA   length = 343
FEATURE                      Location/Qualifiers
source                       1..343
                             mol_type = protein
                             organism = synthetic construct
SEQUENCE: 27
MALPVTALLL PLALLLHAAR PELPTQGTFS NVSTNVSELC GGIYIWAPLA GTCGVLLLSL    60
VITLYCNKRD LIKKHIWPNV PDPSKSHIAQ WSPHTPPRHN FNSKDQMYSD GNFTDVSVVE    120
IEANDKKPFP EDLKSLDLFK KEKINTEGHS SGIGGSSCMS SSRPSISSSD ENESSQNTSS    180
TVQYSTVVHS GYRHQVPSVQ VFSRSESTQP LLDSEERPED LQLVDHVDGG DGILPRQQYF    240
KQNCSQHESS PDISHFERSK QVSSVNEEDF VRLKQQISDH ISQSCGSGQM KMFQEVSAAD    300
AFGPGTEGQV ERFETVGMEA ATDEGMPKSY LPQTVRQGGY MPQ                      343

SEQ ID NO: 28                moltype = AA   length = 382
FEATURE                      Location/Qualifiers
source                       1..382
                             mol_type = protein
                             organism = synthetic construct
SEQUENCE: 28
MALPVTALLL PLALLLHAAR PELPTQGTFS NVSTNVSELC GGIYIWAPLA GTCGVLLLSL    60
VITLYCNKRD LIKKHIWPNV PDPSKSHIAQ WSPHTPPRHN FNSKDQMYSD GNFTDVSVVE    120
IEANDKKPFP EDLKSLDLFK KEKINTEGHS SGIGGSSCMS SSRPSISSSD ENESSQNTSS    180
```

```
TVQYSTVVHS GYRHQVPSVQ VFSRSESTQP LLDSEERPED LQLVDHVDGG DGILPRQQYF   240
KQNCSQHESS PDISHFERSK QVSSVNEEDF VRLKQQISDH ISQSCGSGQM KMFQEVSAAD   300
AFGPGTEGQV ERFETVGMEA ATDEGMPKSY LPQTVRQGGY MPQRIARLEE KVKTLKAQNS   360
ELASTANMLR EQVAQLKQKV MN                                           382

SEQ ID NO: 29              moltype = AA   length = 382
FEATURE                    Location/Qualifiers
source                     1..382
                           mol_type = protein
                           organism = synthetic construct
SEQUENCE: 29
MALPVTALLL PLALLLHAAR PELPTQGTFS NVSTNVSELC GGRIARLEEK VKTLKAQNSE   60
LASTANMLRE QVAQLKQKVM NIYIWAPLAG TCGVLLLSLV ITLYCNKRDL IKKHIWPNVP   120
DPSKSHIAQW SPHTPPRHNF NSKDQMYSDG NFTDVSVVEI EANDKKPFPE DLKSLDLFKK   180
EKINTEGHSS GIGGSSCMSS SRPSISSSDE NESSQNTSST VQYSTVVHSG YRHQVPSVQV   240
FSRSESTQPL LDSEERPEDL QLVDHVDGGD GILPRQQYFK QNCSQHESSP DISHFERSKQ   300
VSSVNEEDFV RLKQQISDHI SQSCGSGQMK MFQEVSAADA FGPGTEGQVE RFETVGMEAA   360
TDEGMPKSYL PQTVRQGGYM PQ                                           382

SEQ ID NO: 30              moltype = AA   length = 595
FEATURE                    Location/Qualifiers
source                     1..595
                           mol_type = protein
                           organism = synthetic construct
SEQUENCE: 30
MLVRRGARAG PRMPRGWTAL CLLSLLPSGF MSLDNNGTAT PELPTQGTFS NVSTNVSYQE   60
TTTPSTLGST SLHPVSQHGN EATTNITETT VKFTSTSVIT SVYGNTNSSV QSQTSVISTV   120
FTTPANVSTP ETTLKPSLSP GNVSDLSTTS TSLATSPTKP YTSSSPILSD IKAEIKCSGI   180
REVKLTQGIC LEQNKTSSCA EFKKDRGEGL ARVLCGEEQA DADAGAQVCS LLLAQSEVRP   240
QCLLLVLANR TEISSKLQLM KKHQSDLKKL GILDFTEQDV ASHQSYSQKT PILLTCPTIS   300
ILSFFSVALL VILACVLWNK RDLIKKHIWP NVPDPSKSHI AQWSPHTPPR HNFNSKDQMY   360
SDGNFTDVSV VEIEANDKKP FPEDLKSLDL FKKEKINTEG HSSGIGGSSC MSSSRPSISS   420
SDENESSQNT SSTVQYSTVV HSGYRHQVPS VQVFSRSEST QPLLDSEERP EDLQLVDHVD   480
GGDGILPRQQ YFKQNCSQHE SSPDISHFER SKQVSSVNEE DFVRLKQQIS DHISQSCGSG   540
QMKMFQEVSA ADAFGPGTEG QVERFETVGM EAATDEGMPK SYLPQTVRQG GYMPQ       595

SEQ ID NO: 31              moltype = AA   length = 595
FEATURE                    Location/Qualifiers
source                     1..595
                           mol_type = protein
                           organism = synthetic construct
SEQUENCE: 31
MLVRRGARAG PRMPRGWTAL CLLSLLPSGF MSLDNNGTAT PELPTQGTFS NVSTNVSYQE   60
TTTPSTLGST SLHPVSQHGN EATTNITETT VKFTSTSVIT SVYGNTNSSV QSQTSVISTV   120
FTTPANVSTP ETTLKPSLSP GNVSDLSTTS TSLATSPTKP YTSSSPILSD IKAEIKCSGI   180
REVKLTQGIC LEQNKTSSCA EFKKDRGEGL ARVLCGEEQA DADAGAQVCS LLLAQSEVRP   240
QCLLLVLANR TEISSKLQLM KKHQSDLKKL GILDFTEQDV ASHQSYSQKT AQGEIEAIVV   300
PVCLAFLLTT LLGVLFCFNK RDLIKKHIWP NVPDPSKSHI AQWSPHTPPR HNFNSKDQMY   360
SDGNFTDVSV VEIEANDKKP FPEDLKSLDL FKKEKINTEG HSSGIGGSSC MSSSRPSISS   420
SDENESSQNT SSTVQYSTVV HSGYRHQVPS VQVFSRSEST QPLLDSEERP EDLQLVDHVD   480
GGDGILPRQQ YFKQNCSQHE SSPDISHFER SKQVSSVNEE DFVRLKQQIS DHISQSCGSG   540
QMKMFQEVSA ADAFGPGTEG QVERFETVGM EAATDEGMPK SYLPQTVRQG GYMPQ       595

SEQ ID NO: 32              moltype = AA   length = 589
FEATURE                    Location/Qualifiers
source                     1..589
                           mol_type = protein
                           organism = synthetic construct
SEQUENCE: 32
MLVRRGARAG PRMPRGWTAL CLLSLLPSGF MSLDNNGTAT PELPTQGTFS NVSTNVSYQE   60
TTTPSTLGST SLHPVSQHGN EATTNITETT VKFTSTSVIT SVYGNTNSSV QSQTSVISTV   120
FTTPANVSTP ETTLKPSLSP GNVSDLSTTS TSLATSPTKP YTSSSPILSD IKAEIKCSGI   180
REVKLTQGIC LEQNKTSSCA EFKKDRGEGL ARVLCGEEQA DADAGAQVCS LLLAQSEVRP   240
QCLLLVLANR TEISSKLQLM KKHQSDLKKL GILDFTEQDV ASHQSYSQKT AIVVPVCLAF   300
LLTTLLGVLF CFNKRDLIKK HIWPNVPDPS KSHIAQWSPH TPPRHNFNSK DQMYSDGNFT   360
DVSVVEIEAN DKKPFPEDLK SLDLFKKEKI NTEGHSSGIG GSSCMSSSRP SISSSDENES   420
SQNTSSTVQY STVVHSGYRH QVPSVQVFSR SESTQPLLDS EERPEDLQLV DHVDGGDGIL   480
PRQQYFKQNC SQHESSPDIS HFERSKQVSS VNEEDFVRLK QQISDHISQS CGSGQMKFQ   540
EVSAADAFGP GTEGQVERFE TVGMEAATDE GMPKSYLPQT VRQGGYMPQ              589

SEQ ID NO: 33              moltype = AA   length = 387
FEATURE                    Location/Qualifiers
source                     1..387
                           mol_type = protein
                           organism = synthetic construct
SEQUENCE: 33
MALPVTALLL PLALLLHAAR PELPTQGTFS NVSTNVSPSS SDYSDLQRVK QELLEEVKKE   60
LQKVKEEIIE AFVQELRKRG SPAQGEIEAI VVPVCLAFLL TTLLGVLFCF NKRDLIKKHI   120
WPNVPDPSKS HIAQWSPHTP PRHNFNSKDQ MYSDGNFTDV SVVEIEANDK KPFPEDLKSL   180
```

-continued

```
DLFKKEKINT EGHSSGIGGS SCMSSSRPSI SSSDENESSQ NTSSTVQYST VVHSGYRHQV   240
PSVQVFSRSE STQPLLDSEE RPEDLQLVDH VDGGDGILPR QQYFKQNCSQ HESSPDISHF   300
ERSKQVSSVN EEDFVRLKQQ ISDHISQSCG SGQMKMFQEV SAADAFGPGT EGQVERFETV   360
GMEAATDEGM PKSYLPQTVR QGGYMPQ                                       387

SEQ ID NO: 34              moltype = AA  length = 387
FEATURE                    Location/Qualifiers
source                     1..387
                           mol_type = protein
                           organism = synthetic construct
SEQUENCE: 34
MALPVTALLL PLALLLHAAR PELPTQGTFS NVSTNVSAQG EIEAIVVPVC LAFLLTTLLG   60
VLFCFNKRDL IKKHIWPNVP DPSKSHIAQW SPHTPPRHNF NSKDQMYSDG NFTDVSVVEI   120
EANDKKPFPE DLKSLDLFKK EKINTEGHSS GIGGSSCMSS SRPSISSSDE NESSQNTSST   180
VQYSTVVHSG YRHQVPSVQV FSRSESTQPL LDSEERPEDL QLVDHVDGGD GILPRQQYFK   240
QNCSQHESSP DISHFERSKQ VSSVNEEDFV RLKQQISDHI SQSCGSGQMK MFQEVSAADA   300
FGPGTEGQVE RFETVGMEAA TDEGMPKSYL PQTVRQGGYM PQPSSSDYSD LQRVKQELLE   360
EVKKELQKVK EEIIEAFVQE LRKRGSP                                       387

SEQ ID NO: 35              moltype = AA  length = 392
FEATURE                    Location/Qualifiers
source                     1..392
                           mol_type = protein
                           organism = synthetic construct
SEQUENCE: 35
MALPVTALLL PLALLLHAAR PELPTQGTFS NVSTNVSELC GGPSSSDYSD LQRVKQELLE   60
EVKKELQKVK EEIIEAFVQE LRKRGSPAQG EIEAIVVPVC LAFLLTTLLG VLFCFNKRDL   120
IKKHIWPNVP DPSKSHIAQW SPHTPPRHNF NSKDQMYSDG NFTDVSVVEI EANDKKPFPE   180
DLKSLDLFKK EKINTEGHSS GIGGSSCMSS SRPSISSSDE NESSQNTSST VQYSTVVHSG   240
YRHQVPSVQV FSRSESTQPL LDSEERPEDL QLVDHVDGGD GILPRQQYFK QNCSQHESSP   300
DISHFERSKQ VSSVNEEDFV RLKQQISDHI SQSCGSGQMK MFQEVSAADA FGPGTEGQVE   360
RFETVGMEAA TDEGMPKSYL PQTVRQGGYM PQ                                 392

SEQ ID NO: 36              moltype = AA  length = 392
FEATURE                    Location/Qualifiers
source                     1..392
                           mol_type = protein
                           organism = synthetic construct
SEQUENCE: 36
MALPVTALLL PLALLLHAAR PELPTQGTFS NVSTNVSELC GGAQGEIEAI VVPVCLAFLL   60
TTLLGVLFCF NKRDLIKKHI WPNVPDPSKS HIAQWSPHTP PRHNFNSKDQ MYSDGNFTDV   120
SVVEIEANDK KPFPEDLKSL DLFKKEKINT EGHSSGIGGS SCMSSSRPSI SSSDENESSQ   180
NTSSTVQYST VVHSGYRHQV PSVQVFSRSE STQPLLDSEE RPEDLQLVDH VDGGDGILPR   240
QQYFKQNCSQ HESSPDISHF ERSKQVSSVN EEDFVRLKQQ ISDHISQSCG SGQMKMFQEV   300
SAADAFGPGT EGQVERFETV GMEAATDEGM PKSYLPQTVR QGGYMPQPSS SDYSDLQRVK   360
QELLEEVKKE LQKVKEEIIE AFVQELRKRG SP                                 392

SEQ ID NO: 37              moltype = AA  length = 594
FEATURE                    Location/Qualifiers
source                     1..594
                           mol_type = protein
                           organism = synthetic construct
SEQUENCE: 37
MLVRRGARAG PRMPRGWTAL CLLSLLPSGF MSLDNNGTAT PELPTQGTFS NVSTNVSYQE   60
TTTPSTLGST SLHPVSQHGN EATTNITETT VKFTSTSVIT SVYGNTNSSV QSQTSVISTV   120
FTTPANVSTP ETTLKPSLSP GNVSDLSTTS TSLATSPTKP YTSSSPILSD IKAEIKCSGI   180
REVKLTQGIC LEQNKTSSCA EFKKDRGEGL ARVLCGEEQA DADAGAQVCS LLLAQSEVRP   240
QCLLLVLANR TEISSKLQLM KKHQSDLKKL GILDFTEQDV ASHQSYSQKT ISLVTALLLV   300
LGLNAVLGLL LLRKQFPAHY RRLRHAIWPN VPDPSKSHIA QWSPHTPPRH NFNSKDQMYS   360
DGNFTDVSVV EIEANDKKPF PEDLKSLDLF KKEKINTEGH SSGIGGSSCM SSSRPSISSS   420
DENESSQNTS STVQYSTVVH SGYRHQVPSV QVFSRSESTQ PLLDSEERPE DLQLVDHVDG   480
GDGILPRQQY FKQNCSQHES SPDISHFERS KQVSSVNEED FVRLKQQISD HISQSCGSGQ   540
MKMFQEVSAA DAFGPGTEGQ VERFETVGME AATDEGMPKS YLPQTVRQGG YMPQ          594

SEQ ID NO: 38              moltype = AA  length = 339
FEATURE                    Location/Qualifiers
source                     1..339
                           mol_type = protein
                           organism = synthetic construct
SEQUENCE: 38
MALPVTALLL PLALLLHAAR PSDPTRVETA TETAWISLVT ALLLVLGLNA VLGLLLLRKQ   60
FPAHYRRLRH AIWPNVPDPS KSHIAQWSPH TPPRHNFNSK DQMYSDGNFT DVSVVEIEAN   120
DKKPFPEDLK SLDLFKKEKI NTEGHSSGIG GSSCMSSSRP SISSSDENES SQNTSSTVQY   180
STVVHSGYRH QVPSVQVFSR SESTQPLLDS EERPEDLQLV DHVDGGDGIL PRQQYFKQNC   240
SQHESSPDIS HFERSKQVSS VNEEDFVRLK QQISDHISQS CGSGQMKMFQ EVSAADAFGP   300
GTEGQVERFE TVGMEAATDE GMPKSYLPQT VRQGGYMPQ                          339

SEQ ID NO: 39              moltype = AA  length = 550
FEATURE                    Location/Qualifiers
```

-continued

```
source                   1..550
                         mol_type = protein
                         organism = synthetic construct
        SEQUENCE: 39
MDHLGASLWP QVGSLCLLLA GAAWAPPPNL PDPKFESKAA LLAARGPEEL LCFTERLEDL    60
VCFWEEAASA GVGPGNYSFS YQLEDEPWKL CRLHQAPTAR GAVRFWCSLP TADTSSFVPL   120
ELRVTAASGA PRYHRVIHIN EVVLLDAPVG LVACLADESG HVVLRWLPPP ETPMTSHIRY   180
EVDVSAGNGA GSVQRVEILE GRTECVLSNL RGRTRYTFAV RARMAEPSFG GFWSAWSEPV   240
SLLTPSDLDP LILTLSLILV VILVLLTVLA LLSNKRDLIK KHIWPNVPDP SKSHIAQWSP   300
HTPPRHNFNS KDQMYSDGNF TDVSVVEIEA NDKKPFPEDL KSLDLFKKEK INTEGHSSGI   360
GGSSCMSSSR PSISSSDENE SSQNTSSTVQ YSTVVHSGYR HQVPSVQVFS RSESTQPLLD   420
SEERPEDLQL VDHVDGGDGI LPRQQYFKQN CSQHESSPDI SHFERSKQVS SVNEEDFVRL   480
KQQISDHISQ SCGSGQMKMF QEVSAADAFG PGTEGQVERF ETVGMEAATD EGMPKSYLPQ   540
TVRQGGYMPQ                                                         550

SEQ ID NO: 40           moltype = AA  length = 549
FEATURE                 Location/Qualifiers
source                  1..549
                        mol_type = protein
                        organism = synthetic construct
        SEQUENCE: 40
MDHLGASLWP QVGSLCLLLA GAAWAPPPNL PDPKFESKAA LLAARGPEEL LCFTERLEDL    60
VCFWEEAASA GVGPGNYSFS YQLEDEPWKL CRLHQAPTAR GAVRFWCSLP TADTSSFVPL   120
ELRVTAASGA PRYHRVIHIN EVVLLDAPVG LVACLADESG HVVLRWLPPP ETPMTSHIRY   180
EVDVSAGNGA GSVQRVEILE GRTECVLSNL RGRTRYTFAV RARMAEPSFG GFWSAWSEPV   240
SLLTPSDLDP AIVVPVCLAF LLTTLLGVLF CFNKRDLIKK HIWPNVPDPS KSHIAQWSPH   300
TPPRHNFNSK DQMYSDGNFT DVSVVEIEAN DKKPFPEDLK SLDLFKKEKI NTEGHSSGIG   360
GSSCMSSSRP SISSSDENES SQNTSSTVQY STVVHSGYRH QVPSVQVFSR SESTQPLLDS   420
EERPEDLQLV DHVDGGDGIL PRQQYFKQNC SQHESSPDIS HFERSKQVSS VNEEDFVRLK   480
QQISDHISQS CGSGQMKMFQ EVSAADAFGP GTEGQVERFE TVGMEAATDE GMPKSYLPQT   540
VRQGGYMPQ                                                          549

SEQ ID NO: 41           moltype = AA  length = 563
FEATURE                 Location/Qualifiers
source                  1..563
                        mol_type = protein
                        organism = synthetic construct
        SEQUENCE: 41
MALPVTALLL PLALLLHAAR PELPTQGTFS NVSTNVSAPP PNLPDPKFES KAALLAARGP    60
EELLCFTERL EDLVCFWEEA ASAGVGPGNY SFSYQLEDEP WKLCRLHQAP TARGAVRFWC   120
SLPTADTSSF VPLELRVTAA SGAPRYHRVI HINEVVLLDA PVGLVACLAD ESGHVVLRWL   180
PPPETPMTSH IRYEVDVSAG NGAGSVQRVE ILEGRTECVL SNLRGRTRYT FAVRARMAEP   240
SFGGFWSAWS EPVSLLTPSD LDPLILTLSL ILVVILVLLT VLALLSNKRD LIKKHIWPNV   300
PDPSKSHIAQ WSPHTPPRHN FNSKDQMYSD GNFTDVSVVE IEANDKKPFP EDLKSLDLFK   360
KEKINTEGHS SGIGGSSCMS SSRPSISSSD ENESSQNTSS TVQYSTVVHS GYRHQVPSVQ   420
VFSRSESTQP LLDSEERPED LQLVDHVDGG DGILPRQQYF KQNCSQHESS PDISHFERSK   480
QVSSVNEEDF VRLKQQISDH ISQSCGSGQM KMFQEVSAAD AFGPGTEGQV ERFETVGMEA   540
ATDEGMPKSY LPQTVRQGGY MPQ                                          563

SEQ ID NO: 42           moltype = AA  length = 562
FEATURE                 Location/Qualifiers
source                  1..562
                        mol_type = protein
                        organism = synthetic construct
        SEQUENCE: 42
MALPVTALLL PLALLLHAAR PELPTQGTFS NVSTNVSAPP PNLPDPKFES KAALLAARGP    60
EELLCFTERL EDLVCFWEEA ASAGVGPGNY SFSYQLEDEP WKLCRLHQAP TARGAVRFWC   120
SLPTADTSSF VPLELRVTAA SGAPRYHRVI HINEVVLLDA PVGLVACLAD ESGHVVLRWL   180
PPPETPMTSH IRYEVDVSAG NGAGSVQRVE ILEGRTECVL SNLRGRTRYT FAVRARMAEP   240
SFGGFWSAWS EPVSLLTPSD LDPAIVVPVC LAFLLTTLLG VLFCFNKRDL IKKHIWPNVP   300
DPSKSHIAQW SPHTPPRHNF NSKDQMYSDG NFTDVSVVEI EANDKKPFPE DLKSLDLFKK   360
EKINTEGHSS GIGGSSCMSS SRPSISSSDE NESSQNTSST VQYSTVVHSG YRHQVPSVQV   420
FSRSESTQPL LDSEERPEDL QLVDHVDGGD GILPRQQYFK QNCSQHESSP DISHFERSKQ   480
VSSVNEEDFV RLKQQISDHI SQSCGSGQMK MFQEVSAADA FGPGTEGQVE RFETVGMEAA   540
TDEGMPKSYL PQTVRQGGYM PQ                                           562

SEQ ID NO: 43           moltype = AA  length = 332
FEATURE                 Location/Qualifiers
source                  1..332
                        mol_type = protein
                        organism = synthetic construct
        SEQUENCE: 43
MGSSKSKPKD PSQRRRRIAR LEEKVKTLKA QNSELASTAN MLREQVAQLK QKVMNNKRDL    60
IKKHIWPNVP DPSKSHIAQW SPHTPPRHNF NSKDQMYSDG NFTDVSVVEI EANDKKPFPE   120
DLKSLDLFKK EKINTEGHSS GIGGSSCMSS SRPSISSSDE NESSQNTSST VQYSTVVHSG   180
YRHQVPSVQV FSRSESTQPL LDSEERPEDL QLVDHVDGGD GILPRQQYFK QNCSQHESSP   240
DISHFERSKQ VSSVNEEDFV RLKQQISDHI SQSCGSGQMK MFQEVSAADA FGPGTEGQVE   300
RFETVGMEAA TDEGMPKSYL PQTVRQGGYM PQ                                332
```

-continued

```
SEQ ID NO: 44              moltype = AA   length = 332
FEATURE                    Location/Qualifiers
source                     1..332
                           mol_type = protein
                           organism = synthetic construct
SEQUENCE: 44
MGSSKSKPKD PSQRRRNKRD LIKKHIWPNV PDPSKSHIAQ WSPHTPPRHN FNSKDQMYSD     60
GNFTDVSVVE IEANDKKPFP EDLKSLDLFK KEKINTEGHS SGIGGSSCMS SSRPSISSSD    120
ENESSQNTSS TVQYSTVVHS GYRHQVPSVQ VFSRSESTQP LLDSEERPED LQLVDHVDGG    180
DGILPRQQYF KQNCSQHESS PDISHFERSK QVSSVNEEDF VRLKQQISDH ISQSCGSGQM    240
KMFQEVSAAD AFGPGTEGQV ERFETVGMEA ATDEGMPKSY LPQTVRQGGY MPQRIARLEE    300
KVKTLKAQNS ELASTANMLR EQVAQLKQKV MN                                  332

SEQ ID NO: 45              moltype = AA   length = 332
FEATURE                    Location/Qualifiers
source                     1..332
                           mol_type = protein
                           organism = synthetic construct
SEQUENCE: 45
MGCVQCKDKE ATKLTERIAR LEEKVKTLKA QNSELASTAN MLREQVAQLK QKVMNNKRDL     60
IKKHIWPNVP DPSKSHIAQW SPHTPPRHNF NSKDQMYSDG NFTDVSVVEI EANDKKPFPE    120
DLKSLDLFKK EKINTEGHSS GIGGSSCMSS SRPSISSSDE NESSQNTSST VQYSTVVHSG    180
YRHQVPSVQV FSRSESTQPL LDSEERPEDL QLVDHVDGGD GILPRQQYFK QNCSQHESSP    240
DISHFERSKQ VSSVNEEDFV RLKQQISDHI SQSCGSGQMK MFQEVSAADA FGPGTEGQVE    300
RFETVGMEAA TDEGMPKSYL PQTVRQGGYM PQ                                  332

SEQ ID NO: 46              moltype = AA   length = 332
FEATURE                    Location/Qualifiers
source                     1..332
                           mol_type = protein
                           organism = synthetic construct
SEQUENCE: 46
MGCVQCKDKE ATKLTENKRD LIKKHIWPNV PDPSKSHIAQ WSPHTPPRHN FNSKDQMYSD     60
GNFTDVSVVE IEANDKKPFP EDLKSLDLFK KEKINTEGHS SGIGGSSCMS SSRPSISSSD    120
ENESSQNTSS TVQYSTVVHS GYRHQVPSVQ VFSRSESTQP LLDSEERPED LQLVDHVDGG    180
DGILPRQQYF KQNCSQHESS PDISHFERSK QVSSVNEEDF VRLKQQISDH ISQSCGSGQM    240
KMFQEVSAAD AFGPGTEGQV ERFETVGMEA ATDEGMPKSY LPQTVRQGGY MPQRIARLEE    300
KVKTLKAQNS ELASTANMLR EQVAQLKQKV MN                                  332

SEQ ID NO: 47              moltype = AA   length = 332
FEATURE                    Location/Qualifiers
source                     1..332
                           mol_type = protein
                           organism = synthetic construct
SEQUENCE: 47
MGCGCSSHPE DDWMENNKRD LIKKHIWPNV PDPSKSHIAQ WSPHTPPRHN FNSKDQMYSD     60
GNFTDVSVVE IEANDKKPFP EDLKSLDLFK KEKINTEGHS SGIGGSSCMS SSRPSISSSD    120
ENESSQNTSS TVQYSTVVHS GYRHQVPSVQ VFSRSESTQP LLDSEERPED LQLVDHVDGG    180
DGILPRQQYF KQNCSQHESS PDISHFERSK QVSSVNEEDF VRLKQQISDH ISQSCGSGQM    240
KMFQEVSAAD AFGPGTEGQV ERFETVGMEA ATDEGMPKSY LPQTVRQGGY MPQRIARLEE    300
KVKTLKAQNS ELASTANMLR EQVAQLKQKV MN                                  332

SEQ ID NO: 48              moltype = AA   length = 332
FEATURE                    Location/Qualifiers
source                     1..332
                           mol_type = protein
                           organism = synthetic construct
SEQUENCE: 48
MGCGCSSHPE DDWMENRIAR LEEKVKTLKA QNSELASTAN MLREQVAQLK QKVMNNKRDL     60
IKKHIWPNVP DPSKSHIAQW SPHTPPRHNF NSKDQMYSDG NFTDVSVVEI EANDKKPFPE    120
DLKSLDLFKK EKINTEGHSS GIGGSSCMSS SRPSISSSDE NESSQNTSST VQYSTVVHSG    180
YRHQVPSVQV FSRSESTQPL LDSEERPEDL QLVDHVDGGD GILPRQQYFK QNCSQHESSP    240
DISHFERSKQ VSSVNEEDFV RLKQQISDHI SQSCGSGQMK MFQEVSAADA FGPGTEGQVE    300
RFETVGMEAA TDEGMPKSYL PQTVRQGGYM PQ                                  332

SEQ ID NO: 49              moltype = AA   length = 340
FEATURE                    Location/Qualifiers
source                     1..340
                           mol_type = protein
                           organism = synthetic construct
SEQUENCE: 49
MGSSKSKPKD PSQRRRPSSS DYSDLQRVKQ ELLEEVKKEL QKVKEEIIEA FVQELRKRGS     60
PGSNKRDLIK KHIWPNVPDP SKSHIAQWSP HTPPRHNFNS KDQMYSDGNF TDVSVVEIEA    120
NDKKPFPEDL KSLDLFKKEK INTEGHSSGI GGSSCMSSSR PSISSSDENE SSQNTSSTVQ    180
YSTVVHSGYR HQVPSVQVFS RSESTQPLLD SEERPEDLQL VDHVDGGDGI LPRQQYFKQN    240
CSQHESSPDI SHFERSKQVS SVNEEDFVRL KQQISDHISQ SCGSGQMKMF QEVSAADAFG    300
PGTEGQVERF ETVGMEAATD EGMPKSYLPQ TVRQGGYMPQ                          340

SEQ ID NO: 50              moltype = AA   length = 340
```

```
FEATURE              Location/Qualifiers
source               1..340
                     mol_type = protein
                     organism = synthetic construct
SEQUENCE: 50
MGSSKSKPKD PSQRRRNKRD LIKKHIWPNV PDPSKSHIAQ WSPHTPPRHN FNSKDQMYSD    60
GNFTDVSVVE IEANDKKPFP EDLKSLDLFK KEKINTEGHS SGIGGSSCMS SSRPSISSSD   120
ENESSQNTSS TVQYSTVVHS GYRHQVPSVQ VFSRSESTQP LLDSEERPED LQLVDHVDGG   180
DGILPRQQYF KQNCSQHESS PDISHFERSK QVSSVNEEDF VRLKQQISDH ISQSCGSGQM   240
KMFQEVSAAD AFGPGTEGQV ERFETVGMEA ATDEGMPKSY LPQTVRQGGY MPQGSPSSSD   300
YSDLQRVKQE LLEEVKKELQ KVKEEIIEAF VQELRKRGSP                        340

SEQ ID NO: 51         moltype = AA  length = 332
FEATURE              Location/Qualifiers
source               1..332
                     mol_type = protein
                     organism = synthetic construct
SEQUENCE: 51
MGSSKSKPKD PSQRRRRIAR LEEKVKTLKA QNSELASTAN MLREQVAQLK QKVMNNKRDL    60
IKKHIWPNVP DPSKSHIAQW SPHTPPRHNF NSKDQMYSDG NFTDVSVVEI EANDKKPFPE   120
DLKSLDLFKK EKINTEGHSS GIGGSSCMSS SRPSISSSDE NESSQNTSST VQYSTVVHSG   180
YRHQVPSVQV FSRSESTQPL LDSEERPEDL QLVDHVDGGD GILPRQQYFK QNCSQHESSP   240
DISHFERSKQ VSSVNEEDFV RLKQQISDHI SQSCGSGQMK MFQEVSAADA FGPGTEGQVE   300
RFETVGMEAA TDEGMPKSYL PQTVRQGGYM PQ                                332

SEQ ID NO: 52         moltype = AA  length = 332
FEATURE              Location/Qualifiers
source               1..332
                     mol_type = protein
                     organism = synthetic construct
SEQUENCE: 52
MGSSKSKPKD PSQRRRNKRD LIKKHIWPNV PDPSKSHIAQ WSPHTPPRHN FNSKDQMYSD    60
GNFTDVSVVE IEANDKKPFP EDLKSLDLFK KEKINTEGHS SGIGGSSCMS SSRPSISSSD   120
ENESSQNTSS TVQYSTVVHS GYRHQVPSVQ VFSRSESTQP LLDSEERPED LQLVDHVDGG   180
DGILPRQQYF KQNCSQHESS PDISHFERSK QVSSVNEEDF VRLKQQISDH ISQSCGSGQM   240
KMFQEVSAAD AFGPGTEGQV ERFETVGMEA ATDEGMPKSY LPQTVRQGGY MPQRIARLEE   300
KVKTLKAQNS ELASTANMLR EQVAQLKQKV MN                                332

SEQ ID NO: 53         moltype = AA  length = 332
FEATURE              Location/Qualifiers
source               1..332
                     mol_type = protein
                     organism = synthetic construct
SEQUENCE: 53
MGCVQCKDKE ATKLTENKRD LIKKHIWPNV PDPSKSHIAQ WSPHTPPRHN FNSKDQMYSD    60
GNFTDVSVVE IEANDKKPFP EDLKSLDLFK KEKINTEGHS SGIGGSSCMS SSRPSISSSD   120
ENESSQNTSS TVQYSTVVHS GYRHQVPSVQ VFSRSESTQP LLDSEERPED LQLVDHVDGG   180
DGILPRQQYF KQNCSQHESS PDISHFERSK QVSSVNEEDF VRLKQQISDH ISQSCGSGQM   240
KMFQEVSAAD AFGPGTEGQV ERFETVGMEA ATDEGMPKSY LPQTVRQGGY MPQRIARLEE   300
KVKTLKAQNS ELASTANMLR EQVAQLKQKV MN                                332

SEQ ID NO: 54         moltype = AA  length = 332
FEATURE              Location/Qualifiers
source               1..332
                     mol_type = protein
                     organism = synthetic construct
SEQUENCE: 54
MGCGCSSHPE DDWMENNKRD LIKKHIWPNV PDPSKSHIAQ WSPHTPPRHN FNSKDQMYSD    60
GNFTDVSVVE IEANDKKPFP EDLKSLDLFK KEKINTEGHS SGIGGSSCMS SSRPSISSSD   120
ENESSQNTSS TVQYSTVVHS GYRHQVPSVQ VFSRSESTQP LLDSEERPED LQLVDHVDGG   180
DGILPRQQYF KQNCSQHESS PDISHFERSK QVSSVNEEDF VRLKQQISDH ISQSCGSGQM   240
KMFQEVSAAD AFGPGTEGQV ERFETVGMEA ATDEGMPKSY LPQTVRQGGY MPQRIARLEE   300
KVKTLKAQNS ELASTANMLR EQVAQLKQKV MN                                332

SEQ ID NO: 55         moltype = AA  length = 332
FEATURE              Location/Qualifiers
source               1..332
                     mol_type = protein
                     organism = synthetic construct
SEQUENCE: 55
MGCGCSSHPE DDWMENRIAR LEEKVKTLKA QNSELASTAN MLREQVAQLK QKVMNNKRDL    60
IKKHIWPNVP DPSKSHIAQW SPHTPPRHNF NSKDQMYSDG NFTDVSVVEI EANDKKPFPE   120
DLKSLDLFKK EKINTEGHSS GIGGSSCMSS SRPSISSSDE NESSQNTSST VQYSTVVHSG   180
YRHQVPSVQV FSRSESTQPL LDSEERPEDL QLVDHVDGGD GILPRQQYFK QNCSQHESSP   240
DISHFERSKQ VSSVNEEDFV RLKQQISDHI SQSCGSGQMK MFQEVSAADA FGPGTEGQVE   300
RFETVGMEAA TDEGMPKSYL PQTVRQGGYM PQ                                332

SEQ ID NO: 56         moltype = AA  length = 340
FEATURE              Location/Qualifiers
```

```
source                  1..340
                        mol_type = protein
                        organism = synthetic construct
SEQUENCE: 56
MGSSKSKPKD PSQRRRPSSS DYSDLQRVKQ ELLEEVKKEL QKVKEEIIEA FVQELRKRGS   60
PGSNKRDLIK KHIWPNVPDP SKSHIAQWSP HTPPRHNFNS KDQMYSDGNF TDVSVVEIEA  120
NDKKPPFPEDL KSLDLFKKEK INTEGHSSGI GGSSCMSSSR PSISSSDENE SSQNTSSTVQ  180
YSTVVHSGYR HQVPSVQVFS RSESTQPLLD SEERPEDLQL VDHVDGGDGI LPRQQYFKQN  240
CSQHESSPDI SHFERSKQVS SVNEEDFVRL KQQISDHISQ SCGSGQMKMF QEVSAADAFG  300
PGTEGQVERF ETVGMEAATD EGMPKSYLPQ TVRQGGYMPQ                         340

SEQ ID NO: 57          moltype = AA  length = 386
FEATURE                Location/Qualifiers
source                 1..386
                       mol_type = protein
                       organism = synthetic construct
SEQUENCE: 57
MALPVTALLL PLALLLHAAR PELPTQGTFS NVSTNVSELC GGRIARLEEK VKTLKAQNSE   60
LASTANMLRE QVAQLKQKVM NAQGEIEAIV VPVCLAFLLT TLLGVLFCFN KRDLIKKHIW  120
PNVPDPSKSH IAQWSPHTPP RHNFNSKDQM YSDGNFTDVS VVEIEANDKK PFPEDLKSLD  180
LFKKEKINTE GHSSGIGGSS CMSSSRPSIS SSDENESSQN TSSTVQYSTV VHSGYRHQVP  240
SVQVFSRSES TQPLLDSEER PEDLQLVDHV DGGDGILPRQ QYFKQNCSQH ESSPDISHFE  300
RSKQVSSVNE EDFVRLKQQI SDHISQSCGS GQMKMFQEVS AADAFGPGTE GQVERFETVG  360
MEAATDEGMP KSYLPQTVRQ GGYMPQ                                       386

SEQ ID NO: 58          moltype = AA  length = 332
FEATURE                Location/Qualifiers
source                 1..332
                       mol_type = protein
                       organism = synthetic construct
SEQUENCE: 58
MGSSKSKPKD PSQRRRRIAR LEEKVKTLKA QNSELASTAN MLREQVAQLK QKVMNNKRDL   60
IKKHIWPNVP DPSKSHIAQW SPHTPPRHNF NSKDQMYSDG NFTDVSVVEI EANDKKPFPE  120
DLKSLDLFKK EKINTEGHSS GIGGSSCMSS SRPSISSSDE NESSQNTSST VQYSTVVHSG  180
YRHQVPSVQV FSRSESTQPL LDSEERPEDL QLVDHVDGGD GILPRQQYFK QNCSQHESSP  240
DISHFERSKQ VSSVNEEDFV RLKQQISDHI SQSCGSGQMK MFQEVSAADA FGPGTEGQVE  300
RFETVGMEAA TDEGMPKSYL PQTVRQGGYM PQ                                332

SEQ ID NO: 59          moltype = AA  length = 918
FEATURE                Location/Qualifiers
source                 1..918
                       mol_type = protein
                       organism = synthetic construct
SEQUENCE: 59
MLTLQTWLVQ ALFIFLTTES TGELLDPCGY ISPESPVVQL HSNFTAVCVL KEKCMDYFHV   60
NANYIVWKTN HFTIPKEQYT IINRTASSVT FTDIASLNIQ LTCNILTFGQ LEQNVYGITI  120
ISGLPPEKPK NLSCIVNEGK KMRCEWDGGR ETHLETNFTL KSEWATHKFA DCKAKRDTPT  180
SCTVDYSTVY FVNIEVWVEA ENALGKVTSD HINFDPVYKV KPNPPHNLSV INSEELSSIL  240
KLTWTNPSIK SVIILKYNIQ YRTKDASTWS QIPPEDTAST RSSFTVQDLK PFTEYVFRIR  300
CMKEDGKGYW SDWSEEASGI TYEDRPSKAP SFWYKIDPSH TQGYRTVQLV WKTLPPFEAN  360
GKILDYEVTL TRWKSHLQNY TVNATKLTVN LTNDRYLATL TVRNLVGKSD AAVLTIPACD  420
FQATHPVMDL KAFPKDNMLW VEWTTPRESV KKYILEWCVL SDKAPCITDW QQEDGTVHRT  480
YLRGNLAESK CYLITVTPVY ADGPGSPESI KAYLKQAPPS KGPTVRTKKV GKNEAVLEWD  540
QLPVDVQNGF IRNYTIFYRT IIGNETAVNV DSSHTEYTLS SLTSDTLYMV RMAAYTDEGG  600
KDGPEFTFTT PKFAQGEIEA IVVPVCLAFL LTTLLGVLFC FNKRDLIKKH IWPNVPDPSK  660
SHIAQWSPHT PPRHNFNSKD QMYSDGNFTD VSVVEIEAND KKPFEDLKS LDLFKKEKIN  720
TEGHSSGIGG SSCMSSSRPS ISSSDENESS QNTSSTVQYS TVVHSGYRHQ VPSVQVFSRS  780
ESTQPLLDSE ERPEDLQLVD HVDGGDGILP RQQYFKQNCS QHESSPDISH FERSKQVSSV  840
NEEDFVRLKQ QISDHISQSC GSGQMKMFQE VSAADAFGPG TEGQVERFET VGMEAATDEG  900
MPKSYLPQTV RQGGYMPQ                                                918

SEQ ID NO: 60          moltype = AA  length = 277
FEATURE                Location/Qualifiers
source                 1..277
                       mol_type = protein
                       organism = synthetic construct
SEQUENCE: 60
NKRDLIKKHI WPNVPDPSKS HIAQWSPHTP PRHNFNSKDQ MYSDGNFTDV SVVEIEANDK   60
KPFPEDLKSL DLFKKEKINT EGHSSGIGGS SCMSSSRPSI SSSDENESSQ NTSSTVQYST  120
VVHSGYRHQV PSVQVFSRSE STQPLLDSEE RPEDLQLVDH VDGGDGILPR QQYFKQNCSQ  180
HESSPDISHF ERSKQVSSVN EEDFVRLKQQ ISDHISQSCG SGQMKMFQEV SAADAFGPGT  240
EGQVERFETV GMEAATDEGM PKSYLPQTVR QGGYMPQ                            277

SEQ ID NO: 61          moltype = AA  length = 22
FEATURE                Location/Qualifiers
source                 1..22
                       mol_type = protein
                       organism = synthetic construct
SEQUENCE: 61
```

```
AIVVPVCLAF LLTTLLGVLF CF                                                    22

SEQ ID NO: 62           moltype = AA  length = 378
FEATURE                 Location/Qualifiers
source                  1..378
                        mol_type = protein
                        organism = synthetic construct
SEQUENCE: 62
MALPVTALLL PLALLLHAAR PDYKDDDDKE LCGGRIARLE EKVKTLKAQN SELASTANML  60
REQVAQLKQK VMNAQGEIEA IVVPVCLAFL LTTLLGVLFC FNKRDLIKKH IWPNVPDPSK  120
SHIAQWSPHT PPRHNFNSKD QMYSDGNFTD VSVVEIEAND KKPFPEDLKS LDLFKKEKIN  180
TEGHSSGIGG SSCMSSSRPS ISSSDENESS QNTSSTVQYS TVVHSGYRHQ VPSVQVFSRS  240
ESTQPLLDSE ERPEDLQLVD HVDGGDGILP RQQYFKQNCS QHESSPDISH FERSKQVSSV  300
NEEDFVRLKQ QISDHISQSC GSGQMKMFQE VSAADAFGPG TEGQVERFET VGMEAATDEG  360
MPKSYLPQTV RQGGYMPQ                                                378

SEQ ID NO: 63           moltype = AA  length = 365
FEATURE                 Location/Qualifiers
source                  1..365
                        mol_type = protein
                        organism = synthetic construct
SEQUENCE: 63
ELPTQGTFSN VSTNVSELCG GRIARLEEKV KTLKAQNSEL ASTANMLREQ VAQLKQKVMN  60
AQGEIEAIVV PVCLAFLLTT LLGVLFCFNK RDLIKKHIWP NVPDPSKSHI AQWSPHTPPR  120
HNFNSKDQMY SDGNFTDVSV VEIEANDKKP FPEDLKSLDL FKKEKINTEG HSSGIGGSSC  180
MSSSRPSISS SDENESSQNT SSTVQFSTVV HSGYRHQVPS VQVFSRSEST QPLLDSEERP  240
EDLQLVDHVD GGDGILPRQQ YFKQNCSQHE SSPDISHFER SKQVSSVNEE DFVRLKQQIS  300
DHISQSCGSG QMKMFQEVSA ADAFGPGTEG QVERFETVGM EAATDEGMPK SYLPQTVRQG  360
GYMPQ                                                             365

SEQ ID NO: 64           moltype = AA  length = 324
FEATURE                 Location/Qualifiers
source                  1..324
                        mol_type = protein
                        organism = synthetic construct
SEQUENCE: 64
ELPTQGTFSN VSTNVSELCG GRIARLEEKV KTLKAQNSEL ASTANMLREQ VAQLKQKVMN  60
AQGEIEAIVV PVCLAFLLTT LLGVLFCFNK RDLIKKHIWP NVPDPSKSHI AQWSPHTPPR  120
HNFNSKDQMY SDGNFTDVSV VEIEANDKKP FPEDLKSLDL FKKEKINTEG HSSGIGGSSC  180
MSSSRPSISS SDENESSQNT SSTVQFSTVV HSGYRHQQQY FKQNCSQHES SPDISHFERS  240
KQVSSVNEED FVRLKQQISD HISQSCGSGQ MKMFQEVSAA DAFGPGTEGQ VERFETVGME  300
AATDEGMPKS YLPQTVRQGG YMPQ                                         324

SEQ ID NO: 65           moltype = AA  length = 324
FEATURE                 Location/Qualifiers
source                  1..324
                        mol_type = protein
                        organism = synthetic construct
SEQUENCE: 65
ELPTQGTFSN VSTNVSELCG GRIARLEEKV KTLKAQNSEL ASTANMLREQ VAQLKQKVMN  60
AQGEIEAIVV PVCLAFLLTT LLGVLFCFNK RDLIKKHIWP NVPDPSKSHI AQWSPHTPPR  120
HNFNSKDQMY SDGNFTDVSV VEIEANDKKP FPEDLKSLDL FKKEKINTEG HSSGIGGSSC  180
MSSSRPSISS SDENESSQNT SSTVQYSTVV HSGYRHQQQY FKQNCSQHES SPDISHFERS  240
KQVSSVNEED FVRLKQQISD HISQSCGSGQ MKMFQEVSAA DAFGPGTEGQ VERFETVGME  300
AATDEGMPKS YLPQTVRQGG YMPQ                                         324

SEQ ID NO: 66           moltype = AA  length = 360
FEATURE                 Location/Qualifiers
source                  1..360
                        mol_type = protein
                        organism = synthetic construct
SEQUENCE: 66
ELPTQGTFSN VSTNVSRIAR LEEKVKTLKA QNSELASTAN MLREQVAQLK QKVMNAQGEI  60
EAIVVPVCLA FLLTTLLGVL FCFNKRDLIK KHIWPNVPDP SKSHIAQWSP HTPPRHNFNS  120
KDQMYSDGNF TDVSVVEIEA NDKKPFPEDL KSLDLFKKEK INTEGHSSGI GGSSCMSSSR  180
PSISSSDENE SSQNTSSTVQ YSTVVHSGYR HQVPSVQVFS RSESTQPLLD SEERPEDLQL  240
VDHVDGGDGI LPRQQYFKQN CSQHESSPDI SHFERSKQVS SVNEEDFVRL KQQISDHISQ  300
SCGSGQMKMF QEVSAADAFG PGTEGQVERF ETVGMEAATD EGMPKSYLPQ TVRQGGYMPQ  360

SEQ ID NO: 67           moltype = AA  length = 360
FEATURE                 Location/Qualifiers
source                  1..360
                        mol_type = protein
                        organism = synthetic construct
SEQUENCE: 67
ELPTQGTFSN VSTNVSRIAR LEEKVKTLKA QNSELASTAN MLREQVAQLK QKVMNAQGEI  60
EAIVVPVCLA FLLTTLLGVL FCFNKRDLIK KHIWPNVPDP SKSHIAQWSP HTPPRHNFNS  120
KDQMYSDGNF TDVSVVEIEA NDKKPFPEDL KSLDLFKKEK INTEGHSSGI GGSSCMSSSR  180
PSISSSDENE SSQNTSSTVQ FSTVVHSGYR HQVPSVQVFS RSESTQPLLD SEERPEDLQL  240
```

-continued

```
VDHVDGGDGI LPRQQYFKQN CSQHESSPDI SHFERSKQVS SVNEEDFVRL KQQISDHISQ  300
SCGSGQMKMF QEVSAADAFG PGTEGQVERF ETVGMEAATD EGMPKSYLPQ TVRQGGYMPQ  360

SEQ ID NO: 68          moltype = AA  length = 319
FEATURE                Location/Qualifiers
source                 1..319
                       mol_type = protein
                       organism = synthetic construct
SEQUENCE: 68
ELPTQGTFSN VSTNVSRIAR LEEKVKTLKA QNSELASTAN MLREQVAQLK QKVMNAQGEI  60
EAIVVPVCLA FLLTTLLGVL FCFNKRDLIK KHIWPNVPDP SKSHIAQWSP HTPPRHNFNS  120
KDQMYSDGNF TDVSVVEIEA NDKKPFPEDL KSLDLFKKEK INTEGHSSGI GGSSCMSSSR  180
PSISSSDENE SSQNTSSTVQ FSTVVHSGYR HQQQYFKQNC SQHESSPDIS HFERSKQVSS  240
VNEEDFVRLK QQISDHISQS CGSGQMKMFQ EVSAADAFGP GTEGQVERFE TVGMEAATDE  300
GMPKSYLPQT VRQGGYMPQ                                              319

SEQ ID NO: 69          moltype = AA  length = 319
FEATURE                Location/Qualifiers
source                 1..319
                       mol_type = protein
                       organism = synthetic construct
SEQUENCE: 69
ELPTQGTFSN VSTNVSRIAR LEEKVKTLKA QNSELASTAN MLREQVAQLK QKVMNAQGEI  60
EAIVVPVCLA FLLTTLLGVL FCFNKRDLIK KHIWPNVPDP SKSHIAQWSP HTPPRHNFNS  120
KDQMYSDGNF TDVSVVEIEA NDKKPFPEDL KSLDLFKKEK INTEGHSSGI GGSSCMSSSR  180
PSISSSDENE SSQNTSSTVQ YSTVVHSGYR HQQQYFKQNC SQHESSPDIS HFERSKQVSS  240
VNEEDFVRLK QQISDHISQS CGSGQMKMFQ EVSAADAFGP GTEGQVERFE TVGMEAATDE  300
GMPKSYLPQT VRQGGYMPQ                                              319

SEQ ID NO: 70          moltype = AA  length = 365
FEATURE                Location/Qualifiers
source                 1..365
                       mol_type = protein
                       organism = synthetic construct
SEQUENCE: 70
ELPTQGTFSN VSTNVSELCG GRIARLEEKV KTLKAQNSEL ASTANMLREQ VAQLKQKVMN  60
AQGEIEAIVV PVCLAFLLTT LLGVLFCFNK RDLIKKHIWP NVPDPSKSHI AQWSPHTPPR  120
HNFNSKDQMY SDGNFTDVSV VEIEANDKKP FPEDLKSLDL FKKEKINTEG HSSGIGGSSC  180
MSSSRPSISS SDENESSQNT SSTVVQYSTVV HSGYRHQVPS VQVFSRSEST QPLLDSEERP  240
EDLQLVDHVD GGDGILPRQQ YFKQNCSQHE SSPDISHFER SKQVSSVNEE DFVRLKQQIS  300
DHISQSCGSG QMKMFQEVSA ADAFGPGTEG QVERFETVGM EAATDEGMPK SYLPQTVRQG  360
GYMPQ                                                            365

SEQ ID NO: 71          moltype = AA  length = 316
FEATURE                Location/Qualifiers
source                 1..316
                       mol_type = protein
                       organism = synthetic construct
SEQUENCE: 71
ELPTQGTFSN VSTNVSELCG GRIARLEEKV KTLKAQNSEL ASTANMLREQ VAQLKQKVMN  60
AQGEIEAIVV PVCLAFLLTT LLGVLFCFNK RDLIKKHIWP NVPDPSKSHI AQWSPHTPPR  120
HNFNSKDQMY SDGNFTDVSV VEIEANDKKP FPETVQYSTV VHSGYRHQVP SVQVFSRSES  180
TQPLLDSEER PEDLQLVDHV DGGDGILPRQ YFKQNCSQH ESSPDISHFE RSKQVSSVNE  240
EDFVRLKQQI SDHISQSCGS GQMKMFQEVS AADAFGPGTE GQVERFETVG MEAATDEGMP  300
KSYLPQTVRQ GGYMPQ                                                316

SEQ ID NO: 72          moltype = AA  length = 324
FEATURE                Location/Qualifiers
source                 1..324
                       mol_type = protein
                       organism = synthetic construct
SEQUENCE: 72
ELPTQGTFSN VSTNVSELCG GRIARLEEKV KTLKAQNSEL ASTANMLREQ VAQLKQKVMN  60
AQGEIEAIVV PVCLAFLLTT LLGVLFCFNK RDLIKKHIWP NVPDPSKSHI AQWSPHTPPR  120
HNFNSKDQMY SDGNFTDVSV VEIEANDKKP FPEDLKSLDL FKKEKINTEG HSSGIGGSSC  180
MSSSRPSISS SDENESSQNT SSTVQYSTVV HSGYRHQQQY FKQNCSQHES SPDISHFERS  240
KQVSSVNEED FVRLKQQISD HISQSCGSGQ MKMFQEVSAA DAFGPGTEGQ VERFETVGME  300
AATDEGMPKS YLPQTVRQGG YMPQ                                        324

SEQ ID NO: 73          moltype = AA  length = 281
FEATURE                Location/Qualifiers
source                 1..281
                       mol_type = protein
                       organism = synthetic construct
SEQUENCE: 73
ELPTQGTFSN VSTNVSELCG GRIARLEEKV KTLKAQNSEL ASTANMLREQ VAQLKQKVMN  60
AQGEIEAIVV PVCLAFLLTT LLGVLFCFNK RDLIKKHIWP NVPDPSKSHI AQWSPHTPPR  120
HNFNSKDQMY SDGNFTDVSV VEIEANDKKP FPEDLKSLDL FKKEKINTEG HSSGIGGSSC  180
MSSSRPSISS SDENESSQNT SSTVQYSTVV HSGYRHQVPS VQVFSRSEST QPLLDSEERP  240
```

```
EDLQLVDHVD GGDGILPRQQ YFKQPKSYLP QTVRQGGYMP Q                281

SEQ ID NO: 74          moltype = AA   length = 275
FEATURE                Location/Qualifiers
source                 1..275
                       mol_type = protein
                       organism = synthetic construct
SEQUENCE: 74
ELPTQGTFSN VSTNVSELCG GRIARLEEKV KTLKAQNSEL ASTANMLREQ VAQLKQKVMN   60
AQGEIEAIVV PVCLAFLLTT LLGVLFCFNK RDLIKKHIWP NVPDPSKSHI AQWSPHTPPR   120
HNFNSKDQMY SDGNFTDVSV VEIEANDKKP FPETVQYSTV VHSGYRHQQQ YFKQNCSQHE   180
SSPDISHFER SKQVSSVNEE DFVRLKQQIS DHISQSCGSG QMKMFQEVSA ADAFGPGTEG   240
QVERFETVGM EAATDEGMPK SYLPQTVRQG GYMPQ                            275

SEQ ID NO: 75          moltype = AA   length = 240
FEATURE                Location/Qualifiers
source                 1..240
                       mol_type = protein
                       organism = synthetic construct
SEQUENCE: 75
ELPTQGTFSN VSTNVSELCG GRIARLEEKV KTLKAQNSEL ASTANMLREQ VAQLKQKVMN   60
AQGEIEAIVV PVCLAFLLTT LLGVLFCFNK RDLIKKHIWP NVPDPSKSHI AQWSPHTPPR   120
HNFNSKDQMY SDGNFTDVSV VEIEANDKKP FPEDLKSLDL FKKEKINTEG HSSGIGGSSC   180
MSSSRPSISS SDENESSQNT SSTVQYSTVV HSGYRHQQQY FKQPKSYLPQ TVRQGGYMPQ   240

SEQ ID NO: 76          moltype = AA   length = 232
FEATURE                Location/Qualifiers
source                 1..232
                       mol_type = protein
                       organism = synthetic construct
SEQUENCE: 76
ELPTQGTFSN VSTNVSELCG GRIARLEEKV KTLKAQNSEL ASTANMLREQ VAQLKQKVMN   60
AQGEIEAIVV PVCLAFLLTT LLGVLFCFNK RDLIKKHIWP NVPDPSKSHI AQWSPHTPPR   120
HNFNSKDQMY SDGNFTDVSV VEIEANDKKP FPETVQYSTV VHSGYRHQVP SVQVFSRSES   180
TQPLLDSEER PEDLQLVDHV DGGDGILPRQ QYFKQPKSYL PQTVRQGGYM PQ           232

SEQ ID NO: 77          moltype = AA   length = 191
FEATURE                Location/Qualifiers
source                 1..191
                       mol_type = protein
                       organism = synthetic construct
SEQUENCE: 77
ELPTQGTFSN VSTNVSELCG GRIARLEEKV KTLKAQNSEL ASTANMLREQ VAQLKQKVMN   60
AQGEIEAIVV PVCLAFLLTT LLGVLFCFNK RDLIKKHIWP NVPDPSKSHI AQWSPHTPPR   120
HNFNSKDQMY SDGNFTDVSV VEIEANDKKP FPETVQYSTV VHSGYRHQQQ YFKQPKSYLP   180
QTVRQGGYMP Q                                                      191

SEQ ID NO: 78          moltype = AA   length = 360
FEATURE                Location/Qualifiers
source                 1..360
                       mol_type = protein
                       organism = synthetic construct
SEQUENCE: 78
ELPTQGTFSN VSTNVSRIAR LEEKVKTLKA QNSELASTAN MLREQVAQLK QKVMNAQGEI   60
EAIVVPVCLA FLLTTLLGVL FCFNKRDLIK KHIWPNVPD SKSHIAQWSP HTPPRHNFNS   120
KDQMYSDGNF TDVSVVEIEA NDKKPFPEDL KSLDLFKKEK INTEGHSSGI GGSSCMSSSR   180
PSISSSDENE SSQNTSSTVQ YSTVVHSGYR HQVPSVQVFS RSESTQPLLD SEERPEDLQL   240
VDHVDGGDGI LPRQQYFKQN CSQHESSPDI SHFERSKQVS SVNEEDFVRL KQQISDHISQ   300
SCGSGQMKMF QEVSAADAFG PGTEGQVERF ETVGMEAATD EGMPKSYLPQ TVRQGGYMPQ   360

SEQ ID NO: 79          moltype = AA   length = 381
FEATURE                Location/Qualifiers
source                 1..381
                       mol_type = protein
                       organism = synthetic construct
SEQUENCE: 79
ELPTQGTFSN VSTNVSMVDP VGFAEAWKAQ FPDSEPPRME LRSVGDIEQE LERCKASIRR   60
LEQEVNQERF RMIYLQTLLA KEAIVVPVCL AFLLTTLLGV LFCFNKRDLI KKHIWPNVPD   120
PSKSHIAQWS PHTPPRHNFN SKDQMYSDGN FTDVSVVEIE ANDKKPFPED LKSLDLFKKE   180
KINTEGHSSG IGGSSCMSSS RPSISSSDEN ESSQNTSSTV QYSTVVHSGY RHQVPSVQVF   240
SRSESTQPLL DSEERPEDLQ LVDHVDGGDG ILPRQQYFKQ NCSQHESSPD ISHFERSKQV   300
SSVNEEDFVR LKQQISDHIS QSCGSGQMKM FQEVSAADAF GPGTEGQVER FETVGMEAAT   360
DEGMPKSYLP QTVRQGGYMP Q                                            381

SEQ ID NO: 80          moltype = AA   length = 326
FEATURE                Location/Qualifiers
source                 1..326
                       mol_type = protein
                       organism = synthetic construct
```

```
SEQUENCE: 80
ELPTQGTFSN VSTNVSELCG GAQGEIEAIV VPVCLAFLLT TLLGVLFCFN KRDLIKKHIW    60
PNVPDPSKSH IAQWSPHTPP RHNFNSKDQM YSDGNFTDVS VVEIEANDKK PFPEDLKSLD   120
LFKKEKINTE GHSSGIGGSS CMSSSRPSIS SSDENESSQN TSSTVQYSTV VHSGYRHQVP   180
SVQVFSRSES TQPLLDSEER PEDLQLVDHV DGGDGILPRQ QYFKQNCSQH ESSPDISHFE   240
RSKQVSSVNE EDFVRLKQQI SDHISQSCGS GQMKMFQEVS AADAFGPGTE GQVERFETVG   300
MEAATDEGMP KSYLPQTVRQ GGYMPQ                                        326

SEQ ID NO: 81          moltype = AA   length = 320
FEATURE                Location/Qualifiers
source                 1..320
                       mol_type = protein
                       organism = synthetic construct
SEQUENCE: 81
ELPTQGTFSN VSTNVSELCG GAIVVPVCLA FLLTTLLGVL FCFNKRDLIK KHIWPNVPDP    60
SKSHIAQWSP HTPPRHNFNS KDQMYSDGNF TDVSVVEIEA NDKKPFPEDL KSLDLFKKEK   120
INTEGHSSGI GGSSCMSSSR PSISSSDENE SSQNTSSTVQ YSTVVHSGYR HQVPSVQVFS   180
RSESTQPLLD SEERPEDLQL VDHVDGGDGI LPRQQYFKQN CSQHESSPDI SHFERSKQVS   240
SVNEEDFVRL KQQISDHISQ SCGSGQMKMF QEVSAADAFG PGTEGQVERF ETVGMEAATD   300
EGMPKSYLPQ TVRQGGYMPQ                                               320

SEQ ID NO: 82          moltype = AA   length = 365
FEATURE                Location/Qualifiers
source                 1..365
                       mol_type = protein
                       organism = synthetic construct
SEQUENCE: 82
ELPTQGTFSN VSTNVSELCG GAQGEIEAIV VPVCLAFLLT TLLGVLFCFN KRDLIKKHIW    60
PNVPDPSKSH IAQWSPHTPP RHNFNSKDQM YSDGNFTDVS VVEIEANDKK PFPEDLKSLD   120
LFKKEKINTE GHSSGIGGSS CMSSSRPSIS SSDENESSQN TSSTVQYSTV VHSGYRHQVP   180
SVQVFSRSES TQPLLDSEER PEDLQLVDHV DGGDGILPRQ QYFKQNCSQH ESSPDISHFE   240
RSKQVSSVNE EDFVRLKQQI SDHISQSCGS GQMKMFQEVS AADAFGPGTE GQVERFETVG   300
MEAATDEGMP KSYLPQTVRQ GGYMPQRIAR LEEKVKTLKA QNSELASTAN MLREQVAQLK   360
QKVMN                                                               365

SEQ ID NO: 83          moltype = AA   length = 359
FEATURE                Location/Qualifiers
source                 1..359
                       mol_type = protein
                       organism = synthetic construct
SEQUENCE: 83
ELPTQGTFSN VSTNVSELCG GAIVVPVCLA FLLTTLLGVL FCFNKRDLIK KHIWPNVPDP    60
SKSHIAQWSP HTPPRHNFNS KDQMYSDGNF TDVSVVEIEA NDKKPFPEDL KSLDLFKKEK   120
INTEGHSSGI GGSSCMSSSR PSISSSDENE SSQNTSSTVQ YSTVVHSGYR HQVPSVQVFS   180
RSESTQPLLD SEERPEDLQL VDHVDGGDGI LPRQQYFKQN CSQHESSPDI SHFERSKQVS   240
SVNEEDFVRL KQQISDHISQ SCGSGQMKMF QEVSAADAFG PGTEGQVERF ETVGMEAATD   300
EGMPKSYLPQ TVRQGGYMPQ RIARLEEKVK TLKAQNSELA STANMLREQV AQLKQKVMN    359

SEQ ID NO: 84          moltype = AA   length = 365
FEATURE                Location/Qualifiers
source                 1..365
                       mol_type = protein
                       organism = synthetic construct
SEQUENCE: 84
ELPTQGTFSN VSTNVSELCG GAQGEIEAIV VPVCLAFLLT TLLGVLFCFN KRDLIKKHRI    60
ARLEEKVKTL KAQNSELAST ANMLREQVAQ LKQKVMNIWP NVPDPSKSHI AQWSPHTPPR   120
HNFNSKDQMY SDGNFTDVSV VEIEANDKKP FPEDLKSLDL FKKEKINTEG HSSGIGGSSC   180
MSSSRPSISS SDENESSQNT SSTVQYSTVV HSGYRHQVPS VQVFSRSEST QPLLDSEERP   240
EDLQLVDHVD GGDGILPRQQ YFKQNCSQHE SSPDISHFER SKQVSSVNEE DFVRLKQQIS   300
DHISQSCGSG QMKMFQEVSA ADAFGPGTEG QVERFETVGM EAATDEGMPK SYLPQTVRQG   360
GYMPQ                                                               365

SEQ ID NO: 85          moltype = AA   length = 359
FEATURE                Location/Qualifiers
source                 1..359
                       mol_type = protein
                       organism = synthetic construct
SEQUENCE: 85
ELPTQGTFSN VSTNVSELCG GAIVVPVCLA FLLTTLLGVL FCFNKRDLIK KHRIARLEEK    60
VKTLKAQNSE LASTANMLRE QVAQLKQKVM NIWPNVPDPS KSHIAQWSPH TPPRHNFNSK   120
DQMYSDGNFT DVSVVEIEAN DKKPFPEDLK SLDLFKKEKI NTEGHSSGIG GSSCMSSSRP   180
SISSSDENES SQNTSSTVQY STVVHSGYRH QVPSVQVFSR SESTQPLLDS EERPEDLQLV   240
DHVDGGDGIL PRQQYFKQNC SQHESSPDIS HFERSKQVSS VNEEDFVRLK QQISDHISQS   300
CGSGQMKMFQ EVSAADAFGP GTEGQVERFE TVGMEAATDE GMPKSYLPQT VRQGGYMPQ    359

SEQ ID NO: 86          moltype = AA   length = 321
FEATURE                Location/Qualifiers
source                 1..321
                       mol_type = protein
```

```
                                organism = synthetic construct
SEQUENCE: 86
ELPTQGTFSN VSTNVSFACD IYIWAPLAGT CGVLLLSLVI TLYCNKRDLI KKHIWPNVPD    60
PSKSHIAQWS PHTPPRHNFN SKDQMYSDGN FTDVSVVEIE ANDKKPFPED LKSLDLFKKE   120
KINTEGHSSG IGGSSCMSSS RPSISSSDEN ESSQNTSSTV QYSTVVHSGY RHQVPSVQVF   180
SRSESTQPLL DSEERPEDLQ LVDHVDGGDG ILPRQQYFKQ NCSQHESSPD ISHFERSKQV   240
SSVNEEDFVR LKQQISDHIS QSCGSGQMKM FQEVSAADAF GPGTEGQVER FETVGMEAAT   300
DEGMPKSYLP QTVRQGGYMP Q                                             321

SEQ ID NO: 87              moltype = AA  length = 362
FEATURE                    Location/Qualifiers
source                     1..362
                           mol_type = protein
                           organism = synthetic construct
SEQUENCE: 87
ELPTQGTFSN VSTNVSTTTP APRPPTPAPT IASQPLSLRP EACRPAAGGA VHTRGLDFAC    60
DIYIWAPLAG TCGVLLLSLV ITLYCNKRDL IKKHIWPNVP DPSKSHIAQW SPHTPPRHNF   120
NSKDQMYSDG NFTDVSVVEI EANDKKPFPE DLKSLDLFKK EKINTEGHSS GIGGSSCMSS   180
SRPSISSSDE NESSQNTSST VQYSTVVHSG YRHQVPSVQV FSRSESTQPL LDSEERPEDL   240
QLVDHVDGGD GILPRQQYFK QNCSQHESSP DISHFERSKQ VSSVNEEDFV RLKQQISDHI   300
SQSCGSGQMK MFQEVSAADA FGPGTEGQVE RFETVGMEAA TDEGMPKSYL PQTVRQGGYM   360
PQ                                                                 362

SEQ ID NO: 88              moltype = AA  length = 322
FEATURE                    Location/Qualifiers
source                     1..322
                           mol_type = protein
                           organism = synthetic construct
SEQUENCE: 88
ELPTQGTFSN VSTNVSELCG GIYIWAPLAG TCGVLLLSLV ITLYCNKRDL IKKHIWPNVP    60
DPSKSHIAQW SPHTPPRHNF NSKDQMYSDG NFTDVSVVEI EANDKKPFPE DLKSLDLFKK   120
EKINTEGHSS GIGGSSCMSS SRPSISSSDE NESSQNTSST VQYSTVVHSG YRHQVPSVQV   180
FSRSESTQPL LDSEERPEDL QLVDHVDGGD GILPRQQYFK QNCSQHESSP DISHFERSKQ   240
VSSVNEEDFV RLKQQISDHI SQSCGSGQMK MFQEVSAADA FGPGTEGQVE RFETVGMEAA   300
TDEGMPKSYL PQTVRQGGYM PQ                                            322

SEQ ID NO: 89              moltype = AA  length = 361
FEATURE                    Location/Qualifiers
source                     1..361
                           mol_type = protein
                           organism = synthetic construct
SEQUENCE: 89
ELPTQGTFSN VSTNVSELCG GIYIWAPLAG TCGVLLLSLV ITLYCNKRDL IKKHIWPNVP    60
DPSKSHIAQW SPHTPPRHNF NSKDQMYSDG NFTDVSVVEI EANDKKPFPE DLKSLDLFKK   120
EKINTEGHSS GIGGSSCMSS SRPSISSSDE NESSQNTSST VQYSTVVHSG YRHQVPSVQV   180
FSRSESTQPL LDSEERPEDL QLVDHVDGGD GILPRQQYFK QNCSQHESSP DISHFERSKQ   240
VSSVNEEDFV RLKQQISDHI SQSCGSGQMK MFQEVSAADA FGPGTEGQVE RFETVGMEAA   300
TDEGMPKSYL PQTVRQGGYM PQRIARLEEK VKTLKAQNSE LASTANMLRE QVAQLKQKVM   360
N                                                                  361

SEQ ID NO: 90              moltype = AA  length = 361
FEATURE                    Location/Qualifiers
source                     1..361
                           mol_type = protein
                           organism = synthetic construct
SEQUENCE: 90
ELPTQGTFSN VSTNVSELCG GRIARLEEKV KTLKAQNSEL ASTANMLREQ VAQLKQKVMN    60
IYIWAPLAGT CGVLLLSLVI TLYCNKRDLI KKHIWPNVPD PSKSHIAQWS PHTPPRHNFN   120
SKDQMYSDGN FTDVSVVEIE ANDKKPFPED LKSLDLFKKE KINTEGHSSG IGGSSCMSSS   180
RPSISSSDEN ESSQNTSSTV QYSTVVHSGY RHQVPSVQVF SRSESTQPLL DSEERPEDLQ   240
LVDHVDGGDG ILPRQQYFKQ NCSQHESSPD ISHFERSKQV SSVNEEDFVR LKQQISDHIS   300
QSCGSGQMKM FQEVSAADAF GPGTEGQVER FETVGMEAAT DEGMPKSYLP QTVRQGGYMP   360
Q                                                                  361

SEQ ID NO: 91              moltype = AA  length = 564
FEATURE                    Location/Qualifiers
source                     1..564
                           mol_type = protein
                           organism = synthetic construct
SEQUENCE: 91
SLDNNGTATP ELPTQGTFSN VSTNVSYQET TTPSTLGSTS LHPVSQHGNE ATTNITETTV    60
KFTSTSVITS VYGNTNSSVQ SQTSVISTVF TTPANVSTPE TTLKPSLSPG NVSDLSTTST   120
SLATSPTKPY TSSSPILSDI KAEIKCSGIR EVKLTQGICL EQNKTSSCAE FKKDRGEGLA   180
RVLCGEEQAD ADAGAQVCSL LLAQSEVRPQ CLLLVLANRT EISSKLQLMK KHQSDLKKLG   240
ILDFTEQDVA SHQSYSQKTP ILLTCPTISI LSFFSVALLV ILACVLWNKR DLIKKHIWPN   300
VPDPSKSHIA QWSPHTPPRH NFNSKDQMYS DGNFTDVSVV EIEANDKKPF PEDLKSLDLF   360
KKEKINTEGH SSGIGGSSCM SSSRPSISSS DENESSQNTS STVQYSTVVH SGYRHQVPSV   420
QVFSRSESTQ PLLDSEERPE DLQLVDHVDG GDGILPRQQY FKQNCSQHES SPDISHFERS   480
KQVSSVNEED FVRLKQQISD HISQSCGSGQ MKMFQEVSAA DAFGPGTEGQ VERFETVGME   540
```

-continued

```
AATDEGMPKS YLPQTVRQGG YMPQ                                              564

SEQ ID NO: 92            moltype = AA   length = 564
FEATURE                  Location/Qualifiers
source                   1..564
                         mol_type = protein
                         organism = synthetic construct
SEQUENCE: 92
SLDNNGTATP ELPTQGTFSN VSTNVSYQET TTPSTLGSTS LHPVSQHGNE ATTNITETTV      60
KFTSTSVITS VYGNTNSSVQ SQTSVISTVF TTPANVSTPE TTLKPSLSPG NVSDLSTTST      120
SLATSPTKPY TSSSPILSDI KAEIKCSGIR EVKLTQGICL EQNKTSSCAE FKKDRGEGLA      180
RVLCGEEQAD ADAGAQVCSL LLAQSEVRPQ CLLLVLANRT EISSKLQLMK KHQSDLKKLG      240
ILDFTEQDVA SHQSYSQKTA QGEIEAIVVP VCLAFLLTTL LGVLFCFNKR DLIKKHIWPN      300
VPDPSKSHIA QWSPHTPPRH NFNSKDQMYS DGNFTDVSVV EIEANDKKPF PEDLKSLDLF      360
KKEKINTEGH SSGIGGSSCM SSSRPSISSS DENESSQNTS STVQYSTVVH SGYRHQVPSV      420
QVFSRSESTQ PLLDSEERPE DLQLVDHVDG GDGILPRQQY FKQNCSQHES SPDISHFERS      480
KQVSSVNEED FVRLKQQISD HISQSCGSGQ MKMFQEVSAA DAFGPGTEGQ VERFETVGME      540
AATDEGMPKS YLPQTVRQGG YMPQ                                              564

SEQ ID NO: 93            moltype = AA   length = 557
FEATURE                  Location/Qualifiers
source                   1..557
                         mol_type = protein
                         organism = synthetic construct
SEQUENCE: 93
LDNNGTATPE LPTQGTFSNV STNVSYQETT TPSTLGSTSL HPVSQHGNEA TTNITETTVK      60
FTSTSVITSV YGNTNSSVQS QTSVISTVFT TPANVSTPET TLKPSLSPGN VSDLSTTSTS      120
LATSPTKPYT SSSPILSDIK AEIKCSGIRE VKLTQGICLE QNKTSSCAEF KKDRGEGLAR      180
VLCGEEQADA DAGAQVCSLL LAQSEVRPQC LLLVLANRTE ISSKLQLMKK HQSDLKKLGI      240
LDFTEQDVAS HQSYSQKTAI VVPVCLAFLL TTLLGVLFCF NKRDLIKKHI WPNVPDPSKS      300
HIAQWSPHTP PRHNFNSKDQ MYSDGNFTDV SVVEIEANDK KPFPEDLKSL DLFKKEKINT      360
EGHSSGIGGS SCMSSSRPSI SSSDENESSQ NTSSTVQYST VVHSGYRHQV PSVQVFSRSE      420
STQPLLDSEE RPEDLQLVDH VDGGDGILPR QQYFKQNCSQ HESSPDISHF ERSKQVSSVN      480
EEDFVRLKQQ ISDHISQSCG SGQMKMFQEV SAADAFGPGT EGQVERFETV GMEAATDEGM      540
PKSYLPQTVR QGGYMPQ                                                     557

SEQ ID NO: 94            moltype = AA   length = 366
FEATURE                  Location/Qualifiers
source                   1..366
                         mol_type = protein
                         organism = synthetic construct
SEQUENCE: 94
ELPTQGTFSN VSTNVSPSSS DYSDLQRVKQ ELLEEVKKEL QKVKEEIIEA FVQELRKRGS      60
PAQGEIEAIV VPVCLAFLLT TLLGVLFCFN KRDLIKKHIW PNVPDPSKSH IAQWSPHTPP      120
RHNFNSKDQM YSDGNFTDVS VVEIEANDKK PFPEDLKSLD LFKKEKINTE GHSSGIGGSS      180
CMSSSRPSIS SSDENESSQN TSSTVQYSTV VHSGYRHQVP SVQVFSRSES TQPLLDSEER      240
PEDLQLVDHV DGGDGILPRQ QYFKQNCSQH ESSPDISHFE RSKQVSSVNE EDFVRLKQQI      300
SDHISQSCGS GQMKMFQEVS AADAFGPGTE GQVERFETVG MEAATDEGMP KSYLPQTVRQ      360
GGYMPQ                                                                 366

SEQ ID NO: 95            moltype = AA   length = 366
FEATURE                  Location/Qualifiers
source                   1..366
                         mol_type = protein
                         organism = synthetic construct
SEQUENCE: 95
ELPTQGTFSN VSTNVSAQGE IEAIVVPVCL AFLLTTLLGV LFCFNKRDLI KKHIWPNVPD      60
PSKSHIAQWS PHTPPRHNFN SKDQMYSDGN FTDVSVVEIE ANDKKPFPED LKSLDLFKKE      120
KINTEGHSSG IGGSSCMSSS RPSISSSDEN ESSQNTSSTV QYSTVVHSGY RHQVPSVQVF      180
SRSESTQPLL DSEERPEDLQ LVDHVDGGDG ILPRQQYFKQ NCSQHESSPD ISHFERSKQV      240
SSVNEEDFVR LKQQISDHIS QSCGSGQMKM FQEVSAADAF GPGTEGQVER FETVGMEAAT      300
DEGMPKSYLP QTVRQGGYMP QPSSSDYSDL QRVKQELLEE VKKELQKVKE EIIEAFVQEL      360
RKRGSP                                                                 366

SEQ ID NO: 96            moltype = AA   length = 371
FEATURE                  Location/Qualifiers
source                   1..371
                         mol_type = protein
                         organism = synthetic construct
SEQUENCE: 96
ELPTQGTFSN VSTNVSELCG GPSSSDYSDL QRVKQELLEE VKKELQKVKE EIIEAFVQEL      60
RKRGSPAQGE IEAIVVPVCL AFLLTTLLGV LFCFNKRDLI KKHIWPNVPD PSKSHIAQWS      120
PHTPPRHNFN SKDQMYSDGN FTDVSVVEIE ANDKKPFPED LKSLDLFKKE KINTEGHSSG      180
IGGSSCMSSS RPSISSSDEN ESSQNTSSTV QYSTVVHSGY RHQVPSVQVF SRSESTQPLL      240
DSEERPEDLQ LVDHVDGGDG ILPRQQYFKQ NCSQHESSPD ISHFERSKQV SSVNEEDFVR      300
LKQQISDHIS QSCGSGQMKM FQEVSAADAF GPGTEGQVER FETVGMEAAT DEGMPKSYLP      360
QTVRQGGYMP Q                                                           371

SEQ ID NO: 97            moltype = AA   length = 371
```

```
FEATURE                   Location/Qualifiers
source                    1..371
                          mol_type = protein
                          organism = synthetic construct
SEQUENCE: 97
ELPTQGTFSN VSTNVSELCG GAQGEIEAIV VPVCLAFLLT TLLGVLFCFN KRDLIKKHIW  60
PNVPDPSKSH IAQWSPHTPP RHNFNSKDQM YSDGNFTDVS VVEIEANDKK PFPEDLKSLD  120
LFKKEKINTE GHSSGIGGSS CMSSSRPSIS SSDENESSQN TSSTVQYSTV VHSGYRHQVP  180
SVQVFSRSES TQPLLDSEER PEDLQLVDHV DGGDGILPRQ QYFKQNCSQH ESSPDISHFE  240
RSKQVSSVNE EDFVRLKQQI SDHISQSCGS GQMKMFQEVS AADAFGPGTE GQVERFETVG  300
MEAATDEGMP KSYLPQTVRQ GGYMPQPSSS DYSDLQRVKQ ELLEEVKKEL QKVKEEIIEA  360
FVQELRKRGS P                                                       371

SEQ ID NO: 98            moltype = AA   length = 563
FEATURE                   Location/Qualifiers
source                    1..563
                          mol_type = protein
                          organism = synthetic construct
SEQUENCE: 98
SLDNNGTATP ELPTQGTFSN VSTNVSYQET TTPSTLGSTS LHPVSQHGNE ATTNITETTV  60
KFTSTSVITS VYGNTNSSVQ SQTSVISTVF TTPANVSTPE TTLKPSLSPG NVSDLSTTST  120
SLATSPTKPY TSSSPILSDI KAEIKCSGIR EVKLTQGICL EQNKTSSCAE FKKDRGEGLA  180
RVLCGEEQAD ADAGAQVCSL LLAQSEVRPQ CLLLVLANRT EISSKLQLMK KHQSDLKKLG  240
ILDFTEQDVA SHQSYSQKTI SLVTALLLVL GLNAVLGLLL LRKQFPAHYR RLRHAIWPNV  300
PDPSKSHIAQ WSPHTPPRHN FNSKDQMYSD GNFTDVSVVE IEANDKKPFP EDLKSLDLFK  360
KEKINTEGHS SGIGGSSCMS SSRPSISSSD ENESSQNTSS TVQYSTVVHS GYRHQVPSVQ  420
VFSRSESTQP LLDSEERPED LQLVDHVDGG DGILPRQQYF KQNCSQHESS PDISHFERSK  480
QVSSVNEEDF VRLKQQISDH ISQSCGSGQM KMFQEVSAAD AFGPGTEGQV ERFETVGMEA  540
ATDEGMPKSY LPQTVRQGGY MPQ                                          563

SEQ ID NO: 99            moltype = AA   length = 318
FEATURE                   Location/Qualifiers
source                    1..318
                          mol_type = protein
                          organism = synthetic construct
SEQUENCE: 99
SDPTRVETAT ETAWISLVTA LLLVLGLNAV LGLLLLRKQF PAHYRRLRHA IWPNVPDPSK  60
SHIAQWSPHT PPRHNFNSKD QMYSDGNFTD VSVVEIEAND KKPFPEDLKS LDLFKKEKIN  120
TEGHSSGIGG SSCMSSSRPS ISSSDENESS QNTSSTVQYS TVVHSGYRHQ VPSVQVFSRS  180
ESTQPLLDSE ERPEDLQLVD HVDGGDGILP RQQYFKQNCS QHESSPDISH FERSKQVSSV  240
NEEDFVRLKQ QISDHISQSC GSGQMKMFQE VSAADAFGPG TEGQVERFET VGMEAATDEG  300
MPKSYLPQTV RQGGYMPQ                                                318

SEQ ID NO: 100           moltype = AA   length = 526
FEATURE                   Location/Qualifiers
source                    1..526
                          mol_type = protein
                          organism = synthetic construct
SEQUENCE: 100
APPPNLPDPK FESKAALLAA RGPEELLCFT ERLEDLVCFW EEAASAGVGP GNYSFSYQLE  60
DEPWKLCRLH QAPTARGAVR FWCSLPTADT SSFVPLELRV TAASGAPRYH RVIHINEVVL  120
LDAPVGLVAC LADESGHVVL RWLPPPETPM TSHIRYEVDV SAGNGAGSVQ RVEILEGRTE  180
CVLSNLRGRT RYTFAVRARM AEPSFGGFWS AWSEPVSLLT PSDLDPLILT LSLILVVILV  240
LLTVLALLSN KRDLIKKHIW PNVPDPSKSH IAQWSPHTPP RHNFNSKDQM YSDGNFTDVS  300
VVEIEANDKK PFPEDLKSLD LFKKEKINTE GHSSGIGGSS CMSSSRPSIS SSDENESSQN  360
TSSTVQYSTV VHSGYRHQVP SVQVFSRSES TQPLLDSEER PEDLQLVDHV DGGDGILPRQ  420
QYFKQNCSQH ESSPDISHFE RSKQVSSVNE EDFVRLKQQI SDHISQSCGS GQMKMFQEVS  480
AADAFGPGTE GQVERFETVG MEAATDEGMP KSYLPQTVRQ GGYMPQ                 526

SEQ ID NO: 101           moltype = AA   length = 525
FEATURE                   Location/Qualifiers
source                    1..525
                          mol_type = protein
                          organism = synthetic construct
SEQUENCE: 101
APPPNLPDPK FESKAALLAA RGPEELLCFT ERLEDLVCFW EEAASAGVGP GNYSFSYQLE  60
DEPWKLCRLH QAPTARGAVR FWCSLPTADT SSFVPLELRV TAASGAPRYH RVIHINEVVL  120
LDAPVGLVAC LADESGHVVL RWLPPPETPM TSHIRYEVDV SAGNGAGSVQ RVEILEGRTE  180
CVLSNLRGRT RYTFAVRARM AEPSFGGFWS AWSEPVSLLT PSDLDPAIVV PVCLAFLLTT  240
LLGVLFCFNK RDLIKKHIWP NVPDPSKSHI AQWSPHTPPR HNFNSKDQMY SDGNFTDVSV  300
VEIEANDKKP FPEDLKSLDL FKKEKINTEG HSSGIGGSSC MSSSRPSISS SDENESSQNT  360
SSTVQYSTVV HSGYRHQVPS VQVFSRSEST QPLLDSEERP EDLQLVDHVD GGDGILPRQQ  420
YFKQNCSQHE SSPDISHFER SKQVSSVNEE DFVRLKQQIS DHISQSCGSG QMKMFQEVSA  480
ADAFGPGTEG QVERFETVGM EAATDEGMPK SYLPQTVRQG GYMPQ                  525

SEQ ID NO: 102           moltype = AA   length = 542
FEATURE                   Location/Qualifiers
source                    1..542
                          mol_type = protein
```

-continued

```
                    organism = synthetic construct
SEQUENCE: 102
ELPTQGTFSN VSTNVSAPPP NLPDPKFESK AALLAARGPE ELLCFTERLE DLVCFWEEAA      60
SAGVGPGNYS FSYQLEDEPW KLCRLHQAPT ARGAVRFWCS LPTADTSSFV PLELRVTAAS     120
GAPRYHRVIH INEVVLLDAP VGLVACLADE SGHVVLRWLP PPETPMTSHI RYEVDVSAGN     180
GAGSVQRVEI LEGRTECVLS NLRGRTRYTF AVRARMAEPS FGGFWSAWSE PVSLLTPSDL     240
DPLILTLSLI LVVILVLLTV LALLSNKRDL IKKHIWPNVP DPSKSHIAQW SPHTPPRHNF     300
NSKDQMYSDG NFTDVSVVEI EANDKKPFPE DLKSLDLFKK EKINTEGHSS GIGGSSCMSS     360
SRPSISSSDE NESSQNTSST VQYSTVVHSG YRHQVPSVQV FSRSESTQPL LDSEERPEDL     420
QLVDHVDGGD GILPRQQYFK QNCSQHESSP DISHFERSKQ VSSVNEEDFV RLKQQISDHI     480
SQSCGSGQMK MFQEVSAADA FGPGTEGQVE RFETVGMEAA TDEGMPKSYL PQTVRQGGYM     540
PQ                                                                   542

SEQ ID NO: 103             moltype = AA   length = 541
FEATURE                    Location/Qualifiers
source                     1..541
                           mol_type = protein
                           organism = synthetic construct
SEQUENCE: 103
ELPTQGTFSN VSTNVSAPPP NLPDPKFESK AALLAARGPE ELLCFTERLE DLVCFWEEAA      60
SAGVGPGNYS FSYQLEDEPW KLCRLHQAPT ARGAVRFWCS LPTADTSSFV PLELRVTAAS     120
GAPRYHRVIH INEVVLLDAP VGLVACLADE SGHVVLRWLP PPETPMTSHI RYEVDVSAGN     180
GAGSVQRVEI LEGRTRYTF AVRARMAEPS FGGFWSAWSE PVSLLTPSDL     240
DPAIVVPVCL AFLLTTLLGV LFCFNKRDLI KKHIWPNVPD PSKSHIAQWS PHTPPRHNFN     300
SKDQMYSDGN FTDVSVVEIE ANDKKPFPED LKSLDLFKKE KINTEGHSSG IGGSSCMSSS     360
RPSISSSDEN ESSQNTSSTV QYSTVVHSGY RHQVPSVQVF SRSESTQPLL DSEERPEDLQ     420
LVDHVDGGDG ILPRQQYFKQ NCSQHESSPD ISHFERSKQV SSVNEEDFVR LKQQISDHIS     480
QSCGSGQMKM FQEVSAADAF GPGTEGQVER FETVGMEAAT DEGMPKSYLP QTVRQGGYMP     540
Q                                                                    541

SEQ ID NO: 104             moltype = AA   length = 365
FEATURE                    Location/Qualifiers
source                     1..365
                           mol_type = protein
                           organism = synthetic construct
SEQUENCE: 104
ELPTQGTFSN VSTNVSELCG GRIARLEEKV KTLKAQNSEL ASTANMLREQ VAQLKQKVMN      60
AQGEIEAIVV PVCLAFLLTT LLGVLFCFNK RDLIKKHIWP NVPDPSKSHI AQWSPHTPPR     120
HNFNSKDQMY SDGNFTDVSV VEIEANDKKP FPEDLKSLDL FKKEKINTEG HSSGIGGSSC     180
MSSSRPSISS SDENESSQNT SSTVQYSTVV HSGYRHQVPS VQVFSRSEST QPLLDSEERP     240
EDLQLVDHVD GGDGILPRQQ YFKQNCSQHE SSPDISHFER SKQVSSVNEE DFVRLKQQIS     300
DHISQSCGSG QMKMFQEVSA ADAFGPGTEG QVERFETVGM EAATDEGMPK SYLPQTVRQG     360
GYMPQ                                                                365

SEQ ID NO: 105             moltype = AA   length = 357
FEATURE                    Location/Qualifiers
source                     1..357
                           mol_type = protein
                           organism = synthetic construct
SEQUENCE: 105
DYKDDDDKEL CGGRIARLEE KVKTLKAQNS ELASTANMLR EQVAQLKQKV MNAQGEIEAI      60
VVPVCLAFLL TTLLGVLFCF NKRDLIKKHI WPNVPDPSKS HIAQWSPHTP PRHNFNSKDQ     120
MYSDGNFTDV SVVEIEANDK KPFPEDLKSL DLFKKEKINT EGHSSGIGGS SCMSSSRPSI     180
SSSDENESSQ NTSSTVQYST VVHSGYRHQV PSVQVFSRSE STQPLLDSEE RPEDLQLVDH     240
VDGGDGILPR QQYFKQNCSQ HESSPDISHF ERSKQVSSVN EEDFVRLKQQ ISDHISQSCG     300
SGQMKMFQEV SAADAFGPGT EGQVERFETV GMEAATDEGM PKSYLPQTVR QGGYMPQ       357

SEQ ID NO: 106             moltype = AA   length = 7
FEATURE                    Location/Qualifiers
source                     1..7
                           mol_type = protein
                           organism = synthetic construct
SEQUENCE: 106
IWPNVDP                                                                7

SEQ ID NO: 107             moltype = AA   length = 13
FEATURE                    Location/Qualifiers
source                     1..13
                           mol_type = protein
                           organism = synthetic construct
SEQUENCE: 107
VSVVEIEAND KKP                                                        13

SEQ ID NO: 108             moltype = AA   length = 21
FEATURE                    Location/Qualifiers
source                     1..21
                           mol_type = protein
                           organism = synthetic construct
SEQUENCE: 108
```

-continued

```
MALPVTALLL PLALLLHAAR P                                               21

SEQ ID NO: 109          moltype = AA   length = 31
FEATURE                 Location/Qualifiers
source                  1..31
                        mol_type = protein
                        organism = synthetic construct
SEQUENCE: 109
MLVRRGARAG PRMPRGWTAL CLLSLLPSGF M                                    31

SEQ ID NO: 110          moltype = AA   length = 24
FEATURE                 Location/Qualifiers
source                  1..24
                        mol_type = protein
                        organism = synthetic construct
SEQUENCE: 110
MDHLGASLWP QVGSLCLLLA GAAW                                            24

SEQ ID NO: 111          moltype = AA   length = 22
FEATURE                 Location/Qualifiers
source                  1..22
                        mol_type = protein
                        organism = synthetic construct
SEQUENCE: 111
MLTLQTWLVQ ALFIFLTTES TG                                              22

SEQ ID NO: 112          moltype = AA   length = 7
FEATURE                 Location/Qualifiers
source                  1..7
                        mol_type = protein
                        organism = synthetic construct
SEQUENCE: 112
ENLYTQS                                                               7

SEQ ID NO: 113          moltype = AA   length = 5
FEATURE                 Location/Qualifiers
source                  1..5
                        mol_type = protein
                        organism = synthetic construct
SEQUENCE: 113
DDDDK                                                                 5

SEQ ID NO: 114          moltype = AA   length = 4
FEATURE                 Location/Qualifiers
source                  1..4
                        mol_type = protein
                        organism = synthetic construct
SEQUENCE: 114
KVPR                                                                  4

SEQ ID NO: 115          moltype = AA   length = 4
FEATURE                 Location/Qualifiers
source                  1..4
                        mol_type = protein
                        organism = synthetic construct
SEQUENCE: 115
CPPC                                                                  4

SEQ ID NO: 116          moltype = RNA   length = 103
FEATURE                 Location/Qualifiers
source                  1..103
                        mol_type = other RNA
                        organism = synthetic construct
SEQUENCE: 116
ggggccacta gggacaggat gttttagagc tagaaatagc aagttaaaat aaggctagtc   60
cgttatcaac ttgaaaaagt ggcaccgagt cggtgctttt ttt                     103

SEQ ID NO: 117          moltype = DNA   length = 20
FEATURE                 Location/Qualifiers
source                  1..20
                        mol_type = genomic DNA
                        organism = Adeno-associated virus
SEQUENCE: 117
ggggccacta gggacaggat                                                20

SEQ ID NO: 118          moltype = RNA   length = 20
FEATURE                 Location/Qualifiers
source                  1..20
                        mol_type = other RNA
```

```
                             organism = synthetic construct
SEQUENCE: 118
gcacctgaat accacgcctg                                                  20

SEQ ID NO: 119              moltype = RNA   length = 20
FEATURE                    Location/Qualifiers
source                     1..20
                           mol_type = other RNA
                           organism = synthetic construct
SEQUENCE: 119
cgcctgcgat gtagtcgatg                                                  20

SEQ ID NO: 120             moltype = RNA   length = 20
FEATURE                    Location/Qualifiers
source                     1..20
                           mol_type = other RNA
                           organism = synthetic construct
SEQUENCE: 120
caggacgggc gagatgtccc                                                  20

SEQ ID NO: 121             moltype = RNA   length = 20
FEATURE                    Location/Qualifiers
source                     1..20
                           mol_type = other RNA
                           organism = synthetic construct
SEQUENCE: 121
ctgaatcttt ggagtacctg                                                  20

SEQ ID NO: 122             moltype = RNA   length = 20
FEATURE                    Location/Qualifiers
source                     1..20
                           mol_type = other RNA
                           organism = synthetic construct
SEQUENCE: 122
ggccacggag cgagacatct                                                  20

SEQ ID NO: 123             moltype = RNA   length = 20
FEATURE                    Location/Qualifiers
source                     1..20
                           mol_type = other RNA
                           organism = synthetic construct
SEQUENCE: 123
aagtcaactt caatgtcgga                                                  20

SEQ ID NO: 124             moltype = RNA   length = 20
FEATURE                    Location/Qualifiers
source                     1..20
                           mol_type = other RNA
                           organism = synthetic construct
SEQUENCE: 124
gcttggaggc ctgatcagcg                                                  20

SEQ ID NO: 125             moltype = RNA   length = 20
FEATURE                    Location/Qualifiers
source                     1..20
                           mol_type = other RNA
                           organism = synthetic construct
SEQUENCE: 125
cttatctctt cgcagcgagg                                                  20

SEQ ID NO: 126             moltype = RNA   length = 20
FEATURE                    Location/Qualifiers
source                     1..20
                           mol_type = other RNA
                           organism = synthetic construct
SEQUENCE: 126
cacacattac tccaacattg                                                  20

SEQ ID NO: 127             moltype = RNA   length = 20
FEATURE                    Location/Qualifiers
source                     1..20
                           mol_type = other RNA
                           organism = synthetic construct
SEQUENCE: 127
ttccgcaaaa tagagcccca                                                  20

SEQ ID NO: 128             moltype = RNA   length = 20
FEATURE                    Location/Qualifiers
source                     1..20
```

-continued

```
                          mol_type = other RNA
                          organism = synthetic construct
SEQUENCE: 128
tgcacagaac tatcgtacca                                        20

SEQ ID NO: 129            moltype = RNA   length = 20
FEATURE                   Location/Qualifiers
source                    1..20
                          mol_type = other RNA
                          organism = synthetic construct
SEQUENCE: 129
gcaataagac tctttaaaga                                        20

SEQ ID NO: 130            moltype = RNA   length = 20
FEATURE                   Location/Qualifiers
source                    1..20
                          mol_type = other RNA
                          organism = synthetic construct
SEQUENCE: 130
caaagagatt acgaatgcct                                        20

SEQ ID NO: 131            moltype = RNA   length = 20
FEATURE                   Location/Qualifiers
source                    1..20
                          mol_type = other RNA
                          organism = synthetic construct
SEQUENCE: 131
caaggcaccc caggtttcca                                        20

SEQ ID NO: 132            moltype = RNA   length = 20
FEATURE                   Location/Qualifiers
source                    1..20
                          mol_type = other RNA
                          organism = synthetic construct
SEQUENCE: 132
ttacgaatgc cttggaaacc                                        20

SEQ ID NO: 133            moltype = RNA   length = 20
FEATURE                   Location/Qualifiers
source                    1..20
                          mol_type = other RNA
                          organism = synthetic construct
SEQUENCE: 133
cagagacgca tctgaccctc                                        20

SEQ ID NO: 134            moltype = RNA   length = 20
FEATURE                   Location/Qualifiers
source                    1..20
                          mol_type = other RNA
                          organism = synthetic construct
SEQUENCE: 134
catgcagttc tcacacactg                                        20

SEQ ID NO: 135            moltype = RNA   length = 20
FEATURE                   Location/Qualifiers
source                    1..20
                          mol_type = other RNA
                          organism = synthetic construct
SEQUENCE: 135
gtgtgagaac tgcatggaga                                        20

SEQ ID NO: 136            moltype = RNA   length = 20
FEATURE                   Location/Qualifiers
source                    1..20
                          mol_type = other RNA
                          organism = synthetic construct
SEQUENCE: 136
tctcatttca ggaaaccact                                        20

SEQ ID NO: 137            moltype = RNA   length = 20
FEATURE                   Location/Qualifiers
source                    1..20
                          mol_type = other RNA
                          organism = synthetic construct
SEQUENCE: 137
agtcatacac cttaaccaag                                        20

SEQ ID NO: 138            moltype = RNA   length = 20
FEATURE                   Location/Qualifiers
```

```
source                    1..20
                          mol_type = other RNA
                          organism = synthetic construct
SEQUENCE: 138
ttcaaggaaa ccagttgagg                                                20

SEQ ID NO: 139            moltype = RNA   length = 20
FEATURE                   Location/Qualifiers
source                    1..20
                          mol_type = other RNA
                          organism = synthetic construct
SEQUENCE: 139
gagccttgcc tggaaatctg                                                20

SEQ ID NO: 140            moltype = RNA   length = 20
FEATURE                   Location/Qualifiers
source                    1..20
                          mol_type = other RNA
                          organism = synthetic construct
SEQUENCE: 140
aagcgtcaaa agtctgccag                                                20

SEQ ID NO: 141            moltype = RNA   length = 20
FEATURE                   Location/Qualifiers
source                    1..20
                          mol_type = other RNA
                          organism = synthetic construct
SEQUENCE: 141
cgttccaact cgaagtgcca                                                20

SEQ ID NO: 142            moltype = RNA   length = 20
FEATURE                   Location/Qualifiers
source                    1..20
                          mol_type = other RNA
                          organism = synthetic construct
SEQUENCE: 142
gagcgactgg gacacggtga                                                20

SEQ ID NO: 143            moltype = RNA   length = 20
FEATURE                   Location/Qualifiers
source                    1..20
                          mol_type = other RNA
                          organism = synthetic construct
SEQUENCE: 143
gctgcgcaag aagggcccta                                                20

SEQ ID NO: 144            moltype = RNA   length = 20
FEATURE                   Location/Qualifiers
source                    1..20
                          mol_type = other RNA
                          organism = synthetic construct
SEQUENCE: 144
ttgttctggc cagcagcccc                                                20

SEQ ID NO: 145            moltype = RNA   length = 20
FEATURE                   Location/Qualifiers
source                    1..20
                          mol_type = other RNA
                          organism = synthetic construct
SEQUENCE: 145
cttccagagc cacatcatcg                                                20

SEQ ID NO: 146            moltype = RNA   length = 20
FEATURE                   Location/Qualifiers
source                    1..20
                          mol_type = other RNA
                          organism = synthetic construct
SEQUENCE: 146
gggactcacc agagagaggt                                                20

SEQ ID NO: 147            moltype = RNA   length = 20
FEATURE                   Location/Qualifiers
source                    1..20
                          mol_type = other RNA
                          organism = synthetic construct
SEQUENCE: 147
cggtcgaaat agaagcccta                                                20

SEQ ID NO: 148            moltype = RNA   length = 20
```

-continued

```
FEATURE              Location/Qualifiers
source               1..20
                     mol_type = other RNA
                     organism = synthetic construct
SEQUENCE: 148
aaaaggatat tgtgcaactg                                              20

SEQ ID NO: 149       moltype = RNA   length = 20
FEATURE              Location/Qualifiers
source               1..20
                     mol_type = other RNA
                     organism = synthetic construct
SEQUENCE: 149
tgtgcatatt tattacatcg                                             20

SEQ ID NO: 150       moltype = RNA   length = 20
FEATURE              Location/Qualifiers
source               1..20
                     mol_type = other RNA
                     organism = synthetic construct
SEQUENCE: 150
tttgtgaaga tcttgaccaa                                             20

SEQ ID NO: 151       moltype = RNA   length = 20
FEATURE              Location/Qualifiers
source               1..20
                     mol_type = other RNA
                     organism = synthetic construct
SEQUENCE: 151
tgtcatgctg aaccgcattg                                             20

SEQ ID NO: 152       moltype = RNA   length = 20
FEATURE              Location/Qualifiers
source               1..20
                     mol_type = other RNA
                     organism = synthetic construct
SEQUENCE: 152
ccactctatg aggatagtca                                             20

SEQ ID NO: 153       moltype = RNA   length = 20
FEATURE              Location/Qualifiers
source               1..20
                     mol_type = other RNA
                     organism = synthetic construct
SEQUENCE: 153
ttgacataga agaggcacaa                                             20

SEQ ID NO: 154       moltype = RNA   length = 20
FEATURE              Location/Qualifiers
source               1..20
                     mol_type = other RNA
                     organism = synthetic construct
SEQUENCE: 154
gagtactaca ctcagcagca                                             20

SEQ ID NO: 155       moltype = RNA   length = 20
FEATURE              Location/Qualifiers
source               1..20
                     mol_type = other RNA
                     organism = synthetic construct
SEQUENCE: 155
tcacgcacaa gaaacgtcca                                             20

SEQ ID NO: 156       moltype = RNA   length = 20
FEATURE              Location/Qualifiers
source               1..20
                     mol_type = other RNA
                     organism = synthetic construct
SEQUENCE: 156
aggtctcggt gaaaccacct                                             20

SEQ ID NO: 157       moltype = RNA   length = 20
FEATURE              Location/Qualifiers
source               1..20
                     mol_type = other RNA
                     organism = synthetic construct
SEQUENCE: 157
agcattatcc aaagagtccg                                             20
```

-continued

```
SEQ ID NO: 158          moltype = RNA   length = 20
FEATURE                 Location/Qualifiers
source                  1..20
                        mol_type = other RNA
                        organism = synthetic construct
SEQUENCE: 158
atattaattc ttaccagtgg                                              20

SEQ ID NO: 159          moltype = RNA   length = 20
FEATURE                 Location/Qualifiers
source                  1..20
                        mol_type = other RNA
                        organism = synthetic construct
SEQUENCE: 159
agctttaaat caaggttcat                                              20

SEQ ID NO: 160          moltype = RNA   length = 20
FEATURE                 Location/Qualifiers
source                  1..20
                        mol_type = other RNA
                        organism = synthetic construct
SEQUENCE: 160
atcccgagcc ctaaggtgca                                              20

SEQ ID NO: 161          moltype = RNA   length = 20
FEATURE                 Location/Qualifiers
source                  1..20
                        mol_type = other RNA
                        organism = synthetic construct
SEQUENCE: 161
ggcagcgcgg aggacagcgt                                              20

SEQ ID NO: 162          moltype = RNA   length = 20
FEATURE                 Location/Qualifiers
source                  1..20
                        mol_type = other RNA
                        organism = synthetic construct
SEQUENCE: 162
ctcaggggggc tactaccacc                                             20

SEQ ID NO: 163          moltype = RNA   length = 20
FEATURE                 Location/Qualifiers
source                  1..20
                        mol_type = other RNA
                        organism = synthetic construct
SEQUENCE: 163
gtcaccgacg agaccagaag                                              20

SEQ ID NO: 164          moltype = RNA   length = 20
FEATURE                 Location/Qualifiers
source                  1..20
                        mol_type = other RNA
                        organism = synthetic construct
SEQUENCE: 164
gtcgtggact tcgtactgct                                              20

SEQ ID NO: 165          moltype = RNA   length = 20
FEATURE                 Location/Qualifiers
source                  1..20
                        mol_type = other RNA
                        organism = synthetic construct
SEQUENCE: 165
taatttttag gcaagtgtcg                                              20

SEQ ID NO: 166          moltype = RNA   length = 20
FEATURE                 Location/Qualifiers
source                  1..20
                        mol_type = other RNA
                        organism = synthetic construct
SEQUENCE: 166
ttagctgtta gacttgaata                                              20

SEQ ID NO: 167          moltype = RNA   length = 20
FEATURE                 Location/Qualifiers
source                  1..20
                        mol_type = other RNA
                        organism = synthetic construct
SEQUENCE: 167
cgagagccgt caacttgcgt                                              20
```

-continued

```
SEQ ID NO: 168            moltype = RNA   length = 20
FEATURE                   Location/Qualifiers
source                    1..20
                          mol_type = other RNA
                          organism = synthetic construct
SEQUENCE: 168
cggcttcaac tgcaaaggtg                                                    20

SEQ ID NO: 169            moltype = RNA   length = 20
FEATURE                   Location/Qualifiers
source                    1..20
                          mol_type = other RNA
                          organism = synthetic construct
SEQUENCE: 169
tatgaaaaag cagagcgact                                                    20

SEQ ID NO: 170            moltype = RNA   length = 20
FEATURE                   Location/Qualifiers
source                    1..20
                          mol_type = other RNA
                          organism = synthetic construct
SEQUENCE: 170
tctggcgggc gagctcacgc                                                    20

SEQ ID NO: 171            moltype = RNA   length = 20
FEATURE                   Location/Qualifiers
source                    1..20
                          mol_type = other RNA
                          organism = synthetic construct
SEQUENCE: 171
ctcacgctgg ttaccgccta                                                    20

SEQ ID NO: 172            moltype = RNA   length = 20
FEATURE                   Location/Qualifiers
source                    1..20
                          mol_type = other RNA
                          organism = synthetic construct
SEQUENCE: 172
aaagattacg aacttccctg                                                    20

SEQ ID NO: 173            moltype = RNA   length = 20
FEATURE                   Location/Qualifiers
source                    1..20
                          mol_type = other RNA
                          organism = synthetic construct
SEQUENCE: 173
gttaaaaaca gacatgccta                                                    20

SEQ ID NO: 174            moltype = RNA   length = 20
FEATURE                   Location/Qualifiers
source                    1..20
                          mol_type = other RNA
                          organism = synthetic construct
SEQUENCE: 174
atgcctaagg aggttgtacc                                                    20

SEQ ID NO: 175            moltype = RNA   length = 20
FEATURE                   Location/Qualifiers
source                    1..20
                          mol_type = other RNA
                          organism = synthetic construct
SEQUENCE: 175
ctccaggtat cccatcgaaa                                                    20

SEQ ID NO: 176            moltype = RNA   length = 20
FEATURE                   Location/Qualifiers
source                    1..20
                          mol_type = other RNA
                          organism = synthetic construct
SEQUENCE: 176
caccaaatac gatagatcag                                                    20

SEQ ID NO: 177            moltype = RNA   length = 20
FEATURE                   Location/Qualifiers
source                    1..20
                          mol_type = other RNA
                          organism = synthetic construct
SEQUENCE: 177
```

-continued

```
tggcggcgtg aatggcaaga                                           20

SEQ ID NO: 178       moltype = RNA   length = 20
FEATURE              Location/Qualifiers
source               1..20
                     mol_type = other RNA
                     organism = synthetic construct
SEQUENCE: 178
taggatggta gcacacaacc                                           20

SEQ ID NO: 179       moltype = RNA   length = 20
FEATURE              Location/Qualifiers
source               1..20
                     mol_type = other RNA
                     organism = synthetic construct
SEQUENCE: 179
cagcagcaga gccccgacgg                                           20

SEQ ID NO: 180       moltype = RNA   length = 20
FEATURE              Location/Qualifiers
source               1..20
                     mol_type = other RNA
                     organism = synthetic construct
SEQUENCE: 180
cggcgtgcga acggaatgtg                                           20

SEQ ID NO: 181       moltype = RNA   length = 20
FEATURE              Location/Qualifiers
source               1..20
                     mol_type = other RNA
                     organism = synthetic construct
SEQUENCE: 181
tatagacgct gcccgacgtc                                           20

SEQ ID NO: 182       moltype = RNA   length = 20
FEATURE              Location/Qualifiers
source               1..20
                     mol_type = other RNA
                     organism = synthetic construct
SEQUENCE: 182
tccaaagaag ggtactgtgg                                           20

SEQ ID NO: 183       moltype = RNA   length = 20
FEATURE              Location/Qualifiers
source               1..20
                     mol_type = other RNA
                     organism = synthetic construct
SEQUENCE: 183
acagtaccct tctttggaat                                           20

SEQ ID NO: 184       moltype = RNA   length = 20
FEATURE              Location/Qualifiers
source               1..20
                     mol_type = other RNA
                     organism = synthetic construct
SEQUENCE: 184
gcgacgggcg catctacgtg                                           20

SEQ ID NO: 185       moltype = RNA   length = 20
FEATURE              Location/Qualifiers
source               1..20
                     mol_type = other RNA
                     organism = synthetic construct
SEQUENCE: 185
cccgacctcc ataagtcctg                                           20

SEQ ID NO: 186       moltype = RNA   length = 20
FEATURE              Location/Qualifiers
source               1..20
                     mol_type = other RNA
                     organism = synthetic construct
SEQUENCE: 186
ggggtcctcg aagcgcacga                                           20

SEQ ID NO: 187       moltype = RNA   length = 20
FEATURE              Location/Qualifiers
source               1..20
                     mol_type = other RNA
                     organism = synthetic construct
```

-continued

```
SEQUENCE: 187
tgctctgttt agaagatgac                                                    20

SEQ ID NO: 188        moltype = RNA  length = 20
FEATURE               Location/Qualifiers
source                1..20
                      mol_type = other RNA
                      organism = synthetic construct
SEQUENCE: 188
atattctttt ctagttaaag                                                    20

SEQ ID NO: 189        moltype = RNA  length = 20
FEATURE               Location/Qualifiers
source                1..20
                      mol_type = other RNA
                      organism = synthetic construct
SEQUENCE: 189
cctgtaaaga aacaaaagac                                                    20

SEQ ID NO: 190        moltype = RNA  length = 20
FEATURE               Location/Qualifiers
source                1..20
                      mol_type = other RNA
                      organism = synthetic construct
SEQUENCE: 190
tggagaaaga cgtaacttcg                                                    20

SEQ ID NO: 191        moltype = RNA  length = 20
FEATURE               Location/Qualifiers
source                1..20
                      mol_type = other RNA
                      organism = synthetic construct
SEQUENCE: 191
tctgccctga ggtatgcgat                                                    20

SEQ ID NO: 192        moltype = RNA  length = 20
FEATURE               Location/Qualifiers
source                1..20
                      mol_type = other RNA
                      organism = synthetic construct
SEQUENCE: 192
attccgcttg gtgaaaacga                                                    20

SEQ ID NO: 193        moltype = RNA  length = 20
FEATURE               Location/Qualifiers
source                1..20
                      mol_type = other RNA
                      organism = synthetic construct
SEQUENCE: 193
caggcacaat agaaacaacg                                                    20

SEQ ID NO: 194        moltype = RNA  length = 20
FEATURE               Location/Qualifiers
source                1..20
                      mol_type = other RNA
                      organism = synthetic construct
SEQUENCE: 194
ccatttgtaa tgctgacttg                                                    20

SEQ ID NO: 195        moltype = RNA  length = 20
FEATURE               Location/Qualifiers
source                1..20
                      mol_type = other RNA
                      organism = synthetic construct
SEQUENCE: 195
ctgggtcact tgtgccgtgg                                                    20

SEQ ID NO: 196        moltype = RNA  length = 20
FEATURE               Location/Qualifiers
source                1..20
                      mol_type = other RNA
                      organism = synthetic construct
SEQUENCE: 196
gtcagggttc tggatatctg                                                    20

SEQ ID NO: 197        moltype = RNA  length = 20
FEATURE               Location/Qualifiers
source                1..20
                      mol_type = other RNA
```

-continued

```
                         organism = synthetic construct
SEQUENCE: 197
tggatttaga gtctctcagc                                                       20

SEQ ID NO: 198         moltype = RNA   length = 20
FEATURE                Location/Qualifiers
source                 1..20
                       mol_type = other RNA
                       organism = synthetic construct
SEQUENCE: 198
ctgcggctgt ggtccagctg                                                       20

SEQ ID NO: 199         moltype = RNA   length = 20
FEATURE                Location/Qualifiers
source                 1..20
                       mol_type = other RNA
                       organism = synthetic construct
SEQUENCE: 199
acaaaactgt gctagacatg                                                       20

SEQ ID NO: 200         moltype = RNA   length = 20
FEATURE                Location/Qualifiers
source                 1..20
                       mol_type = other RNA
                       organism = synthetic construct
SEQUENCE: 200
ttcttcccca gcccaggtaa                                                       20

SEQ ID NO: 201         moltype = RNA   length = 20
FEATURE                Location/Qualifiers
source                 1..20
                       mol_type = other RNA
                       organism = synthetic construct
SEQUENCE: 201
cgtcatgagc agattaaacc                                                       20

SEQ ID NO: 202         moltype = RNA   length = 20
FEATURE                Location/Qualifiers
source                 1..20
                       mol_type = other RNA
                       organism = synthetic construct
SEQUENCE: 202
gagagcgcct gcgacccgag                                                       20

SEQ ID NO: 203         moltype = RNA   length = 20
FEATURE                Location/Qualifiers
source                 1..20
                       mol_type = other RNA
                       organism = synthetic construct
SEQUENCE: 203
ccagcgggtg aagtacacca                                                       20

SEQ ID NO: 204         moltype = RNA   length = 20
FEATURE                Location/Qualifiers
source                 1..20
                       mol_type = other RNA
                       organism = synthetic construct
SEQUENCE: 204
ggagcgcttt tcgccgccag                                                       20

SEQ ID NO: 205         moltype = RNA   length = 20
FEATURE                Location/Qualifiers
source                 1..20
                       mol_type = other RNA
                       organism = synthetic construct
SEQUENCE: 205
tgaggcctgg accttatgca                                                       20

SEQ ID NO: 206         moltype = RNA   length = 20
FEATURE                Location/Qualifiers
source                 1..20
                       mol_type = other RNA
                       organism = synthetic construct
SEQUENCE: 206
cctggtggag tgaaccatga                                                       20

SEQ ID NO: 207         moltype = RNA   length = 20
FEATURE                Location/Qualifiers
source                 1..20
```

```
                        mol_type = other RNA
                        organism = synthetic construct
SEQUENCE: 207
caagcactta ggttcccctg                                        20

SEQ ID NO: 208         moltype = RNA   length = 20
FEATURE                Location/Qualifiers
source                 1..20
                       mol_type = other RNA
                       organism = synthetic construct
SEQUENCE: 208
ggtctcccta caattcagcg                                        20

SEQ ID NO: 209         moltype = RNA   length = 20
FEATURE                Location/Qualifiers
source                 1..20
                       mol_type = other RNA
                       organism = synthetic construct
SEQUENCE: 209
cacagcgcgt gactgcaatg                                        20

SEQ ID NO: 210         moltype = RNA   length = 20
FEATURE                Location/Qualifiers
source                 1..20
                       mol_type = other RNA
                       organism = synthetic construct
SEQUENCE: 210
tctggggcac caattctagg                                        20

SEQ ID NO: 211         moltype = RNA   length = 20
FEATURE                Location/Qualifiers
source                 1..20
                       mol_type = other RNA
                       organism = synthetic construct
SEQUENCE: 211
gagccatgct tggcttacga                                        20

SEQ ID NO: 212         moltype = RNA   length = 20
FEATURE                Location/Qualifiers
source                 1..20
                       mol_type = other RNA
                       organism = synthetic construct
SEQUENCE: 212
gtacaagtac ttatctcatg                                        20

SEQ ID NO: 213         moltype = RNA   length = 20
FEATURE                Location/Qualifiers
source                 1..20
                       mol_type = other RNA
                       organism = synthetic construct
SEQUENCE: 213
gagataacaa cataacaaca                                        20

SEQ ID NO: 214         moltype = RNA   length = 20
FEATURE                Location/Qualifiers
source                 1..20
                       mol_type = other RNA
                       organism = synthetic construct
SEQUENCE: 214
catattccat agtctttggg                                        20

SEQ ID NO: 215         moltype = RNA   length = 20
FEATURE                Location/Qualifiers
source                 1..20
                       mol_type = other RNA
                       organism = synthetic construct
SEQUENCE: 215
ctgcccctta gcaacttagg                                        20

SEQ ID NO: 216         moltype = RNA   length = 20
FEATURE                Location/Qualifiers
source                 1..20
                       mol_type = other RNA
                       organism = synthetic construct
SEQUENCE: 216
tgtttaaaaa tatgttgaca                                        20

SEQ ID NO: 217         moltype = RNA   length = 20
FEATURE                Location/Qualifiers
```

-continued

```
source                  1..20
                        mol_type = other RNA
                        organism = synthetic construct
SEQUENCE: 217
ccaggaatgg aaactcacgc                                              20

SEQ ID NO: 218          moltype = RNA   length = 20
FEATURE                 Location/Qualifiers
source                  1..20
                        mol_type = other RNA
                        organism = synthetic construct
SEQUENCE: 218
gaggccgctg aattaacccg                                              20

SEQ ID NO: 219          moltype = RNA   length = 20
FEATURE                 Location/Qualifiers
source                  1..20
                        mol_type = other RNA
                        organism = synthetic construct
SEQUENCE: 219
atacacgcac acttgcagaa                                              20

SEQ ID NO: 220          moltype = RNA   length = 20
FEATURE                 Location/Qualifiers
source                  1..20
                        mol_type = other RNA
                        organism = synthetic construct
SEQUENCE: 220
gagcagacag aaacccaggg                                              20

SEQ ID NO: 221          moltype = RNA   length = 20
FEATURE                 Location/Qualifiers
source                  1..20
                        mol_type = other RNA
                        organism = synthetic construct
SEQUENCE: 221
tgagtctcca aacagaacag                                              20

SEQ ID NO: 222          moltype = RNA   length = 20
FEATURE                 Location/Qualifiers
source                  1..20
                        mol_type = other RNA
                        organism = synthetic construct
SEQUENCE: 222
taatatcact gacttcacgg                                              20

SEQ ID NO: 223          moltype = RNA   length = 20
FEATURE                 Location/Qualifiers
source                  1..20
                        mol_type = other RNA
                        organism = synthetic construct
SEQUENCE: 223
tacacacaat gtaagcagca                                              20

SEQ ID NO: 224          moltype = RNA   length = 20
FEATURE                 Location/Qualifiers
source                  1..20
                        mol_type = other RNA
                        organism = synthetic construct
SEQUENCE: 224
gggagctcaa ttcgaaacca                                              20

SEQ ID NO: 225          moltype = RNA   length = 20
FEATURE                 Location/Qualifiers
source                  1..20
                        mol_type = other RNA
                        organism = synthetic construct
SEQUENCE: 225
ttggacaggt gagacagtcg                                              20

SEQ ID NO: 226          moltype = RNA   length = 20
FEATURE                 Location/Qualifiers
source                  1..20
                        mol_type = other RNA
                        organism = synthetic construct
SEQUENCE: 226
aagctcactc agatagtgtg                                              20

SEQ ID NO: 227          moltype = RNA   length = 20
```

-continued

```
FEATURE                 Location/Qualifiers
source                  1..20
                        mol_type = other RNA
                        organism = synthetic construct
SEQUENCE: 227
caggagaacc accttacacg                                           20

SEQ ID NO: 228          moltype = RNA   length = 20
FEATURE                 Location/Qualifiers
source                  1..20
                        mol_type = other RNA
                        organism = synthetic construct
SEQUENCE: 228
ggacagaccc tgattcacaa                                           20

SEQ ID NO: 229          moltype = RNA   length = 20
FEATURE                 Location/Qualifiers
source                  1..20
                        mol_type = other RNA
                        organism = synthetic construct
SEQUENCE: 229
acatggcagt ctatgaacag                                           20

SEQ ID NO: 230          moltype = RNA   length = 20
FEATURE                 Location/Qualifiers
source                  1..20
                        mol_type = other RNA
                        organism = synthetic construct
SEQUENCE: 230
cctatagaga gtactacttg                                           20

SEQ ID NO: 231          moltype = RNA   length = 20
FEATURE                 Location/Qualifiers
source                  1..20
                        mol_type = other RNA
                        organism = synthetic construct
SEQUENCE: 231
ccaaccgggt cttcattacg                                           20

SEQ ID NO: 232          moltype = RNA   length = 20
FEATURE                 Location/Qualifiers
source                  1..20
                        mol_type = other RNA
                        organism = synthetic construct
SEQUENCE: 232
tcaagcgtag agttccgagt                                           20

SEQ ID NO: 233          moltype = RNA   length = 20
FEATURE                 Location/Qualifiers
source                  1..20
                        mol_type = other RNA
                        organism = synthetic construct
SEQUENCE: 233
tcatgcaatt atggacccag                                           20

SEQ ID NO: 234          moltype = RNA   length = 20
FEATURE                 Location/Qualifiers
source                  1..20
                        mol_type = other RNA
                        organism = synthetic construct
SEQUENCE: 234
cgggaaagtg actggccatg                                           20

SEQ ID NO: 235          moltype = RNA   length = 20
FEATURE                 Location/Qualifiers
source                  1..20
                        mol_type = other RNA
                        organism = synthetic construct
SEQUENCE: 235
tgagattgaa atcaaatcgg                                           20
```

-continued

```
SEQ ID NO: 236          moltype = RNA  length = 20
FEATURE                 Location/Qualifiers
source                  1..20
                        mol_type = other RNA
                        organism = synthetic construct
SEQUENCE: 236
tatgcaatat tcatcacgcg                                           20

SEQ ID NO: 237          moltype = RNA  length = 20
FEATURE                 Location/Qualifiers
source                  1..20
                        mol_type = other RNA
                        organism = synthetic construct
SEQUENCE: 237
aatgtgttaa atcaaatgca                                           20

SEQ ID NO: 238          moltype = AA  length = 16
FEATURE                 Location/Qualifiers
source                  1..16
                        mol_type = protein
                        organism = synthetic construct
SEQUENCE: 238
ELPTQGTFSN VSTNVS                                               16

SEQ ID NO: 239          moltype = AA  length = 66
FEATURE                 Location/Qualifiers
source                  1..66
                        mol_type = protein
                        organism = synthetic construct
SEQUENCE: 239
MVDPVGFAEA WKAQFPDSEP PRMELRSVGD IEQELERCKA SIRRLEQEVN QERFRMIYLQ  60
TLLAKE                                                          66

SEQ ID NO: 240          moltype = AA  length = 51
FEATURE                 Location/Qualifiers
source                  1..51
                        mol_type = protein
                        organism = synthetic construct
SEQUENCE: 240
PSSSDYSDLQ RVKQELLEEV KKELQKVKEE IIEAFVQELR KRGSPAQGEI E          51

SEQ ID NO: 241          moltype = AA  length = 226
FEATURE                 Location/Qualifiers
source                  1..226
                        mol_type = protein
                        organism = synthetic construct
SEQUENCE: 241
APPPNLPDPK FESKAALLAA RGPEELLCFT ERLEDLVCFW EEAASAGVGP GNYSFSYQLE  60
DEPWKLCRLH QAPTARGAVR FWCSLPTADT SSFVPLELRV TAASGAPRYH RVIHINEVVL  120
LDAPVGLVAC LADESGHVVL RWLPPPETPM TSHIRYEVDV SAGNGAGSVQ RVEILEGRTE  180
CVLSNLRGRT RYTFAVRARM AEPSFGGFWS AWSEPVSLLT PSDLDP                226

SEQ ID NO: 242          moltype = AA  length = 259
FEATURE                 Location/Qualifiers
source                  1..259
                        mol_type = protein
                        organism = synthetic construct
SEQUENCE: 242
SLDNNGTATP ELPTQGTFSN VSTNVSYQET TTPSTLGSTS LHPVSQHGNE ATTNITETTV  60
KFTSTSVITS VYGNTNSSVQ SQTSVISTVF TTPANVSTPE TTLKPSLSPG NVSDLSTTST  120
SLATSPTKPY TSSSPILSDI KAEIKCSGIR EVKLTQGICL EQNKTSSCAE FKKDRGEGLA  180
RVLCGEEQAD ADAGAQVCSL LLAQSEVRPQ CLLLVLANRT EISSKLQLMK KHQSDLKKLG  240
ILDFTEQDVA SHQSYSQKT                                            259

SEQ ID NO: 243          moltype = AA  length = 22
FEATURE                 Location/Qualifiers
source                  1..22
                        mol_type = protein
                        organism = synthetic construct
SEQUENCE: 243
ISLVTALLLV LGLNAVLGLL LL                                        22
```

SYNTHETIC PATHWAY ACTIVATORS

CROSS REFERENCE TO RELATED APPLICATIONS

This application is a continuation of Internation Application No. PCT/US2024/019690 filed Mar. 13, 2024, which claims the benefit of U.S. Provisional Application No. 63/489,842, filed Mar. 13, 2023; U.S. Provisional Application No. 63/495,865, filed Apr. 13, 2023; and U.S. Provisional Application No. 63/613,713, filed Dec. 21, 2023; each of which are hereby incorporated in their entirety by reference.

SEQUENCE LISTING

The instant application contains a Sequence Listing which is hereby incorporated by reference in its entirety. Said XML copy, created on Feb. 28, 2024, is named ANB-219WO_SL, and is 252,803 bytes in size.

BACKGROUND

Cancer is a disease characterized by uncontrollable growth of cells. Many approaches to treating cancer have been tried, including drugs and radiation therapies. Recent cancer treatments have sought to use the body's own immune cells to attack cancer cells. One promising approach uses T cells that are taken from a patient and genetically engineered to produce chimeric antigen receptors, or CARs, receptor proteins that give the T cells a new ability to target a specific protein. The receptors are chimeric because they combine antigen-binding and T-cell activating functions into a single receptor.

Immunotherapy using CAR-T cells is promising because the modified T cells have the potential to recognize cancer cells in order to more effectively target and destroy them.

After the T cells are engineered with the CARs, the resulting CAR-T cells are introduced into patients to attack tumor cells. CAR-T cells can be either derived from T cells in a patient's own blood (autologous) or derived from the T cells of another healthy donor (allogeneic). Once CAR-T cells are infused into a patient, they come in contact with their targeted antigen on a cell. The CAR-T cells bind to the antigen and become activated. Upon antigen engagement, CAR T cells can proliferate exponentially, initiate antitumor cytokine production, and target tumor cell killing.

However, there remain some concerns and limitations to CAR T cell-based immunotherapy. Clinically effective adoptive T cell therapy for the treatment of solid tumors will use robust T cell expansion, persistence, and potency. Thus, additional therapies that increase T cell expansion, persistence, and potency remain desirable.

SUMMARY

In one aspect, provided herein are synthetic pathway activator (SPA) peptides comprising a chimeric polypeptide comprising:

i. optionally, an extracellular domain;
    ii. a lipid anchor or a transmembrane domain;
    iii. an intracellular signaling domain; and
    iv. a multimerization region.

In some embodiments, multimerization of the chimeric polypeptide via the multimerization region results in constitutive activity of the intracellular signaling domain.

In some embodiments, the multimerization region comprises at least one of an unpaired cysteine residue, a leucine zipper, a BCR domain, and a VASP domain.

In some embodiments, the multimerization region comprises at least an unpaired cysteine residue.

In some embodiments, the multimerization region comprises at least an unpaired cysteine residue and a leucine zipper.

In some embodiments, the multimerization region is intracellular when expressed by a cell.

In some embodiments, the multimerization region is extracellular when expressed by a cell.

In some embodiments, the intracellular signaling domain induces phosphorylation of STAT1, STAT3, or STAT5.

In some embodiments, the intracellular signaling domain comprises a type I cytokine receptor superfamily box1 (IWPNVDP (SEQ ID NO: 106)) or box2 (VSVVEIEAN-DKKP (SEQ ID NO: 107)) peptide motif.

In some embodiments, the intracellular signaling domain comprises a tyrosine phosphorylation motif comprising YXXQ or YXPQ.

In some embodiments, the intracellular signaling domain comprises a polypeptide sequence from an interleukin receptor.

In some embodiments, the interleukin receptor comprises a gp130 intracellular signaling domain.

In some embodiments, the intracellular signaling domain comprises a polypeptide sequence comprising amino acids 642 to 918 of gp130 (SEQ ID NO: 59).

In some embodiments, the intracellular signaling domain comprises a polypeptide sequence comprising the sequence set forth as SEQ ID NO: 60.

In some embodiments, the interleukin receptor comprises a truncated gp130 intracellular signaling domain.

In some embodiments, the truncated gp130 intracellular signaling domain comprises a deletion of amino acids 771 to 811 of gp130 (SEQ ID NO: 59).

In some embodiments, the truncated gp130 intracellular signaling domain comprises the truncated gp130 intracellular domain of a sequence selected from the group set forth in SEQ ID NOs: 10-16 and 71-77.

In some embodiments, the gp130 intracellular signaling domain further comprises a Y759F mutation of gp130 (SEQ ID NO: 59).

In some embodiments, wherein the intracellular signaling domain further comprises a prenylation motif at the C terminus.

In some embodiments, the lipid anchor or a transmembrane domain comprises a gp130 transmembrane domain, a CD8-alpha transmembrane domain, a prenylation motif, or a myristoylation domain derived from src, fyn, or lck.

In some embodiments, the transmembrane domain comprises a gp130 transmembrane domain.

In some embodiments, the transmembrane domain comprises a polypeptide sequence comprising amino acids 620 to 641 of gp130 (SEQ ID NO: 59)

In some embodiments, the transmembrane domain comprises a polypeptide sequence comprising the sequence set forth as SEQ ID NO: 61.

In some embodiments, the SPA peptides further comprise a CD8-alpha hinge domain.

In some embodiments, the extracellular domain comprises one or more of a CD34 epitope, a CD34 ectodomain, a BCR ectodomain, a thrombopoietin receptor (TpoR) ectodomain, or an erythropoietin receptor (EpoR) ectodomain.

In some embodiments, the thrombopoietin receptor (TpoR) ectodomain or erythropoietin receptor (EpoR) ectodomain comprise an unpaired cysteine.

In some embodiments, the extracellular domain conveys constitutive activity to the intracellular signaling domain.

In some embodiments, comprising, from N terminus to C terminus, an extracellular domain comprising a CD34 epitope, a multimerization region comprising an unpaired cysteine residue, a gp130 transmembrane domain, and a gp130 intracellular signaling domain.

In some embodiments, the SPA peptide comprises a sequence selected from the sequences set forth in SEQ ID NOs: 1-58 or 63-104.

In some embodiments, the SPA peptide comprises a sequence as set forth in SEQ ID NO: 20.

In another aspect, provided herein are multimers of the SPA peptides disclosed herein.

In another aspect, provided herein are nucleic acids encoding the SPA peptides disclosed herein.

In another aspect, provided herein are vectors comprising the nucleic acids disclosed herein.

In another aspect, provided herein are systems comprising:
  i. a first chimeric polypeptide comprising a priming receptor;
  ii. a second chimeric polypeptide comprising a chimeric antigen receptor (CAR); and
  iii. the SPA peptides disclosed herein.

In some embodiments, the CAR induces expression of the SPA peptide.

In some embodiments, the SPA peptide is constitutively expressed.

In another aspect, provided herein are cells or populations of cells comprising the SPA peptides disclosed herein, the multimers disclosed herein, the nucleic acids disclosed herein, the vectors disclosed herein, or the systems disclosed herein.

In some embodiments, the cell is an immune cell, optionally wherein the immune cell is a primary human immune cell.

In another aspect, provided herein are pharmaceutical composition comprising the cell or population of cells disclosed herein, and a pharmaceutically acceptable excipient.

In another aspect, provided herein are pharmaceutical compositions comprising the nucleic acids disclosed herein or the vectors disclosed herein, and a pharmaceutically acceptable excipient.

In another aspect, provided herein are method of editing a cell, comprising:
  i. providing a ribonucleoprotein complex (RNP)-nucleic acid complex, wherein the RNP comprises a nuclease domain and a guide RNA, wherein the nucleic acid comprises the nucleic acids disclosed herein, and wherein the 5' and 3' ends of the nucleic acid comprise nucleotide sequences that are homologous to genomic sequences flanking an insertion site in the genome of the immune cell;
  ii. non-virally introducing the RNP-nucleic acid complex into the immune cell, wherein the guide RNA specifically hybridizes to a target region of the genome of the primary immune cell, and wherein the nuclease domain cleaves the target region to create the insertion site in the genome of the immune cell; and
  iii. editing the immune cell via insertion of the nucleic acids disclosed herein into the insertion site in the genome of the immune cell.

In another aspect, provided herein are methods of treating a disease in a subject comprising administering the cells disclosed herein or the pharmaceutical compositions disclosed herein to the subject.

In another aspect, provided herein are methods of inhibiting a target cell in a subject comprising administering the cells disclosed herein to the subject, wherein the cell inhibits the target cell.

In another aspect, provided herein are methods of modulating the activity of an immune cell comprising:
  i. obtaining a cell comprising
    1. SPA peptides disclosed herein;
    2. the systems disclosed herein;
    3. the nucleic acids disclosed herein; and/or
    4. the vectors disclosed herein; and
  ii. contacting the immune cell with a target cell, wherein the synthetic pathway activator modulates the activity of the immune cell.

In another aspect, provided herein are methods of modulating the activity of an immune cell comprising:
  i. obtaining a cell comprising
    1. SPA peptides disclosed herein;
    2. the systems disclosed herein;
    3. the nucleic acids disclosed herein; and/or
    4. the vectors disclosed herein; and
  ii. contacting the immune cell with a target cell expressing a priming receptor antigen and a CAR antigen, wherein binding of the priming receptor to the priming receptor antigen on the target cell induces activation of the priming receptor and expression of the chimeric antigen receptor, wherein binding of the chimeric antigen receptor to CAR antigen on the target cell modulates the activity of the immune cell, and wherein the synthetic pathway activator also modulates the activity of the immune cell.

In some aspects, provided herein are methods of treating a disease in a subject in need thereof comprising: determining or having determined the expression of CD11c in a cell comprising the synthetic pathway activator (SPA) peptide disclosed herein or the nucleic acid disclosed herein; and administering or having administered to the subject the cell.

In some aspects, provided herein are methods of determining expression of a SPA in a cell, comprising expressing one or more SPA peptides disclosed herein in the cell and determining CD11c expression in the cell.

In some embodiments, the expression of CD11c in the cell comprises an mRNA expression level of CD11c or a protein expression level of CD11c.

In some embodiments, the cell is an immune cell, a primary human immune cell, a natural killer (NK) cell, a T cell, a CD8+ T cell, a CD4+ T cell, a primary T cell, or a T cell progenitor cell.

BRIEF DESCRIPTION OF THE SEVERAL VIEWS OF THE DRAWINGS

These and other features, aspects, and advantages of the present disclosure will become better understood with regard to the following description, and accompanying drawings, where.

DETAILED DESCRIPTION

Definitions

Figure 1:
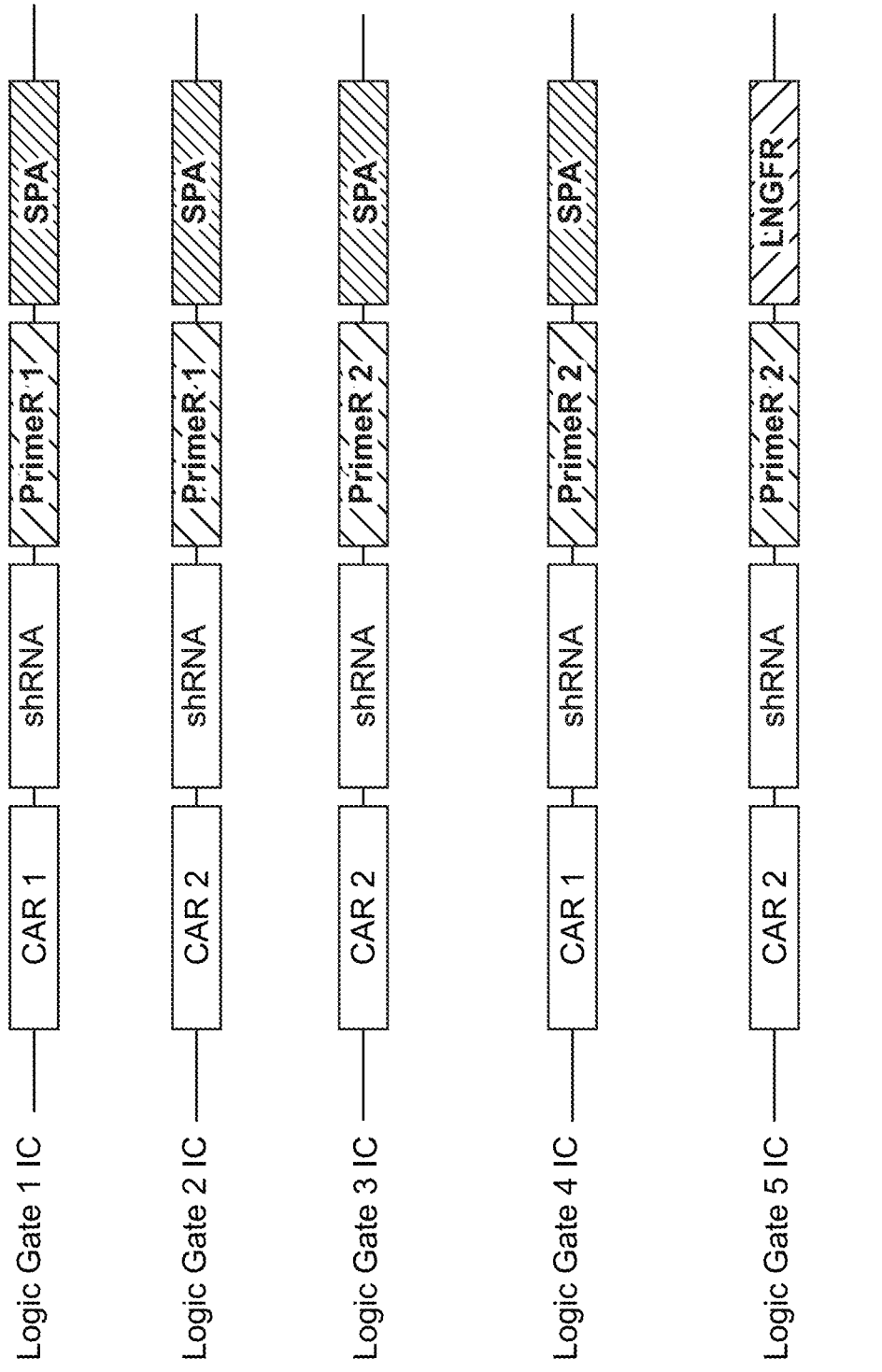
FIG. 1 provides diagram of the various ICT transgene cassettes expressing Logic Gate 1-5 ICs, shRNA, and SPAs.

Terms used in the claims and specification are defined as set forth below unless otherwise specified.

As used herein, the term "gene" refers to the basic unit of heredity, consisting of a segment of DNA arranged along a chromosome, which codes for a specific protein or segment of protein. A gene typically includes a promoter, a 5' untranslated region, one or more coding sequences (exons), optionally introns, and a 3' untranslated region. The gene may further comprise a terminator, enhancers and/or silencers.

As used herein, the term "locus" refers to a specific, fixed physical location on a chromosome where a gene or genetic marker is located.

The term "safe harbor locus" refers to a locus at which genes or genetic elements can be incorporated without disruption to expression or regulation of adjacent genes. These safe harbor loci are also referred to as safe harbor sites (SHS). As used herein, a safe harbor locus refers to an "integration site" or "knock-in site" at which a sequence encoding a transgene, as defined herein, can be inserted. In some embodiments the insertion occurs with replacement of a sequence that is located at the integration site. In some embodiments, the insertion occurs without replacement of a sequence at the integration site. Examples of integration sites contemplated are provided in Table D.

As used herein, the term "insert" refers to a nucleotide sequence that is integrated (inserted) at a target locus or safe harbor site. The insert can be used to refer to the genes or genetic elements that are incorporated at the target locus or safe harbor site using, for example, homology-directed repair (HDR) CRISPR/Cas9 genome-editing or other methods for inserting nucleotide sequences into a genomic region known to those of ordinary skill in the art.

The term "inserting" refers to a manipulation of a nucleotide sequence to introduce a non-native sequence. This is done, for example, via the use of restriction enzymes and ligases whereby the DNA sequence of interest, usually encoding the gene of interest, can be incorporated into another nucleic acid molecule by digesting both molecules with appropriate restriction enzymes in order to create compatible overlaps and then using a ligase to join the molecules together. One skilled in the art is very familiar with such manipulations and examples may be found in Sambrook et al. (Sambrook, Fritsch, & Maniatis, "Molecular Cloning: A Laboratory Manual", $2^{nd}$ ed., Cold Spring Harbor Laboratory, 1989), which is hereby incorporated by reference in its entirety including any drawings, figures and tables.

The "CRISPR/Cas" system refers to a widespread class of bacterial systems for defense against foreign nucleic acid. CRISPR/Cas systems are found in a wide range of eubacterial and archacal organisms. CRISPR/Cas systems include type I, II, and III sub-types. Wild-type type II CRISPR/Cas systems utilize an RNA-mediated nuclease, Cas9 in complex with guide and activating RNA to recognize and cleave foreign nucleic acid. Guide RNAs having the activity of both a guide RNA and an activating RNA are also known in the art. In some cases, such dual activity guide RNAs are referred to as a small guide RNA (sgRNA).

Cas9 homologs are found in a wide variety of cubacteria, including, but not limited to bacteria of the following taxonomic groups: Actinobacteria, Aquificae, Bacteroidetes-Chlorobi, Chlamydiae-Verrucomicrobia, Chlroflexi, Cyano-bacteria, Firmicutes, Proteobacteria, Spirochaetes, and Ther-motogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10 (5): 726-737; Nat. Rev. Micro-biol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. The Cas9 nucle-ase domain can be optimized for efficient activity or enhanced stability in the host cell.

As used herein, the term "Cas9" refers to an RNA-mediated nuclease (e.g., of bacterial or archeal origin, or derived therefrom). Exemplary RNA-mediated nucleases include the foregoing Cas9 proteins and homologs thereof, and include but are not limited to, CPF1 (See, e.g., Zetsche et al., Cell, Volume 163, Issue 3, p 759-771, 22 Oct. 2015). Similarly, as used herein, the term "Cas9 ribonucleoprotein" complex and the like refers to a complex between the Cas9 protein and a crRNA (e.g., guide RNA or small guide RNA), the Cas9 protein and a trans-activating crRNA (tracrRNA), the Cas9 protein and a small guide RNA, or a combination thereof (e.g., a complex containing the Cas9 protein, a tracrRNA, and a crRNA guide RNA).

As used herein, the phrase "immune cell" is inclusive of all cell types that can give rise to immune cells, including hematopoietic cells such hematopoietic stem cells, pluripo-tent stem cells, and induced pluripotent stem cells (iPSCs). In some embodiments, the immune cell is a B cell, macro-phage, a natural killer (NK) cell, an induced pluripotent stem cell (iPSC), a human pluripotent stem cell (HSPC), a T cell or a T cell progenitor cell, or dendritic cell. In some embodiments, the cell is an innate immune cell.

As used herein, the term "primary" in the context of a primary cell or primary stem cell refers to a cell that has not been transformed or immortalized. Such primary cells can be cultured, sub-cultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized, e.g., directly without culturing or sub-culturing. In some cases, the primary cells are stimulated, activated, or differentiated. For example, primary T cells can be activated by contact with (e.g., culturing in the presence of) CD3, CD28 agonists, IL-2, IFN-γ, or a combination thereof.

As used herein, the terms "T lymphocyte" and "T cell" are used interchangeably and refer to cells that have completed maturation in the thymus, and identify certain foreign anti-gens in the body. The terms also refer to the major leukocyte types that have various roles in the immune system, includ-ing activation and deactivation of other immune cells. The T cell can be any T cell such as a cultured T cell, e.g., a primary T cell, or a T cell derived from a cultured T cell line, e.g., a Jurkat, SupT1, etc., or a T cell obtained from a mammal. T cells include, but are not limited to, naïve T cells, stimulated T cells, primary T cells (e.g., uncultured), cul-tured T cells, immortalized T cells, helper T cells, cytotoxic T cells, memory T cells, regulatory T cells, natural killer T cells, combinations thereof, or sub-populations thereof. The T cell can be a CD3+ cell. T cells can be CD4$^+$, CD8$^+$, or CD4$^+$ and CD8$^+$. The T cell can be any type of T cell, CD4+/CD8+ double positive T cells, CD4+ helper T cells (e.g. Th1 and Th2 cells), CD8+ T cells (e.g. cytotoxic T cells), peripheral Including but not limited to blood mono-nuclear cells (PBMC), peripheral blood leukocytes (PBL), tumor infiltrating lymphocytes (TIL), memory T cells, naïve T cells, T cells, regulatory T cells, γδ T cells, etc. It can be any T cell at any stage of development. Additional types of helper T cells include Th3 (Treg) cells, Th17 cells, Th9 cells, or Tfh cells. Additional types of memory T cells include cells such as central memory T cells (Tem cells), effector memory T cells (Tem cells and TEMRA cells). A T cell can also refer to a genetically modified T cell, such as a T cell that has been modified to express a T cell receptor (TCR) or a chimeric antigen receptor (CAR). T cells can also be differentiated from stem cells or progenitor cells.

"CD4+ T cells" refers to a subset of T cells that express CD4 on their surface and are associated with a cellular immune response. CD4+ T cells are characterized by a post-stimulation secretion profile that can include secretion of cytokines such as IFN-γ, TNF-α, IL-2, IL-4 and IL-10. "CD4" is a 55 kD glycoprotein originally defined as a differentiation antigen on T lymphocytes, but was also found on other cells including monocytes/macrophages. The CD4 antigen is a member of the immunoglobulin superfamily and has been implicated as an associative recognition element in MHC (major histocompatibility complex) class II restricted immune responses. On T lymphocytes, the CD4 antigen defines a helper/inducer subset.

"CD8+ T cells" refers to a subset of T cells that express CD8 on their surface, are MHC class I restricted, and function as cytotoxic T cells. The "CD8" molecule is a differentiation antigen present on thymocytes, as well as on cytotoxic and suppressor T lymphocytes. The CD8 antigen is a member of the immunoglobulin superfamily and is an associative recognition element in major histocompatibility complex class I restriction interactions.

As used herein, the phrase "hematopoietic stem cell" refers to a type of stem cell that can give rise to a blood cell. Hematopoietic stem cells can give rise to cells of the myeloid or lymphoid lineages, or a combination thereof. Hematopoietic stem cells are predominantly found in the bone marrow, although they can be isolated from peripheral blood, or a fraction thereof. Various cell surface markers can be used to identify, sort, or purify hematopoietic stem cells. In some cases, hematopoietic stem cells are identified as c-kit$^+$ and lin$^-$. In some cases, human hematopoietic stem cells are identified as CD34$^+$, CD59$^+$, Thy1/CD90$^+$, CD38$^{lo/-}$, C-kit/CD117$^+$, lin$^-$. In some cases, human hema-topoietic stem cells are identified as CD34$^-$, CD59$^+$, Thy1/CD90$^+$, CD38$^{lo/-}$, C-kit/CD117$^+$, lin$^-$. In some cases, human hematopoietic stem cells are identified as CD133$^+$, CD59$^+$, Thy1/CD90$^+$, CD38$^{lo/-}$, C-kit/CD117$^+$, lin$^-$. In some cases, mouse hematopoietic stem cells are identified as CD34$^{lo/-}$, SCA-1$^+$, Thy1$^{+/lo}$, CD38$^+$, C-kit$^+$, lin$^-$. In some cases, the hematopoietic stem cells are CD150$^+$CD48$^-$CD244$^-$.

As used herein, the phrase "hematopoietic cell" refers to a cell derived from a hematopoietic stem cell. The hema-topoietic cell may be obtained or provided by isolation from an organism, system, organ, or tissue (e.g., blood, or a fraction thereof). Alternatively, an hematopoietic stem cell can be isolated and the hematopoietic cell obtained or provided by differentiating the stem cell. Hematopoietic cells include cells with limited potential to differentiate into further cell types. Such hematopoietic cells include, but are not limited to, multipotent progenitor cells, lineage-re-stricted progenitor cells, common myeloid progenitor cells, granulocyte-macrophage progenitor cells, or megakaryocyte-erythroid progenitor cells. Hematopoietic cells include cells of the lymphoid and myeloid lineages, such as lymphocytes, erythrocytes, granulocytes, monocytes, and thrombocytes.

As used herein, the term "construct" refers to a complex of molecules, including macromolecules or polynucleotides.

As used herein, the term "integration" refers to the process of stably inserting one or more nucleotides of a construct into the cell genome, i.e., covalently linking to a nucleic acid sequence in the chromosomal DNA of the cell. It may also refer to nucleotide deletions at a site of integration. Where there is a deletion at the insertion site, "integration" may further include substitution of the endogenous sequence or nucleotide deleted with one or more inserted nucleotides.

As used herein, the term "exogenous" refers to a molecule or activity that has been introduced into a host cell and is not native to that cell. The molecule can be introduced, for example, by introduction of the encoding nucleic acid into host genetic material, such as by integration into a host chromosome, or as non-chromosomal genetic material, such as a plasmid. Thus, the term, when used in connection with expression of an encoding nucleic acid, refers to the introduction of the encoding nucleic acid into a cell in an expressible form. The term "endogenous" refers to a molecule or activity that is present in a host cell under natural, unedited conditions. Similarly, the term, when used in connection with expression of the encoding nucleic acid, refers to expression of the encoding nucleic acid that is contained within the cell and not introduced exogenously.

The term "heterologous" refers to a nucleic acid or polypeptide sequence or domain which is not native to a flanking sequence, e.g., wherein the heterologous sequence is not found in nature coupled to the nucleic acid or polypeptide sequences occurring at one or both ends.

The term "homologous" refers to a nucleic acid or polypeptide sequence or domain which is native to a flanking sequence, e.g., wherein the homologous sequence is found in nature coupled to the nucleic acid or polypeptide sequences occurring at one or both ends.

As used herein, a "polynucleotide donor construct" refers to a nucleotide sequence (e.g. DNA sequence) that is genetically inserted into a polynucleotide and is exogenous to that polynucleotide. The polynucleotide donor construct is transcribed into RNA and optionally translated into a polypeptide. The polynucleotide donor construct can include prokaryotic sequences, cDNA from eukaryotic mRNA, genomic DNA sequences from eukaryotic (e.g., mammalian) DNA, and synthetic DNA sequences. For example, the polynucleotide donor construct can be a miRNA, shRNA, natural polypeptide (i.e., a naturally occurring polypeptide) or fragment thereof or a variant polypeptide (e.g. a natural polypeptide having less than 100% sequence identity with the natural polypeptide) or fragments thereof.

As used herein, the term "complementary" or "complementarity" refers to specific base pairing between nucleotides or nucleic acids. Complementary nucleotides are, generally, A and T (or A and U), and G and C. The guide RNAs described herein can comprise sequences, for example, DNA targeting sequence that are perfectly complementary or substantially complementary (e.g., having 1-4 mismatches) to a genomic sequence in a cell.

As used herein, the term "transgene" refers to a polynucleotide that has been transferred naturally, or by any of a number of genetic engineering techniques from one organism to another. It is optionally translated into a polypeptide. As used, transgene can refer to a polynucleotide that encodes a polypeptide.

The terms "protein," "polypeptide," and "peptide" are used herein interchangeably.

As used herein, the term "operably linked" or "operatively linked" refers to the binding of a nucleic acid sequence to a single nucleic acid fragment such that one function is affected by the other. For example, if a promoter is capable of affecting the expression of a coding sequence or functional RNA (i.e., the coding sequence or functional RNA is under transcriptional control by the promoter), the promoter is operably linked thereto. Coding sequences can be operably linked to control sequences in both sense and antisense orientation.

As used herein, the term "developmental cell states" refers to, for example, states when the cell is inactive, actively expressing, differentiating, senescent, etc. developmental cell state may also refer to a cell in a precursor state (e.g., a T cell precursor).

As used, the term "encoding" refers to a sequence of nucleic acids which codes for a protein or polypeptide of interest. The nucleic acid sequence may be either a molecule of DNA or RNA. In preferred embodiments, the molecule is a DNA molecule. In other preferred embodiments, the molecule is a RNA molecule. When present as a RNA molecule, it will comprise sequences which direct the ribosomes of the host cell to start translation (e.g., a start codon, ATG) and direct the ribosomes to end translation (e.g., a stop codon). Between the start codon and stop codon is an open reading frame (ORF). Such terms are known to one of ordinary skill in the art.

As used herein, the term "subject" refers to a mammalian subject. Exemplary subjects include humans, monkeys, dogs, cats, mice, rats, cows, horses, camels, goats, rabbits, pigs and sheep. In certain embodiments, the subject is a human. In some embodiments the subject has a disease or condition that can be treated with an engineered cell provided herein or population thereof. In some aspects, the disease or condition is a cancer.

As used herein, the term "promoter" refers to a nucleotide sequence (e.g. DNA sequence) capable of controlling the expression of a coding sequence or functional RNA. The promoter sequence consists of proximal and more distal upstream elements, the latter elements often referred to as enhancers. A promoter can be derived from natural genes in its entirety, can be composed of different elements from different promoters found in nature, and/or may comprise synthetic DNA segments. A promoter, as contemplated herein, can be endogenous to the cell of interest or exogenous to the cell of interest. It is appreciated by those skilled in the art that different promoters can induce gene expression in different tissue or cell types, or at different developmental stages, or in response to different environmental conditions. As is known in the art, a promoter can be selected according to the strength of the promoter and/or the conditions under which the promoter is active, e.g., constitutive promoter, strong promoter, weak promoter, inducible/repressible promoter, tissue specific Or developmentally regulated promoters, cell cycle-dependent promoters, and the like.

A promoter can be an inducible promoter (e.g., a heat shock promoter, tetracycline-regulated promoter, steroid-regulated promoter, metal-regulated promoter, estrogen receptor-regulated promoter, HNF1α promoter, etc.). The promoter can be a constitutive promoter (e.g., CMV promoter, UBC promoter). In some embodiments, the promoter can be a spatially restricted and/or temporally restricted promoter (e.g., a tissue specific promoter, a cell type specific promoter, etc.). See for example US Publication 20180127786, the disclosure of which is herein incorporated by reference in its entirety.

Gene editing, as contemplated herein, may involve a gene (or nucleotide sequence) knock-in or knock-out. As used herein, the term "knock-in" refers to an addition of a DNA sequence, or fragment thereof into a genome. Such DNA sequences to be knocked-in may include an entire gene or genes, may include regulatory sequences associated with a gene or any portion or fragment of the foregoing. For example, a polynucleotide donor construct encoding a protein may be inserted into the genome of a cell carrying a mutant gene. In some embodiments, a knock-in strategy involves substitution of an existing sequence with the provided sequence, e.g., substitution of a mutant allele with a wild-type copy. On the other hand, the term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant (e.g., non-coding) sequence.

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term "homology directed repair" or HDR refers to a cellular process in which cut or nicked ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR-induced change of the sequence at the target site. In this way, specific mutations can be introduced at the cut site.

As used herein, a single-stranded DNA template or a double-stranded DNA template refers to a DNA oligonucleotide that can be used by a cell as a template for HDR. Generally, the single-stranded DNA template or a double-stranded DNA template has at least one region of homology to a target site. In some cases, the single-stranded DNA template or double-stranded DNA template has two homologous regions flanking a region that contains a heterologous sequence to be inserted at a target cut site.

The terms "vector" and "plasmid" are used interchangeably and as used herein refer to polynucleotide vehicles useful to introduce genetic material into a cell. Vectors can be linear or circular. Vectors can integrate into a target genome of a host cell or replicate independently in a host cell. Vectors can comprise, for example, an origin of replication, a multicloning site, and/or a selectable marker. An expression vector typically comprises an expression cassette. Vectors and plasmids include, but are not limited to, integrating vectors, prokaryotic plasmids, eukaryotic plasmids, plant synthetic chromosomes, episomes, cosmids, and artificial chromosomes.

As used herein, the phrase "introducing" in the context of introducing a nucleic acid or a complex comprising a nucleic acid, for example, an RNP-DNA template complex, refers to the translocation of the nucleic acid sequence or the RNP-DNA template complex from outside a cell to inside the cell. In some cases, introducing refers to translocation of the nucleic acid or the complex from outside the cell to inside the nucleus of the cell. Various methods of such translocation are contemplated, including but not limited to, electroporation, contact with nanowires or nanotubes, receptor mediated internalization, translocation via cell penetrating peptides, liposome mediated translocation, and the like.

As used herein the term "expression cassette" is a polynucleotide construct, generated recombinantly or chemically synthesized, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

As used herein, the phrase "subject in need thereof" refers to a subject that exhibits and/or is diagnosed with one or more symptoms or signs of a disease or disorder as described herein.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "composition" refers to a mixture that contains, e.g., an engineered cell or protein contemplated herein. In some embodiments, the composition may contain additional components, such as adjuvants, stabilizers, excipients, and the like. The term "composition" or "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The term "in situ" refers to processes that occur in a living cell growing separate from a living organism, e.g., growing in tissue culture.

The term "in vivo" refers to processes that occur in a living organism.

As used herein, the term "ex vivo" generally includes experiments or measurements made in or on living tissue, preferably in an artificial environment outside the organism, preferably with minimal differences from natural conditions.

The term "mammal" as used herein includes both humans and non-humans and include but is not limited to humans, non-human primates, canines, felines, murines, bovines, equines, and porcines.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc' Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease.

The term "ameliorating" refers to any therapeutically beneficial result in the treatment of a disease state, e.g., a cancer disease state, lessening in the severity or progression, remission, or cure thereof.

As used herein, the term "effective amount" refers to the amount of a compound (e.g., a compositions described herein, cells described herein) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). For example, an antibody that "selectively binds" or "specifically binds" an antigen is an antigen-binding moiety that binds the antigen with high affinity and does not significantly bind other unrelated antigens. Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including, but not limited to, surface plasmon resonance (SPR) technology (e.g., BIACORE®) or biolayer interferometry (e.g., FORTEBIO®).

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at bioinf.org.uk/abs/abnum/, and described in Abhinandan and Martin, *Immunology*, 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

As used herein, the term "single chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')₂" fragments contain two Fab' fragments joined, near the hinge region, by disulfide bonds. F(ab')₂ fragments may be generated, for example, by recombinant or synthetic methods or by pepsin digestion of an intact antibody. The F(ab') fragments can be dissociated, for example, by treatment with β-mercaptoethanol.

"Fv" fragments comprise a non-covalently-linked dimer of one heavy chain variable domain and one light chain variable domain.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (20"7).

"Properties, production, and applications of camelid single-domain antibody frag" ents". Appl. Microbiol Biotechnol. 77 (1): 13-22).

It must be noted that, as used in the specification and the appended claims, the singular forms "a," "an" and "the" include plural referents unless the context clearly dictates otherwise.

Synthetic Pathway Activators

In various aspects, systems disclosed herein employ one or more "synthetic pathway activator" (SPA) peptides. CAR-expressing immune cells can be limited by the necessity for in vivo expansion following infusion. To achieve robust expansion, T cells use three signals: antigen-stimulation, co-stimulation, and cytokine-induced stimulation. Activation of CARs is sufficient to induce the first two signals, but cannot recapitulate cytokine signaling. Furthermore, the tumor microenvironment is often immunosuppressive and devoid of pro-inflammatory cytokines. SPA peptides can thus be used to stimulate robust in vivo expansion and enhance desirable properties (i.e., increased survival, persistence, and potency) of T cells, e.g., expressing priming receptors and/or CARs as described herein.

In one aspect, provided herein are synthetic pathway activator (SPA) peptides comprising a chimeric polypeptide comprising: a lipid anchor or a transmembrane domain; an intracellular signaling domain; and a multimerization region. In another aspect, provided herein are synthetic pathway activator (SPA) peptides comprising a chimeric polypeptide comprising: an extracellular domain, a lipid anchor or a transmembrane domain; an intracellular signaling domain; and a multimerization region. In some embodiments, a SPA peptide further comprises a CD8-alpha hinge domain. In some embodiments, the SPA peptide is constitutively expressed in a cell. In some embodiments, expression of the SPA peptide in a cell is induced, e.g., by T cell activation. For example, an inducible SPA can be expressed after engagement of a CAR T cell with the CAR cognate ligand on a target cell. In some embodiments, expression of the SPA peptide in a cell is induced by the priming receptor and/or CAR signaling.

SPA Structure

In various embodiments, a SPA peptide mimics activation of interleukin signaling. Interleukin receptors are cytokine receptors that signal through Signal Transducer and Activator of Transcription (STAT) transcription factors (e.g., STAT1, STAT3, and STAT5). Interleukin receptors typically function by dimerization in response to ligand binding. Once dimerized, receptors can bind janus-associated kinases (JAKs) to induce JAK cross-phosphorylation and downstream "JAK/STAT" signaling. Accordingly, induced receptor agonism or ligand-independent dimerization of receptors can be utilized t Synthetic Pathway Activators induce constitutive receptor activity and thus, constitutive cytokine signaling.

In various embodiments, SPA peptides comprise interleukin receptors or functional fragments thereof. In some embodiments, SPAs comprise or are derived from interleukin receptor intracellular signaling domains or functional fragments thereof. In some embodiments, SPA peptides comprise or are derived from interleukin-6 signal transducer (IL6ST) polypeptides or functional fragments thereof. Interleukin-6 signal transducer (IL6ST) is also known as glycoprotein 130 (gp130). A SPA can comprise multimerized SPA peptides, e.g., two SPA peptides that are dimerized, e.g., homodimerized. Multimerization encompasses dimerization, trimerization, tetramerization, or higher order combinations of SPA peptides that interact with each other.

Intracellular Signaling Domain

In some embodiments, the intracellular signaling domain induces phosphorylation of STAT1, STAT3, and/or STAT5. In some embodiments, a functional SPA induces phosphorylation of STAT1, STAT3, and/or STAT5. In some embodiments, the intracellular signaling domain comprises a type I cytokine receptor superfamily box1 (IWPNVDP (SEQ ID NO: 106)) or box2 (VSVVEIEANDKKP (SEQ ID NO: 107)) peptide motif. In some embodiments, the intracellular signaling domain comprises a tyrosine phosphorylation motif comprising YXXQ or YXPQ. In some embodiments, the intracellular signaling domain comprises one or more minimum STAT binding motif from a STAT1, STAT3 and/or STAT5 protein. In some embodiments, the intracellular signaling domain comprises one or more minimum STAT binding motif from a STAT1 and STAT3 protein. In some embodiments, the intracellular signaling domain comprises one or more minimum STAT binding motif from a STAT1 and STAT5 protein. In some embodiments, the intracellular signaling domain comprises one or more minimum STAT binding motif from a STAT3 and STAT5 protein.

In some embodiments, the intracellular signaling domain comprises a polypeptide sequence from an interleukin receptor.

In some embodiments, the interleukin receptor comprises a gp130 intracellular signaling domain. In some embodiments, the intracellular signaling domain comprises a polypeptide sequence comprising amino acids 642 to 918 of gp130 (SEQ ID NO: 59).

In some embodiments, the interleukin receptor comprises a truncated gp130 intracellular signaling domain. In some embodiments, the SPA peptides comprise truncated gp130 intracellular domains. In some embodiments, the truncated gp130 intracellular signaling domain comprises the truncated gp130 intracellular domain of a sequence selected from the group set forth in SEQ ID NOs: 10-16 and 71-77. In some embodiments, the truncated gp130 intracellular signaling domain comprises a sequence with at least about 5%, 10%, 15%, 20%, 25%, 30%, 35%, 40%, 45%, 50%, 55%, 60%, 65%, 70%, 75%, 80%, 85%, 90%, 95%, or 99% identity to the gp130 intracellular signaling domain as provide in the sequence set forth in SEQ ID NO: 60.

In some embodiments, the truncated gp130 intracellular domain comprises a GP130Δ771-811 fragment. In some embodiments, the truncated gp130 intracellular domain comprises a GP130Δ707-755 fragment. In some embodiments, the truncated gp130 intracellular domain comprises a GP130Δ818-901 fragment. In some embodiments, the truncated gp130 intracellular domain comprises one or more truncation selected from the group consisting of GP130Δ707-755, GP130Δ771-811, and GP130Δ818-901. In some embodiments, the truncated gp130 intracellular signaling domain comprises a deletion of amino acids 771 to 811 of gp130 (SEQ ID NO: 59). In some embodiments, the truncated gp130 intracellular signaling domain comprises a deletion of amino acids 707 to 755 of gp130 (SEQ ID NO: 59). In some embodiments, the truncated gp130 intracellular signaling domain comprises a deletion of amino acids 818 to 901 of gp130 (SEQ ID NO: 59). In some embodiments, the truncated gp130 intracellular signaling domain comprises one or more (e.g., one, two, or three) deletions of amino acids selected from the group consisting of amino acids 707 to 755, 771 to 811, and 818-901 of gp130 (SEQ ID NO: 59). In other embodiments, the gp130 intracellular domain comprises a Y759F mutation (resulting in a SOCS-proof mutant). In some embodiments, the gp130 intracellular signaling domain further comprises a Y759F mutation of gp130 (SEQ ID NO: 59). In other embodiments, the gp130 intracellular domain comprises a a Y759F mutation and a 4771-811 truncation (gp130Y759FΔ771-811) of gp130 (SEQ ID NO: 59). In other embodiments, the gp130 intracellular domain comprises a a Y759F mutation and a 4707-755 truncation (gp130Y759FΔ707-755) of gp130 (SEQ ID NO: 59). In other embodiments, the gp130 intracellular domain comprises a a Y759F mutation and a 4818-901 truncation (gp130Y759FΔ818-901) of gp130 (SEQ ID NO: 59).

In some embodiments, the gp130 intracellular signaling domain comprises an amino acid sequence at least 80%, at least 85%, at least 90%, at least 91%, at least 92%, at least 93%, at least 94%, at least 95%, at least 96%, at least 97%, at least 98%, or at least 99% identical to the sequence set forth in SEQ ID NO: 60. In some embodiments, the gp130 intracellular signaling domain comprises the amino acid sequence set forth in SEQ ID NO: 60.

In some embodiments, a SPA peptide can comprise a ligand agonist (e.g., a cytokine, e.g., an interleukin) that allows constitutive activation of the SPA. In some embodiments, the cytokine receptor and a soluble agonist are expressed simultaneously. In some embodiments, the cytokine receptor and a membrane-bound agonist are expressed simultaneously.

Lipid Anchors and Transmembrane Domains

In various embodiments, SPA peptides are anchored to the cellular membrane via a lipid anchor. In other embodiments, SPA peptides comprise a transmembrane domain. In various embodiments, a SPA peptide comprises a lipid anchor or a transmembrane domain comprising a gp130 transmembrane domain, a CD8-alpha transmembrane domain, a prenylation motif, or a myristoylation domain derived from src, fyn, or lck.

In some embodiments, a SPA peptide comprises a src-derived myristoylation domain, fyn-derived myristoylation domain, or lck-derived myristoylation domain. In other embodiments, a SPA peptide comprises a prenylation motif. In some embodiments, a SPA peptide comprises an extracellular domain, a transmembrane domain, and an intracellular signaling domain. In some embodiments, a SPA peptide comprises comprise a transmembrane domain of an interleukin receptor.

In some embodiments, the transmembrane domain comprises an amino acid sequence at least 80%, at least 85%, at least 90%, at least 91%, at least 92%, at least 93%, at least 94%, at least 95%, at least 96%, at least 97%, at least 98%, or at least 99% identical to the sequence set forth in SEQ ID NO: 61. In some embodiments, the transmembrane domain comprises the amino acid sequence set forth in SEQ ID NO: 61.

Multimerization Regions

In various embodiments, one or more structural alterations can be made to confer constitutive activity to a SPA or functional fragment thereof. In some embodiments, structures or mutations can be added to induce SPA multimerization (e.g, dimerization, trimerization, tetramerization, or higher order multimers). In some embodiments, one or more amino acids can be mutated to a cysteine to allow formation of one or more disulfide bond(s), e.g., between two receptor monomers. In some embodiments, one or more amino acids can be inserted into a wild-type receptor polypeptide to promote dimerization, e.g., through formation of one or more disulfide bond(s). In some embodiments, the multimerization domain comprises one or more unpaired cysteine residues. The one or more amino acids mutated to an unpaired cysteine can be in the extracellular domain, the transmembrane domain, a hinge domain, the intracellular signaling domain, or any linker used to link such domains. In some embodiments, the multimerization domain comprises one or more VASP domains. In some embodiments, the multimerization domain comprises one or more VASP tetramerization domains. In some embodiments, the multimerization domain comprises one or more leucine zippers. In some embodiments, the multimerization domain is intracellular or extracellular.

In some embodiments, an exogenous polypeptide is operatively linked to a cytokine receptor or functional fragment thereof to cause their multimerization or dimerization. In some embodiments, a leucine zipper polypeptide is operatively linked to a cytokine receptor or functional fragment thereof. In some embodiments, the leucine zipper polypeptide is a c-Jun leucine zipper. In some embodiments, an exogenous scaffold is operatively linked to a cytokine receptor or functional fragment thereof. In some embodiments, the exogenous scaffold is a CD34 ectodomain (e.g., SEQ ID NO: 242), erythropoietin receptor (EpoR) ectodomain, or thrombopoietin receptor (TpoR) ectodomain.

In some embodiments, multimerization of the chimeric polypeptide via the multimerization region results in constitutive activity of the intracellular signaling domain. In some embodiments, the SPA peptide comprises one or more multimerization region. In some embodiments, the SPA peptide comprises two or more multimerization regions. In some embodiments, the multimerization region comprises at least one of one or more unpaired cysteine residues, a leucine zipper, a BCR domain, and a VASP domain. An exemplary BCR domain is provided in SEQ ID NO: 239. An exemplary VASP domain is provided in SEQ ID NO: 240. In some embodiments, the multimerization region comprises at least one or more unpaired cysteine residues. In some embodiments, the multimerization region comprises at least one or more unpaired cysteine residue and a leucine zipper. In some embodiments, the SPA peptide comprises one or more VASP domain polypeptides to promote multimerization (e.g., SEQ ID NO: 240). In some embodiments, the VASP domain is the tetramerization domain of VASP. In some embodiments, the BCR domain comprises a coiled coil tetramerization region. In such embodiments, the BCR ectodomain can result in multimerization through non-covalent interactions.

In some embodiments, the multimerization region is intracellular when expressed by a cell. In some embodiments, the multimerization region is extracellular when expressed by a cell. For example, the SPA peptide can comprise, in an N terminus to C terminus direction, i) one or more multimerization domains—an extracellular domain—a transmembrane domain—an intracellular signaling domain, ii) an extracellular domain—one or more multimerization domains—a transmembrane domain—an intracellular signaling domain, iii) one or more multimerization domains—a transmembrane domain—an intracellular signaling domain, iv) one or more multimerization domains—a lipid anchor—an intracellular signaling domain, v) an extracellular domain—a transmembrane domain—one or more multimerization domains—an intracellular signaling domain, vi) a lipid anchor—one or more multimerization domains—an intracellular signaling domain, vii) an extracellular domain—a transmembrane domain—an intracellular signaling domain-one or more multimerization domains, or viii) a lipid anchor—an intracellular signaling domain—one or more multimerization domains, or any combination thereof.

Extracellular Domain

A SPA peptide disclosed herein can also comprise an extracellular domain. In some embodiments, the extracellular domain conveys constitutive activity to the intracellular signaling domain. In some embodiments, the extracellular domain comprises a CD34 ectodomain (e.g., a CD34 extracellular domain, SEQ ID NO: 238). In some embodiments, the extracellular domain comprises a CD34 epitope (e.g. a QBEND10 epitope, SEQ ID NO: 238). In some embodiments, the extracellular domain comprises a type I cytokine receptor extracellular domain (e.g., a thrombopoietin receptor (TpoR) ectodomain or erythropoietin receptor (EpoR) ectodomain). In some embodiments, the type I cytokine receptor extracellular domain (e.g., a thrombopoietin receptor (TpoR) ectodomain or erythropoietin receptor (EpoR) ectodomain) further comprises a type I cytokine receptor transmembrane domain (e.g., a thrombopoietin receptor (TpoR) transmembrane domain or erythropoietin receptor (EpoR) transmembrane domain). In some embodiments, the extracellular domain comprises one or more of a CD34 epitope (e.g. a QBEND10 epitope, SEQ ID NO: 238), a CD34 ectodomain (SEQ ID NO: 242), a BCR ectodomain (SEQ ID NO: 239), a thrombopoietin receptor (TpoR) domain (SEQ ID NO: 243), or an erythropoietin receptor (EpoR) ectodomain (SEQ ID NO: 241). In various embodiments, the thrombopoietin receptor (TpoR) ectodomain or erythropoietin receptor (EpoR) ectodomain further comprise one or more unpaired cysteines. In some embodiments, the BCR ectodomain comprises a coiled coil tetramerization region. In such embodiments, the BCR ectodomain can result in multimerization through non-covalent interactions.

Exemplary SPAs

In some embodiments, the SPA peptide comprises a leucine zipper-gp130 (referred to interchangeably herein as "L-gp130" or "gp130") or an L-gp130 intracellular signaling domain. L-gp130 comprises a homodimer, with each monomer comprising (a) an extracellular domain comprising an inserted cysteine residue that forms a disulfide linkage with another monomer and a c-Jun leucine zipper; and (b) an IL6ST (GP130) transmembrane domain and intracellular signaling domain. The cysteine residue and the leucine zipper on each polypeptide can induce the formation of stable homodimers that mimic constitutive IL-6R activation. Additional details on the construction of L-gp130 are described in Stuhlmann-Laeisz et al. Mol Biol Cell. 2006 July; 17 (7): 2986-95 and in WO2020200325, which are hereby incorporated by reference in their entirety. Diagrams of L-gp130 and other exemplary SPAs described herein are provided in FIG. 2B.

In some embodiments, the SPA peptide comprises, from N terminus to C terminus, an extracellular domain comprising a CD34 epitope or CD34 extracellular domain, a multimerization region comprising one or more unpaired cysteine residues, a GP130 (IL6ST) transmembrane domain, and a GP130 (IL6ST) intracellular signaling domain. In some embodiments, the SPA peptide further comprises a leader sequence at the N terminus. In some embodiments, the leader sequence is a CD8a signal sequence, a GP130 (IL6ST) signal sequence, a CD34 signal sequence, or an Erythropoietin receptor (EpoR) signal sequence. In some embodiments, the leader sequence comprises (SEQ ID NO: 108)
MALPVTALLLPLALLLHAARP, -continued

```
                                      (SEQ ID NO: 109)
MLVRRGARAGPRMPRGWTALCLLSLLPSGFM, (SEQ ID NO: 110)
MDHLGASLWPQVGSLCLLLAGAAW,
or (SEQ ID NO: 111)
MLTLQTWLVQALFIFLTTESTG.
```

In some embodiments, the SPA peptide comprises a sequence selected from the group set forth in SEQ ID NOs: 1-58 or 63-104. SPAs with a leader sequence at the N terminus are provided in SEQ ID NOs: 1-58. SPAs without a leader sequence at the N terminus are provided in SEQ ID NOs: 63-104. In some embodiments, the SPA peptide comprises a sequence as set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, or 104. In some embodiments, the SPA peptide comprises a sequence selected from the group set forth in SEQ ID NOs: 1-58 or 63-104. In some embodiments, the SPA peptide comprises a sequence with about 5%, 10%, 15%, 20%, 25%, 30%, 35%, 40%, 45%, 50%, 55%, 60%, 65%, 70%, 75%, 80%, 85%, 90%, 95%, or 99% identity to a sequence as set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, or 104. In some embodiments, the SPA peptide comprises the sequence set forth in SEQ ID NO: 20. In some embodiments, the SPA peptide comprises the sequence set forth in SEQ ID NO: 81. In some embodiments, the SPA peptide comprises a sequence with about 5%, 10%, 15%, 20%, 25%, 30%, 35%, 40%, 45%, 50%, 55%, 60%, 65%, 70%, 75%, 80%, 85%, 90%, 95%, or 99% identity to a sequence as set forth in SEQ ID NOs: 20 or 81.

Logic Gate Systems

As used herein, a "logic gate," "circuit," "circuit receptor," "system" or "system receptor" refers to a two part protein expression system comprising a priming receptor and a chimeric antigen receptor. The system can be encoded on at least one nucleic acid inserted into a cell, where the priming receptor is expressed in the cell. The intracellular domain of the priming receptor is cleaved from the trans-membrane domain upon binding of the priming receptor to its target antigen. The intracellular domain is then capable of translocating into a cell nucleus where it induces expression of the chimeric antigen receptor.

In one aspect, provided herein are systems comprising a priming receptor that binds to a target antigen and a chimeric antigen receptor that binds to a target antigen, wherein the transcription factor of the intracellular domain of the priming receptor is capable of inducing expression of the CAR and/or SPA. Such systems are alternatively termed "logic gates" or "circuits." In some aspects, the system is encoded by nucleic acid transgenes inserted into an immune cell. The system can be encoded on a single nucleic acid insert or fragment that comprises both transgenes, or can be encoded on two nucleic acids that encode the system transgenes individually. The priming receptor and CAR of the system can be placed in any order on the single nucleic acid. For example, the priming receptor can be at the 5' end and the CAR can be at the 3' end, or the CAR can be at the 5' end and the priming receptor can be at the 3' end.

A constitutive promoter can be operably linked to the nucleotide sequence encoding the priming receptor and/or SPA. An inducible promoter can also be operably linked to the nucleotide sequence encoding the CAR. In some embodiments, when the system is encoded on a single nucleic acid insert or fragment that comprises both transgenes, the nucleic acid can comprise, in a 5' to 3' direction, the constitutive promoter; the nucleotide sequence encoding priming receptor; the inducible promoter; and the nucleotide sequence encoding chimeric antigen receptor. Alternatively, the nucleic acid can comprise, in a 5' to 3' direction, the inducible promoter; the nucleotide sequence encoding chimeric antigen receptor; the constitutive promoter; the nucleotide sequence encoding priming receptor. In some embodiments, the inducible promoter comprises one or more HNF1α enhancer elements (e.g., one or more, two or more, three or more, four or more, five or more, six or more, seven or more, eight or more, nine or more, or ten or more HNF1α enhancer elements). In some embodiments, the constitutive promoter comprises an EF1α promoter.

Priming Receptors

Provided herein are priming receptors comprising an extracellular antigen-binding domain that specifically binds target antigens and one or more intracellular domains from or derived from a transcriptional regulator and/or a DNA-binding domain.

In certain aspects of the present disclosure, the priming receptor is a synthetic receptor based on the Notch protein. Binding of a natural Notch receptor to a cognate ligand, such as those from the Delta family of proteins, causes intramembrane proteolysis that cleaves an intracellular fragment of the Notch protein. This intracellular fragment is a transcriptional regulator that only functions when cleaved from Notch. Cleavage may occur by sequential proteolysis by ADAM metalloprotease and the gamma-secretase complex. This intracellular fragment enters the nucleus of a cell and activates cell-cell signaling genes. In contrast to a natural Notch protein, a synthetic notch priming receptor replaces the natural Notch intracellular fragment with one that causes a gene encoding a protein of choice, such as a CAR, to be transcribed upon release of the intracellular fragment from the priming receptor.

Notch receptors have a modular domain organization. The ectodomains of Notch receptors consist of a series of N-terminal epidermal growth factor (EGF)-like repeats that are responsible for ligand binding. In synthetic Notch receptors or priming receptors, the Notch ligand-binding domain is replaced with a ligand binding domain that binds a selected target ligand or antigen. The EGF repeats are followed by three LIN-12/Notch repeat (LNR) modules, which are unique to Notch receptors, and are widely reported to participate in preventing premature receptor activation. The heterodimerization (HD) domain of Notch1 is divided by furin cleavage, so that its N-terminal part terminates the extracellular subunit, and its C-terminal half constitutes the beginning of the transmembrane subunit. Following the extracellular region, the receptor has a transmembrane segment and an intracellular domain (ICD), which includes a transcriptional regulator.

Multiple forms of priming receptors can be used in the methods, cells, and nucleic acids as described herein. One type of priming receptor contemplated for use in the methods and cells herein comprise a heterologous extracellular ligand binding domain, a linking polypeptide having substantial sequence identity with a Notch receptor including the NRR, a TMD, and an ICD. "Fn Notch" receptors comprise a heterologous extracellular ligand binding domain, a linking polypeptide having substantial sequence identity with a Robo receptor (such as a mammalian Robo1, Robo2, Robo3, or Robo4), followed by 1, 2, or 3 fibronectin repeats ("Fn"), a TMD, and an ICD. "Mini Notch" receptors comprise a heterologous extracellular ligand binding domain, a linking polypeptide having substantial sequence identity with a Notch receptor (lacking the NRR), a TMD, and an ICD. "Minimal Linker Notch" receptors comprise a heterologous extracellular ligand binding domain, a linking polypeptide lacking substantial sequence identity with a Notch receptor (e.g., a synthetic (GGS) n polypeptide sequence), a TMD, and an ICD. "Hinge Notch" receptors comprise a heterologous extracellular ligand binding domain, a hinge sequence comprising an oligomerization domain (i.e., a domain that promotes dimerization, trimerization, or higher order multimerization with a synthetic receptor and/or an existing host receptor), a TMD, and an ICD. All of these receptor classes are synthetic, recombinant, and do not occur in nature. In some embodiments, the non-naturally occurring receptors disclosed herein bind a target cell-surface displayed ligand, which triggers proteolytic cleavage of the receptors and release of a transcriptional regulator that modulates a custom transcriptional program in the cell. In some embodiments, the priming receptor does not include a LIN-12-Notch repeat (LNR) and/or a heterodimerization domain (HD) of a Notch receptor.

Priming Receptor Extracellular Domain

In some embodiments, the extracellular domain includes the ligand-binding portion of a receptor. In some embodiments, the extracellular domain includes an antigen-binding moiety that binds to one or more target antigens. In some embodiments, the antigen-binding moiety includes one or more antigen-binding determinants of an antibody or a functional antigen-binding fragment thereof. In some embodiments, the antigen-binding moiety is selected from the group consisting of an antibody, a nanobody, a diabody, a triabody, or a minibody, a F(ab')2 fragment, a Fab fragment, a single chain variable fragment (scFv), and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

In various embodiments, a priming receptor comprises means for binding a target protein, optionally binding a human target protein. In some embodiments, the means binds a target protein. In some embodiments, the means binds a human target protein. In some embodiments, the means is an antibody or antigen-binding fragment or equivalent thereof (e.g., a full length antibody or a F(ab')2 fragment, a Fab fragment, a single chain variable fragment (scFv), and a single domain antibody (sdAb), or a functional fragment thereof).

Transmembrane Domain

In some embodiments, the priming receptor comprises a hinge domain. In some embodiments, the hinge domain is a CD8 hinge.

As described above, the priming receptor comprises a transmembrane domain (TMD) comprising one or more ligand-inducible proteolytic cleavage sites.

In some embodiments, the TMD comprises a Notch1 transmembrane domain.

Generally, the TMD suitable for the chimeric receptors disclosed herein can be any transmembrane domain of a Type 1 transmembrane receptor including at least one gamma-secretase cleavage site. Detailed description of the structure and function of the gamma-secretase complex as well as its substrate proteins, including amyloid precursor protein (APP) and Notch, can, for example, be found in a recent review by Zhang et al, Frontiers Cell Neurosci (2014). Non limiting suitable TMDs from Type 1 transmembrane receptors include those from CLSTN1, CLSTN2, APLP1, APLP2, LRP8, APP, BTC, TGBR3, SPN, CD44, CSF1R, CXCL16, CX3CL1, DCC, DLL1, DSG2, DAG1, CDH1, EPCAM, EPHA4, EPHB2, EFNB1, EFNB2, ErbB4, GHR, HLA-A, and IFNAR2, wherein the TMD includes at least one gamma secretase cleavage site. Additional TMDs suitable for the compositions and methods described herein include, but are not limited to, transmembrane domains from Type 1 transmembrane receptors ILIR1, ILIR2, IL6R, INSR, ERN1, ERN2, JAG2, KCNE1, KCNE2, KCNE3, KCNE4, KL, CHL1, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, YASN, FLT1, CDH5, PKHD1, NECTIN1, PCDHGC3, NRG1, LRP1B, CDH2, NRG2, PTPRK, SCN2B, Nradd, and PTPRM. In some embodiments, the TMD of the chimeric polypeptides or Notch receptors of the disclosure is a TMD derived from the TMD of a member of the calsyntenin family, such as, alcadein alpha and alcadein gamma. In some embodiments, the TMD of the chimeric polypeptides or Notch receptors of the disclosure is a TMD known for Notch receptors. In some embodiments, the TMD of the chimeric polypeptides or Notch receptors of the disclosure is a TMD derived from a different Notch receptor. For example, in a Mini Notch based on human Notch1, the Notch1 TMD can be substituted with a Notch2 TMD, Notch3 TMD, Notch4 TMD, or a Notch TMD from a non-human animal such as *Danio rerio, Drosophila melanogaster, Xenopus lacvis*, or *Gallus gallus*.

In some embodiments, the priming receptor comprises a Notch cleavage site, such as S2 or S3. Additional proteolytic cleavage sites suitable for the compositions and methods disclosed herein include, but are not limited to, ADAM10, a metalloproteinase cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). Another example of a suitable protease cleavage site is a plasminogen activator cleavage site, e.g., a urokinase plasminogen activator (uPA) or a tissue plasminogen activator (tPA) cleavage site. Another example of a suitable protease cleavage site is a prolactin cleavage site. Specific examples of cleavage sequences of uPA and tPA include sequences comprising Yal-Gly-Arg. Another example of a protease cleavage site that can be included in a proteolytically cleavable linker is a tobacco etch vims (TEV) protease cleavage site, e.g., Glu-Asn-Leu-Tyr-Thr-Gln-Ser (SEQ ID NO: 112), where the protease cleaves between the glutamine and the serine. Another example of a protease cleavage site that can be included in a proteolytically cleavable linker is an enterokinase cleavage site, e.g., Asp-Asp-Asp-Asp-Lys (SEQ ID NO: 113), where cleavage occurs after the lysine residue. Another example of a protease cleavage site that can be included in a proteolytically cleavable linker is a thrombin cleavage site, e.g., Leu-Val-Pro-Arg (SEQ ID NO: 114). Additional suitable linkers comprising protease cleavage sites include sequences cleavable by the following proteases: a PreScission™ protease (a fusion protein comprising human rhinovirus 3C protease and glutathione-S-transferase), a thrombin, cathepsin B, Epstein-Barr vims proteas, MMP-3 (stromelysin), MMP-7 (matrilysin), MMP-9; thermolysin-like MMP, matrix metalloproteinase 2 (MMP-2), cathepsin L; cathepsin D, matrix metalloproteinase 1 (MMP-1), urokinase-type plasminogen activator, membrane type 1 matrixmetalloprotemase (MT-MMP), stromelysin 3 (or MMP-11), thermo lysin, fibroblast collagenase and stromelysin-1, matrix metalloproteinase 13 (collagenase-3), tissue-type plasminogen activator (tPA), human prostate-specific antigen, kallikrein (hK3), neutrophil elastase, and calpain (calcium activated neutral protease). Proteases that are not native to the host cell in which the receptor is expressed (for example, TEV) can be used as a further regulatory mechanism, in which activation of the receptor is reduced until the protease is expressed or otherwise provided. Additionally, a protease may be tumor-associated or disease-associated (expressed to a significantly higher degree than in normal tissue), and serve as an independent regulatory mechanism. For example, some matrix metalloproteases are highly expressed in certain cancer types.

In some embodiments, the amino acid substitution(s) within the TMD includes one or more substitutions within a "GV" motif of the TMD. In some embodiments, at least one of such substitution(s) comprises a substitution to alanine. Additional sequences and substitutions are described in WO2021061872, hereby incorporated by reference in its entirety.

Intracellular Domain

In some embodiments, the priming receptor comprises one or more intracellular domains from or derived from a transcriptional regulator and/or a DNA-binding domain. In some embodiments, the intracellular domain comprises means for modulating transcription of one or more genes. In some embodiments, the means for modulating transcription of one or more genes comprises a transcriptional regulator, e.g., a transcriptional regulator provided herein or an equivalent thereof. In some embodiments, the priming receptor comprises one or more intracellular domains from or derived from a transcriptional regulator and/or a DNA-binding domain. In some embodiments, the intracellular domain comprises an HNF1α/p65 domain or a Gal4/VP64 domain.

Transcriptional regulators either activate or repress transcription from cognate promoters. Transcriptional activators typically bind nearby to transcriptional promoters and recruit RNA polymerase to directly initiate transcription. Transcriptional repressors bind to transcriptional promoters and sterically hinder transcriptional initiation by RNA polymerase. Other transcriptional regulators serve as either an activator or a repressor depending on where it binds and cellular conditions. Accordingly, as used herein, a "transcriptional activation domain" refers to the domain of a transcription factor that interacts with transcriptional control elements and/or transcriptional regulatory proteins (i.e., transcription factors, RNA polymerases, etc.) to increase and/or activate transcription of one or more genes. Non-limiting examples of transcriptional activation domains include: a herpes simplex virus VP16 activation domain, VP64 (which is a tetrameric derivative of VP16), HIV TAT, a NFkB p65 activation domain, p53 activation domains 1 and 2, a CREB (CAMP response element binding protein) activation domain, an E2A activation domain, NFAT (nuclear factor of activated T-cells) activation domain, yeast Gal4, yeast GCN4, yeast HAP1, MLL, RTG3, GLN3, OAF1, PIP2, PDR1, PDR3, PHO4, LEU3 glucocorticoid receptor transcription activation domain, B-cell POU homeodomain protein Oct2, plant Ap2, or any others known to one or ordinary skill in the art. In some embodiments, the transcriptional regulator is selected from Gal4-VP16, Gal4-VP64, tetR-VP64, ZFHD1-YP64, Gal4-KRAB, and HAP1-VP16. In some embodiments, the transcriptional regulator is Gal4-VP64. A transcriptional activation domain can comprise a wild-type or naturally occurring sequence, or it can be a modified, mutant, or derivative version of the original transcriptional activation domain that has the desired ability to increase and/or activate transcription of one or more genes. In some embodiments, the transcriptional regulator can further include a nuclear localization signal.

In some embodiments, the priming receptor comprises one or more intracellular "DNA-binding domains" (or "DB domains"). Such "DNA-binding domains" refer to sequence-specific DNA binding domains that bind a particular DNA sequence element. Accordingly, as used herein, a "sequence-specific DNA-binding domain" refers to a protein domain portion that has the ability to selectively bind DNA having a specific, predetermined sequence. A sequence-specific DNA binding domain can comprise a wild-type or naturally occurring sequence, or it can be a modified, mutant, or derivative version of the original domain that has the desired ability to bind to a desired sequence. In some embodiments, the sequence-specific DNA binding domain is engineered to bind a desired sequence. Non-limiting examples of proteins having sequence-specific DNA binding domains that can be used in synthetic proteins described herein include HNF1a, Gal4, GCN4, reverse tetracycline receptor, THY1, SYN1, NSE/RU5', AGRP, CALB2, CAMK2A, CCK, CHAT, DLX6A, EMX1, zinc finger proteins or domains thereof, CRISPR/Cas proteins, such as Cas9, Cas3, Cas4, Cas5, Cas5e (or CasD), Cash, Cas6e, Cas6f, Cas7, Cas8a1, Cas8a2, Cas8b, Cas8c, Cas10, Cas10d, CasF, CasG, CasH, Csy1, Csy2, Csy3, Cse1 (or CasA), Csc2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu196, and TALES.

In those embodiments where a CRISPR/Cas-like protein is used, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the functions of the systems described herein. For example, a CRISPR enzyme that is used as a DNA binding protein or domain thereof can be mutated with respect to a corresponding wild-type enzyme such that the mutated CRISPR or domain thereof lacks the ability to cleave a nucleic acid sequence containing a DNA binding domain target site. For example, a D10A mutation can be combined with one or more of H840A, N854A, or N863A mutations to produce a Cas9 enzyme substantially lacking all DNA cleavage activity.

Juxtamembrane Domain

The ECD and the TMD, or the TMD and the ICD, can be linked to each other with a linking polypeptide, such as a juxtamembrane domain. "SynNotch" or synthetic notch receptors comprise a heterologous extracellular ligand-binding domain, a linking polypeptide having substantial sequence identity with a Notch receptor JMD (including the NRR), a TMD, and an ICD. "Fn Notch" receptors comprise a heterologous extracellular ligand binding domain, a linking polypeptide having substantial sequence identity with a Robo receptor (such as a mammalian Robo1, Robo2, Robo3, or Robo4), followed by 1, 2, or 3 fibronectin repeats ("Fn"), a TMD, and an ICD. "Mini Notch" receptors comprise a heterologous extracellular ligand binding domain, a linking polypeptide having substantial sequence identity with a Notch receptor JMD but lacking the NRR (the LIN-12-Notch repeat (LNR) modules, and the heterodimerization domain), a TMD, and an ICD. "Minimal Linker Notch" receptors comprise a heterologous extracellular ligand-binding domain, a linking polypeptide lacking substantial sequence identity with a Notch receptor (for example, without limitation, having a synthetic (GGS) n polypeptide sequence), a TMD, and an ICD. "Hinge Notch" receptors comprise a heterologous extracellular ligand-binding domain, a hinge sequence comprising an oligomerization domain (i.e., a domain that promotes dimerization, trimerization, or higher order multimerization with a synthetic receptor and/or an existing host receptor), a TMD, and an ICD.

In some embodiments, the priming receptor comprises a juxtamembrane domain (JMD) peptide in between the extracellular domain and the transmembrane domain. In some embodiments, the priming receptor comprises a juxtamembrane domain (JMD) peptide in between the transmembrane domain and the intracellular domain. In some embodiments, the JMD peptide comprises an LWF motif. The use of LWF motifs in receptor constructs is described in U.S. Pat. No. 10,858,443, hereby incorporated by reference in its entirety. In some embodiments, the JMD peptide has substantial sequence identity to the JMD of Notch1, Notch2, Notch3, and/or Notch4. In some embodiments, the JMD peptide has substantial sequence identity to the Notch1, Notch2, Notch3, and/or Notch4 JMD, but does not include a LIN-12-Notch repeat (LNR) and/or a heterodimerization domain (HD) of a Notch receptor. In some embodiments, the JMD peptide does not have substantial sequence identity to the Notch1, Notch2, Notch3, and/or Notch4 JMD. In some embodiments, the JMD peptide includes an oligimerization domain which promotes formation of dimers, trimers, or higher order assemblages of the receptor. Such JMD peptides are described in WO2021061872, hereby incorporated by reference in its entirety.

In the Mini Notch receptor, the linking polypeptide is derived from a Notch JMD sequence after deletion of the NRR and HD domain. The Notch JMD sequence may be the sequence from Notch1, Notch2, Notch3, or Notch4, and can be derived from a non-human homolog, such as those from *Drosophila, Gallus, Danio*, and the like. Four to 50 amino acid residues of the remaining Notch sequence can be used as a polypeptide linker. In some embodiments, the length and amino acid composition of the linker polypeptide sequence are varied to alter the orientation and/or proximity of the ECD and the TMD relative to one another to achieve a desired activity of the chimeric polypeptide, such as the signal transduction level when ligand induced or in the absence of ligand.

In the Minimal Linker Notch receptor, the linking polypeptide does not have substantial sequence identity to a Notch JMD sequence, including the Notch JMD sequence from Notch1, Notch2, Notch3, or Notch4, or a non-human homolog thereof. Four to 50 amino acid residues can be used as a polypeptide linker. In some embodiments, the length and amino acid composition of the linker polypeptide sequence are varied to alter the orientation and/or proximity of the ECD and the TMD relative to one another to achieve a desired activity of the chimeric polypeptide of the disclosure. The Minimal Linker sequence can be designed to include or omit a protease cleavage site, and can include or omit a glycosylation site or sites for other types of post-translational modification. In some embodiments, the Minimal Linker does not comprise a protease cleavage site or a glysosylation site.

In some embodiments, the priming receptor further comprises a hinge. Hinge linkers that can be used in the priming receptor can include an oligomerization domain (e.g., a hinge domain) containing one or more polypeptide motifs that promote oligomer formation of the chimeric polypeptides via intermolecular disulfide bonding. In these instances, within the chimeric receptors disclosed herein, the hinge domain generally includes a flexible polypeptide connector region disposed between the ECD and the TMD. Thus, the hinge domain provides flexibility between the ECD and TMD and also provides sites for intermolecular disulfide bonding between two or more chimeric polypeptide monomers to form an oligomeric complex. In some embodiments, the hinge domain includes motifs that promote dimer formation of the chimeric polypeptides disclosed herein. In some embodiments, the hinge domain includes motifs that promote trimer formation of the chimeric polypeptides disclosed herein (e.g., a hinge domain derived from OX40). Hinge polypeptide sequences suitable for the compositions and methods of the disclosure can be naturally-occurring hinge polypeptide sequences (e.g., those from naturally-occurring immunoglobulins) or can be engineered, designed, or modified so as to provide desired and/or improved properties, e.g., modulating transcription. Suitable hinge polypeptide sequences include, but are not limited to, those derived from IgA, IgD, and IgG subclasses, such as IgG1 hinge domain, IgG2 hinge domain, IgG3 hinge domain, and IgG4 hinge domain, or a functional variant thereof. In some embodiments, the hinge polypeptide sequence contains one or more CXXC motifs. In some embodiments, the hinge polypeptide sequence contains one or more CPPC motifs (SEQ ID NO: 115).

Hinge polypeptide sequences can also be derived from a CD8a hinge domain, a CD28 hinge domain, a CD152 hinge domain, a PD-1 hinge domain, a CTLA4 hinge domain, an OX40 hinge domain, and functional variants thereof. In some embodiments, the hinge domain includes a hinge polypeptide sequence derived from a CD8 α hinge domain or a functional variant thereof. In some embodiments, the hinge domain includes a hinge polypeptide sequence derived from a CD28 hinge domain or a functional variant thereof. In some embodiments, the hinge domain includes a hinge polypeptide sequence derived from an OX40 hinge domain or a functional variant thereof. In some embodiments, the hinge domain includes a hinge polypeptide sequence derived from an IgG4 hinge domain or a functional variant thereof.

The Fn Notch linking polypeptide is derived from the Robo1 JMD, which contains a fibronectin repeat (Fn) domain, with a short polypeptide sequence between the Fn repeats and the TMD. The Fn Notch linking polypeptide does not contain a Notch negative regulatory region (NRR), or the Notch HD domain. The Fn linking polypeptide can contain 1, 2, 3, 4, or 5 Fn repeats. In some embodiments, the chimeric receptor comprises a Fn linking polypeptide having about 1 to about 5 Fn repeats, about 1 to about 3 Fn repeats, or about 2 to about 3 Fn repeats. The short polypeptide sequence between the Fn repeats and the TMD can be from about 2 to about 30 amino acid residues. In some embodiments, the short polypeptide sequence can be between about 5 and about 20 amino acids, of any sequence. In some embodiments, the short polypeptide sequence can be between about 5 and about 20 naturally-occurring amino acids, of any sequence. In some embodiments, the short polypeptide sequence can be between about 5 and about 20 amino acids, of any sequence but having no more than one proline. In some embodiments, the short polypeptide sequence can be between about 5 and about 20 amino acids, and about 50% or more of the amino acids are glycine. In some embodiments, the short polypeptide sequence can be between about 5 and about 20 amino acids, where the amino acids are selected from glycine, serine, threonine, and alanine. In some embodiments, the length and amino acid composition of the Fn linking polypeptide sequence can be varied to alter the orientation and/or proximity of the ECD and the TMD relative to one another to achieve a desired activity of the chimeric polypeptide of the disclosure.

Stop-Transfer Sequence

In some embodiments, the priming receptor further comprises a stop-transfer sequence (STS) in between the transmembrane domain and the intracellular domains. The STS comprises a charged, lipophobic sequence. Without being bound by any theory, the STS serves as a membrane anchor, and is believed to prevent passage of the intracellular domain into the plasma membrane. The use of STS domains in priming receptors is described in WO2021061872, hereby incorporated by reference in its entirety. Non-limiting exemplary STS sequences include APLP1, APLP2, APP, TGBR3, CSF1R, CXCL16, CX3CL1, DAG1, DCC, DNER, DSG2, CDH1, GHR, HLA-A, IFNAR2, IGF1R, ILIR1, ERN2, KCNE1, KCNE2, CHL1, LRP1, LRP2, LRP18, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, VASN, FLT1, CDH5, PKTFD1, NEC-TIN1, KL, IL6R, EFNB1, CD44, CLSTN1, LRP8, PCDHGC3, NRG1, LRP1B, JAG2, EFNB2, DLL1, CLSTN2, EPCAM, ErbB4, KCNE3, CDH2, NRG2, PTPRK, BTC, EPHA4, ILIR2, KCNE4, SCN2B, Nradd, PTPRM, Notch1, Notch2, Notch3, and Notch4 STS sequences. In some embodiments, the STS is heterologous to the transmembrane domain. In some embodiments, the STS is homologous to the transmembrane domain. STS sequences are described in WO2021061872, hereby incorporated by reference in its entirety.

Chimeric Antigen Receptors

In another aspect, provided herein are chimeric antigen receptors comprising an extracellular antigen-binding domain that specifically binds to a target antigen or ligand.

In some embodiments, the chimeric antigen receptor includes an extracellular portion comprising an antigen binding domain. The antigen recognition domain of a receptor such as a CAR can be linked to one or more intracellular signaling components, such as signaling components that mimic activation through an antigen receptor complex, such as a TCR complex, in the case of a CAR, and/or signal via another cell surface receptor. Thus, in some embodiments, the extracellular binding component (e.g., ligand-binding or antigen-binding domain) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

In some aspects, the chimeric antigen receptor includes an extracellular portion comprising an antigen binding domain described herein and an intracellular signaling domain. In some embodiments, an antibody or fragment includes an scFv, a VH, or a single-domain VH antibody and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain.

In some aspects, the transmembrane domain contains a transmembrane portion of CD8a or CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

Chimeric Antigen Receptor Extracellular Domain

In some embodiments, the extracellular domain includes the ligand-binding portion of a receptor. In some embodiments, the extracellular domain includes an antigen-binding moiety that binds to one or more target antigens. In some embodiments, the antigen-binding moiety includes one or more antigen-binding determinants of an antibody or a functional antigen-binding fragment thereof. In some embodiments, the antigen-binding moiety is selected from the group consisting of an antibody, a nanobody, a diabody, a triabody, or a minibody, a F(ab')₂ fragment, a Fab fragment, a single chain variable fragment (scFv), and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

In various embodiments, a CAR comprises means for binding a target protein. In some embodiments, the means binds a target protein. In some embodiments, the means binds a human target protein. In some embodiments, the means is an antibody or antigen-binding fragment or equivalent thereof (e.g., a full length antibody or a F(ab') 2 fragment, a Fab fragment, a single chain variable fragment (scFv), and a single domain antibody (sdAb), or a functional fragment thereof) means for binding a target protein.

CAR Transmembrane Domain

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, and/or CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

In some embodiments, the transmembrane domain of the receptor, e.g., the CAR, is a transmembrane domain of human CD28 or variant thereof, e.g., a 27-amino acid transmembrane domain of a human CD28 (Accession No.: P10747.1).

In some embodiments, the CAR comprises a CD8a or CD28 TMD.

CAR Hinge

In some embodiments, the CAR further includes a spacer, which may be or include at least a portion of an immunoglobulin constant region or variant or modified version thereof, such as a hinge region, e.g., a CD8a hinge, an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include CD8a hinge, IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687. In some embodiments, the CAR hinge comprises a CD8a CD8a, truncated CD8a, or CD28 hinge domain.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the receptor.

CAR Intracellular Domain

In some embodiments, upon ligation of the CAR, the cytoplasmic domain or intracellular signaling domain of the receptor activates at least one of the normal effector functions or responses of the immune cell, e.g., T cell engineered to express the receptor. In some embodiments, the CAR comprises means for activating at least one of the normal effector functions or responses of the immune cell, e.g., T cell engineered to express the receptor. For example, in some contexts, the receptor induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability. In some embodiments, the means for at least one of the normal effector functions or responses of the immune cell comprises an CAR intracellular activation domain, e.g., an intracellular activation domain provided herein or an equivalent thereof. In some embodiments, the means for at least one of the normal effector functions or responses of the immune cell comprises an CAR intracellular activation domain and a CAR co-stimulatory domain, e.g., a co-stimulatory domain provided herein or an equivalent thereof.

In some aspects, the receptor includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta. In some embodiments, the intracellular activation domain comprises a CD33 domain.

In some embodiments, the intracellular signaling domain comprises a human CD3 zeta stimulatory signaling domain or functional variant thereof, such as a 112 AA cytoplasmic domain of isoform 3 of human CD3.zeta. (Accession No.: P20963.2) or a CD3 zeta signaling domain as described in U.S. Pat. No. 7,446,190 or U.S. Pat. No. 8,911,993.

The receptor, e.g., the CAR, can include at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the extracellular domain is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor-gamma, CD8, CD4, CD25, or CD16. For example, in some aspects, the CAR includes a chimeric molecule between CD3-zeta or Fc receptor-gamma and CD8, CD4, CD25 or CD16.

In some embodiments, the intracellular domain comprises an intracellular costimulatory signaling domain of 41BB or functional variant or portion thereof, such as a 42-amino acid cytoplasmic domain of a human 4-1BB (Accession No. Q07011.1) or functional variant or portion thereof.

In some embodiments, the receptor encompasses one or more, e.g., two or more, costimulatory domains and an activation domain, e.g., primary activation domain, in the cytoplasmic portion. Exemplary receptors include intracellular components of CD3-zeta, CD28, and 4-1BB. In some embodiments, the chimeric antigen receptor contains an intracellular domain of a T cell costimulatory molecule. In some aspects, the T cell costimulatory molecule is 4-1BB.

In some embodiments, the receptor includes a signaling domain and/or transmembrane portion of a costimulatory receptor, such as CD28, 4-1BB, OX40, DAP10, and ICOS. In some aspects, the same receptor includes both the activating and costimulatory components.

In certain embodiments, the intracellular signaling domain comprises a CD8a transmembrane and signaling domain linked to a CD3 (e.g., CD3-zeta) intracellular domain. In some embodiments, the intracellular signaling domain comprises a 4-1BB (CD137, TNFRSF9) co-stimulatory domains, linked to a CD3 zeta intracellular domain. In some embodiments, the CAR comprises a 4-1BB co-stimulatory domain.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a nerve growth factor receptor (NGFR), or epidermal growth factor receptor (e.g., tEGFR). In some embodiments, the nucleic acid encoding the marker is operably linked to a polynucleotide encoding for a linker sequence, such as a cleavable linker sequence or a ribosomal skip sequence, e.g., T2A. See WO2014031687. In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published patent application No. WO2014031687. For example, the marker can be a truncated EGFR (tEGFR) that is, optionally, linked to a linker sequence, such as a T2A ribosomal skip sequence.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

The CAR may comprise one or modified synthetic amino acids in place of one or more naturally-occurring amino acids. Exemplary modified amino acids include, but are not limited to, aminocyclohexane carboxylic acid, norleucine, α-amino n-decanoic acid, homoserine, S-acetylaminomethylcysteine, trans-3- and trans-4-hydroxyproline, 4-aminophenylalanine, 4-nitrophenylalanine, 4-chlorophenylalanine, 4-carboxyphenylalanine, (3-phenylserine (3-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbomane)-carboxylic acid, α,γ-diaminobutyric acid, α,γ-diaminopropionic acid, homophenylalanine, and α-tertbutylglycine.

For example, in some embodiments, the CAR includes an antibody or fragment thereof, including single chain antibodies (sdAbs, e.g. containing only the VH region), VH domains, and scFvs, described herein, a spacer such as a CD8a hinge, a CD8a transmembrane domain, a 4-1BB intracellular signaling domain, and a CD3 zeta signaling domain. In some embodiments, the CAR includes an antibody or fragment, including sdAbs and scFvs described herein, a spacer such as a CD8a hinge, a CD8a transmembrane domain, a 4-1BB intracellular signaling domain, and a CD3 zeta signaling domain.

Transgenes expressing the priming receptor and CAR system may be introduced into cells, such as a T cell, using, for example, a site-specific technique. With site specific integration of the transgenes (e.g. priming receptor and CAR), the transgenes may be targeted to a safe harbor locus or TRAC. Examples of site-specific techniques for integration into the safe harbor loci include, without limitation, homology-dependent engineering using nucleases and homology independent targeted insertion using Cas9.

The engineered cells have applications to immune-oncology. The priming receptor and CAR, for example, can be selected to target different specific tumor antigens. Examples of cancers that can be effectively targeted using such cells are blood cancers or solid cancers. In some embodiments, immune cell therapy can be used to treat solid tumors.

Nucleic Acids and Vectors

In another aspect, provided herein are one or more nucleic acids, wherein the one or more nucleic acids encode a synthetic pathway activator described herein. In another aspect, provided herein are one or more nucleic acids, wherein the one or more nucleic acids encode a sequence selected from the group consisting of SEQ ID NOS: 1-58 or 63-104.

In some embodiments, the one or more nucleic acid(s) further comprises a 5' homology directed repair arm and/or a 3' homology directed repair arm complementary to an insertion site in a host cell chromosome. In some embodiments, the one or more nucleic acid(s) comprises the 5' homology directed repair arm and the 3' homology directed repair arm. In some embodiments, the one or more nucleic acid(s) is incorporated into an expression cassette or an expression vector. In some embodiments, the expression cassette or the expression vector further comprises a constitutive promoter upstream of the one or more nucleic acid(s).

In some embodiments, the priming receptor, CAR, and synthetic pathway activator are incorporated into a single expression cassette or a single expression vector. In some embodiments, the priming receptor, CAR, and synthetic pathway activator are incorporated into two or more expression cassettes or expression vectors. In some embodiments, the expression vector(s) is a non-viral vector.

In some embodiments, the present disclosure contemplates nucleic acid DNA template inserts that comprise one or more transgenes encoding the synthetic pathway activators as described herein. In some embodiments, the DNA template insert encodes a synthetic pathway activator. In some embodiments, the nucleic acid DNA template further comprises a priming receptors and/or CAR. In some embodiments, the DNA template insert encodes a priming receptor transgene. In some embodiments, the DNA template insert encodes a chimeric antigen receptor transgene.

In some embodiments, the DNA template insert comprises a synthetic pathway activator, a priming receptor transgene, and a chimeric antigen receptor transgene.

In some embodiments, the one or more nucleic acid(s) are encoded on a single DNA template insert. In some embodiments, the one or more nucleic acid(s) are encoded on multiple DNA template inserts. For example, the one or more nucleic acid(s) can be encoded on two, three, or four DNA template inserts.

The DNA template insert can also comprise a self-cleaving peptide. Examples of self-cleaving peptides include, but are not limited to, self-cleaving viral 2A peptides, for example, a porcine teschovirus-1 (P2A) peptide, a Thosea asigna virus (T2A) peptide, an equine rhinitis A virus (E2A) peptide, or a foot-and-mouth disease virus (F2A) peptide. Self-cleaving 2A peptides allow expression of multiple gene products from a single construct. (See, for example, Chang et al. "Cleavage efficient 2A peptides for high level monoclonal antibody expression in CHO cells," *MAbs* 7 (2): 403-412 (2015)).

The DNA template insert can also comprise a WPRE element. WPRE elements are generally described in Higashimoto, T., et al. Gene Ther 14, 1298-1304 (2007); and Zufferey, R., et al. J Virol. 1999 April; 73 (4): 2886-92, both of which are hereby incorporated by reference.

The DNA template insert can also comprise an SV40 polyA tail.

Cells

Also provided herein are cells or immune cells comprising at least one DNA template non-virally inserted into a target region of the genome of the cell, wherein DNA template encodes one or more of the synthetic pathway activators as described herein. In some embodiments, the DNA template further encodes a priming receptor and CAR system as described herein.

A cell comprising a DNA template insert at a target locus or safe harbor site as described in the present disclosure can be referred to as an engineered cell. In some embodiments, the cell or immune cell is any cell that can give rise to a pluripotent immune cell. In some embodiments, the immune cell is a primary immune cell. In some embodiments, the immune cell can be an induced pluripotent stem cell (iPSC) or a human pluripotent stem cell (HSPC). In some embodiments, the immune cell comprises primary hematopoietic cells or primary hematopoietic stem cells. In some embodiments, that engineered cell is a stem cell, a human cell, a primary cell, an hematopoietic cell, an adaptive immune cell, an innate immune cell, a natural killer (NK) cell, a T cell, a CD8+ cell, a CD4+ cell, or a T cell progenitor cell. In some embodiments, the immune cells are T cells. In some embodiments, the T cells are regulatory T cells, effector T cells, or naïve T cells. In some embodiments, the T cells are CD8$^+$ T cells. In some embodiments, the T cells are CD4$^+$ T cells. In some embodiments, the T cells are CD4$^+$CD8$^+$ T cells.

In some embodiments, the engineered cell is a stem cell, a human cell, a primary cell, an hematopoietic cell, an hematopoietic stem cell, an adaptive immune cell, an innate immune cell, a T cell or a T cell progenitor. Non-limiting examples of immune cells that are contemplated in the present disclosure include T cell, B cell, natural killer (NK) cell, NKT/INKT cell, macrophage, myeloid cell, and dendritic cells. Non-limiting examples of stem cells that are contemplated in the present disclosure include pluripotent stem cells (PSCs), embryonic stem cells (ESCs), induced pluripotent stem cells (iPSCs), embryo-derived embryonic stem cells obtained by nuclear transfer (ntES; nuclear transfer ES), male germline stem cells (GS cells), embryonic germ cells (EG cells), hematopoietic stem/progenitor stem cells (HSPCs), somatic stem cells (adult stem cells), hemangioblasts, neural stem cells, mesenchymal stem cells and stem cells of other cells (including osteocyte, chondrocyte, myocyte, cardiac myocyte, neuron, tendon cell, adipocyte, pancreocyte, hepatocyte, nephrocyte and follicle cells and so on). In some embodiments, the engineered cells is a T cell, NK cells, iPSC, and HSPC. In some embodiments, the engineered cells used in the present disclosure are human cell lines grown in vitro (e.g. deliberately immortalized cell lines, cancer cell lines, etc.).

Also provided herein are populations of cells comprising a plurality of the cells or immune cell. In some embodiments, the genome of at least 20%, 30%, 40%, 50%, 60%, 70%, 80%, 90%, 95%, 99% or greater of the cells comprises the priming receptor and CAR system as described herein.

Method of Treating Immune-Related Condition of Disease

In another aspect, the disclosure provides methods of treating an immune-related condition (e.g., cancer) in an individual comprising administering to the individual an effective amount of a composition comprising a synthetic pathway activator described herein, such as a cell comprising a synthetic pathway activator described herein. In some embodiments, the composition further comprises a priming receptor that specifically binds to a target antigen and a chimeric antigen receptor that specifically binds to a target antigen. In another aspect, the disclosure provides methods of enhancing an immune response in an individual comprising administering to the individual an effective amount of a composition comprising a synthetic pathway activator described herein, such as such as a cell comprising a synthetic pathway activator described herein. In some embodiments, the composition further comprises a priming receptor that specifically binds to a target antigen and a chimeric antigen receptor that specifically binds to a target antigen.

In some embodiments, the methods provided herein are useful for the treatment of an immune-related condition in an individual. In one embodiment, the individual is a human.

In some embodiments, the methods provided herein (such as methods of enhancing an immune response) are useful for the treatment of cancer and as such an individual receiving the synthetic pathway activator described herein has cancer. In some embodiments, the cancer is a solid cancer. In some embodiments, the cancer is immunoevasive. In some embodiments, the cancer is immunoresponsive. In some embodiments, the cancer is immunoresponsive. In particular embodiments, the cancer is kidney cancer, renal cell carcinoma, clear cell renal cell carcinoma (ccRcc), colorectal cancer, or lung cancer. In some embodiments, the cancer is mesothelioma.

In another aspect, the disclosure provides methods of inhibiting (e.g., killing, disabling, or preventing growth or expansion) a target cell that expresses both of the CAR antigen and the priming receptor antigen. In another aspect, the invention provides methods of killing a target cell that expresses both of the CAR antigen and the priming receptor antigen. In some embodiments, the target cell is a cancer cell.

In some embodiments, the treatment results in a decrease in the cancer volume or size. In some embodiments, the treatment is effective at reducing a cancer volume as compared to the cancer volume prior to administration of the antibody. In some embodiments, the treatment results in a decrease in the cancer growth rate. In some embodiments, the treatment is effective at reducing a cancer growth rate as compared to the cancer growth rate prior to administration of the antibody. In some embodiments, the treatment is effective at eliminating the cancer.

In some embodiments, the CAR antigen and/or the priming receptor antigen are expressed at a higher level in the cancer as compared to a non-cancer cell. Levels of CAR antigen and/or the priming receptor antigen can be assessed by any technique known in the field, including, but not limited to, protein assays or nucleic assays such as FACS, Western blot, ELISA, immunoprecipitation, immunohisto-chemistry, immunofluorescence, radioimmunoassay, dot blotting, immunodetection methods, HPLC, surface plas-mon resonance, optical spectroscopy, mass spectrometry, HPLC, qPCR, RT-qPCR, multiplex qPCR or RT-qPCR, RNA-seq, microarray analysis, SAGE, MassARRAY tech-nique, and FISH, and combinations thereof.

Method of Immune Modulation

Methods of administration of a cell comprising a synthetic pathway activator described herein can result in modulation of an immune response. Modulation can be an increase or decrease in an immune response. In some embodiments, modulation is an increase in an immune response.

In one aspect, administration of a cell comprising a synthetic pathway activator described herein can result in induction of pro-inflammatory molecules, such as cytokines or chemokines. Generally, induced pro-inflammatory mol-ecules are present at levels greater than that achieved with isotype control. Such pro-inflammatory molecules in turn result in activation of anti-tumor immunity, including, but not limited to, T cell activation, T cell proliferation, T cell differentiation, MI-like macrophage activation, and NK cell activation. Thus, the administration of a cell comprising a synthetic pathway activator described herein can induce multiple anti-tumor immune mechanisms that lead to tumor destruction. In some embodiments, the immune activity of the cell is cytolytic activity.

In another aspect, provided herein are methods of increas-ing an immune response in an individual comprising admin-istering to the individual an effective amount of a cell comprising a synthetic pathway activator described herein. In some embodiments, the method of increasing an immune response in a subject comprises administering to the subject a cell comprising a synthetic pathway activator described herein.

In some embodiments, the cell is present in a pharma-ceutical composition further comprising a pharmaceutically acceptable excipient.

In any and all aspects of increasing an immune response as described herein, any increase or decrease or alteration of an aspect of characteristic(s) or function(s) is as compared to a cell not comprising a composition comprising a synthetic pathway activator described herein.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodi-ments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response. In some embodiments, the immune response is started or initiated by administration of a cell comprising a synthetic pathway activator described herein. In some embodiments, the immune response is enhanced by administration of cell comprising a synthetic pathway acti-vator described herein. In some embodiments, the immune response is enhanced by administration of cell comprising a synthetic pathway activator and a priming receptor and CAR system described herein.

In another aspect, the present application provides meth-ods of genetically editing a cell with a synthetic pathway activator described herein, which results in the modulation of the immune function of the cell. The modulation can be increasing an immune response. In some embodiments, the modulation is an increase in immune function. In some embodiments, the modulation of function leads to the expression of cytokine or interleukin. In some embodiments, the modulation of function leads to the activation of an immune cell.

In some embodiments, the cell is a natural killer (NK) cell, a T cell, a CD8+ T cell, a CD4+ T cell, a primary T cell, or a T cell progenitor.

In some embodiments, the modulation of function of the cells comprising a synthetic pathway activator as described herein leads to an increase in the cells' abilities to stimulate both native and activated T-cells, for example, by increasing cytokine or chemokine secretion by the cells expressing the synthetic pathway activator described herein. In some embodiments, the modulation of function enhances or increases the cells' ability to produce cytokines, chemok-ines, CARs, or costimulatory or activating receptors. In some embodiments, the modulation increases the T-cell stimulatory function of the cells expressing a synthetic pathway activator described herein, including, for example, the cells' abilities to trigger T-cell receptor (TCR) signaling, T-cell proliferation, or T-cell cytokine production.

In some embodiments, the increased immune response is secretion of cytokines and chemokines. In some embodi-ments, a synthetic pathway activator described herein induces increased expression of at least one cytokine or chemokine in a cell as compared to an isotype control cell. In some embodiments, the at least one cytokine or chemo-kine is selected from the group consisting of: IL-2 and IFNγ. In some embodiments, the cytokine or chemokine is IL-2. In some embodiments, the cytokine or chemokine is IFNγ. In some embodiments, the cytokine or chemokine secretion is increased a between bout 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody. In some embodiments, the chemokine is IL-2 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody. In some embodiments, the cytokine is IFNγ and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody.

In some embodiments, the enhanced immune response is anti-tumor immune cell recruitment and activation.

In some embodiments, the cell expressing a synthetic pathway activator described herein induces a memory immune response as compared to an isotype control cell. In general, a memory immune response is a protective immune response upon a subsequent exposure to pathogens or antigens that the immune system encountered previously. Exemplary memory immune responses include the immune response after infection or vaccination with an antigen. In general, memory immune responses are mediated by lymphocytes such as T cells or B cells. In some embodiments, the memory immune response is a protective immune response to cancer, including cancer cell growth, proliferation, or metastasis. In some embodiments, the memory immune response inhibits, prevents, or reduces cancer cell growth, proliferation, or metastasis.

Methods of Editing Cells

The terms "gene editing" or "genome editing", as used herein, refer to a type of genetic manipulation in which DNA is inserted, replaced, or removed from the genome using artificially manipulated nucleases or "molecular scissors". It is a useful tool for elucidating the function and effect of sequence-specific genes or proteins or altering cell behavior (e.g. for therapeutic purposes).

Currently available genome editing tools include zinc finger nucleases (ZFN) and transcription activator-like effector nucleases (TALENs) to incorporate genes at safe harbor loci (e.g. the adeno-associated virus integration site 1 (AAVS1) safe harbor locus). The DICE (dual integrase cassette exchange) system utilizing phiC31 integrase and Bxb1 integrase is a tool for target integration. Additionally, clustered regularly interspaced short palindromic repeat/Cas9 (CRISPR/Cas9) techniques can be used for targeted gene insertion.

Site specific gene editing approaches can include homology dependent mechanisms or homology independent mechanisms.

All methods known in the art for targeted insertion of gene sequences are contemplated in the methods described herein to insert constructs at gene targets or safe harbor loci.

Provided herein are methods of inserting nucleotide sequences greater than about 5 kilobases in length into the genome of a cell, in the absence of a viral vector. In some embodiments, the nucleotide sequence greater than about 5 kilobase in length can be inserted into the genome of a primary immune cell, in the absence of a viral vector Integration of large nucleic acids, for example nucleic acids greater than 5 kilobase in size, into cells, can be limited by low efficiency of integration, off-target effects and/or loss of cell viability. Described herein are methods and compositions for achieving integration of a nucleotide sequence, for example, a nucleotide sequence greater than about 5 kilobases in size, into the genome of a cell. In some methods the efficiency of integration is increased, off-target effects are reduced and/or loss of cell viability is reduced.

The plasmid can be introduced into an immune cell with a nuclease, such as a CRISPR-associated system (Cas). The nuclease can be introduced in a ribonucleoprotein format with a guide RNA (gRNA) that targets a specific site on the genome of the immune cell. The nuclease cuts the genomic DNA at this specific site. The specific site may be a portion of the genome that encodes an endogenous immune cell receptor. Thus, cutting the genome at this site will cause the immune cell to no longer express an endogenous immune cell receptor.

The plasmid may include 5' and 3' homology-directed repair arms complementary to sequences at a specific site on the genome of the immune cell. The complementary sequences are on either side of the site cut by the nuclease, which allows the plasmid to be incorporated at a specified insertion site on the immune cell's genome. Once the plasmid is incorporated, the cell will express the SPA peptide. In examples where the SPA peptide is also co-expressed with a system comprising a priming receptor and CAR, the priming receptor is also expressed by the cell. However, as explained, the design of the transgene cassette ensures that non-virally delivered circuit system receptors do not express CAR until the priming receptor binds to its cognate ligand and releases the cleavable transcription factor.

Initially, a T cell is activated. The T cell may be obtained from a patient. Thus, the present disclosure provides methods in which immune cells, such as T cells, are harvested from a patient. Then, the plasmid that encodes the CAR and priming receptor are introduced into a T cell. Advantageously, the plasmids of the present disclosure can be introduced using electroporation. When introducing the plasmid via electroporation, the nuclease may also be introduced. By using electroporation, methods of the present disclosure avoid the use of viral vectors for introducing transgenes, which is a known bottleneck in immune cell engineering. The T cells are then expanded and co-cultured to create a sufficient quantity of engineered immune cells to be used as a therapeutic treatment.

Methods for editing the genome of a cell can include a) providing a Cas9 ribonucleoprotein complex (RNP)-DNA template complex comprising: (i) the RNP, wherein the RNP comprises a Cas9 nuclease domain and a guide RNA, wherein the guide RNA specifically hybridizes to a target region of the genome of the cell, and wherein the Cas9 nuclease domain cleaves the target region to create an insertion site in the genome of the cell; and (ii) a double-stranded or single-stranded DNA template, wherein the size of the DNA template is greater than about 200 nucleotides, wherein the 5' and 3' ends of the DNA template comprise nucleotide sequences that are homologous to genomic sequences flanking the insertion site, and wherein the molar ratio of RNP to DNA template in the complex is from about 3:1 to about 100:1; and b) introducing the RNP-DNA template complex into the cell.

In some embodiments, the methods described herein provide an efficiency of delivery of the RNP-DNA template complex of at least about 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the efficiency is determined with respect to cells that are viable after introducing the RNP-DNA template into the cell. In some cases, the efficiency is determined with respect to the total number of cells (viable or non-viable) in which the RNP-DNA template is introduced into the cell.

As another example, the efficiency of delivery can be determined by quantifying the number of genome edited cells in a population of cells (as compared to total cells or total viable cells obtained after the introducing step). Various methods for quantifying genome editing can be utilized. These methods include, but are not limited to, the use of a mismatch-specific nuclease, such as T7 endonuclease I; sequencing of one or more target loci (e.g., by sanger sequencing of cloned target locus amplification fragments); and high-throughput deep sequencing.

In some embodiments, loss of cell viability is reduced as compared to loss of cell viability after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages. In some embodiments, off-target effects of integration are reduced as compared to off-target integration after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages.

In some cases, the methods described herein provide for high cell viability of cells to which the RNP-DNA template has been introduced. In some cases, the viability of the cells to which the RNP-DNA template has been introduced is at least about 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the viability of the cells to which the RNP-DNA template has been introduced is from about 20% to about 99%, from about 30% to about 90%, from about 35% to about 85% or 90% or higher, from about 40% to about 85% or 90% or higher, from about 50% to about 85% or 90% or higher, from about 50% to about 85% or 90% or higher, from about 60% to about 85% or 90% or higher, or from about 70% to about 85% or 90% or higher.

In the methods provided herein, the molar ratio of RNP to nucleic acid (e.g., DNA template) can be from about 3:1 to about 100:1. For example, the molar ratio can be from about 3:1 to 10:1, from about 3:1 to about 15:1, 3:1 to about 20:1; 3:1 to about 25:1; from about 3:1 to 50:1, from about 3:1 to 75:1, from about 3:1 to 100:1; from about 5:1 to 10:1, from about 5:1 to about 15:1, 5:1 to about 20:1; 5:1 to about 25:1; from about 5:1 to 50:1, from about 5:1 to 75:1, from about 5:1 to 100:1; from about 8:1 to about 12:1; from about 8:1 to about 15:1, from about 8:1 to about 20:1, from about 8:1 to about 25:1, from about 8:1 to 50:1, from about 8:1 to 75:1, from about 8:1 to 100:1; from about 10:1 to about 15:1, 10:1 to about 20:1, 10:1 to about 25:1; from about 10:1 to 50:1, from about 10:1 to 75:1, or from about 10:1 to 100:1.

In some embodiments, the DNA template is at a concentration of about 2.5 pM to about 25 pM. For example, the concentration of DNA template can be about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25 pM or any concentration in between these concentrations.

In some embodiments, the size or length of the nucleic acid (e.g., DNA template) is greater than about 4.5 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.1 kb, 9.2 kb, 9.3 kb, 9.4 kb, 9.5 kb, 9.6 kb, 9.7 kb, 9.8 kb, 9.9 kb, 10 kb, 11 kb, 12 kb, 13 kb, 14 kb, 15 kb, or 16 kb or any size of nucleic acid (e.g., DNA template) in between these sizes. For example, the size of the DNA template can be about 4.5 kb to about 15 kb, about 4.5 kb to about 14 kb, about 4.5 kb to about 10 kb, about 5 kb to about 15 kb, about 5 kb to about 14 kb, about 5 kb to about 10 kb, about 5 kb to about 9 kb, about 5 kb to about 8 kb, about 5 kb to about 7 kb, about 5 kb to about 6 kb, about kb 6 to about 15 kb, about kb 6 to about 14 kb, about kb 6 to about 10 kb, about 6 kb to about 9 kb, about 6 kb to about 8 kb, about 6 kb to about 7 kb, about 7 kb to about 15 kb, about 7 kb to about 14 kb, about 7 kb to about 10 kb, about 7 kb to about 9 kb, about 7 kb to about 8 kb, about 8 kb to about 15 kb, about 8 kb to about 14 kb, about 8 kb to about 10 kb, about 8 kb to about 9 kb, about 9 kb to about 15 kb, about 9 kb to about 14 kb, about 9 kb to about 13 kb, about 9 kb to about 12 kb, about 9 kb to about 11 kb, about 9 kb to about 10 kb, about 10 kb to about 15 kb, about 10 kb to about 14 kb, about 10 kb to about 13 kb, about 10 kb to about 12 kb, or about 10 kb to about 11 kb.

In some embodiments, the amount of DNA template is about 1 µg to about 10 µg. For example, the amount of DNA template can be about 1 µg to about 2 µg, about 1 µg to about 3 µg, about 1 µg to about 4 µg, about 1 µg to about 5 µg, about 1 µg to about 6 µg, about 1 µg to about 7 µg, about 1 µg to about 8 µg, about 1 µg to about 9 µg, about 1 µg to about 10 µg. In some embodiments the amount of DNA template is about 2 µg to about 3 µg, about 2 µg to about 4 µg, about 2 µg to about 5 µg, about 2 µg to about 6 µg, about 2 µg to about 7 µg, about 2 µg to about 8 µg, about 2 µg to about 9 µg, or 2 µg to about 10 µg. In some embodiments the amount of DNA template is about 3 µg to about 4 µg, about 3 µg to about 5 µg, about 3 µg to about 6 µg, about 3 µg to about 7 µg, about 3 µg to about 8 µg, about 3 µg to about 9 µg, or about 3 µg to about 10 µg. In some embodiments, the amount of DNA template is about 4 µg to about 5 µg, about 4 µg to about 6 µg, about 4 µg to about 7 µg, about 4 µg to about 8 µg, about 4 µg to about 9 µg, or about 4 µg to about 10 µg. In some embodiments, the amount of DNA template is about 5 µg to about 6 µg, about 5 µg to about 7 µg, about 5 µg to about 8 µg, about 5 µg to about 9 µg, or about 5 µg to about 10 µg. In some embodiments, the amount of DNA template is about 6 µg to about 7 µg, about 6 µg to about 8 µg, about 6 µg to about 9 µg, or about 6 µg to about 10 µg. In some embodiments, the amount of DNA template is about 7 µg to about 8 µg, about 7 µg to about 9 µg, or about 7 µg to about 10 µg. In some embodiments, the amount of DNA template is about 8 µg to about 9 µg, or about 8 µg to about 10 µg. In some embodiments, the amount of DNA template is about 9 µg to about 10 µg.

In some cases, the size of the DNA template is large enough and in sufficient quantity to be lethal as naked DNA. In some embodiments, the DNA template encodes a heterologous protein or a fragment thereof. In some embodiments, the DNA template encodes at least one gene. In some embodiments, the DNA template encodes at least two genes. In some embodiments, the DNA template encodes one, two, three, four, five, six, seven, eight, nine, ten, or more genes. In some embodiments, the DNA template includes regulatory sequences, for example, a promoter sequence and/or an enhancer sequence to regulate expression of the heterologous protein or fragment thereof after insertion into the genome of a cell.

In some cases, the DNA template is a linear DNA template. In some cases, the DNA template is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA.

In some cases, the RNP-DNA template complex is formed by incubating the RNP with the DNA template for less than about one minute to about thirty minutes, at a temperature of about 20° C. to about 25° C. For example, the RNP can be incubated with the DNA template for about 5 seconds, 10 seconds, 15 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes or 30 minutes or any amount of time in between these times, at a temperature of about 20° C., 21° C., 22° C., 23° C., 24° C., or 25° C. In another example, the RNP can be incubated with the DNA template for less than about one minute to about one minute, for less than about one minute to about 5 minutes, for less than about 1 minute to about 10 minutes, for about 10 5 minutes to 10 minutes, for about 5 minutes to 15 minutes, for about 10 to about 15 minutes, for about 10 minutes to about 20 minutes, or for about 10 minutes to about 30 minutes, at a temperature of about 20° C. to about 25° C. In some embodiments, the RNP-DNA template complex and the cell are mixed prior to introducing the RNP-DNA template complex into the cell.

In some embodiments introducing the RNP-DNA template complex comprises electroporation. Methods, compositions, and devices for electroporating cells to introduce a RNP-DNA template complex can include those described in the examples herein. Additional or alternative methods, compositions, and devices for electroporating cells to introduce a RNP-DNA template complex can include those described in WO/2006/001614 or Kim, J. A. et al. Biosens. Bioelectron. 23, 1353-1360 (2008). Additional or alternative methods, compositions, and devices for electroporating cells to introduce a RNP-DNA template complex can include those described in U.S. Patent Appl. Pub. Nos. 2006/0094095; 2005/0064596; or 2006/0087522. Additional or alternative methods, compositions, and devices for electroporating cells to introduce a RNP-DNA template complex can include those described in Li, L. H. et al. Cancer Res. Treat. 1, 341-350 (2002); U.S. Pat. Nos. 6,773,669; 7,186, 559; 7,771,984; 7,991,559; 6,485,961; 7,029,916; and U.S. Patent Appl. Pub. Nos: 2014/0017213; and 2012/0088842, all of which are hereby incorporated by reference. Additional or alternative methods, compositions, and devices for electroporating cells to introduce a RNP-DNA template complex can include those described in Geng, T. et al., J. Control Release 144, 91-100 (2010); and Wang, J., et al. Lab. Chip 10, 2057-2061 (2010), all of which are hereby incorporated by reference.

In some embodiments, the Cas9 protein can be in an active endonuclease form, such that when bound to target nucleic acid as part of a complex with a guide RNA or part of a complex with a DNA template, a double strand break is introduced into the target nucleic acid. The double strand break can be repaired by NHEJ to introduce random mutations, or HDR to introduce specific mutations. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to any region of a genome that contains an NGG sequence. As another example, Cas9 proteins with orthogonal PAM motif requirements can be utilized to target sequences that do not have an adjacent NGG PAM sequence. Exemplary Cas9 proteins with orthogonal PAM sequence specificities include, but are not limited to, CFP1, those described in Nature Methods 10, 1116-1121 (2013), and those described in Zetsche et al., Cell, Volume 163, Issue 3, p759-771, 22 Oct. 2015, both of which are hereby incorporated by reference.

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by baseexcision repair mechanisms. Exemplary Cas9 nickases include Cas9 nucleases having a D10A or H840A mutation.

In some embodiments, the RNP comprises a Cas9 nuclease. In some embodiments, the RNP comprises a Cas9 nickase. In some embodiments, the RNP-DNA template complex comprises at least two structurally different RNP complexes. In some embodiments, the at least two structurally different RNP complexes contain structurally different Cas9 nuclease domains In some embodiments, the at least two structurally different RNP complexes contain structurally different guide RNAs. In some embodiments, wherein the at least two structurally different RNP complexes contain structurally different guide RNAs, each of the structurally different RNP complexes comprises a Cas9 nickase, and the structurally different guide RNAs hybridize to opposite strands of the target region.

In some cases, a plurality of RNP-DNA templates comprising structurally different ribonucleoprotein complexes is introduced into the cell. For example a Cas9 protein can be complexed with a plurality (e.g., 2, 3, 4, 5, or more, e.g., 2-10, 5-100, 20-100) of structurally different guide RNAs to target insertion of a DNA template at a plurality of structurally different target genomic regions.

In the methods and compositions provided herein, cells include, but are not limited to, eukaryotic cells, prokaryotic cells, animal cells, plant cells, fungal cells and the like. Optionally, the cell is a mammalian cell, for example, a human cell. The cell can be in vitro, ex vivo or in vivo. The cell can also be a primary cell, a germ cell, a stem cell or a precursor cell. The precursor cell can be, for example, a pluripotent stem cell, or a hematopoietic stem cell. In some embodiments, the cell is a primary hematopoietic cell or a primary hematopoietic stem cell. In some embodiments, the primary hematopoietic cell is an immune cell. In some embodiments, the immune cell is a T cell. In some embodiments, the T cell is a regulatory T cell, an effector T cell, or a naïve T cell. In some embodiments, the T cell is a CD4$^+$ T cell. In some embodiments, the T cell is a CD8$^+$ T cell. In some embodiments, the T cell is a CD4$^+$CD8$^+$ T cell. In some embodiments, the T cell is a CD4$^-$CD8$^-$T cell. Populations of any of the cells modified by any of the methods described herein are also provided. In some embodiments, the methods further comprise expanding the population of modified cells.

In some cases, the cells are removed from a subject, modified using any of the methods described herein and administered to the patient. In other cases, any of the constructs described herein is delivered to the patient in vivo. See, for example, U.S. Pat. No. 9,737,604 and Zhang et al. "Lipid nanoparticle-mediated efficient delivery of CRISPR/Cas9 for tumor therapy," *NPG Asia Materials* Volume 9, page e441 (2017), both of which are hereby incorporated by reference.

In some embodiments, the RNP-DNA template complex is introduced into about $1 \times 10^5$ to about $2 \times 10^6$ cells. For example, the RNP-DNA template complex can be introduced into about $1 \times 10^5$ to about $5 \times 10^5$ cells, about $1 \times 10^5$ to about $1 \times 10^6$, $1 \times 10^5$ to about $1.5 \times 10^6$, $1 \times 10^5$ to about $2 \times 10^6$, about $1 \times 10^6$ to about $1.5 \times 10^6$ cells or about $1 \times 10^6$ to about $2 \times 10^6$.

In some cases, the methods and compositions described herein can be used for generation, modification, use, or control of recombinant T cells, such as chimeric antigen receptor T cells (CAR T cells). Such CAR T cells can be used to treat or prevent cancer, an infectious disease, or autoimmune disease in a subject. For example, in some embodiments, one or more gene products are inserted or knocked-in to a T cell to express a heterologous protein (e.g., a chimeric antigen receptor (CAR) or a priming receptor).

Insertion Sites

Methods for editing the genome of a T cell, specifically, include a method of editing the genome of a human T cell comprise inserting a nucleic acid sequence or construct into a target region in exon 1 of the TCR-α subunit (TRAC) gene in the human T cell. In some embodiments, the target region is in exon 1 of the constant domain of TRAC gene. In other embodiments, the target region is in exon 1, exon 2 or exon 3, prior to the start of the sequence encoding the TCR-α transmembrane domain. In some embodiments, the target region is the GS94 genomic safe harbor.

Methods for editing the genome of a T cell also include a method of editing the genome of a human T cell comprise inserting a nucleic acid sequence or construct into a target region in exon 1 of a TCR-β subunit (TRBC) gene in the human T cell. In some embodiments, the target region is in exon 1 of the TRBC1 or TRBC2 gene.

Methods for editing the genome of a T cell, specifically, include a method of editing the genome of a human T cell comprise inserting a nucleic acid sequence or construct into a target region of a genomic safe harbor (GSH).

Methods for editing the genome of a T cell also include a method of editing the genome of a human T cell comprise inserting a nucleic acid sequence or construct into a GS94 target region (locus chr11: 128340000-128350000).

In some embodiments, the target region is the GS94 locus.

Gene editing therapies include, for example, vector integration and site specific integration. Site-specific integration is a promising alternative to random integration of viral vectors, as it mitigates the risks of insertional mutagenesis or insertional oncogenesis (Kolb et al. Trends Biotechnol. 2005 23:399-406; Porteus et al. Nat Biotechnol. 2005 23:967-973; Paques et al. Curr Gen Ther. 2007 7:49-66). However, site specific integration continues to face challenges such as poor knock-in efficiency, risk of insertional oncogenesis, unstable and/or anomalous expression of adjacent genes or the transgene, low accessibility (e.g. within 20 KB of adjacent genes), etc., These challenges can be addressed, in part, through the identification and use of safe harbor loci or safe harbor sites (SHS), which are sites in which genes or genetic elements can be incorporated without disruption to expression or regulation of adjacent genes.

The most widely used of the putative human safe harbor sites is the AAVS1 site on chromosome 19q, which was initially identified as a site for recurrent adenoassociated virus insertion. Other potential SHS have been identified on the basis of homology, with sites first identified in other species (e.g., the human homolog of the permissive murine Rosa26 locus) or among the growing number of human genes that appear non-essential under some circumstances. One putative SHS of this type is the CCR5 chemokine receptor gene, which, when disrupted, confers resistance to human immunodeficiency virus infection. Additional potential genomic SHS have been identified in human and other cell types on the basis of viral integration site mapping or gene-trap analyses, as was the original murine Rosa26 locus. The three top SHS, AAVS1, CCR5, and Rosa26, are in close proximity to many protein coding genes and regulatory elements. (See Sadelain, M., et al. (2012). Safe harbours for the integration of new DNA in the human genome. Nature reviews Cancer, 12 (1), 51-58, the relevant disclosures of which are herein incorporated by reference in their entirety).

The AAVS1 (also known as the PPP1R12C locus) on human chromosome 19 is a known SHS for hosting transgenes (e.g. DNA transgenes) with expected function. It is at position 19q13.42. It has an open chromatin structure and is transcription-competent. The canonical SHS locus for AAVS1 is chr19: 55,625,241-55,629,351. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference. An exemplary AAVS1 target gRNA and target sequence are provided below:

```
AAVS1-gRNA sequence:
                                   (SEQ ID NO: 116)
ggggccactagggacaggatGTTTTAGAGCTAGAAATAGCAAGTTAAAA

TAAGGCTAGTCCGTTATCAACTTGAAAAAGTGGCACCGAGTCGGTGCTT

TTTTT

AAVS1 target sequence:
                                   (SEQ ID NO: 117)
ggggccactagggacaggat.
```

CCR5, which is located on chromosome 3 at position 3p21.31, encodes the major co-receptor for HIV-1. Disruption at this site in the CCR5 gene has been beneficial in HIV/AIDS therapy and prompted the development of zinc-finger nucleases that target its third exon. The canonical SHS locus for CCR5 is chr3: 46,414,443-46,414,942. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference.

The mouse Rosa26 locus is particularly useful for genetic modification as it can be targeted with high efficiency and is expressed in most cell types tested. Irion et al. 2007 ("Identification and targeting of the ROSA26 locus in human embryonic stem cells." Nature biotechnology 25.12 (2007): 1477-1482, the relevant disclosure of which are herein incorporated by reference) identified the human homolog, human ROSA26, in chromosome 3 (position 3p25.3). The canonical SHS locus for human Rosa26 (hRosa26) is chr3: 9,415,082-9,414,043. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference.

Additional examples of safe harbor sites are provided in Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference. Examples of additional integration sites are provided in Table D.

In some embodiments, the safe harbor sites allow for high transgene expression (sufficient to allow for transgene functionality or treatment of a disease of interest) and stable expression of the transgene over several days, weeks or months. In some embodiments, knockout of the gene at the safe harbor locus confers benefit to the function of the cell, or the gene at the safe harbor locus has no known function within the cell. In some embodiments the safe harbor locus results in stable transgene expression in vitro with or without CD3/CD28 stimulation, negligible off-target cleavage as detected by iGuide-Seq or CRISPR-Seq, less off-target cleavage relative to other loci as detected by iGuide-Seq or CRISPR-Seq, negligible transgene-independent cytotoxicity, negligible transgene-independent cytokine expression, negligible transgene-independent chimeric antigen receptor expression, negligible deregulation or silencing of nearby genes, and positioned outside of a cancer-related gene.

As used, a "nearby gene" can refer to a gene that is within about 100 KB, about 125 kB, about 150 kB, about 175 kB, about 200 kB, about 225 kB, about 250 kB, about 275 kB, about 300 KB, about 325 kB, about 350 KB, about 375 KB, about 400 kB, about 425 kB, about 450 kB, about 475 kB, about 500 KB, about 525 kB, about 550 kB away from the safe harbor locus (integration site).

In some embodiments, the present disclosure contemplates inserts that comprise one or more transgenes. The transgene can encode a therapeutic protein, an antibody, a peptide, or any other gene of interest. The transgene integration can result in, for example, enhanced therapeutic properties. These enhanced therapeutic properties, as used herein, refer to an enhanced therapeutic property of a cell when compared to a typical immune cell of the same normal cell type. For example, a T cell having "enhanced therapeutic properties" has an enhanced, improved, and/or increased treatment outcome when compared to a typical, unmodified and/or naturally occurring T cell. The therapeutic properties of immune cells can include, but are not limited to, cell transplantation, transport, homing, viability, self-renewal, persistence, immune response control and regulation, survival, and cytotoxicity. The therapeutic properties of immune cells are also manifested by: antigen-targeted receptor expression; HLA presentation or lack thereof; tolerance to the intratumoral microenvironment; induction of bystander immune cells and immune regulation; improved target specificity with reduction; resistance to treatments such as chemotherapy.

As used herein, the term "insert size" refers to the length of the nucleotide sequence being integrated (inserted) at the target locus or safe harbor site. In some embodiments, the insert size comprises at least about 4.5 kilobasepairs (kb) to about 10 kilobasepairs (kb). In some embodiments, the insert size comprises about 5000 nucleotides or more basepairs. In some embodiments, the insert size comprises up to 4.5, 4.8, 5, 6, 7, 8, 9, 10, 11, 12, 13, 14, 15, 16, 17, 18, 19, 20 kbp (kilo basepairs) or the sizes in between. In some embodiments, the insert size is greater than 4.5, 4.8, 5, 6, 7, 8, 9, 10, 11, 12, 13, 14, 15, 16, 17, 18, 19, 20 kbp or the sizes in between. In some embodiments, the insert size is within the range of 4.5-15 kbp or is any number in that range. In some embodiments, the insert size is within the range of 4.8-8.3 kbp or is any number in that range. In some embodiments, the insert size is within the range of 5-8.3 kbp or is any number in that range. In some embodiments, the insert size is within the range of 5-15 kbp or is any number in that range. In some embodiments, the insert size is within the range of 4.5-20 kbp or is any number in that range. In some embodiments, the insert size is 5-10 kbp. In some embodiments, the insert size is 4.5-10, 5-10, 6-10, 7-10, 8-10, 9-10 kbp. In some embodiments, the insert size is 4.5-11, 6-11, 7-11, 8-11, 9-11, or 10-11 kbp. In some embodiments, the insert size is 4.5-12, 6-12, 7-12, 8-12, 9-12, 10-12, or 11-12 kbp. In some embodiments, the insert size is 4.5-13, 6-13, 7-13, 8-13, 9-13, 10-13, 11-13, or 12-13 kbp. In some embodiments, the insert size is 4.5-14, 6-14, 7-14, 8-14, 9-14, 10-14, 11-14, 12-14 or 13-14 kbp. In some embodiments, the insert size is 4.5-15, 6-15, 7-15, 8-15, 9-15, 10-15, 11-15, 12-15, 13-15, or 14-15 kbp. In some embodiments, the insert size is 4.5-16, 6-16, 7-16, 8-16, 9-16, 10-16, 11-16, 12-16, 13-16, 14-16 or 15-16 kbp. In some embodiments, the insert size is 4.5-17, 6-17, 7-17, 8-17, 9-17, 10-17, 11-17, 12-17, 13-17, or 14-17, 15-17 or 16-17 kbp. In some embodiments, the insert size is 4.5-18, 6-18, 7-18, 8-18, 9-18, 10-18, 11-18, 12-18, 13-18, 14-18, 15-18, 16-18 or 17-18 kbp. In some embodiments, the insert size is 4.5-19, 6-19, 7-19, 8-19, 9-19, 10-19, 11-19, 12-19, 13-19, 14-19, 15-19, 16-19, 17-19, or 18-19 kbp. In some embodiments, the insert size is 4.5-20, 6-20, 7-20, 8-20, 9-20, 10-20, 11-20, 12-20, 13-20, 14-20, 15-20, 16-20, 17-20, 18-20, or 19-20 kbp.

The inserts of the present disclosure refer to nucleic acid molecules or polynucleotide inserted at a target locus or safe harbor site. In some embodiments, the nucleotide sequence is a DNA molecule, e.g., genomic DNA, or comprises deoxy-ribonucleotides. In some embodiments, the insert comprises a smaller fragment of DNA, such as a plastid DNA, mitochondrial DNA, or DNA isolated in the form of a plasmid, a fosmid, a cosmid, a bacterial artificial chromosome (BAC), a yeast artificial chromosome (YAC), and/or any other sub-genome segment of DNA. In some embodiments, the insert is an RNA molecule or comprises ribonucleotides. The nucleotides in the insert are contemplated as naturally occurring nucleotides, non-naturally occurring, and modified nucleotides. Nucleotides may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications. The polynucleotides can be in any topological conformation, including single-stranded, double-stranded, partially duplexed, triplexed, hairpinned, circular conformations, and other three-dimension conformations contemplated in the art.

The inserts can have coding and/or non-coding regions. The insert can comprises a non-coding sequence (e.g., control elements, e.g., a promoter sequence). In some embodiments, the insert encodes transcription factors. In some embodiments, the insert encodes an antigen binding receptors such as single receptors, T-cell receptors (TCRs), priming receptors, CARs, mAbs, etc. In some embodiments, the the insert is a human sequence. In some embodiments, the insert is chimeric. In some embodiments, the insert is a multi-gene/multi-module therapeutic cassette. A multi-gene/multi-module therapeutic cassette refers to an insert or cassette having one or more than one receptor (e.g., synthetic receptors such as a CAR or a priming receptor), other exogenous protein coding sequences, non-coding RNAs, transcriptional regulatory elements, and/or insulator sequences, etc.

In some embodiments, the nucleic acid sequence is inserted into the genome of the cell such as an immune cell or T cell via non-viral delivery. In non-viral delivery methods, the nucleic acid can be naked DNA, or in a non-viral plasmid or vector. Non-viral delivery techniques can be site-specific integration techniques, as described herein or known to those of ordinary skill in the art. Examples of site-specific techniques for integration into the safe harbor loci include, without limitation, homology-dependent engineering using nucleases and homology independent targeted insertion using Cas9 or other CRISPR endonucleases.

In some embodiments, the insert is integrated at a safe harbor site by introducing into the engineered cell, (a) a targeted nuclease that cleaves a target region in the safe harbor site to create the insertion site; and (b) the nucleic acid sequence (insert), wherein the insert is incorporated at the insertion site by, e.g., HDR. Examples of non-viral delivery techniques that can be used in the methods of the present disclosure are provided in U.S. Pat. Nos. 11,033, 584B2 and 11,814,624B2, the relevant disclosures of which are herein incorporated by reference in their entirety.

Examples of integration sites contemplated are provided in Table D.

TABLE D

| sgRNA sequences | | | | | | |
|---|---|---|---|---|---|---|
| sgRNA ID | sgRNA Sequence | SEQ ID NO: | sgRNA start coor GRCH38 | sgRNA Target Loci | Integration Site | Median (% Modified), summarized from 2 donors, 2 primersets |
| sgRNA_1 | GCACCTGAATACC ACGCCTG | 118 | chr16: 88811818 | APRT | APRT | 79.28 |
| sgRNA_2 | CGCCTGCGATGTA GTCGATG | 119 | chr16: 88811551 | APRT | APRT | 78.60 |
| sgRNA_3 | CAGGACGGGCGA GATGTCCC | 120 | chr16: 88811640 | APRT | APRT | 85.25 |
| sgRNA_4 | CTGAATCTTTGGA GTACCTG | 121 | chr15: 44715425 | B2M | B2M | 78.51 |
| sgRNA_5 | GGCCACGGAGCGA GACATCT | 122 | chr15: 44711550 | B2M | B2M | 94.75 |
| sgRNA_6 | AAGTCAACTTCAA TGTCGGA | 123 | chr15: 44715515 | B2M | B2M | 70.97 |
| sgRNA_7 | GCTTGGAGGCCTG ATCAGCG | 124 | chr19: 36141111 | CAPNS1 | CAPNS1 | 89.34 |
| sgRNA_8 | CTTATCTCTTCGC AGCGAGG | 125 | chr19: 36142301 | CAPNS1 | CAPNS1 | 91.09 |
| sgRNA_9 | CACACATTACTCC AACATTG | 126 | chr19: 36142676 | CAPNS1 | CAPNS1 | 71.98 |
| sgRNA_10 | TTCCGCAAAATAG AGCCCCA | 127 | chr3: 105746019 | CBLB | CBLB | 91.55 |
| sgRNA_11 | TGCACAGAACTAT CGTACCA | 128 | chr3: 105751622 | CBLB | CBLB | 91.43 |
| sgRNA_12 | GCAATAAGACTCT TTAAAGA | 129 | chr3: 105853470 | CBLB | CBLB | 76.18 |
| sgRNA_13 | CAAAGAGATTACG AATGCCT | 130 | chr1: 116754658 | CD2 | CD2 | 89.80 |
| sgRNA_14 | CAAGGCACCCCAG GTTTCCA | 131 | chr1: 116754663 | CD2 | CD2 | 92.70 |
| sgRNA_15 | TTACGAATGCCTT GGAAACC | 132 | chr1: 116754666 | CD2 | CD2 | 92.82 |
| sgRNA_16 | CAGAGACGCATCT GACCCTC | 133 | chr11: 118315540 | CD3E | CD3E | 90.96 |
| sgRNA_17 | CATGCAGTTCTCA CACACTG | 134 | chr11: 118313715 | CD3E | CD3E | 87.47 |
| sgRNA_18 | GTGTGAGAACTGC ATGGAGA | 135 | chr11: 118313715 | CD3E | CD3E | 86.65 |
| sgRNA_19 | TCTCATTTCAGGA AACCACT | 136 | chr11: 118349748 | CD3G | CD3G | 87.24 |
| sgRNA_20 | AGTCATACACCTT AACCAAG | 137 | chr11: 118349754 | CD3G | CD3G | 87.99 |
| sgRNA_21 | TTCAAGGAAACCA GTTGAGG | 138 | chr11: 118352458 | CD3G | CD3G | 86.55 |

TABLE D-continued

| sgRNA ID | sgRNA Sequence | SEQ ID NO: | sgRNA start coor GRCH38 | sgRNA Target Loci | Integration Site | Median (% Modified), summarized from 2 donors, 2 primersets |
|---|---|---|---|---|---|---|
| sgRNA_22 | GAGCCTTGCCTGG AAATCTG | 139 | chr11: 61118177 | CD5 | CD5 | 84.03 |
| sgRNA_23 | AAGCGTCAAAAGT CTGCCAG | 140 | chr11: 61118324 | CD5 | CD5 | 89.19 |
| sgRNA_24 | CGTTCCAACTCGA AGTGCCA | 141 | chr11: 61118121 | CD5 | CD5 | 83.11 |
| sgRNA_25 | GAGCGACTGGGAC ACGGTGA | 142 | chr9: 136866246 | EDF1 | EDF1 | 88.84 |
| sgRNA_26 | GCTGCGCAAGAAG GGCCCTA | 143 | chr9: 136866211 | EDF1 | EDF1 | 91.04 |
| sgRNA_27 | TTGTTCTGGCCAG CAGCCCC | 144 | chr9: 136863433 | EDF1 | EDF1 | 85.98 |
| sgRNA_28 | CTTCCAGAGCCAC ATCATCG | 145 | chr19: 48965791 | FTL | FTL | 93.10 |
| sgRNA_29 | GGGACTCACCAGA GAGAGGT | 146 | chr19: 48965601 | FTL | FTL | 88.86 |
| sgRNA_30 | CGGTCGAAATAGA AGCCCTA | 147 | chr19: 48965770 | FTL | FTL | 93.14 |
| sgRNA_31 | AAAAGGATATTGT GCAACTG | 148 | chr10: 87933015 | PTEN | PTEN | 92.37 |
| sgRNA_32 | TGTGCATATTTAT TACATCG | 149 | chr10: 87933183 | PTEN | PTEN | 90.64 |
| sgRNA_33 | TTTGTGAAGATCT TGACCAA | 150 | chr10: 87933087 | PTEN | PTEN | 85.36 |
| sgRNA_34 | TGTCATGCTGAAC CGCATTG | 151 | chr18: 12830972 | PTPN2 | PTPN2 | 87.94 |
| sgRNA_35 | CCACTCTATGAGG ATAGTCA | 152 | chr18: 12859219 | PTPN2 | PTPN2 | 92.45 |
| sgRNA_36 | TTGACATAGAAGA GGCACAA | 153 | chr18: 12836828 | PTPN2 | PTPN2 | 93.96 |
| sgRNA_37 | GAGTACTACACTC AGCAGCA | 154 | chr12: 6952098 | PTPN6 | PTPN6 | 89.61 |
| sgRNA_38 | TCACGCACAAGAA ACGTCCA | 155 | chr12: 6954872 | PTPN6 | PTPN6 | 82.74 |
| sgRNA_39 | AGGTCTCGGTGAA ACCACCT | 156 | chr12: 6951610 | PTPN6 | PTPN6 | 91.27 |
| sgRNA_40 | AGCATTATCCAAA GAGTCCG | 157 | chr1: 198696873 | PTPRC | PTPRC | 88.88 |
| sgRNA_41 | ATATTAATTCTTA CCAGTGG | 158 | chr1: 198692370 | PTPRC | PTPRC | 88.95 |
| sgRNA_42 | AGCTTTAAATCAA GGTTCAT | 159 | chr1: 198756176 | PTPRC | PTPRC | 96.89 |
| sgRNA_43 | ATCCCGAGCCCTA AGGTGCA | 160 | chr11: 67436325 | PTPRCAP | PTPRCAP | 84.08 |
| sgRNA_44 | GGCAGCGCGGAG GACAGCGT | 161 | chr11: 67436285 | PTPRCAP | PTPRCAP | 97.74 |

TABLE D-continued

| | | | | | Median (% Modified), summarized |
|---|---|---|---|---|---|
| sgRNA ID | sgRNA Sequence | SEQ ID NO: | sgRNA start coor GRCH38 | sgRNA Target Loci | Integration Site | from 2 donors, 2 primersets |
| sgRNA_45 | CTCAGGGGGCTAC TACCACC | 162 | chr11: 67436170 | PTPRCAP | PTPRCAP | 91.50 |
| sgRNA_46 | GTCACCGACGAGA CCAGAAG | 163 | chr5: 82277810 | RPS23 | RPS23 | 79.40 |
| sgRNA_47 | GTCGTGGACTTCG TACTGCT | 164 | chr5: 82277843 | RPS23 | RPS23 | 83.07 |
| sgRNA_48 | TAATTTTTAGGCA AGTGTCG | 165 | chr5: 82277860 | RPS23 | RPS23 | 61.94 |
| sgRNA_49 | TTAGCTGTTAGAC TTGAATA | 166 | chr14: 51993810 | RTRAF | RTRAF | 85.50 |
| sgRNA_50 | CGAGAGCCGTCAA CTTGCGT | 167 | chr14: 51989652 | RTRAF | RTRAF | 85.64 |
| sgRNA_51 | CGGCTTCAACTGC AAAGGTG | 168 | chr14: 51989700 | RTRAF | RTRAF | 88.77 |
| sgRNA_52 | TATGAAAAAGCAG AGCGACT | 169 | chr15: 43793025 | SERF2 | SERF2 | 89.61 |
| sgRNA_53 | TCTGGCGGGCGAG CTCACGC | 170 | chr15: 43792989 | SERF2 | SERF2 | 86.73 |
| sgRNA_54 | CTCACGCTGGTTA CCGCCTA | 171 | chr15: 43792977 | SERF2 | SERF2 | 80.57 |
| sgRNA_55 | AAAGATTACGAAC TTCCCTG | 172 | chr12: 46207559 | SLC38A1 | SLC38A1 | 92.24 |
| sgRNA_56 | GTTAAAAACAGAC ATGCCTA | 173 | chr12: 46229232 | SLC38A1 | SLC38A1 | 91.51 |
| sgRNA_57 | ATGCCTAAGGAGG TTGTACC | 174 | chr12: 46229246 | SLC38A1 | SLC38A1 | 79.48 |
| sgRNA_58 | CTCCAGGTATCCC ATCGAAA | 175 | chr18: 47869418 | SMAD2 | SMAD2 | 79.53 |
| sgRNA_59 | CACCAAATACGAT AGATCAG | 176 | chr18: 47870532 | SMAD2 | SMAD2 | 86.61 |
| sgRNA_60 | TGGCGGCGTGAAT GGCAAGA | 177 | chr18: 47896729 | SMAD2 | SMAD2 | 82.91 |
| sgRNA_61 | TAGGATGGTAGCA CACAACC | 178 | chr16: 11255478 | SOCS1 | SOCS1 | 92.25 |
| sgRNA_62 | CAGCAGCAGAGCC CCGACGG | 179 | chr16: 11255432 | SOCS1 | SOCS1 | 83.79 |
| sgRNA_63 | CGGCGTGCGAACG GAATGTG | 180 | chr16: 11255296 | SOCS1 | SOCS1 | 84.24 |
| sgRNA_64 | TATAGACGCTGCC CGACGTC | 181 | chr15: 40038895 | SRP14 | SRP14 | 95.12 |
| sgRNA_65 | TCCAAAGAAGGGT ACTGTGG | 182 | chr15: 40038368 | SRP14 | SRP14 | 92.14 |
| sgRNA_66 | ACAGTACCCTTCT TTGGAAT | 183 | chr15: 40038358 | SRP14 | SRP14 | 65.82 |
| sgRNA_67 | GCGACGGGCGCAT CTACGTG | 184 | chr12: 120469572 | SRSF9 | SRSF9 | 83.68 |

TABLE D-continued sgRNA sequences

| sgRNA ID | sgRNA Sequence | SEQ ID NO: | sgRNA start coor GRCH38 | sgRNA Target Loci | Integration Site | Median (% Modified), summarized from 2 donors, 2 primersets |
|---|---|---|---|---|---|---|
| sgRNA_68 | CCCGACCTCCATA AGTCCTG | 185 | chr12: 120465700 | SRSF9 | SRSF9 | 92.56 |
| sgRNA_69 | GGGGTCCTCGAAG CGCACGA | 186 | chr12: 120469426 | SRSF9 | SRSF9 | 89.94 |
| sgRNA_70 | TGCTCTGTTTAGA AGATGAC | 187 | chr5: 32591641 | SUB1 | SUB1 | 79.36 |
| sgRNA_71 | ATATTCTTTTCTAG TTAAAG | 188 | chr5: 32591566 | SUB1 | SUB1 | 70.93 |
| sgRNA_72 | CCTGTAAAGAAAC AAAAGAC | 189 | chr5: 32591614 | SUB1 | SUB1 | 93.66 |
| sgRNA_73 | TGGAGAAAGACGT AACTTCG | 190 | chr4: 105234315 | TET2 | TET2 | 83.53 |
| sgRNA_74 | TCTGCCCTGAGGT ATGCGAT | 191 | chr4: 105234747 | TET2 | TET2 | 90.97 |
| sgRNA_75 | ATTCCGCTTGGTG AAAACGA | 192 | chr4: 105235656 | TET2 | TET2 | 89.62 |
| sgRNA_76 | CAGGCACAATAGA AACAACG | 193 | chr3: 114295571 | TIGIT | TIGIT | 92.65 |
| sgRNA_77 | CCATTTGTAATGC TGACTTG | 194 | chr3: 114295700 | TIGIT | TIGIT | 60.75 |
| sgRNA_78 | CTGGGTCACTTGT GCCGTGG | 195 | chr3: 114295634 | TIGIT | TIGIT | 87.99 |
| sgRNA_79 | GTCAGGGTTCTGG ATATCTG | 196 | chr14: 22547508 | TRAC | TRAC | 98.20 |
| sgRNA_80 | TGGATTTAGAGTC TCTCAGC | 197 | chr14: 22547541 | TRAC | TRAC | 88.15 |
| sgRNA_81 | CTGCGGCTGTGGT CCAGCTG | 198 | chr14: 22550661 | TRAC | TRAC | 94.77 |
| sgRNA_82 | ACAAAACTGTGCT AGACATG | 199 | chr14: 22547658 | TRAC | TRAC | 87.86 |
| sgRNA_83 | TTCTTCCCCAGCC CAGGTAA | 200 | chr14: 22547778 | TRAC | TRAC | 89.85 |
| sgRNA_84 | CGTCATGAGCAGA TTAAACC | 201 | chr14: 22550625 | TRAC | TRAC | 95.81 |
| sgRNA_85 | GAGAGCGCCTGCG ACCCGAG | 202 | chr19: 58544980 | TRIM28 | TRIM28 | 89.44 |
| sgRNA_86 | CCAGCGGGTGAAG TACACCA | 203 | chr19: 58544869 | TRIM28 | TRIM28 | 94.79 |
| sgRNA_87 | GGAGCGCTTTTCG CCGCCAG | 204 | chr19: 58544839 | TRIM28 | TRIM28 | 91.81 |
| sgRNA_88 | TGAGGCCTGGACC TTATGCA | 205 | chr10: 33134193 | chr10: 33130000- 33140000 | desert_1 (GS88) | 69.44 |
| sgRNA_89 | CCTGGTGGAGTGA ACCATGA | 206 | chr10: 33132917 | chr10: 33130000- 33140000 | desert_1 (GS89) | 95.25 |

TABLE D-continued

| | | | | | Median (% |
|---|---|---|---|---|---|
| | | | | | Modified), |
| | | | sgRNA | | summarized |
| | | SEQ | start | sgRNA | | from 2 |
| sgRNA | | ID | coor | Target | Integration | donors, 2 |
| ID | sgRNA Sequence | NO: | GRCH38 | Loci | Site | primersets |

| sgRNA_90 | CAAGCACTTAGGT TCCCCTG | 207 | chr10: 33134633 | chr10: 33130000- 33140000 | desert_1 (GS90) | 91.13 |
| sgRNA_91 | GGTCTCCCTACAA TTCAGCG | 208 | chr10: 72294568 | chr10: 72290000- 72300000 | desert_2 (GS91) | 92.02 |
| sgRNA_92 | CACAGCGCGTGAC TGCAATG | 209 | chr10: 72298268 | chr10: 72290000- 72300000 | desert_2 (GS92) | 90.22 |
| sgRNA_93 | TCTGGGGCACCAA TTCTAGG | 210 | chr10: 72292786 | chr10: 72290000- 72300000 | desert_2 (GS93) | 86.35 |
| sgRNA_94 | GAGCCATGCTTGG CTTACGA | 211 | chr11: 128342576 | chr11: 128340000- 128350000 | desert_3 (GS94) | 91.24 |
| sgRNA_95 | GTACAAGTACTTA TCTCATG | 212 | chr11: 128343592 | chr11: 128340000- 128350000 | desert_3 (GS95) | 89.02 |
| sgRNA_96 | GAGATAACAACAT AACAACA | 213 | chr11: 128347170 | chr11: 128340000- 128350000 | desert_3 (GS96) | 96.47 |
| sgRNA_97 | CATATTCCATAGT CTTTGGG | 214 | chr11: 65425000 | chr11: 65425000- 65427000 (NEAT1) | desert_4 (GS97) | 88.54 |
| sgRNA_98 | CTGCCCCTTAGCA ACTTAGG | 215 | chr11: 65425507 | chr11: 65425000- 65427000 (NEAT1) | desert_4 (GS98) | 92.76 |
| sgRNA_99 | TGTTTAAAAATAT GTTGACA | 216 | chr11: 65426264 | chr11: 65425000- 65427000 (NEAT1) | desert_4 (GS99) | 90.76 |
| sgRNA_100 | CCAGGAATGGAAA CTCACGC | 217 | chr15: 92830315 | chr15: 92830000- 92840000 | desert_5 (GS100) | 87.84 |
| sgRNA_101 | GAGGCCGCTGAAT TAACCCG | 218 | chr15: 92831850 | chr15: 92830000- 92840000 | desert_5 (GS101) | 85.32 |
| sgRNA_102 | ATACACGCACACT TGCAGAA | 219 | chr15: 92831131 | chr15: 92830000- 92840000 | desert_5 (GS102) | 99.92 |
| sgRNA_103 | GAGCAGACAGAA ACCCAGGG | 220 | chr16: 11225670 | chr16: 11220000- 11230000 | desert_6 (GS103) | 87.92 |
| sgRNA_104 | TGAGTCTCCAAAC AGAACAG | 221 | chr16: 11226284 | chr16: 11220000- 11230000 | desert_6 (GS104) | 88.53 |
| sgRNA_105 | TAATATCACTGAC TTCACGG | 222 | chr16: 11225029 | chr16: 11220000- 11230000 | desert_6 (GS105) | 87.65 |
| sgRNA_106 | TACACACAATGTA AGCAGCA | 223 | chr2: 87467461 | chr2: 87460000- 87470000 | desert_7 (GS106) | 71.79 |

TABLE D-continued sgRNA sequences

| sgRNA ID | sgRNA Sequence | SEQ ID NO: | sgRNA start coor GRCH38 | sgRNA Target Loci | Integration Site | Median (% Modified), summarized from 2 donors, 2 primersets |
|---|---|---|---|---|---|---|
| sgRNA_107 | GGGAGCTCAATTC GAAACCA | 224 | chr2: 87468809 | chr2: 87460000- 87470000 | desert_7 (GS107) | 65.89 |
| sgRNA_108 | TTGGACAGGTGAG ACAGTCG | 225 | chr2: 87467001 | chr2: 87460000- 87470000 | desert_7 (GS108) | 72.64 |
| sgRNA_109 | AAGCTCACTCAGA TAGTGTG | 226 | chr3: 186511316 | chr3: 186510000- 186520000 | desert_8 GS109) | 76.89 |
| sgRNA_110 | CAGGAGAACCACC TTACACG | 227 | chr3: 186515260 | chr3: 186510000- 186520000 | desert_8 (GS110) | 86.31 |
| sgRNA_111 | GGACAGACCCTGA TTCACAA | 228 | chr3: 186519655 | chr3: 186510000- 186520000 | desert_8 (GS111) | 85.47 |
| sgRNA_112 | ACATGGCAGTCTA TGAACAG | 229 | chr3: 59451154 | chr3: 59450000- 59460000 | desert_9 (GS112) | 87.77 |
| sgRNA_113 | CCTATAGAGAGTA CTACTTG | 230 | chr3: 59456416 | chr3: 59450000- 59460000 | desert_9 (GS113) | 79.33 |
| sgRNA_114 | CCAACCGGGTCTT CATTACG | 231 | chr3: 59457029 | chr3: 59450000- 59460000 | desert_9 (GS114) | 92.21 |
| sgRNA_115 | TCAAGCGTAGAGT TCCGAGT | 232 | chr8: 127993006 | chr8: 127980000- 128000000 | desert_10 (GS115) | 93.07 |
| sgRNA_116 | TCATGCAATTATG GACCCAG | 233 | chr8: 127994663 | chr8: 127980000- 128000000 | desert_10 (GS116) | 89.40 |
| sgRNA_117 | CGGGAAAGTGACT GGCCATG | 234 | chr8: 127996766 | chr8: 127980000- 128000000 | desert_10 (GS117) | 87.45 |
| sgRNA_118 | TGAGATTGAAATC AAATCGG | 235 | chr9: 7974159 | chr9: 7970000- 7980000 | desert_11 (GS118) | 84.84 |
| sgRNA_119 | TATGCAATATTCA TCACGCG | 236 | chr9: 7977914 | chr9: 7970000- 7980000 | desert_11 (GS119) | 85.44 |
| sgRNA_120 | AATGTGTTAAATC AAATGCA | 237 | chr9: 7976895 | chr9: 7970000- 7980000 | desert_11 (GS120) | 83.48 |

CRISPR-Cas Editing

One effective example of gene editing is the CRISPR-Cas approach (e.g. CRISPR-Cas9). This approach incorporates the use of a guide polynucleotide (e.g. guide ribonucleic acid or gRNA) and a cas endonuclease (e.g. Cas9 endonuclease).

As used herein, a polypeptide referred to as a "Cas endonuclease" or having "Cas endonuclease activity" refers to a CRISPR-related (Cas) polypeptide encoded by a Cas gene, wherein a Cas polypeptide is a target DNA sequence that can be cleaved when operably linked to one or more guide polynucleotides (see, e.g., U.S. Pat. No. 8,697,359).

Also included in this definition are variants of Cas endonuclease that retain guide polynucleotide-dependent endonuclease activity. The Cas endonuclease used in the donor DNA insertion method detailed herein is an endonuclease that introduces double-strand breaks into DNA at the target site (e.g., within the target locus or at the safe harbor site).

As used herein, the term "guide polynucleotide" relates to a polynucleotide sequence capable of complexing with a Cas endonuclease and allowing the Cas endonuclease to recognize and cleave a DNA target site. The guide polynucleotide can be a single molecule or a double molecule. The guide polynucleotide sequence can be an RNA sequence, a DNA sequence, or a combination thereof (RNA-DNA combination sequence). A guide polynucleotide comprising only ribonucleic acid is also referred to as "guide RNA". In some embodiments, a polynucleotide donor construct is inserted at a safe harbor locus using a guide RNA (gRNA) in combination with a cas endonuclease (e.g. Cas9 endonuclease).

The guide polynucleotide includes a first nucleotide sequence domain (also referred to as a variable targeting domain or VT domain) that is complementary to a nucleotide sequence in the target DNA, and a second nucleotide that interacts with a Cas endonuclease polypeptide. It can be a double molecule (also referred to as a double-stranded guide polynucleotide) comprising a sequence domain (referred to as a Cas endonuclease recognition domain or CER domain). The CER domain of this double molecule guide polynucleotide comprises two separate molecules that hybridize along the complementary region. The two separate molecules can be RNA sequences, DNA sequences and/or RNA-DNA combination sequences.

Genome editing using CRISPR-Cas approaches relies on the repair of site-specific DNA double-strand breaks (DSBs) induced by the RNA-guided Cas endonuclease (e.g. Cas 9 endonuclease). Homology-directed repair (HDR) of these DSBs enables precise editing of the genome by introducing defined genomic changes, including base substitutions, sequence insertions, and deletions. Conventional HDR-based CRISPR/Cas9 genome-editing involves transfecting cells with Cas9, gRNA and donor DNA containing homologous arms matching the genomic locus of interest.

HITI (homology independent targeted insertion) uses a non-homologous end joining (NHEJ)-based homology-independent strategy and the method can be more efficient than HDR. Guide RNAs (gRNAs) target the insertion site. For HITI, donor plasmids lack homology arms and DSB repair does not occur through the HDR pathway. The donor polynucleotide construct can be engineered to include Cas9 cleavage site(s) flanking the gene or sequence to be inserted. This results in Cas9 cleavage at both the donor plasmid and the genomic target sequence. Both target and donor have blunt ends and the linearized donor DNA plasmid is used by the NHEJ pathway resulting integration into the genomic DSB site. (See, for example, Suzuki, K., et al. (2016). In vivo genome editing via CRISPR/Cas9 mediated homology-independent targeted integration. Nature, 540 (7631), 144-149, the relevant disclosures of which are herein incorporated in their entirety).

Methods for conducing gene editing using CRISPR-Cas approaches are known to those of ordinary skill in the art. (See, for example, U.S. application Ser. Nos. 16/312,676, 15/303,722, and 15/628,533, the disclosures of which are herein incorporated by reference in their entirety). Additionally, uses of endonucleases for inserting transgenes into safe harbor loci are described, for example, in U.S. application Ser. No. 13/036,343, the disclosures of which are herein incorporated by reference in their entirety.

The guide RNAs and/or mRNA (or DNA) encoding an endonuclease can be chemically linked to one or more moieties or conjugates that enhance the activity, cellular distribution, or cellular uptake of the oligonucleotide. Non-limiting examples of such moieties include lipid moieties such as a cholesterol moiety, cholic acid, a thioether, a thiocholesterol, an aliphatic chain (e.g., dodecandiol or undecyl residues), a phospholipid, e.g., di-hexadecyl-rac-glycerol or triethylammonium 1,2-di-O-hexadecyl-rac-glycero-3-H-phosphonate, a polyamine or a polyethylene glycol chain, adamantane acetic acid, a palmityl moiety and an octadecylamine or hexylamino-carbonyl-t oxycholesterol moiety. See for example US Patent Publication No. 20180127786, the disclosure of which is herein incorporated by reference in its entirety.

Therapeutic Applications

For therapeutic applications, the engineered cells, populations thereof, or compositions thereof are administered to a subject, generally a mammal, generally a human, in an effective amount. The engineered cells may be administered to a subject by infusion (e.g., continuous infusion over a period of time) or other modes of administration known to those of ordinary skill in the art.

The engineered cells provided herein not only find use in gene therapy but also in non-pharmaceutical uses such as, e.g., production of animal models and production of recombinant cell lines expressing a protein of interest.

The engineered cells of the present disclosure can be any cell, generally a mammalian cell, generally a human cell that has been modified by integrating a transgene at a safe harbor locus described herein. Exemplary cells are provided in the Recombinant Cells section.

The engineered cells, compositions and methods of the present disclosure are useful for therapeutic applications such as CAR T cell therapy and TCR T cell therapy. In some embodiments, the insertion of a sequence encoding a transgene within a safe harbor locus maintains the TCR expression relative to instances when there is no insertion and enables transgene expression while maintaining TCR function.

In some embodiments, the present disclosure provides methods of treating a subject in need of treatment by administering to the subject a composition comprising any of the engineered cells described herein. In some embodiments, administration of the engineered cell composition results in a desired pharmacological and/or physiological effect. That effect can be partial or complete cure of the disease and/or adverse effects resulting from the disease. In some embodiments, treatment encompasses any treatment of a disease in a subject (e.g., mammal, e.g., human). Further, treatment may stabilize or reduce undesirable clinical symptoms in subjects (e.g., patients). The cells provided herein populations thereof, or compositions thereof may be administered during or after the occurrence of the disease.

In certain embodiments, the subject has a disease, condition, and/or injury that can be treated and/or ameliorated by cell therapy. In some embodiments, the subject in need of cell therapy is a subject having an injury, disease, or condition, thereby causing cell therapy (e.g., therapy in which cellular material is administered to the subject). However, it is contemplated that it is possible to treat, ameliorate and/or reduce the severity of at least one symptom associated with the injury, disease or condition.

Method of Administration

An effective amount of the immune cell comprising the SPA peptide comprises may be administered for the treatment of cancer. The appropriate dosage of the immune cell comprising the SPA peptide may be determined based on the type of cancer to be treated, the type of the immune cell comprising the SPA peptide, the severity and course of the cancer, the clinical condition of the individual, the individual's clinical history and response to the treatment, and the discretion of the attending physician.

Determining Expression of CD11c

Also provided herein are methods of treating a cancer in a subject in need thereof comprising: determining or having determined the expression of CD11c in a cell comprising a synthetic pathway activator (SPA) peptide disclosed herein, optionally wherein the SPA is inserted into a target region of the genome of the cell; and administering or having administered to the subject the cell comprising the SPA.

CD11c is also known as Integrin Subunit Alpha X, Integrin, Alpha X (Complement Component 3 Receptor 4 Subunit), or ITGAX (HGNC: 6152, NCBI Gene: 3687, UniProtKB/Swiss-Prot: P20702).

In some aspects, provided herein are methods of determining an expression level of CD11c protein in a sample from a subject comprising contacting the sample with an anti-CD11c antibody and performing a FACS, Western blot, ELISA, immunoprecipitation, immunohistochemistry, monoplex immunohistochemistry, multiplex immunohistochemistry, immunofluorescence, radioimmunoassay, dot blotting, immunodetection methods, surface plasmon resonance, optical spectroscopy, mass spectrometry assay, or any combination thereof. In some aspects, provided herein are methods of determining an expression level of CD11c mRNA in a sample from a subject comprising performing qPCR, RT-qPCR, multiplex qPCR or RT-qPCR, RNA-seq, microarray analysis, SAGE, MassARRAY technique, Luminex, MSD, or FISH, and combinations thereof.

In some aspects, provided herein are methods of producing a CD11c-positive (CD11c+) cell comprising inserting a nucleic acid encoding for any SPA peptide disclosed herein and expressing the SPA peptide in the cell. In other aspects, provided herein are methods of detecting a SPA, optionally a functional SPA, in a cell comprising a SPA peptide disclosed herein, optionally wherein the SPA is inserted into the genome of the cell.

In some aspects, provided herein are methods of screening a cell for expression of a SPA, optionally wherein the SPA is a functional SPA, comprising expressing one or more SPAs in a cell and detecting CD11c expression in the cell, wherein the detection of CD11c indicates a functional SPA peptide. In such embodiments, a functional SPA is one that has functional signaling (e.g., can stimulate the cell, such as a T cell, via phosphorylation of STAT1, STAT3, and/or STAT5).

In some aspects, provided herein are assays to detect cells, such as primary cells and/or immune cells, engineered to express a SPA comprising: determining or having determined CD11c expression in the primary cell, wherein CD11c expression indicates that the cell expresses the SPA.

In some aspects, provided herein are methods of treating a patient with an engineered CD11c-expressing T cell comprising: administering a T cell comprising a SPA disclosed herein to the patient.

In some embodiments, the CD11c expression is determined in the T cell, from a biological sample from a patient administered the cell expressing the SPA peptide, or in the tumor of a patient administered the cell expressing the SPA peptide. In some embodiments, the cell is an immune cell. In some embodiments, the immune cell is a primary immune cell. In some embodiments, the immune cell is a hematopoietic cell, an adaptive immune cell, an innate immune cell, a natural killer (NK) cell, a T cell, a CD8+ cell, a CD4+ cell, or a T cell progenitor cell. In some embodiments, the immune cells are T cells. In some embodiments, the T cells are regulatory T cells, effector T cells, or naïve T cells. In some embodiments, the T cells are CD8$^+$ T cells. In some embodiments, the T cells are CD4$^+$ T cells. In some embodiments, the T cells are CD4$^+$CD8$^+$ T cells.

In some embodiments, the expression level of CD11c comprises the mRNA expression level of CD11c. In some embodiments, the expression level of CD11c comprises the protein expression level of CD11c. In some embodiments the expression level of CD11c is detected in the sample using a method selected from the group consisting of FACS, Western blot, ELISA, immunoprecipitation, immunohistochemistry, monoplex immunohistochemistry, multiplex immunohistochemistry, immunofluorescence, radioimmunoassay, dot blotting, immunodetection methods, HPLC, surface plasmon resonance, optical spectroscopy, mass spectrometry, qPCR, RT-qPCR, multiplex qPCR or RT-qPCR, RNA-seq, microarray analysis, SAGE, MassARRAY technique, Luminex, MSD, and FISH, and combinations thereof.

Pharmaceutical Compositions

The engineered recombinant cells provided herein can be administered as part of a pharmaceutical compositions. These compositions can comprise, in addition to one or more of the recombinant cells, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes. The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the Handbook of Pharmaceutical Excipients, Rowe et al. (Eds.) 6th Ed. (2009), incorporated by reference in its entirety.

Various modes of administering the additional therapeutic agents are contemplated herein. In some embodiments, the additional therapeutic agent is administered by any suitable mode of administration.

A composition can be administered alone or in combination with other treatments, either simultaneously or sequentially dependent upon the condition to be treated.

Kits and Articles of Manufacture

The present application provides kits comprising any one or more of the SPA peptides or cell compositions described herein along with instructions for use. The instructions for use can be present in the kits as a package insert, in the labeling of the container of the kit or components thereof, or can be in digital form (e.g. on a CD-ROM, via a link on the internet). A kit can include one or more of a genome-targeting nucleic acid, a polynucleotide encoding a genome-targeting nucleic acid, a site-directed polypeptide, and/or a polynucleotide encoding a site-directed polypeptide. Additional components within the kits are also contemplated, for example, buffer (such as reconstituting buffer, stabilizing buffer, diluting buffer), and/or one or more control vectors.

In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

EXAMPLES

Below are examples of specific embodiments for carrying out the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Synthesis and In Vitro Characterization of Logic Gate Circuits Comprising Synthetic Pathway Activators

Materials and Methods

ICT Construct Expression in T Cells

Integrated circuit T (ICT) cells were generated through site directed CRISPR mediated knock in (KI). T cells were activated for two days using CD3-CD28 beads. At day 2, beads were removed followed by the delivery of the ICT transgene to the GS94 site in the genome of the T cells. Transgene integration was performed using a CRISPR-based process and electroporation step that combined activated T cells, CRISPR/Cas9 RNP targeting the GS94 non-coding autosomal integration site, and plasmid DNA constituting a repair template to effect insertion of the transgene cassette via cellular DNA repair machinery.

The GS94 CRISPR/Cas9 RNP used was generated by complexing single guide RNA (sgRNA) with recombinant *Streptococcus pyogenes* Cas9 (SpCas9). The sgRNA contained a protospacer sequence directing the CRISPR/Cas9 RNP to the GS94-transgene integration site. The plasmid DNA repair template contained the ICT transgene cassette, flanked by 450 base pair (bp) sequences homologous to the regions flanking the integration site to effect repair-mediated insertion.

A diagram of five ICT transgene cassettes generated is provided in FIG. 1. The ICT constructs 1, 2, 3, and 4 comprised a constitutively expressed priming receptor, an inducible CAR (collectively forming a Logic Gate or "LG"), constitutively expressed shRNAs, and a synthetic pathway activator (SPA). ICT 5 included LNGFR in place of the SPA.

Following electroporation, cells were recovered and expanded in T cell media for 7 days. When indicated, negative control T cells were generated using a mock electroporation process that edited T cells with ribonucleoprotein (RNP) in the absence of donor plasmid and are referred to as "RNP control".

ICT cells were assessed for transgene KI and the expression of the PrimeR and CAR using flow based staining. Constructs contained tags myc and flag on the distal extracellular portion of the PrimeR and CAR respectively following the signal peptide. ICT cells at day 7 post activation were stained with myc, flag and CD3 antibodies for 30 min at 4c. Following activation, cells were washed in FACs buffer and run by flow cytometry. ICTs were analyzed for PrimeR and CAR expression following gating each sample for live CD3+ cells.

ICT Induction of CARS

ICTs were generated as described above from the T cells of 2 donors. On day 11 post activation, ICTs were measured for CAR and PrimeR expression by Flag and Myc staining. % KI was quantify by summing the % of T cells in a sample that were PrimeR+ or CAR+. Before co-culture setup, ICTs were normalized to the same % KI using the addition of donor matched RNP only cell. $1\times10^7$ ICTs were co-cultured with $1\times10^7$ target cells or media for 72 hours and stained to calculate the % of CAR+ cells using flag staining. Basal CAR expression was measured during assay set up.

Synthetic Pathway Activators

Figure 2A:
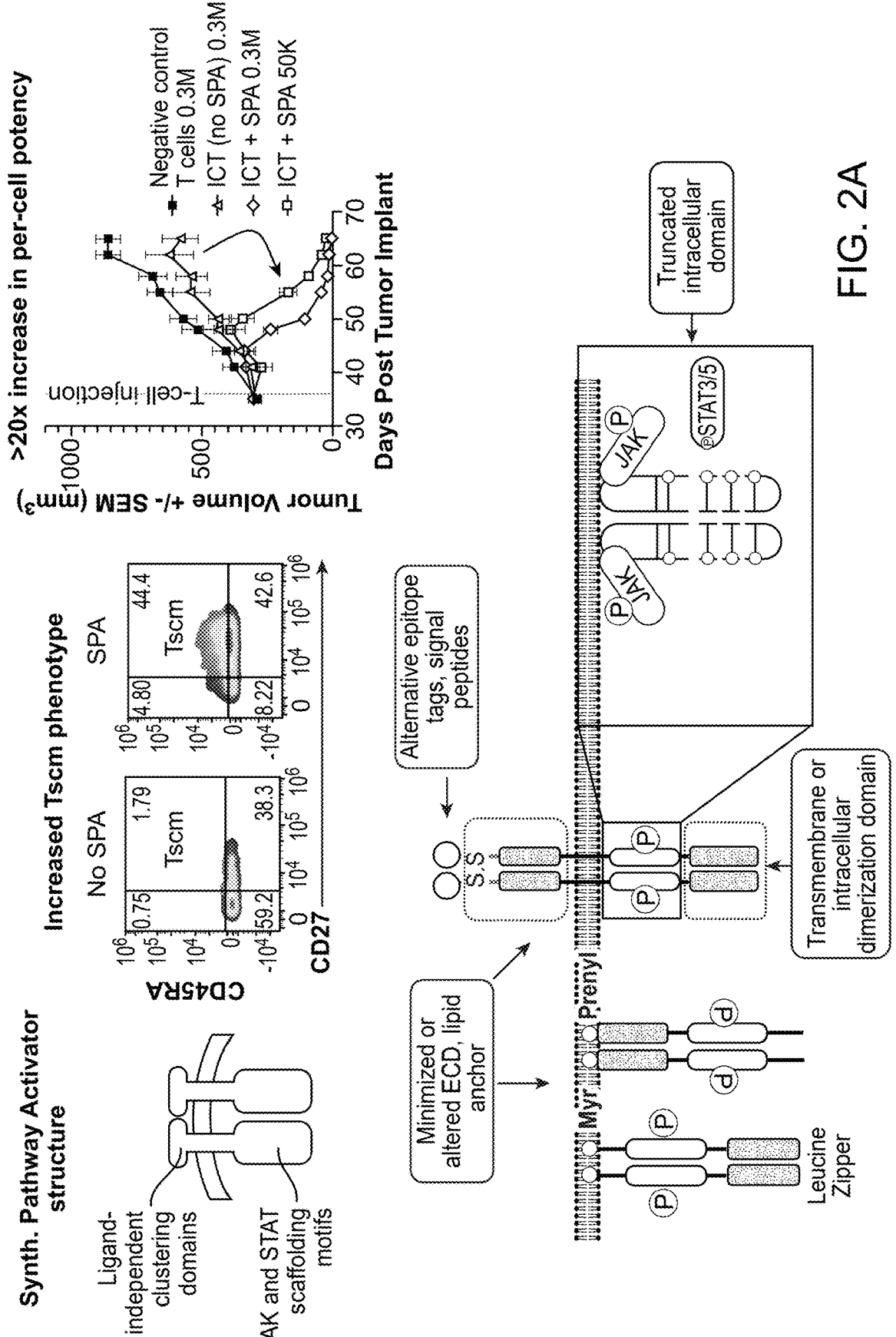
FIG. 2A shows exemplary synthetic pathway activators and that synthetic pathway activators increase potency and T stem memory phenotype.
Figure 2B:
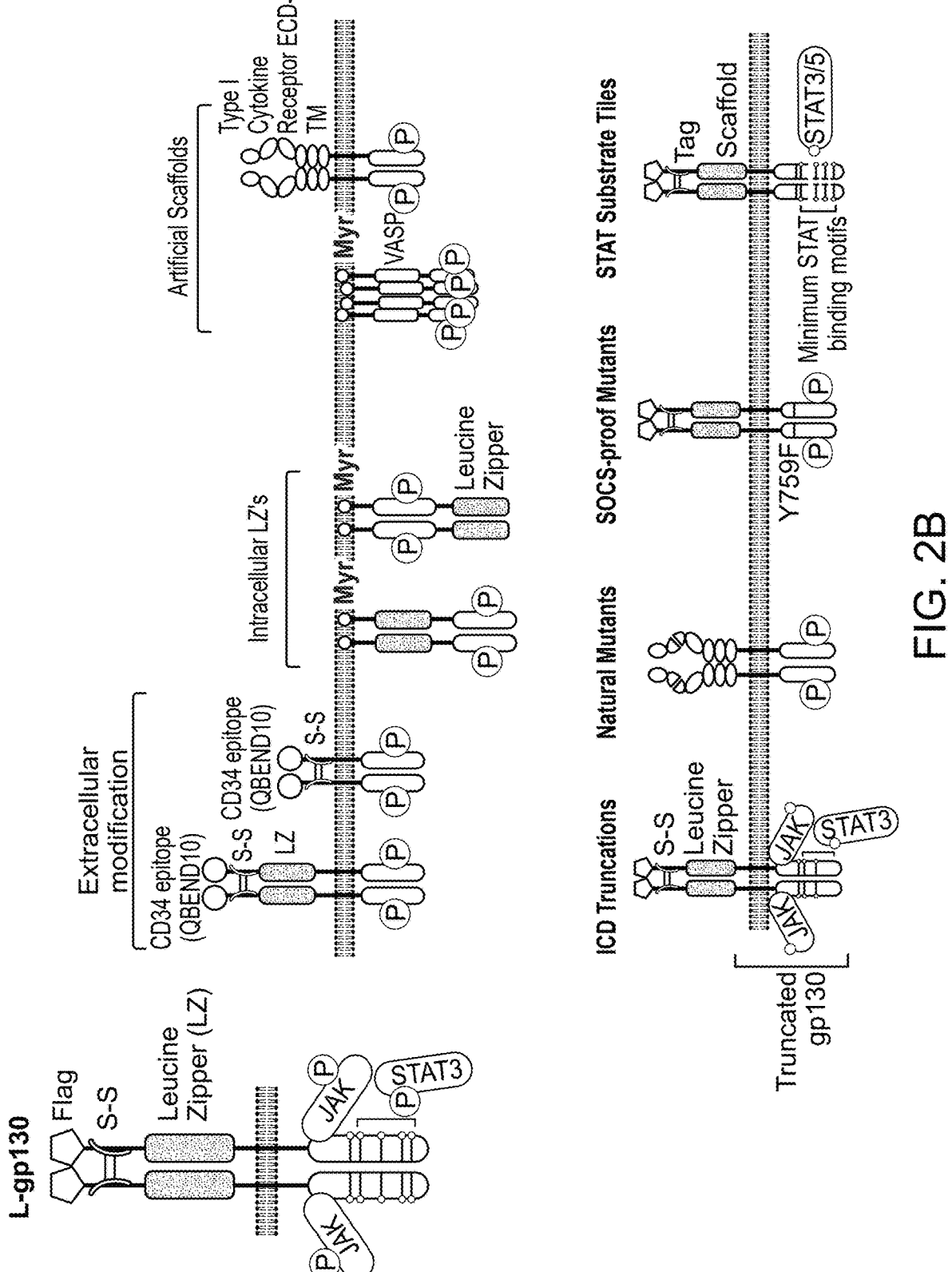
FIG. 2B shows additional exemplary synthetic pathway activators

Synthetic Pathway Activators (SPAs) constitutively drive STAT signaling without the need for external cytokine input. SPAs can be designed to engage activity of multiple STAT family transcription factors at variable levels through rational design. Exemplary Class I SPAs primarily increase pSTAT3 activity and exemplary Class II SPAs primarily increase pSTAT5 activity. FIG. 2 shows the structures of exemplary synthetic pathway activators.

Figure 5:
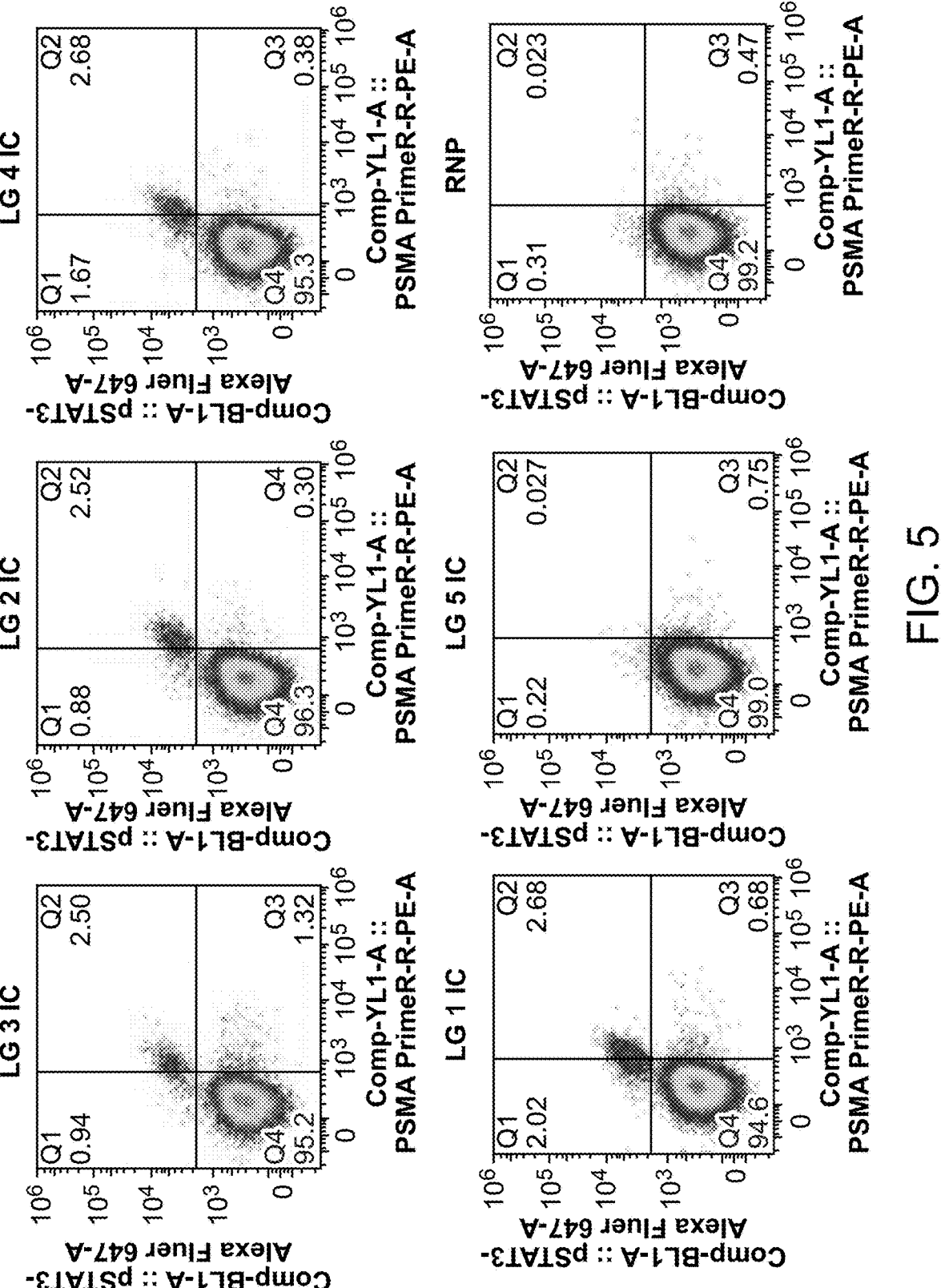
FIG. 5 shows that ICT cells expressing the SPA exhibit approximately two logs higher pSTAT3 expression when compared to the PrimeR-cells lacking a SPA (EGFRt).

A synthetic pathway activator (SPA) based on gp130 was constructed as shown in SEQ ID NOs: 20 and 81. SEQ ID NO: 20 includes a leader sequence. The SPA comprises the transmembrane region and intracellular domain of gp130 linked to an ectodomain derived from the cell adhesion protein CD34. An unpaired cysteine residue was introduced into the receptor ectodomain to permit formation of a covalent bond and subsequent dimerization of individual synthetic gp130 monomers. The SPA drives constitutive recruitment and phosphorylation of STAT1 and STAT3 transcription factors. (FIG. 5 and data not shown)

To demonstrate the ability of the SPA module to drive constitutive STAT3 phosphorylation, ICTs expressing the SPA module under non-stimulated conditions were fixed, permeabilized, and stained for pSTAT3 and the myc epitope tag to distinguish between edited and non-edited cells expressing the ICT.

Cytotoxicity, Engineered K562 Cells

ICT cells expressing the integrated circuits comprising Logic Gate 1 IC, Logic Gate 2 IC, Logic Gate 3 IC, Logic Gate 4 IC, or Logic Gate 5 IC (LG-15 IC) with shRNA and a SPA were co-cultured with K562_EFG, K562_EFG_CAR, K562_EFG_primeR, or K562_EFG_CAR_primeR target antigens at varying E:T ratios for 72 hours at 37° C. Following incubation, cytotoxicity was measured using a luciferase reporter assay. Data are presented as the mean±standard deviation of 4 donors.

Cytokine Secretion

To further assess the specificity and function of ICT cells expressing Logic Gates 1-5, supernatants were collected from K562 target cytotoxicity co-cultures (Effector:Target ratio of 1:1, 72 hour co-culture). Following incubation, supernatants were collected at endpoint and cytokine release levels were measured using a Luminex assay. Data from 4 donors are shown.

Cytotoxicity in Endogenous CAR Cells

ICT cells expressing Logic Gates 1-5 were co-cultured with cells endogenously expressing a CAR target and engineered to express a primeR target at varying E:T ratios for 72 hours at 37° C. Following incubation, cytotoxicity was measured using a luciferase reporter assay. Data are presented as the mean±standard deviation of 4 donors. Prior to luciferase readout described above, supernatants were collected at endpoint and cytokines IFN-g, TNFa, GM-CSF, and IL-2 were measured using a Luminex assay. Data from 4 donors are shown.

Mixed Co-Culture Cytotoxicity

ICT cells expressing LG 1-5 ICs were co-cultured with primeR target+/CAR target– HUVEC and luciferase expressing primeR target–/CAR target+ cells (K562-EFG-CAR) at varying E:T ratios for 72 hours at 37° C. Following incubation, cytotoxicity was measured using a luciferase reporter assay. Data are from one normal donor. ICT-mediated CAR+ target cell killing was evaluated relative to an RNP-electroporated negative control using a luciferase reporter assay.

Results

Figure 3:
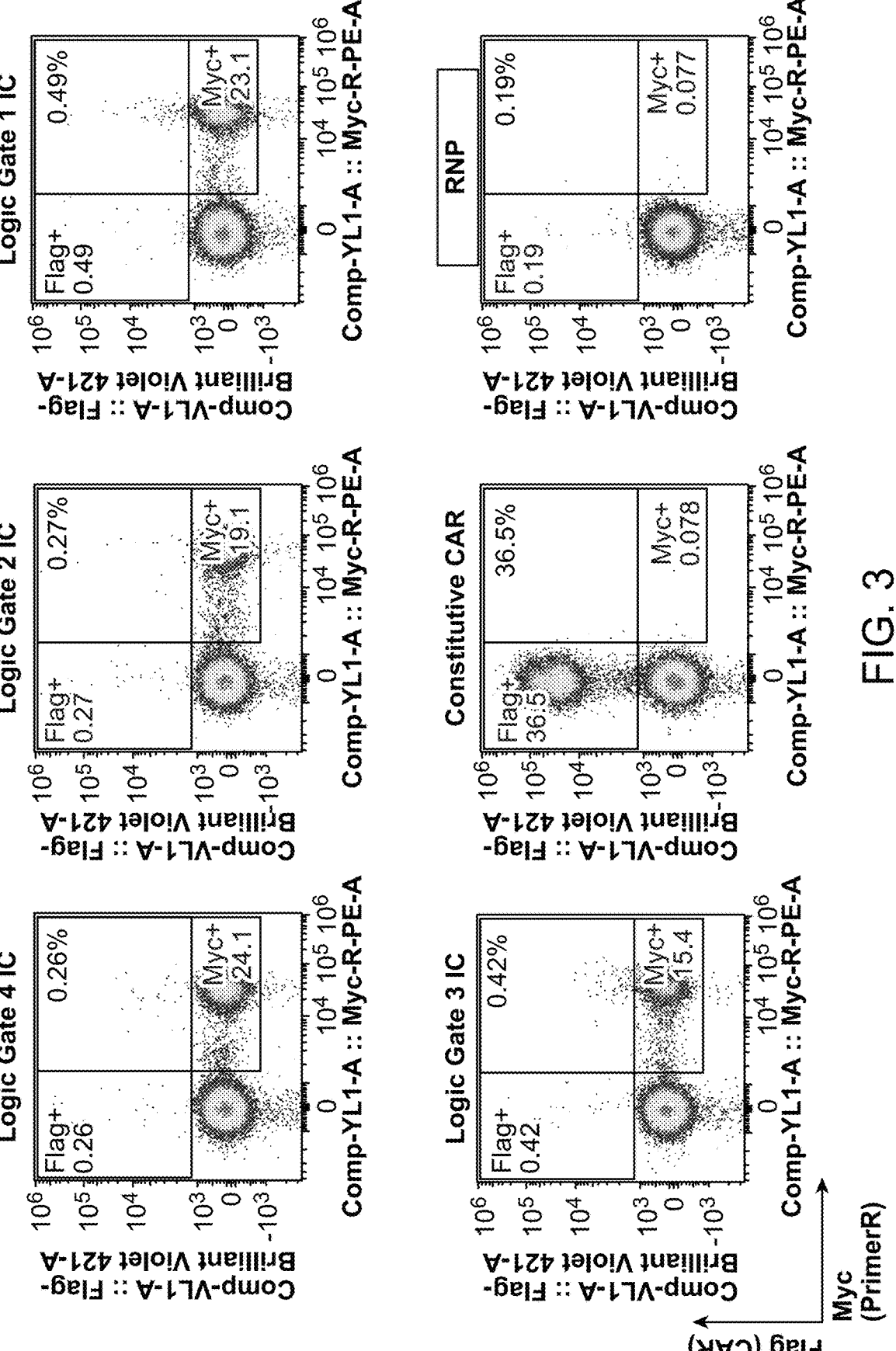
FIG. 3 shows that all ICT cells constitutively expressed the PrimeR construct.

All ICT cells constitutively expressed the PrimeR construct as shown by myc expression (FIG. 3). The inducible CAR was not expressed at basal state in the ICT cells, as indicated by the lack of FLAG expression (FIG. 3), indicating that the priming receptor had not induced expression of the CAR.

Figure 4:
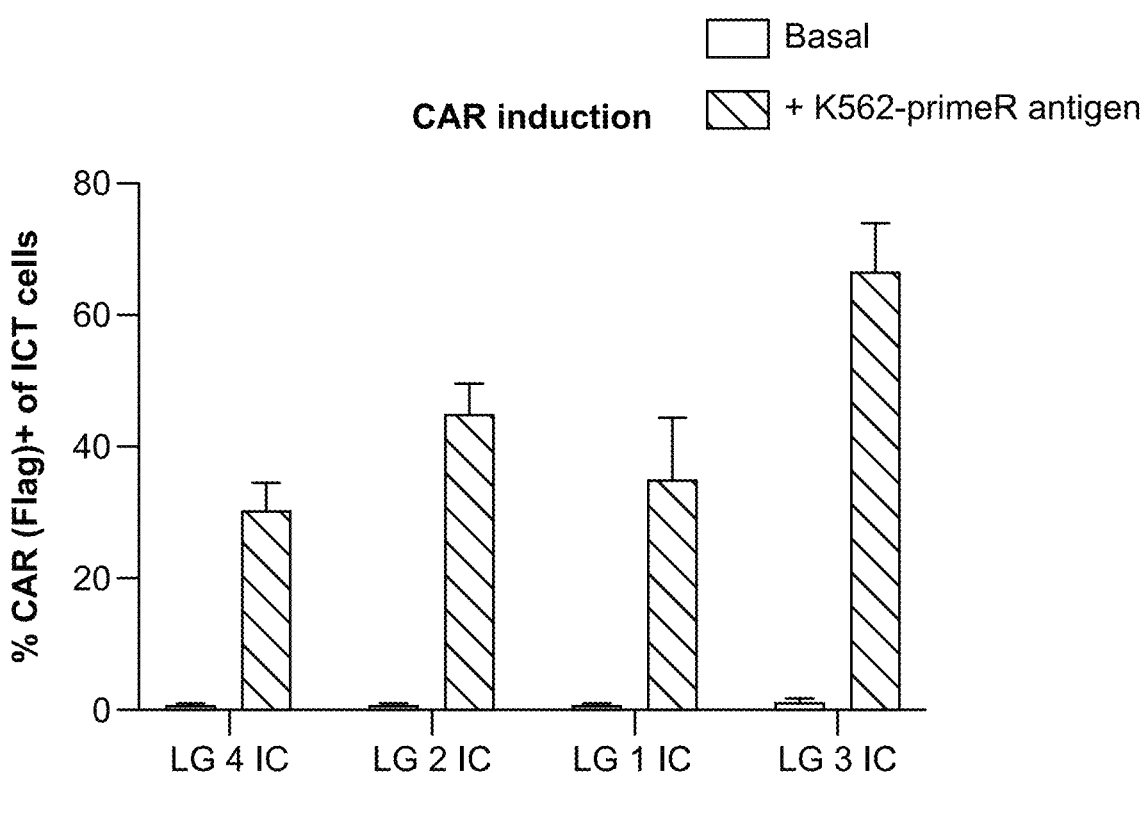
FIG. 4 shows that the ICT cells induced CAR expression when co-cultured with primeR-antigen expressing cell lines.

As shown in FIG. 4, the ICT cells induced CAR expression when co-cultured with primeR target antigen expressing cell lines. Numbers shown in FIG. 4 are the (% CAR)/(% KI normalized to at the start of the assay)*100. Thus, the logic gate circuit functioned correctly by not expressing the CAR in the absence of binding of the primeR to primeR target antigen (FIG. 3) and induction of expression of the CAR upon binding of the primeR to its cognate ligand on a target cell (FIG. 4).

As shown in FIG. 5, flow cytometry analysis revealed that ICT cells expressing the SPA (LG 1-4 ICs) exhibit approximately one log higher pSTAT3 expression when compared to the PrimeR-cells lacking a SPA (EGFRt). Edited T cells with a EGFRt (non-signaling) module in the place of a SPA does not exhibit increased pSTAT3 staining when compared to PrimeR-cells. Overall, the results indicate that ICTs expressing the SPA module exhibit increased STAT3 phosphorylation.

Figures 6A, 6B, 6C, 6D:
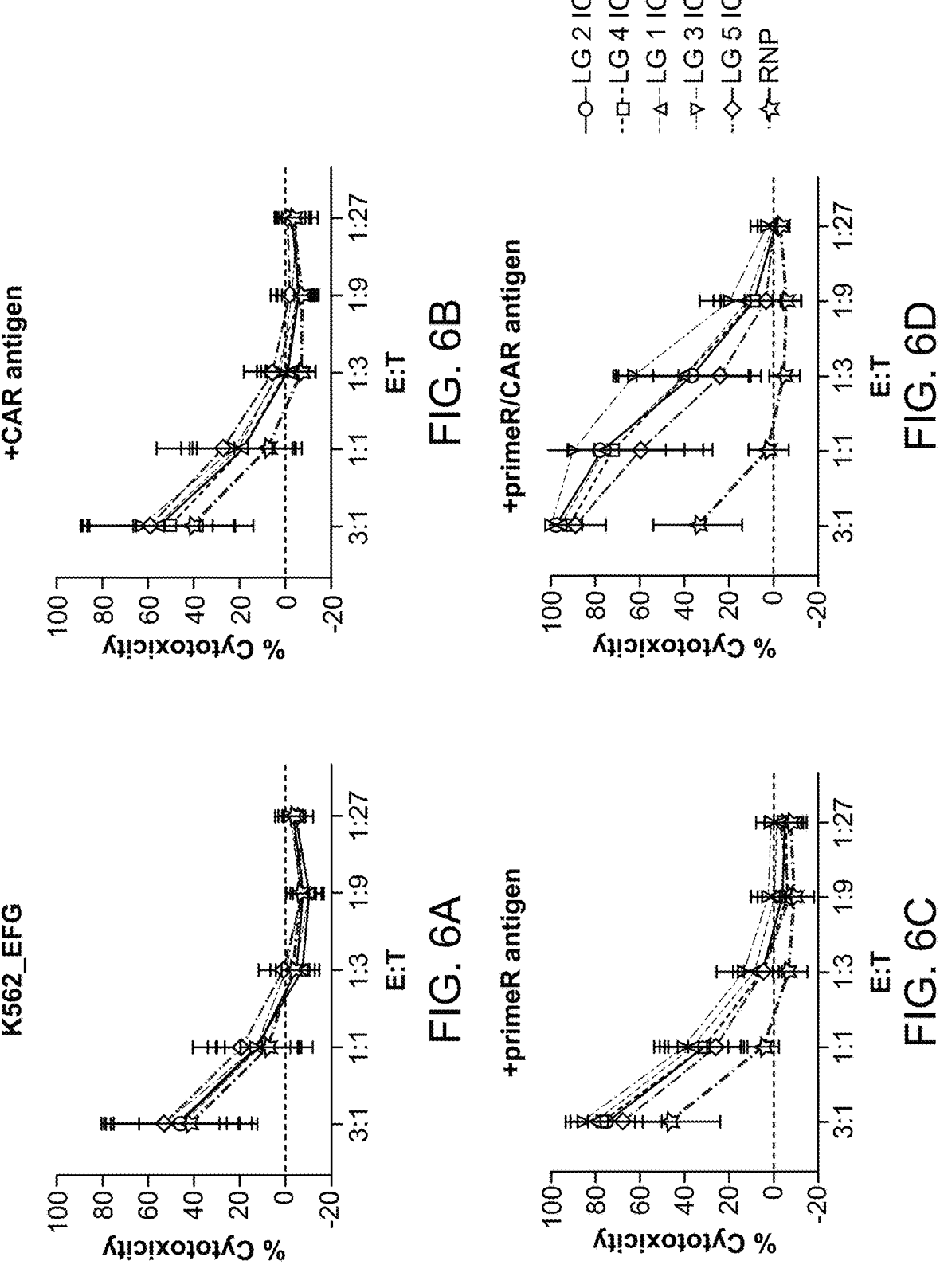
FIG. 6A shows cytotoxicity against parental K562 cells expressing neither CAR or primeR antigen.
FIG. 6B shows cytotoxicity against K562 cells expressing only CAR antigen, FIG. 6C cytotoxicity against K562 cells expressing only primeR antigen.
FIG. 6D shows cytotoxicity against K562 cells expressing both primeR antigen and CAR antigen.

ICTs expressing LG 1-5 IC's demonstrated cytotoxicity against only dual CAR target antigen and primeR target antigen expressing cells as compared to unedited control cells (RNP). FIG. 6A shows cytotoxicity against parental K562 cells expressing neither target antigen, FIG. 6B shows cytotoxicity against K562 cells expressing only CAR target antigen, FIG. 6C shows cytotoxicity against K562 cells expressing only primeR target antigen, and FIG. 6D shows cytotoxicity against K562 cells expressing both primeR target antigen and CAR target antigen. As shown in FIG. 6D, the ICTs exhibited cytotoxicity against only cells expressing both primeR target antigen and CAR target antigen as compared to unedited cells (RNP).

Figure 7:
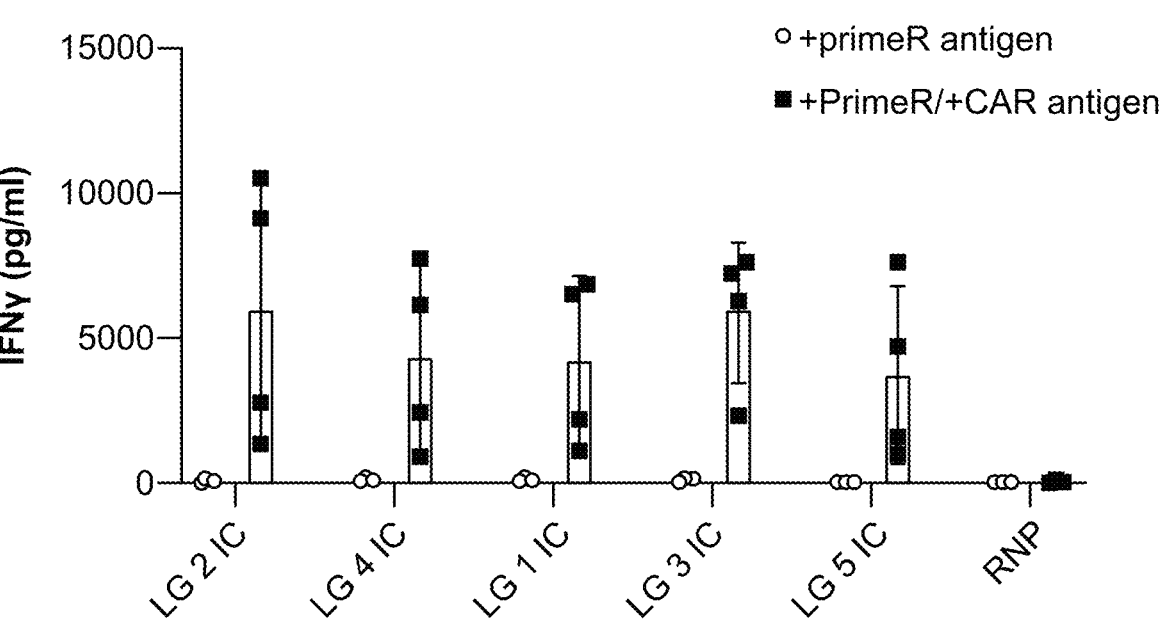
FIG. 7 shows IFN-γ production from ICTs expressing Logic Gates 1-5 only in supernatants taken from co-cultures where the target cells expressed both primeR antigen and CAR antigen.

IFN-γ production from ICTs expressing LG 1-5 ICs was observed only in supernatants taken from co-cultures where the target cells expressed both primeR target antigen and CAR target antigen (FIG. 7). Results from the cytokine analysis were consistent with the cytotoxicity data. Together, these data further demonstrate that ICT activity is driven by co-expression of primeR target antigen and CAR target antigen.

Figure 8A:
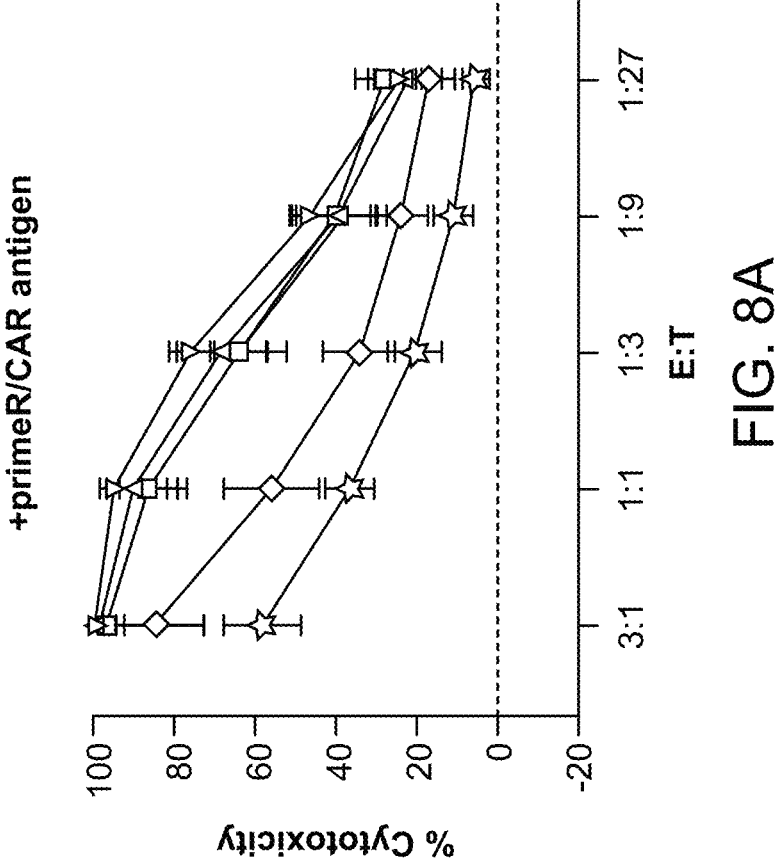
FIG. 8A shows that ICTs expressing LG 1-5 ICs demonstrated in vitro cytotoxicity against the endogenous +CAR/+ primeR antigen cell line.
Figure 8B:
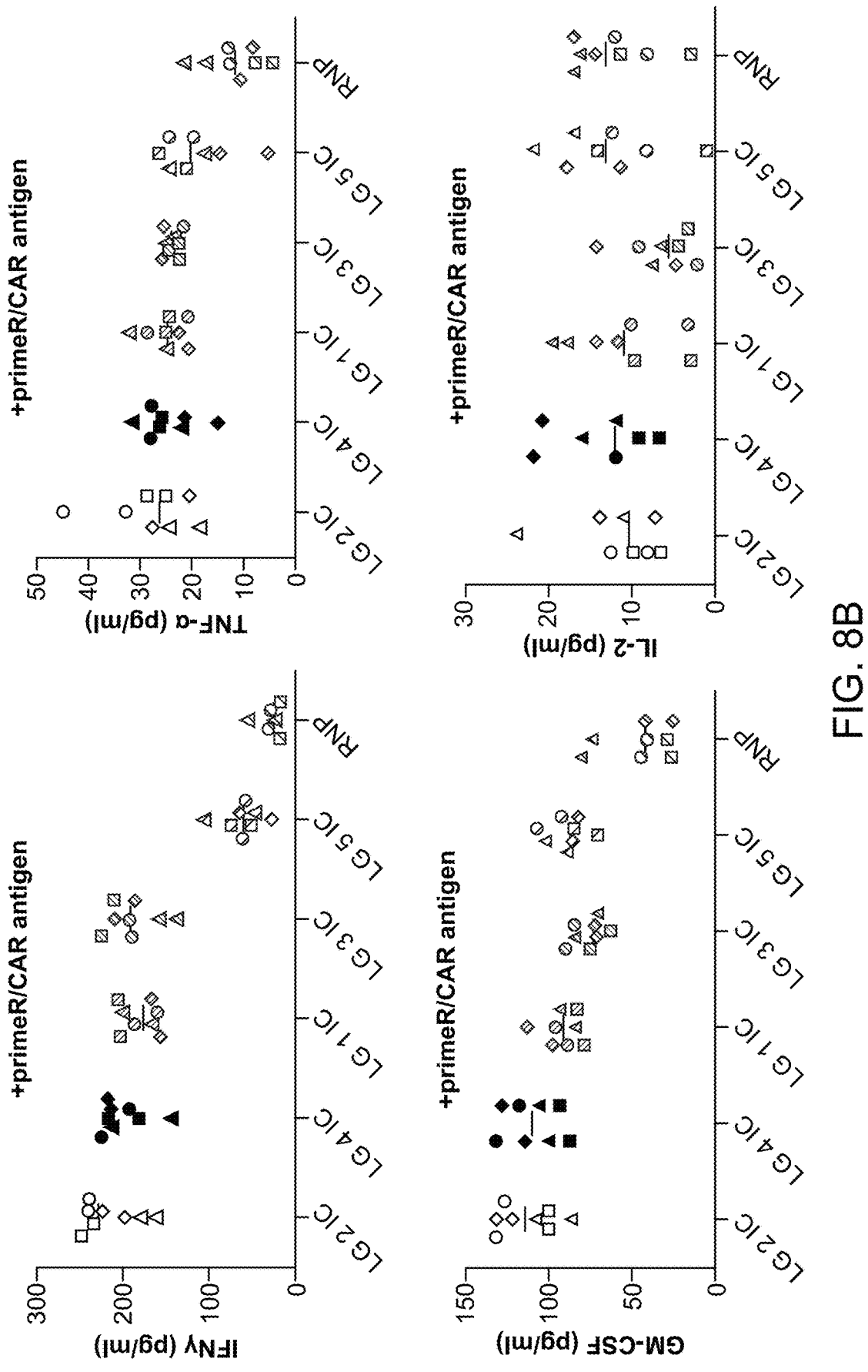
FIG. 8B shows IFNγ, TNFα, GM-CSF, and IL-2 secretion by ICT cells after co-culture with endogenous +CAR/+primeR antigen cells.

ICTs expressing LG 1-5 ICs demonstrated in vitro cytotoxicity against the cell line expressing endogenous CAR target antigen and engineered primeR target antigen (FIG. 8A). ICTs also secrete cytokines after co-culture with the CAR/primeR target antigen cell line. FIG. 8B shows IFNγ, TNFα, GM-CSF, and IL-2 secretion by ICT cells after co-culture with +CAR/+primeR target antigen cells. Thus, ICTs expressing Logic Gate 1-5 ICs secreted cytokines and killed ccRCC cell lines that express endogenous CAR antigen in the presence of primeR target antigen.

Figure 9:
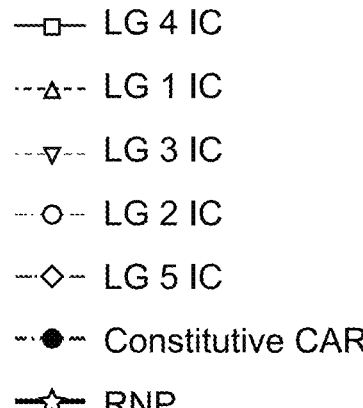
FIG. 9 shows that co-culture with HUVEC-primeR antigen cells induced expression of the CAR protein on ICT cells and specific killing of CAR antigen+ cells.
Figure 9:
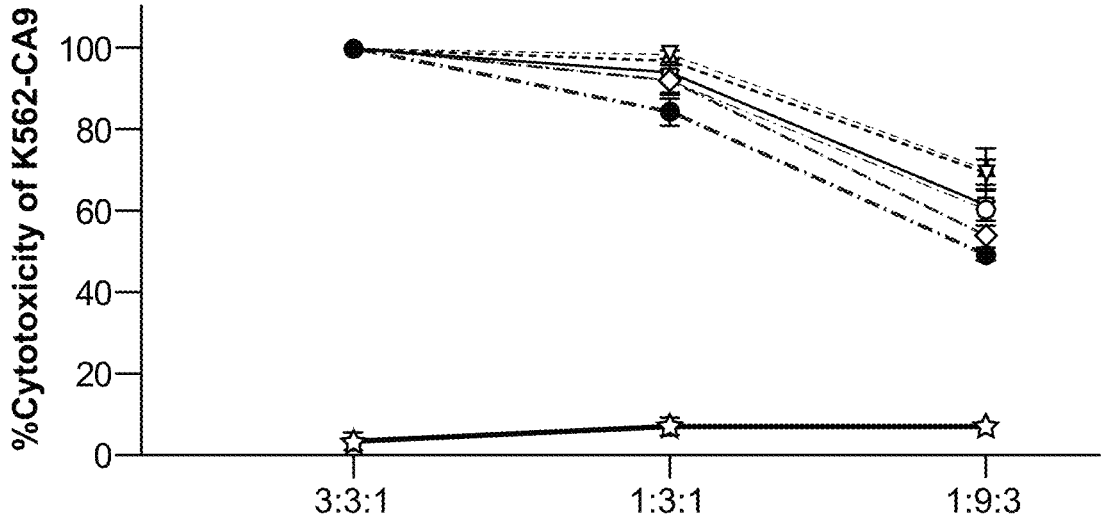

Co-culture with HUVEC-primeR antigen+ cells induced expression of the CAR protein on ICT cells and specific killing of CAR antigen positive cells was confirmed (FIG. 9). Thus, ICTs expressing Logic Gates 1-5 were capable of inducing CAR expression through interaction with primeR target antigen positive endothelial cells and subsequently specifically engaging and killing CAR target antigen positive tumor cells. Therefore, without wishing to be bound by theory, ICTs can be primed by binding to endothelial cells expressing primeR target antigen in order to express the CAR and then kill CAR target tumor cells.

Thus, logic gated ICT cells with signal pathway activators that utilize the presence of two antigens to trigger tumor cell killing to improve the therapeutic index of CAR T cells were developed, thereby enhancing tumor specificity. Induction of the CAR was gated on the expression of primeR target antigen found on the tumor neovasculature of ccRCC. When the priming receptor (PrimeR) binds the primeR target antigen, PrimeR engagement triggers proteolytic release of a transcription factor that induces expression of a CAR. The feasibility of vascular priming was confirmed using a transwell assay where ICTs were primed by a primeR target antigen expressing endothelial cell line and then migrated across the transwell membrane to kill CAR antigen expressing RCC cells.

When constitutively expressed in the ICT cells, the SPA resulted in significant enhancements in T-cell potency and expansion. Repetitive stimulation assays, wherein T cells were challenged with tumor cells every 2 days, show that Class I SPAs result in 6-log or higher improved tumor cell clearance over a 2-week assay period. (data not shown) Across various mouse xenograft models (FIGS. 2, 10A, 10D, 11B, and data not shown), SPA-expressing ICTs reach at least 6-fold improved tumor growth inhibition. RNAseq and ATACseq analysis indicate changes to gene expression profiles in T cells expressing Class I SPAs, with maintenance of T cell stem-like phenotypes, and restricted accessibility of various exhaustion marker genes (FIG. 2 and data not shown). Importantly, despite significantly increased levels of expansion, ICTs equipped with SPAs are not immortalized, showing no signs of cytokine-independent outgrowth. (data not shown) In addition, SPA-expressing ICT cells rapidly contract following tumor clearance in-vivo (FIGS. 10B, 10C, 10E, 10F).

Collectively, these results demonstrate that primeR/CAR plus SPA ICT cells can (i) selectively target antigens that cannot generally be safely targeted by conventional CARs; and (ii) overcome multiple suppressive mechanisms in the tumor microenvironment.

Example 2: In Vivo Efficacy of primeR and CAR Logic Gate T Cells Expressing a Synthetic Pathway Activator Materials and Methods RCC Efficacy Model Human ccRCC cells express endogenous levels of the CAR target antigen and were engineered to express physiological levels of the primeR target antigen. $2 \times 10^6$ primeR target antigen cells were inoculated into the right dorsal flank of five-six weeks old, female NSG MHC I/II DKO mice. Day 35 post tumor inoculation, mean tumor volume of 150 mm$^3$ was reached and tumor-bearing animals were randomized into various treatment groups such that mean tumor volume per group was within 10% of the overall mean. Seven mice/group were injected intravenously with a single dose of $0.15 \times 10^6$ of PrimeR+ ICT cells expressing one of the five LG ICTs described in Example 1 (LG 1 IC, LG 2 IC, LG 3 IC, LG 4 IC, or LG 5 IC) RNP or PBS. The study was repeated with ICTs generated from two different normal donors. Tumor volumes and body weight were recorded bi-weekly. Tumor volume was calculated as per formula $\frac{1}{2} * L * W^2$, where L is tumor length and W is tumor width.

Blood pharmacokinetics demonstrated the expansion of ICTs on day 14 followed by complete contraction by day 42 post T cell injection. PrimeR+ ICTs in mouse blood were quantified to track expansion of ICTs using flow cytometry with count bright beads for T cell quantification/volume. Mean and SEM plotted.

Dual Flank Model

Human ccRCC 786-O cells were engineered to express either the CAR target antigen and primeR target antigen or the CAR target antigen only. $2 \times 10^6$ 786-O-CAR+ and 786-O-CAR antigen+-primeR antigen+ cells were inoculated into the left and right dorsal flank respectively of five-six weeks old, female NSG MHC I/II DKO mice. Day 35 post tumor inoculation, mean tumor volume of 150-200 mm$^3$ was reached on each flank and tumor-bearing animals were randomized into various treatment groups such that mean tumor volume per group on the right flank was within 10% of the overall mean. Seven mice/group were injected intravenously with a single dose of $0.25 \times 10^6$ or $1 \times 10^6$ of PrimeR+ ICT cells, constitutive CAR T cells, RNP or PBS control. Tumor volumes and body weight were recorded bi-weekly. Tumor volume was calculated as per formula $\frac{1}{2} * L * W^2$, where L is tumor length and W is tumor width. (B) tumor volumes on the 786-O CAR only flank (left), and (C) tumor volumes on the 786-O-CAR+primeR+ flank (right). Data represents a single donor study with 7 mice per group, mean and SEM plotted.

Results

A498 RCC Efficacy Model

Figure 10A:
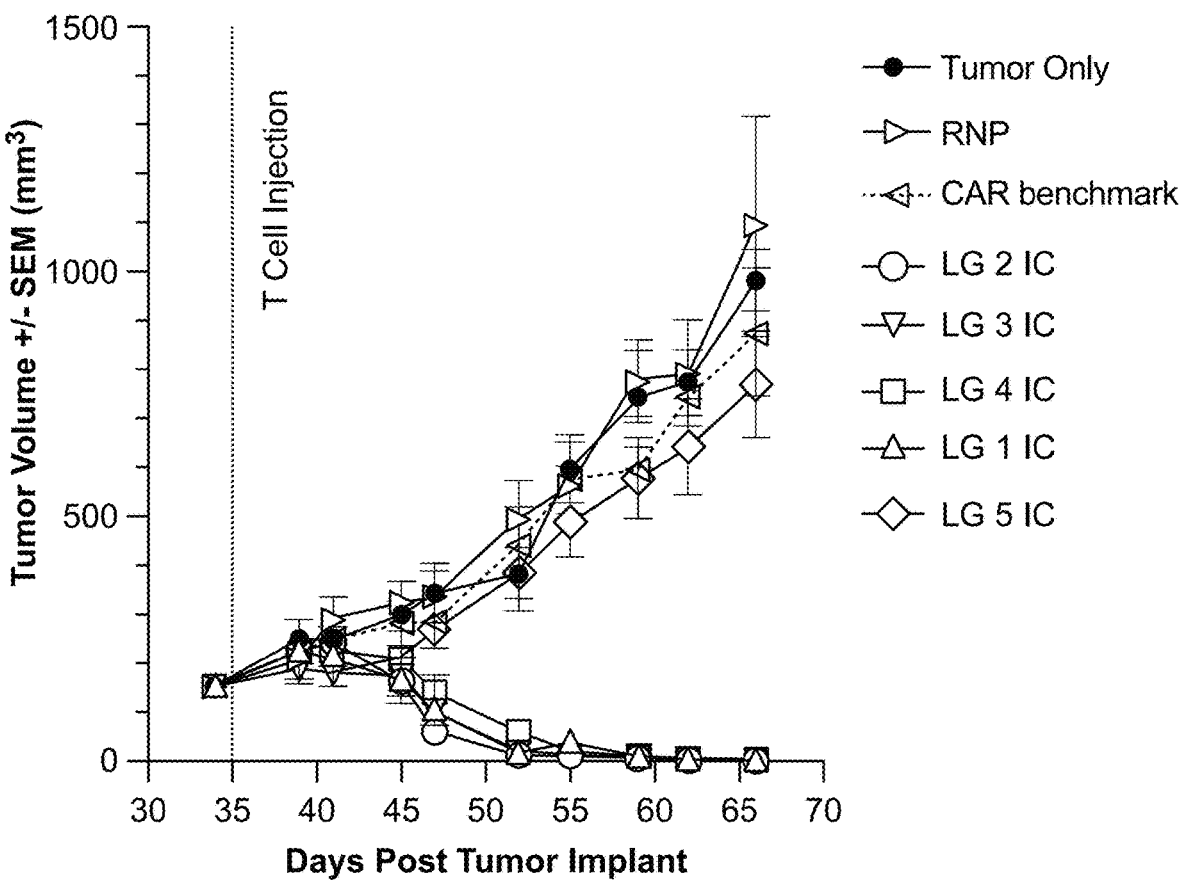
FIG. 10A shows the tumor volume post tumor implant in mice treated with ICTs expressing Logic Gates 1-5, RNP or PBS generated from donor 1.
Figure 10B:
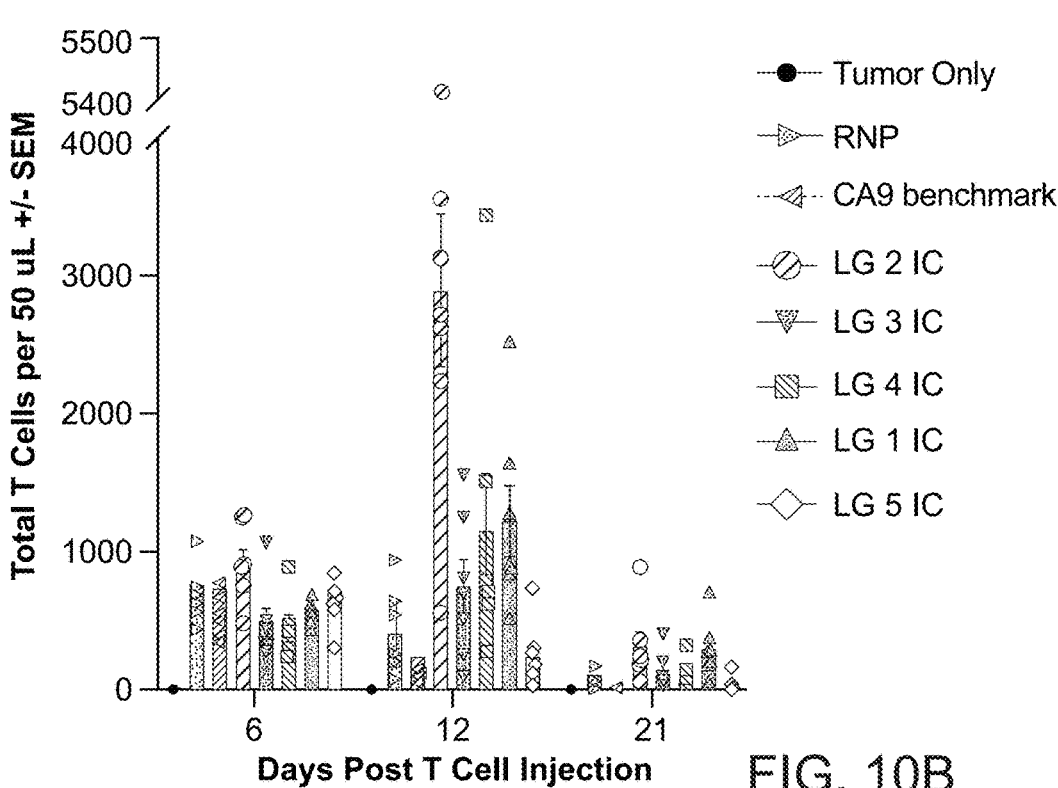
FIG. 10B shows the total T cells and expansion of the ICTs on day 12 post inoculation followed by contraction by day 21.
Figure 10C:
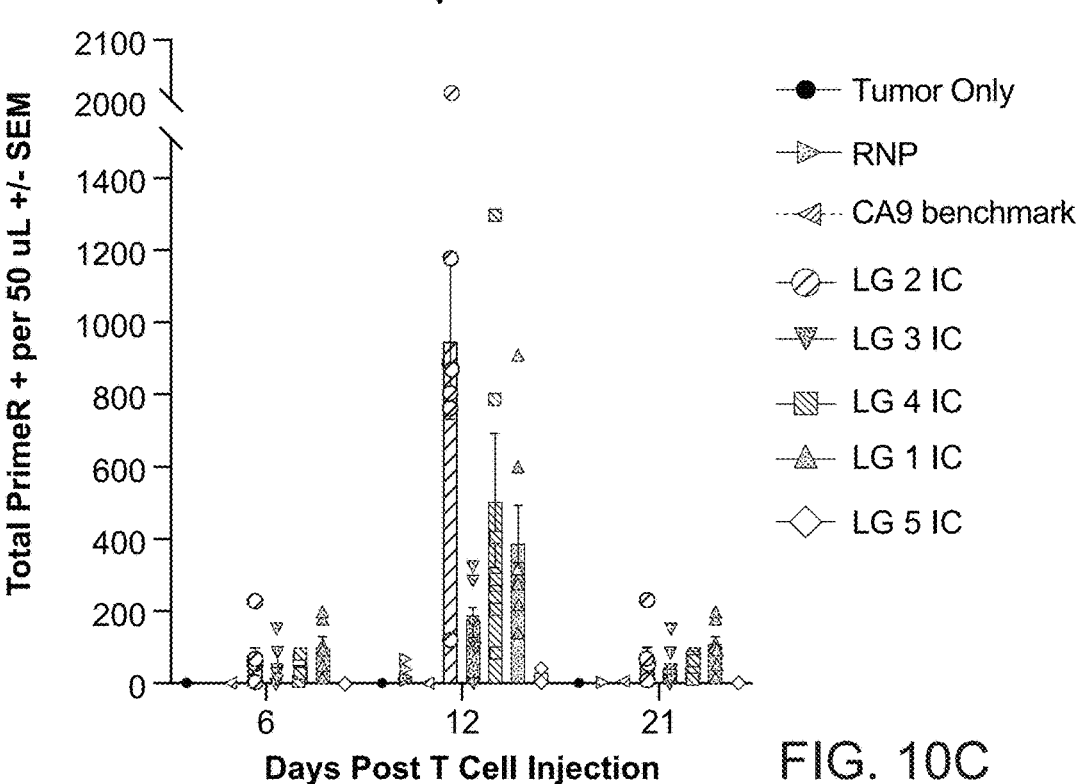
FIG. 10C shows total T cells expressing the priming receptor on days 12 and 21.
Figure 10D:
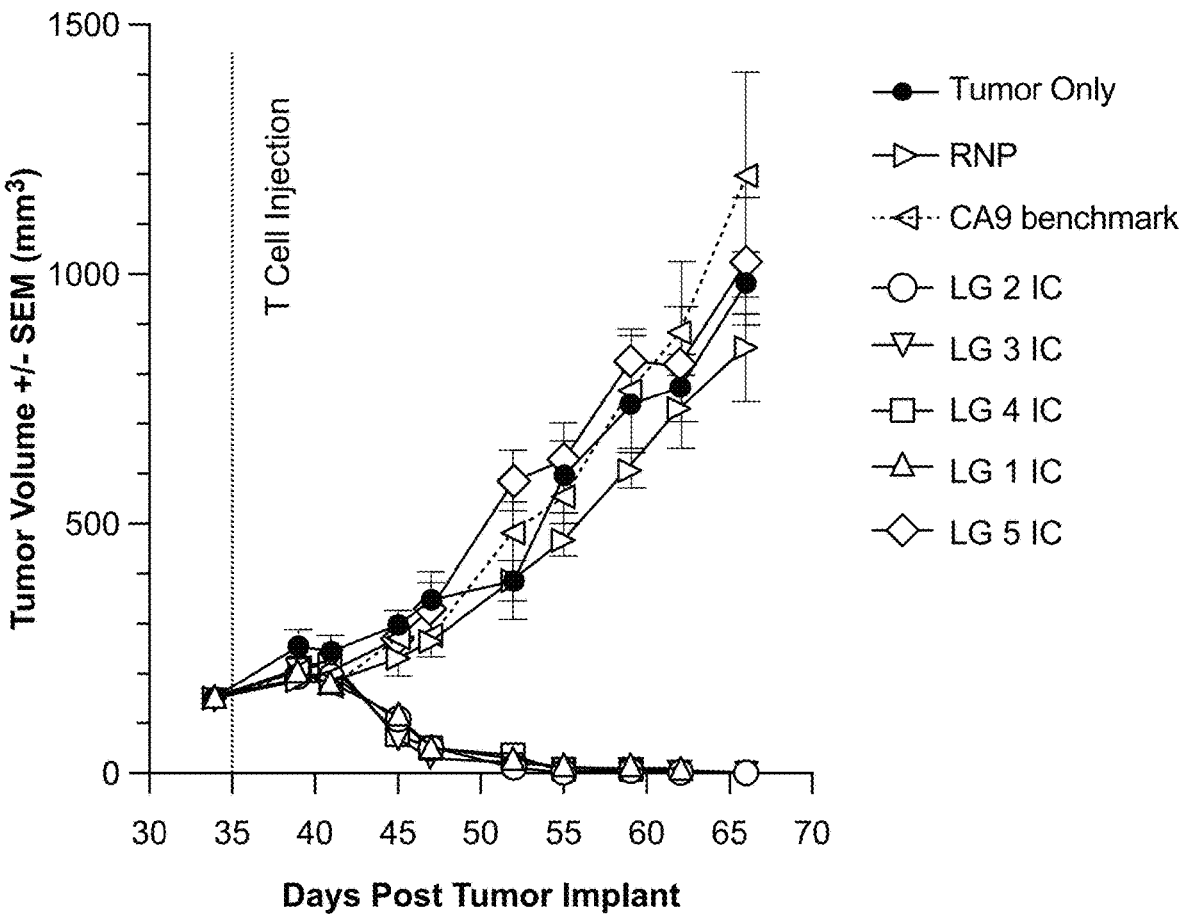
FIG. 10D show the tumor volume post tumor implant in mice treated with ICTs expressing Logic Gates 1-5, RNP or PBS generated from donor 2.
Figure 10E:
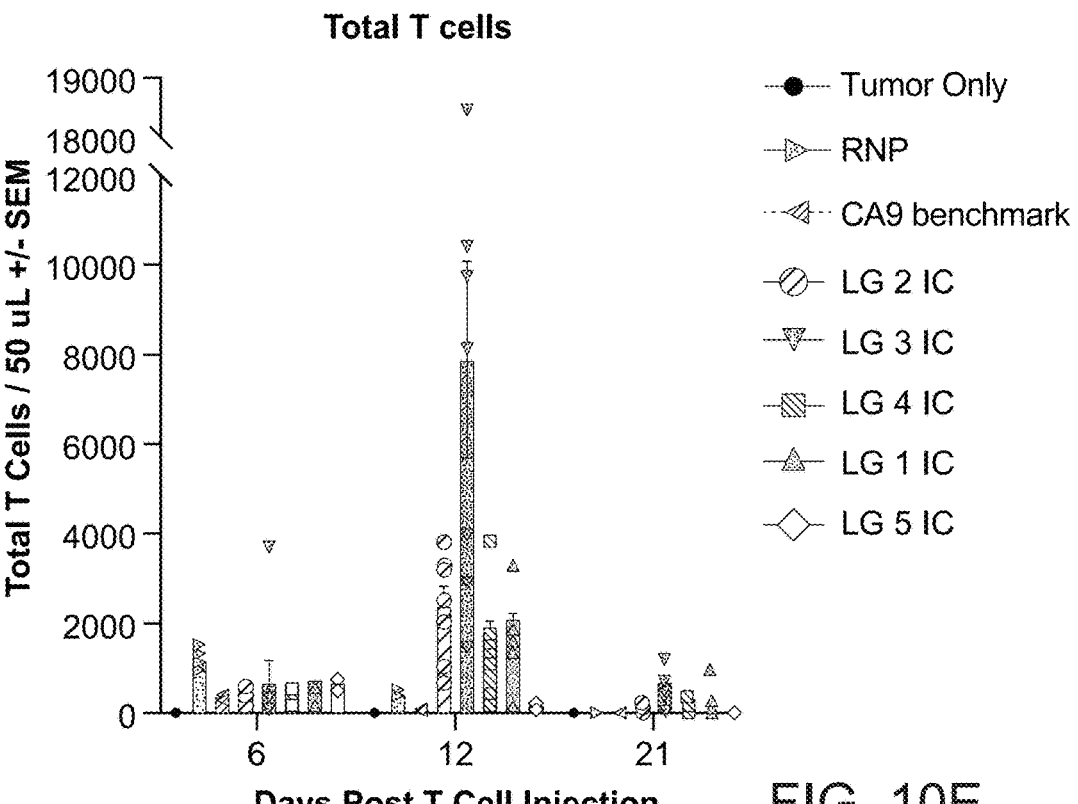
FIG. 10E shows the total T cells and expansion of the ICTs on day 12 post inoculation followed by contraction by day 21.
Figure 10F:
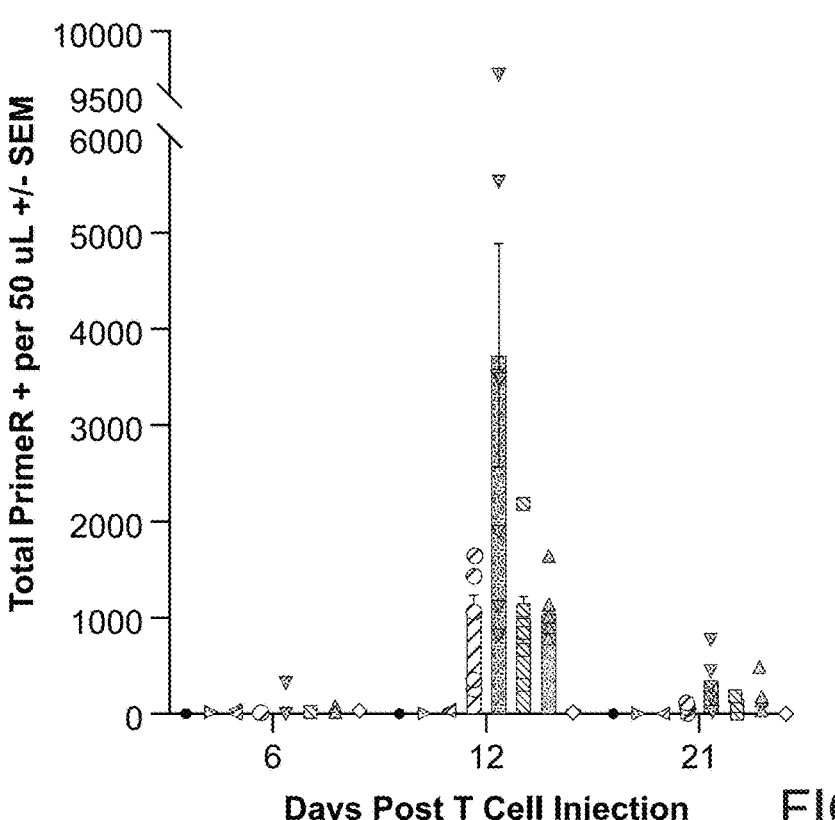
FIG. 10F shows total T cells expressing the priming receptor on days 12 and 21.

ICTs expressing LG 1-5 ICs showed tumor elimination in a ccRCC model. FIGS. 10A and 10D show the tumor volume post tumor implant in mice treated with ICTs expressing Logic Gates 1-5, RNP or PBS generated from T cells from either donor 1 (FIGS. 10A-C) or donor 2 (FIGS. 10D-F). FIGS. 10B and 10E show the total T cells and expansion of the ICTs on day 12 post inoculation followed by contraction by day 21. FIGS. 10C and 10F show total T cells expressing the priming receptor on days 12 and 21. In both replicates, the ICT cells demonstrated significant tumor-growth inhibition in mice (P<0.05).

Dual Flank Model

Figures 11A, 11B:
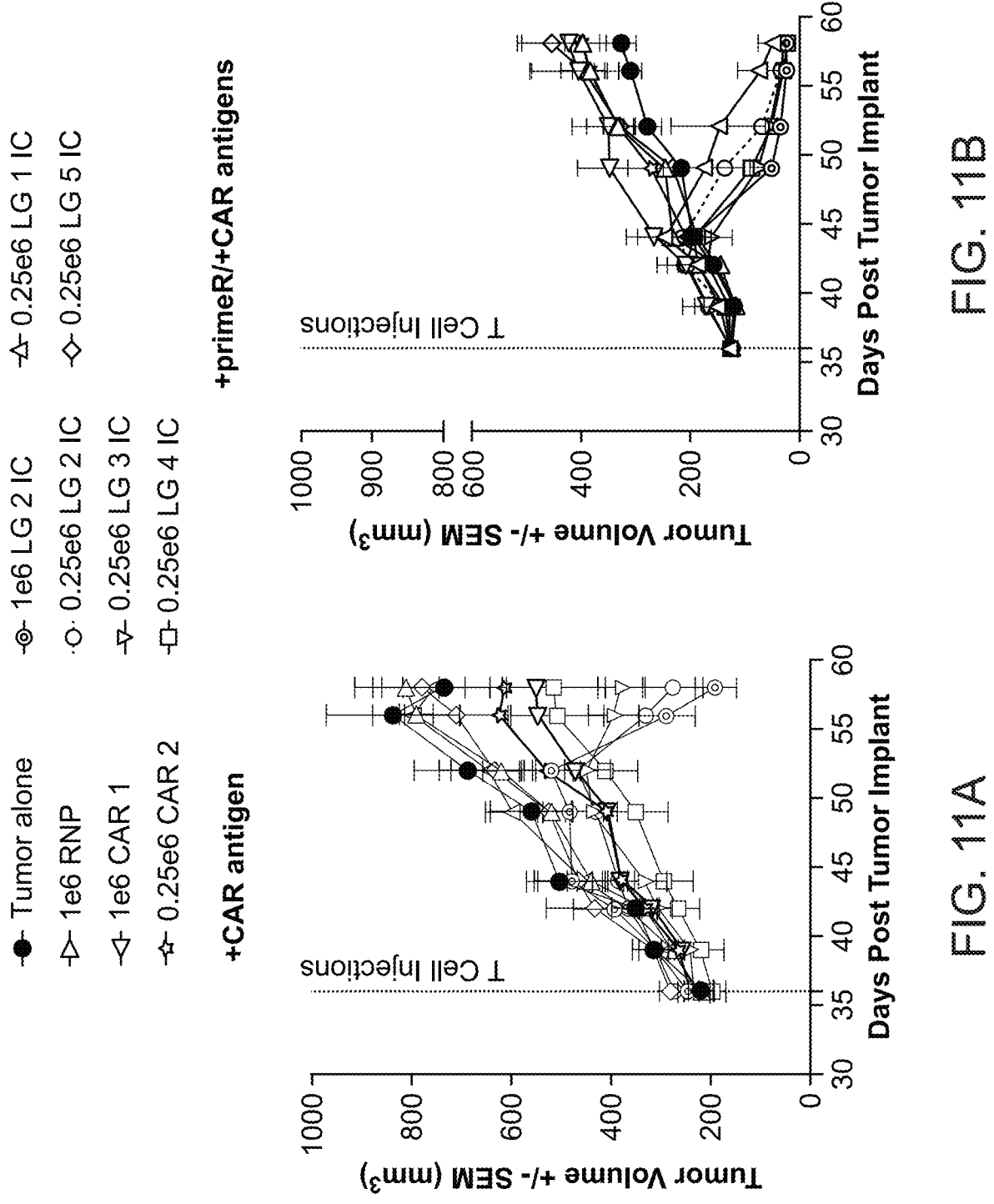
FIG. 11A shows tumor growth inhibition (TGI) in the single positive CAR antigen-only flank.
FIG. 11B shows tumor growth inhibition (TGI) in the dual positive primeR antigen/CAR antigen flank.

The ICTs expressing LG 1-5 ICs showed specificity in a dual flank model (FIG. 11A-B). Greater tumor growth inhibition (TGI) was observed in the dual positive primeR/CAR flank (FIG. 11B) than the single positive CAR-only flank (FIG. 11A). Thus, the dual flank xenograft model shows that logic gated circuits (ICTs) more selectively killed tumors that express both CAR and primeR target antigens, and not tumors that express CAR alone.

Example 3: Generation and Characterization of Novel Synthetic Pathway Activators Methods Generation and Synthesis A library of novel gp130-based STAT1/3 synthetic pathway activators (SPAs) was generated through diversification of extracellular and intracellular domains, multimerization modalities, membrane anchor modalities, and epitope tags/signaling peptides. The SPAs were generated to explore the optimization and improvement of SPA performance such as enhanced potency, reduced immunogenicity, detection capabilities, and reduced gene size. Various forms of the gp130 intracellular domain (ICD) were used, including the full length gp130 ICD, as well as truncations comprising deletions of the gp130 ICD Δ707-755, Δ771-811, Δ818-901, and combinations therein. A gp130 Y759F mutation was also included in some ICD constructs. Multimerization modalities used were unpaired cysteines, a leucine zipper, a BCR ectodomain (SEQ ID NO: 239), and a VASP tetramerization domain (SEQ ID NO: 240). Extracellular domains used were the full CD34 ectodomain (SEQ ID NO: 242), a CD34 epitope (SEQ ID NO: 238), a BCR ectodomain (SEQ ID NO: 239), a thrombopoetin receptor domain (SEQ ID NO: 243), and an erythropoietin receptor (EpoR) ectodomain (SEQ ID NO: 241). Membrane anchor modalities used were prenylation and myristoylation domains derived from src, fyn, or lck. The prenylation modification was also used at the C terminus of some SPAs. Some SPAs also comprised a CD8alpha hinge domain (FACD). In some SPAs, the SPA expression was inducible based on T cell activation. Other SPAs were constitutively expressed. The sequences of the novel SPAs are provided in SEQ ID NOs: 1-58 and 63-104. The SPAs were screened first by a pSTAT activation screen, then an in vitro functional assessment, and finally an in vivo efficacy assessment.

Activity of the novel pathway activators were assessed by intracellular pSTAT staining following a 24 hour serum starve. ICTs expressing a SPA construct module were starved for 24 hours with no antigen stimulation or cytokine support, then fixed, permeabilized, and stained for pSTAT proteins. pSTAT3 and pSTAT1 MFI values were measured for two independent donors and the average value was plotted in a heat map.

Cytokine Induction

A diverse range of ICTs expressing novel STAT1/STAT3 SPAs were cultured with K562 cells at a 1:1 ratio. Following 72 hours of co-culture, supernatants were isolated and analyzed by Luminex for granzyme B and IL10 production. Representative cytokines displaying diverse expression levels are shown (plotted in groups according to pSTAT1 levels).

Repetitive Stimulation and Memory Phenotype

T cells expressing a logic gate (ICTs) and a diverse range of novel Class I STAT1/STAT3 SPAs were challenged in a 14-day repetitive stimulation assay with K562 cells expressing primeR and CAR antigens with IL-2 supplementation. ICTs and tumor cells were re-normalized to a fixed number every other day to maintain a 1:1 E:T ratio. The total tumor cell growth and T-cell expansion over the course of the experiment was normalized to the EGFRt control and plotted in groups according to pSTAT1 levels. L-gp130 was used as a control SPA. Additional controls included expressing cJun, EGFRt, mbIL-15, and IL7Ra-IL7 in the ICTs.

Memory phenotype was measured by flow cytometry for CD45RA and CD27 expression at day 0 and repetitive stimulation assay endpoint (day 14) and plotted in groups according to pSTAT1 profile.

Results

Figure 12A:
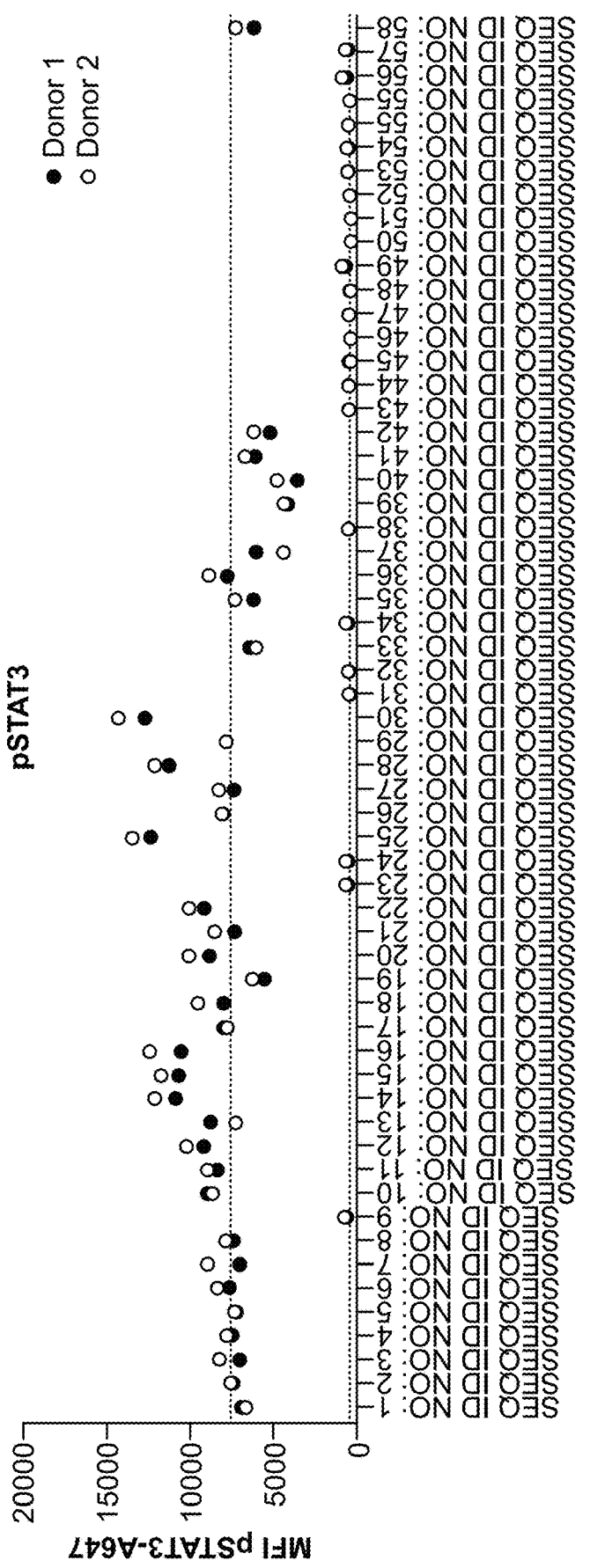
FIG. 12A shows level of pSTAT3 signaling induced by expression of the indicated SPA in a T cell after serum starvation.
Figure 12B:
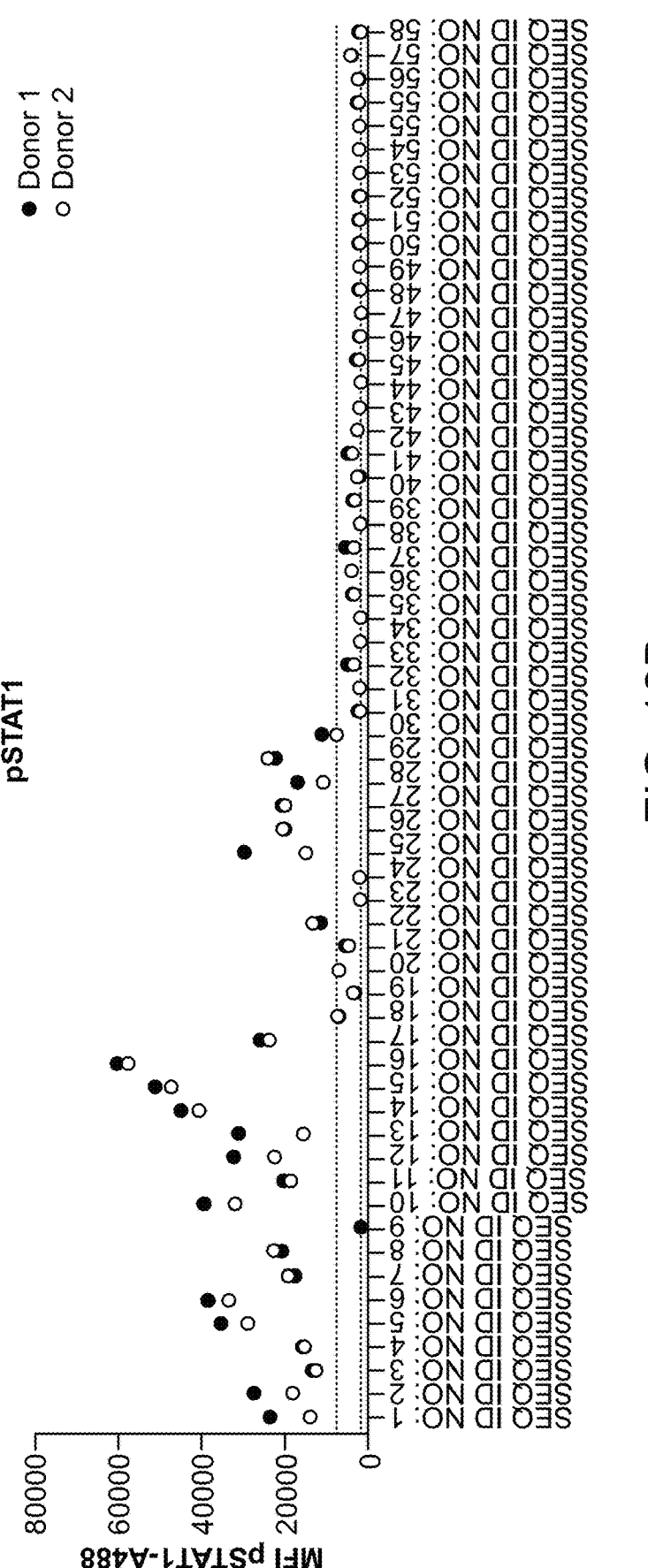
FIG. 12B shows level of pSTAT1 signaling induced by expression of the indicated SPA in a T cell after serum starvation FIG. 13 provides a pSTAT1 vs pSTAT3 heatmap for the indicated SPAs.
Figure 13:
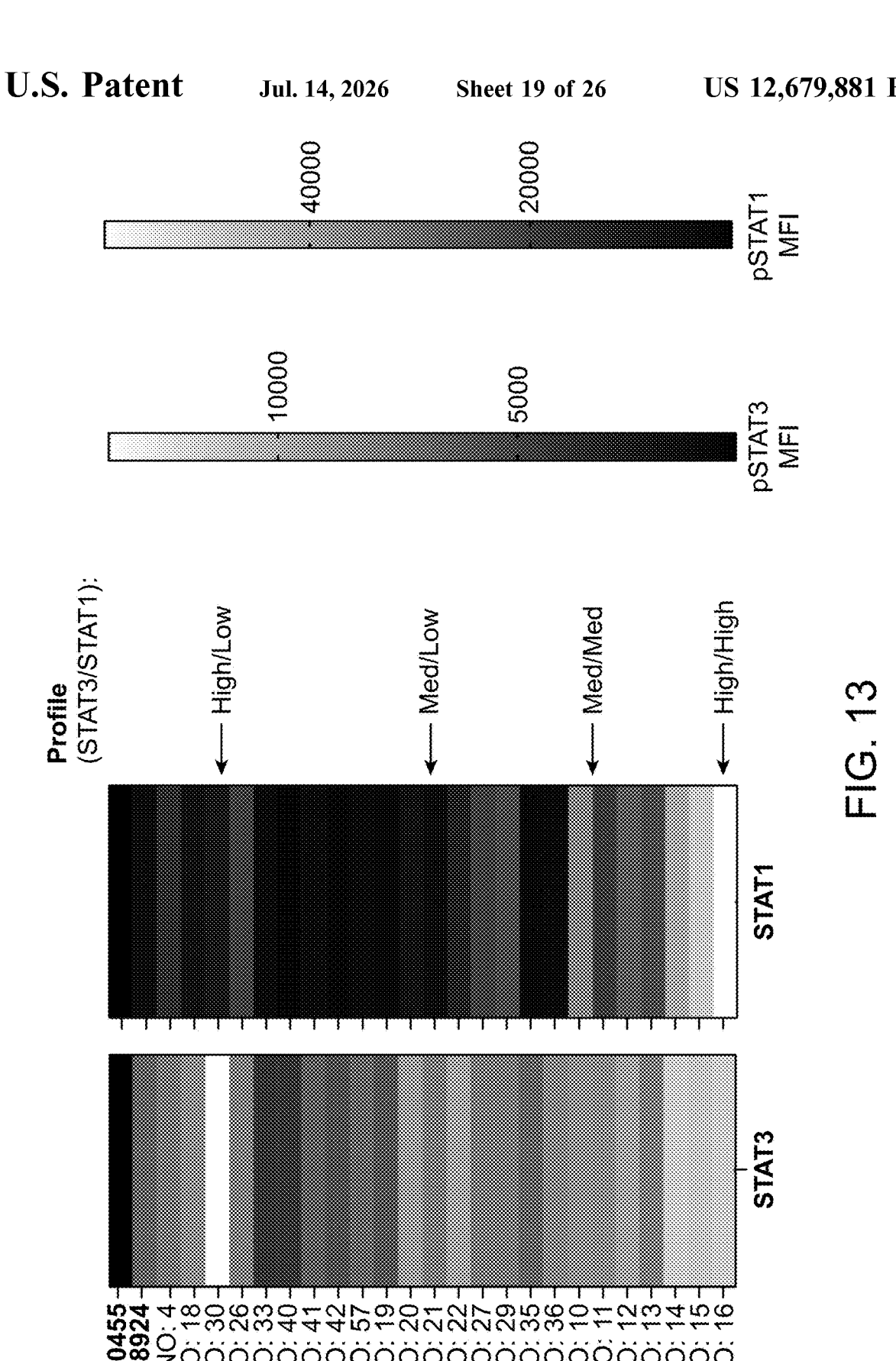

Approximately 60% of the novel SPAs demonstrated elevated levels of pSTAT1 (FIG. 12B) and/or pSTAT3 (FIG. 12A) relative to a logic gate ICT expressing an inert truncated EGFR molecule in place of a SPA. The pSTAT1 vs pSTAT3 heatmap highlights the combinatorial diversity achieved through modification of the SPA architecture (FIG. 13). Thus, without wishing to be bound by theory, STAT-inducing cell-surface receptors demonstrate remarkable flexibility in their architecture, permitting diversification of STAT profiles.

Figure 14:
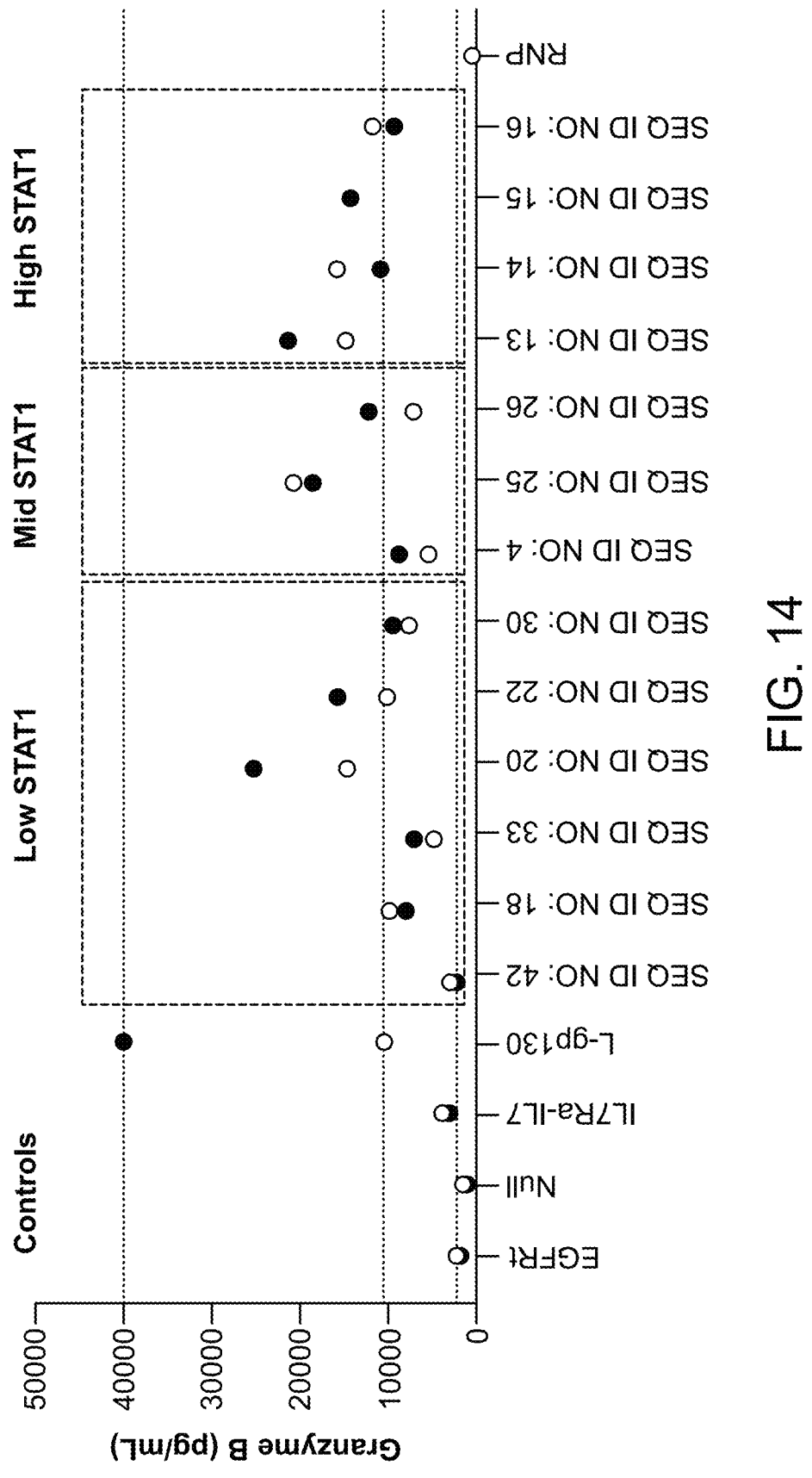
FIG. 14 shows the levels of granzyme B (top panel) and IL-10 (bottom panel) induced by the indicated SPA.
Figure 14:
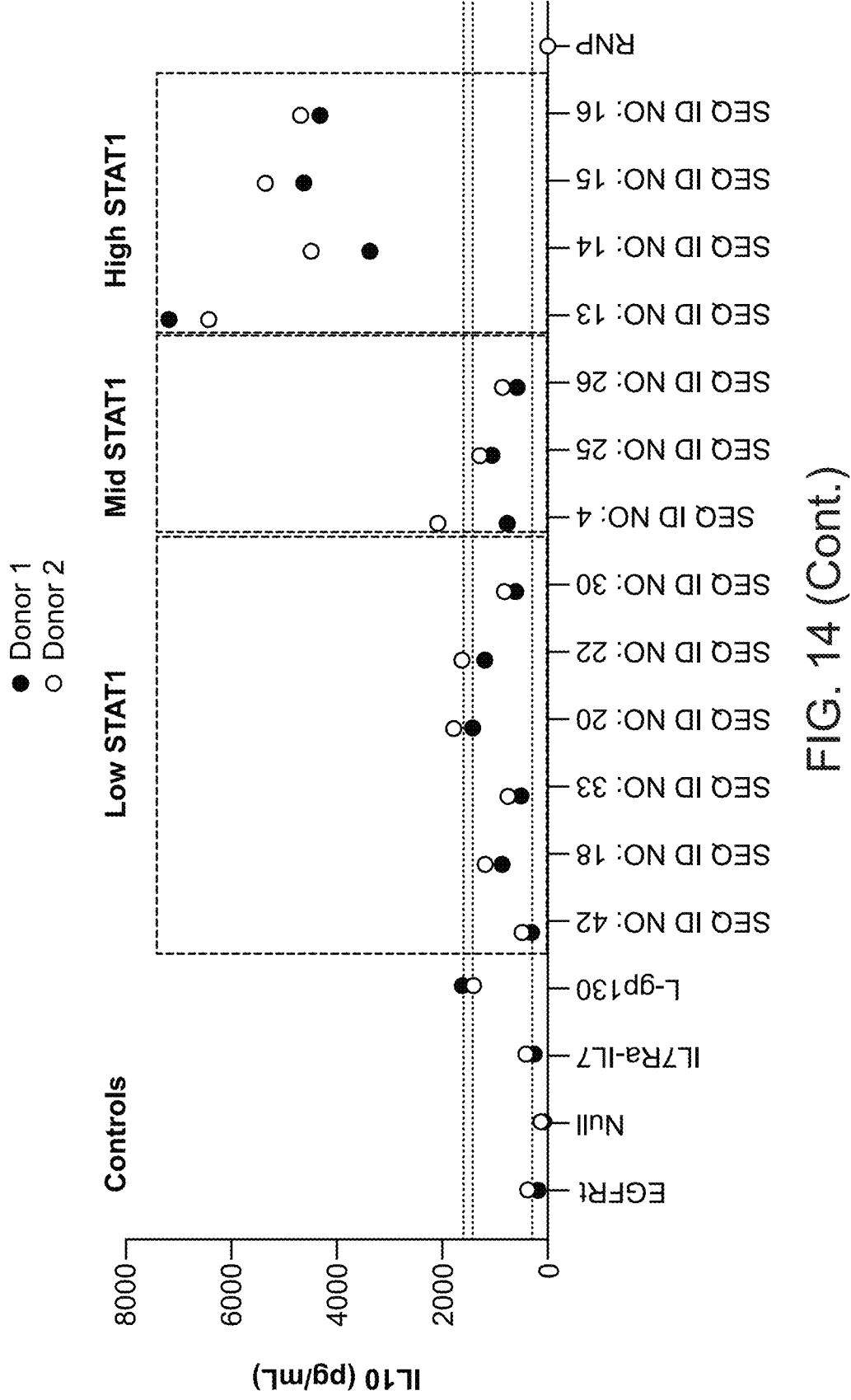

The diversity in pSTAT1 and pSTAT3 signaling resulted in varied cytokine secretion, including Granzyme B (top panel FIG. 14) and IL-10 (bottom panel FIG. 14). Thus, pSTAT1/3 signaling diversity achieved through the novel SPAs drove cytokine responses.

Figure 15:
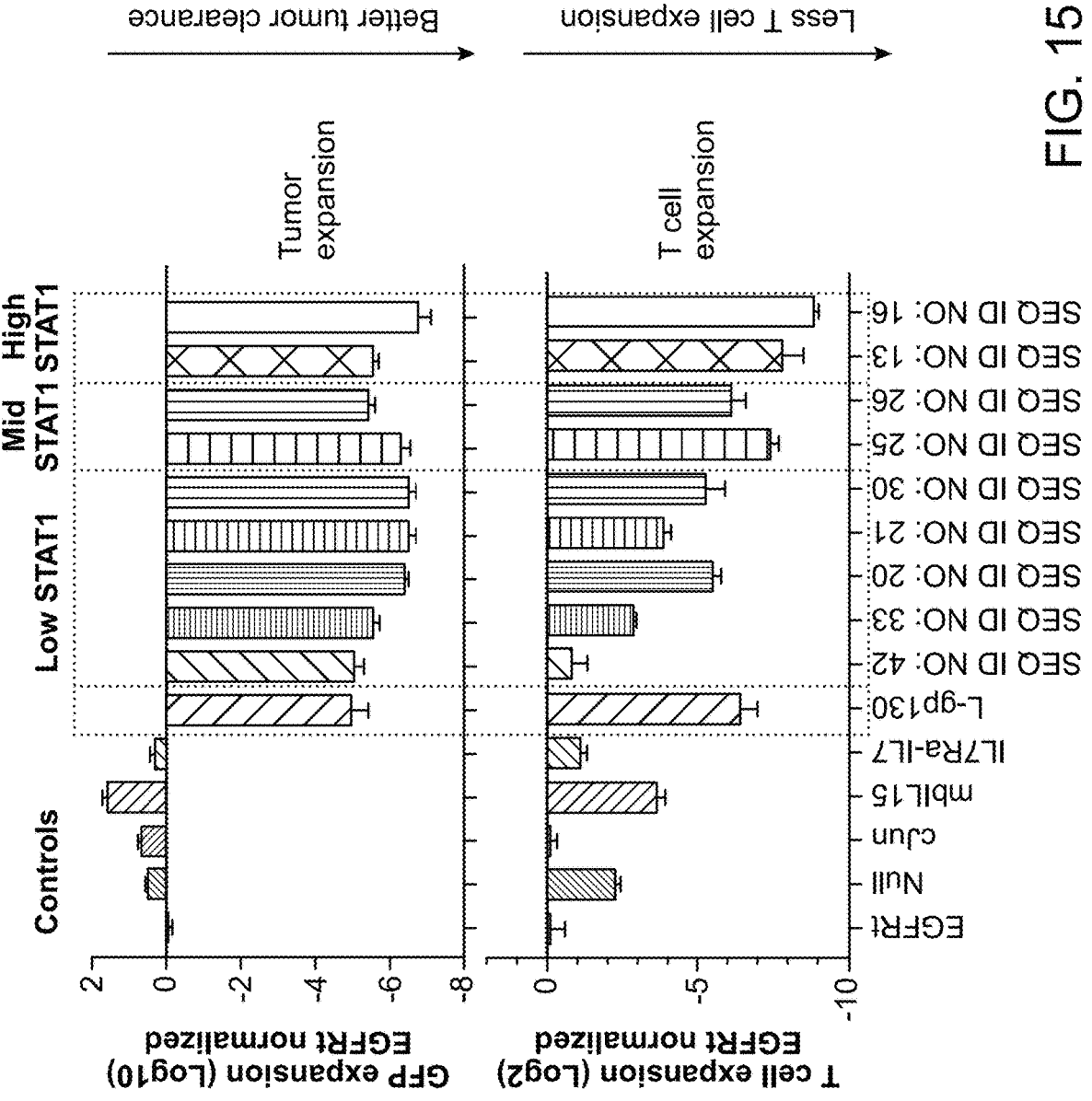
FIG. 15 shows the tumor cell clearance (top panel) and T cell expansion (bottom panel) of tumor cells expressing the logic gate antigens in a repetitive stimulation assay.

All of the novel STAT1/STAT3 SPAs demonstrated dramatic levels of tumor clearance in the repetitive stimulation assay. FIG. 15 (top panel) shows the tumor expansion as compared to the control ICTs under chronic antigen stimulation. ICTs expressing the novel SPAs significantly reduced tumor expansion and resulted in increased tumor clearance as compared to control ICTs. FIG. 15 (bottom panel) shows T cell expansion. Without wishing to be bound by theory, the novel Class I SPAs thus demonstrated both superior anti-tumor activity as compared to L-gp130 (SEQ ID NO: 62) and also demonstrated a favorable safety profile by rapidly contracting after tumor clearance.

Figure 16:
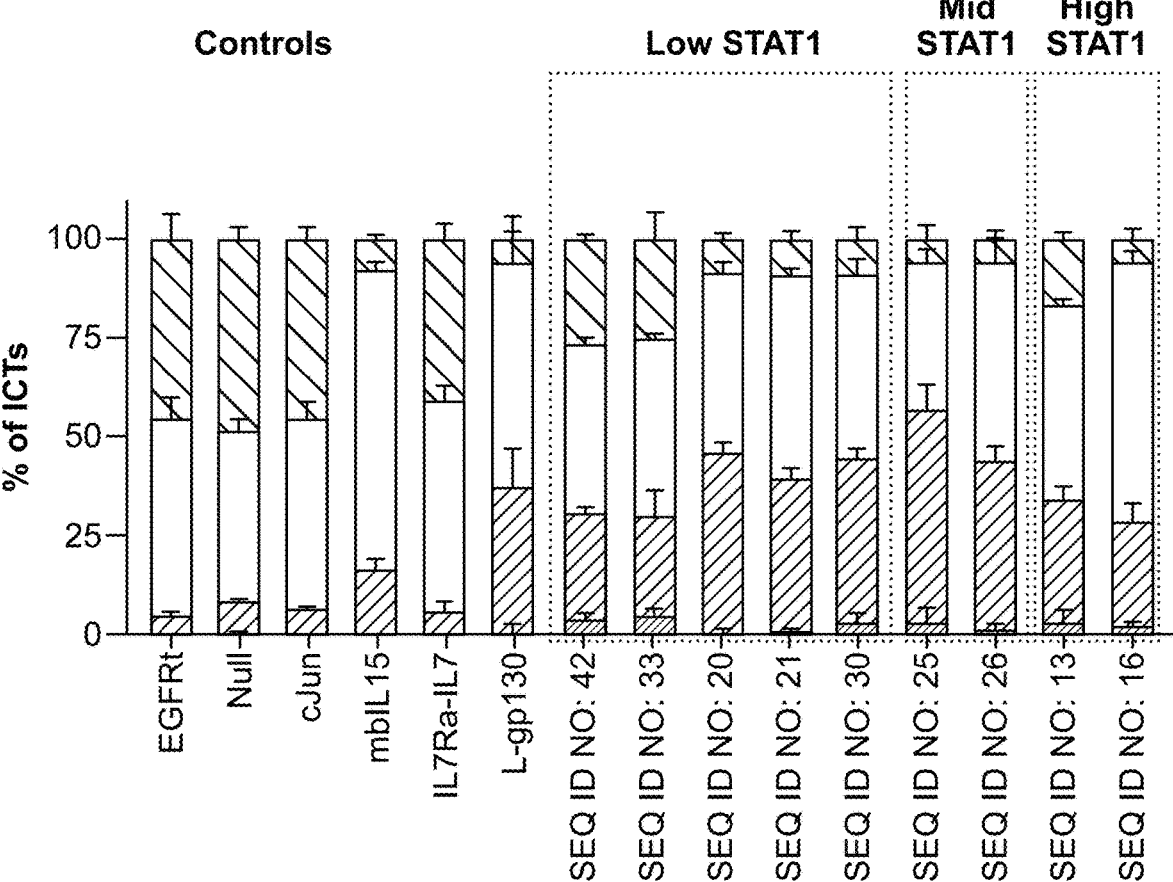
FIG. 16 shows the percent of ICT cells expressing that indicated SPA that expressed the indicated cell markers after a repetitive stimulation assay.

The novel SPAs drove diverse memory phenotypes and functional phenotypes based on pSTAT profiles (FIG. 16). FIG. 16 shows the percent of ICT cells expressing the novel SPAs that expressed CD45RA and/or CD27 and the corresponding T cell type (e.g., Tscm, Tem, Teff) after the repetitive stimulation assay.

Without wishing to be bound by theory, the novel SPAs thus represent a novel, improved, tunable, T cell intrinsic approach for engineering cell fates that result in potent anti-tumor properties, e.g., as compared to L-gp130.

Example 4: In Vivo Efficacy of Second primeR and CAR Logic Gate T Cells Expressing a Synthetic Pathway Activator

Materials and Methods

In a mesothelioma (MSTO) solid tumor model, mice were engrafted with MSTO tumors expressing different primeR and CAR antigens as compared to Example 2. 300,000 ICT cells expressing the exemplary primeR and CAR logic gate and the novel Class I SPAs (SPAs of SEQ ID NOs: 20, 30, or 16) or the exemplary primeR and CAR logic gate and no additional SPA were administered intravenously when tumors reached 100 mm³. T cells expressing the exemplary primeR and CAR logic gate and L-gp130 (SPA001, SEQ ID NO: 62) were used as an additional control. Blood was drawn weekly for pharmacokinetics (PK) studies on days 7, 14, 21, and 28 post T cell injection. Tumor growth inhibition (TGI) was measured 3× weekly for 45 days post T cell injection.

Results

Figure 17:
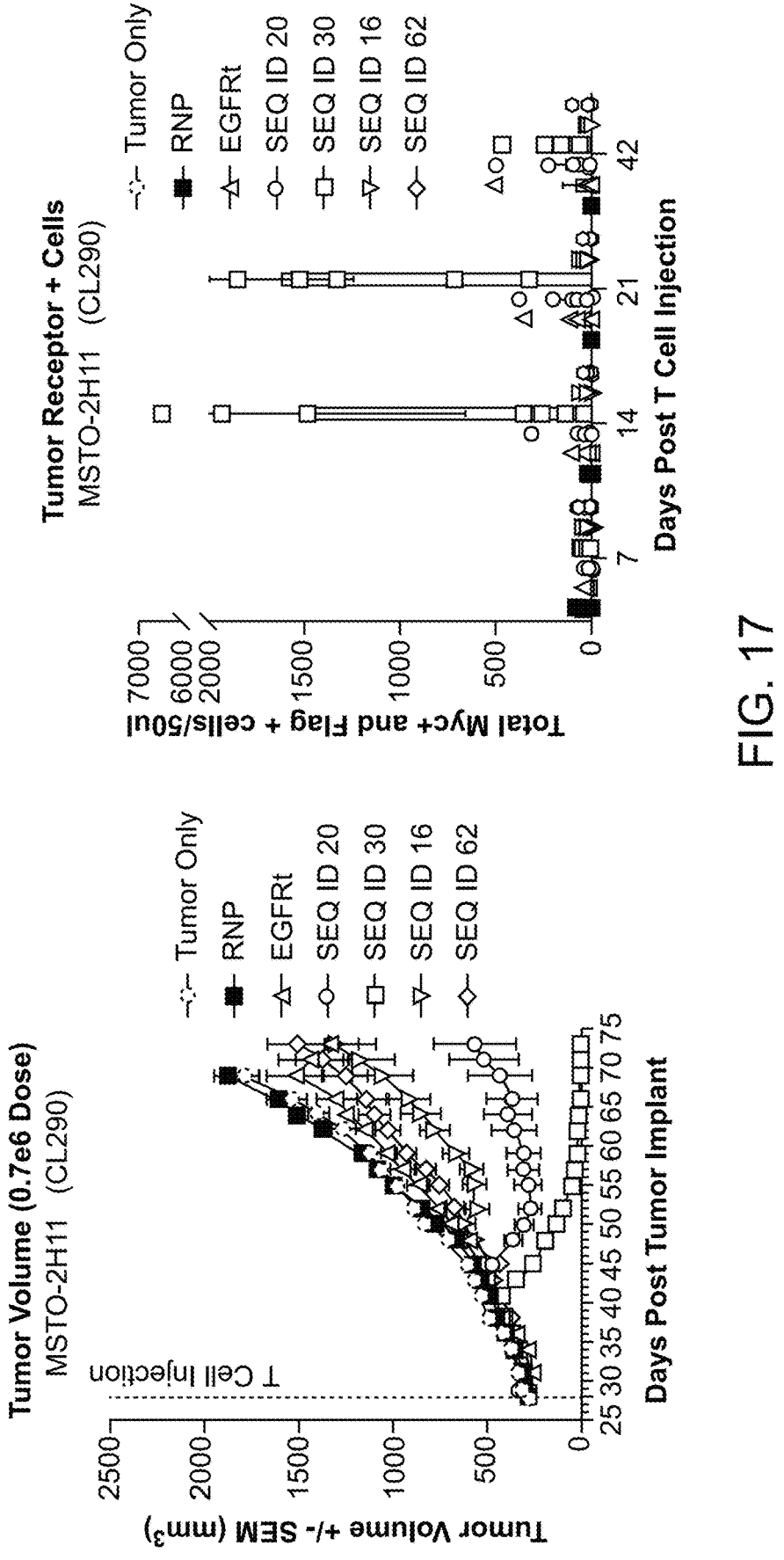
FIG. 17 shows the tumor volume in vivo after treatment with ICTs expressing the indicated SPA.

The ICT cells expressing the logic gate and the novel Class I SPA variants of SEQ ID NOs: 20, 30, and 16 showed improved anti-tumor efficacy as compared to ICT cells expressing a logic gate and L-gp130 (SPA01, FIG. 17). The novel Class I SPA variants also exhibited improved T-cell expansion compared to the foundation SPA01 molecule. Thus, the novel SPAs outperformed L-gp130 in an in vivo experiment assessing anti-cancer efficacy.

Example 5: SPA Expression in T Cells Induces CD11c Expression

Materials and Methods 5-6 week old female NSG MHC DKO mice were implanted with 786-O B2M KO tumors expressing the primeR antigen and CAR antigen from Example 2. Day 36 post tumor implant mice were intravenously injected with LG 1 IC T cells or the non-SPA IC T cells (LG 5 ICT). Tumor and spleen samples were harvested from 15 mice treated with either LG 1 IC T cells (2 donors) or non-SPA ICT (1 donor) at day 7 post ICT injection. Tumors were lysed in DMEM containing Dnase/Collagenase/hyaluronidase. Tumor dissociation was performed in gentleMacs (Octo) using a custom built program. Spleen was mechanically digested using a syringe plunger "handle-end" over 70 μm filter. Post digestion, cell suspension was filtered and subjected to RBC lysis and staining with live dead Zombie NIR dye for 15 min at RT in dark. After live-dead staining cells were centrifuged, washed and stained with cell surface antibody cocktail containing murineCD45, murineGR-1, humanCD3, CAR idiotype (CAR receptor), Prime idiotype (Prime receptor) in the presence of human and mouse Fc blocks for 30 minutes at RT in dark. Cells were then centrifuged at 400 g for 10 min, washed and suspended in flow staining buffer (BD Biosciences). Cells were then sorted using BD FACS Aria. Receptor positive cells were sorted and subjected to RNA seq and CITE seq.

CITE Labeling Protocol

TotalSeq-C Human Universal Cocktail, V1.0 (Biolegend Cat #399905) antibody mix was reconstituted in 26 ul PBS with 1% BSA. Cells were blocked with Fc Block and 13 uL antibody mix was added to 500,000 cells. Following 30 min. incubation on ice cells were washed, resuspended and transferred for GEM generation and barcoding with the 10× Genomics Chromium Next Gem 5' Single Cell kit (Cat #1000263). Cells were combined with GEM Master mix, loaded on a 10×K chip into the Chromium X controller for GEM generation, then incubated in a thermal cycler for reverse transcription. Following GEM clean up and cDNA amplification, gene expression sequencing libraries were generated according to 10× Genomics published protocols. Using the supernatant fraction from the cDNA amplification clean up step, CITE-Seq libraries were constructed using Dual Index Plate TN Set A from 10× Genomics (Cat #1000250) with 8 cycles of PCR amplification. Following library preparation, samples were sequenced on an Illumina NovaSeq 6000.

Bioinformatics Analysis

Single-cell RNA-seq and CITE-seq data was first analyze by Cellranger 7.0 to generate gene by cell matrix. Cells were filtered to exclude low UMI cells, high mitochondrial content cells and non T cells. The filtered matrix was analyzed by scvi 0.20 to generate low dimensional visualizations for the individual cells. The filtered matrix was also analyzed by Seurat 5.0 to define differentially expressed genes, which are genes significantly up or down-regulated in SPA positive cells compared to SPA negative cells (SPA-vs-no SPA). The genes that up-regulated in SPA-vs-no SPA all of D0, D7 Tumor and D7 Spleen samples were intersected to generate a shared list. The same analysis was performed for both RNA-seq and CITE-seq to generate two shared lists. The two shared lists were further intersected to nominate the final list of cell surface protein genes that are most associated with SPA expression. CD11c was nominated by manually examining the final nominated genes.

CD11c Detection by Flow Cytometry

Peripheral blood samples were collected into EDTA-coated tubes. Red blood cells were lysed with ammonium chloride and the remaining cellular fraction was stained with a fixable amine-reactive viability dye and Fc receptors were blocked using anti-CD16/CD32 monoclonal antibodies. After washing, cell surface antigens were stained using fluorochrome-conjugated monoclonal antibodies against humanCD45, murineCD45, murineGr-1, Flag tag (chimeric antigen receptor) & Myc tag (priming receptor). The cells were then fixed with Cytofix fixation buffer (BD Biosciences) and permeabilized with Phosflow Perm Buffer III (BD Biosciences) following the manufacturers recommendation. After permeabilization, the cells were stained using fluorochrome-conjugated monoclonal antibodies against CD11c (CD11c is also known as Integrin, alpha X or ITGAX) and intracellular pSTAT3. Samples were analyzed on an Attune N×T flow cytometer (Thermo Fisher Scientific).

Results

Figure 18A:
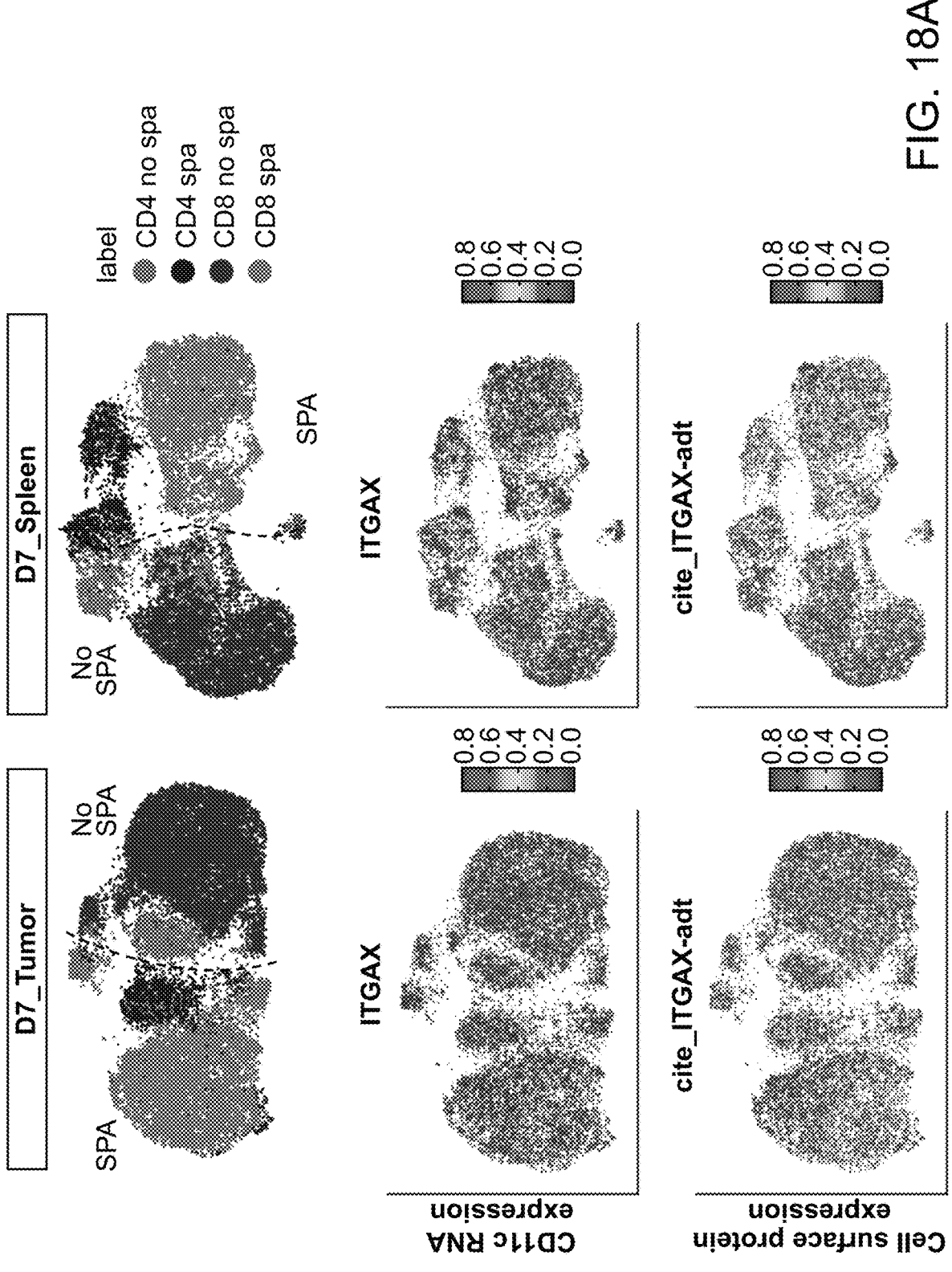
FIG. 18A shows CD11c RNA and cell surface expression and SPA expression in both CD4+ and CD8+ cells at Day 7 in both tumor and spleen cells. Cells with increased CD11c RNA and cell surface expression correlated with cells expressing the SPA.
Figure 18B:
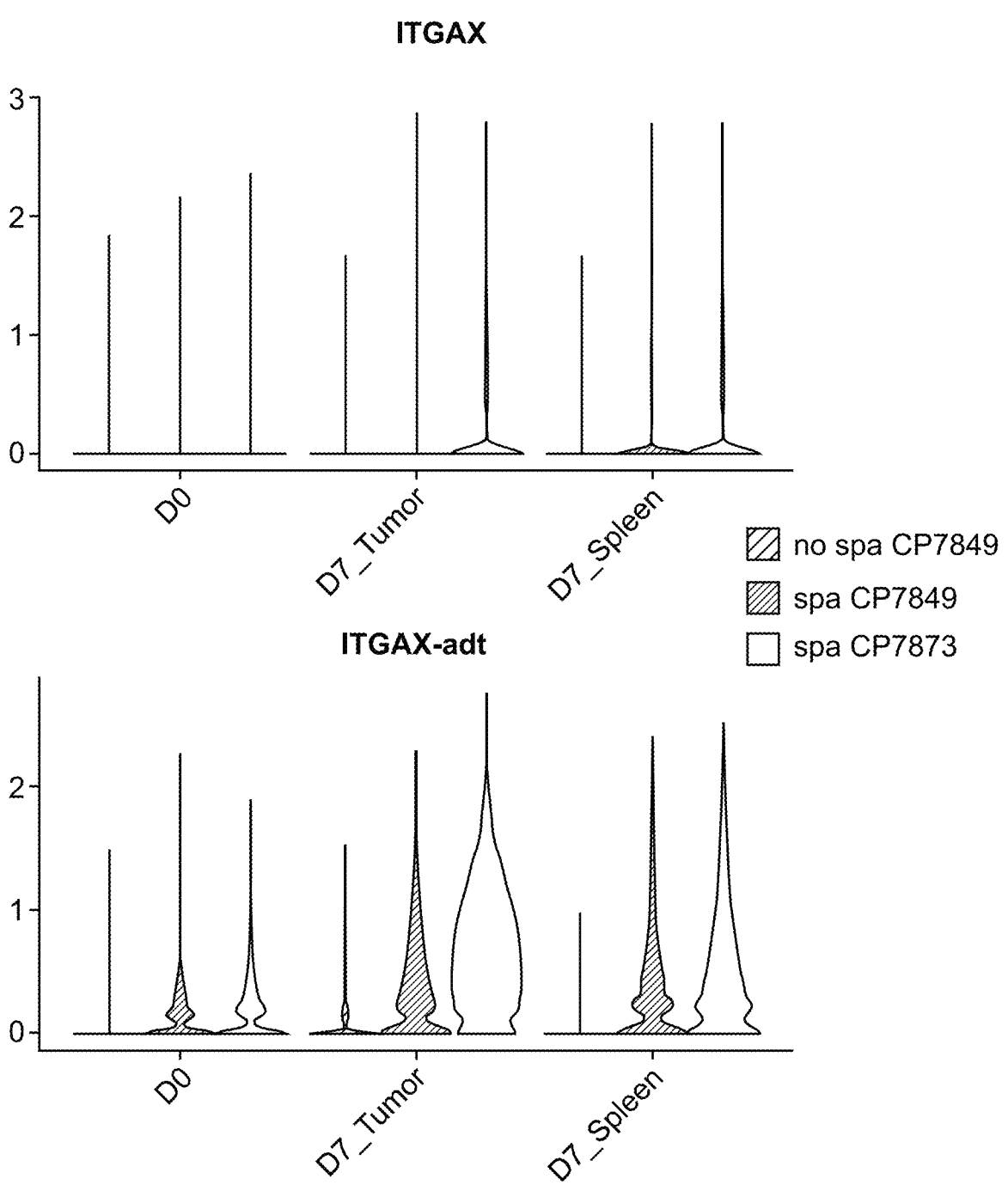
FIG. 18B shows CD11c (ITGAX) expression in spleen or tumor cells from mice treated with cells expressing a SPA ICT (two donors) as compared to cells that do not express a SPA ICT (one donor) collected on Day 0 and Day 7 post treatment.

There is a strong correlation of CD11c RNA and cell surface expression with SPA expression in both CD4+ and CD8+ cells at D7 in both tumor and spleen samples (FIG. 18A). Increased expression of CD11c was observed in the CD8 and CD4 cells expressing the SPA as compared to the CD8 and CD4 cells that did not express the SPA. FIG. 18B shows CD11c (ITGAX) expression in spleen or tumor cells from mice treated with cells expressing a SPA ICT (two donors) as compared to cells that do not express a SPA ICT (one donor) collected on Day 0 and Day 7 post treatment. CD11c (i.e., ITGAX) was expressed at higher levels in SPA containing T cells isolated from the tumor and spleen as compared to non-SPA containing T cells (FIG. 18B). Thus, quantification of expression of CD11c (mRNA or protein) can be used as a marker for SPA expression in both CD4+ and CD8+ cells.

While the disclosure has been particularly shown and described with reference to a preferred embodiment and various alternate embodiments, it will be understood by persons skilled in the relevant art that various changes in form and details can be made therein without departing from the spirit and scope of the disclosure.

All references, issued patents and patent applications cited within the body of the instant specification are hereby incorporated by reference in their entirety, for all purposes.

informal sequence listing

| SEQ ID NO | Name | Sequence |
|---|---|---|
| 1 | QBEND10-Cys-L-GP130Y759F with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQFSTVVH SGYRHQVPSVQVFSRSESTQPLLDSEERPEDLQLVDHVDGGDGILPRQQYFKQNCSQH ESSPDISHFERSKQVSSVNEEDFVRLKQQISDHISQSCGSGQMKMFQEVSAADAFGPG TEGQVERFETVGMEAATDEGMPKSYLPQTVRQGGYMPQ |
| 2 | QBEND10-Cys-L-GP130Y759F 4771-811 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQFSTVVH SGYRHQQQYFKQNCSQHESSPDISHFERSKQVSSVNEEDFVRLKQQISDHISQSCGSG QMKMFQEVSAADAFGPGTEGQVERFETVGMEAATDEGMPKSYLPQTVRQGGYMPQ |
| 3 | QBEND10-Cys-L-GP1304771-811 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQYSTVVH SGYRHQQQYFKQNCSQHESSPDISHFERSKQVSSVNEEDFVRLKQQISDHISQSCGSG QMKMFQEVSAADAFGPGTEGQVERFETVGMEAATDEGMPKSYLPQTVRQGGYMPQ |
| 4 | QBEND10-L-GP130 with leader sequence | MALPVTALLLPLALLLHAARPELPTQGTFSNVSTNVSRIARLEEKVKTLKAQNSELAS TANMLREQVAQLKQKVMNAQGEIEAIVVPVCLAFLLTTLLGVLFCFNKRDLIKKHIWP NVPDDPSKSHIAQWSPHTPPRHNFNSKDQMYSDGNFTDVSVVEIEANDKKPFPEDLKSL DLFKKEKINTEGHSSGIGGSSCMSSSRPSISSSDENESSQNTSSTVQYSTVVHSGYRH QVPSVQVFSRSESTQPLLDSEERPEDLQLVDHVDGGDGILPRQQYFKQNCSQHESSPD ISHFERSKQVSSVNEEDFVRLKQQISDHISQSCGSGQMKMFQEVSAADAFGPGTEGQV ERFETVGMEAATDEGMPKSYLPQTVRQGGYMPQ |
| 5 | QBEND10-L-GP130Y759F with leader sequence | MALPVTALLLPLALLLHAARPELPTQGTFSNVSTNVSRIARLEEKVKTLKAQNSELAS TANMLREQVAQLKQKVMNAQGEIEAIVVPVCLAFLLTTLLGVLFCFNKRDLIKKHIWP NVPDDPSKSHIAQWSPHTPPRHNFNSKDQMYSDGNFTDVSVVEIEANDKKPFPEDLKSL DLFKKEKINTEGHSSGIGGSSCMSSSRPSISSSDENESSQNTSSTVQFSTVVHSGYRH QVPSVQVFSRSESTQPLLDSEERPEDLQLVDHVDGGDGILPRQQYFKQNCSQHESSPD ISHFERSKQVSSVNEEDFVRLKQQISDHISQSCGSGQMKMFQEVSAADAFGPGTEGQV ERFETVGMEAATDEGMPKSYLPQTVRQGGYMPQ |
| 6 | QBEND10-L-GP130Y759F 4771-811 with leader sequence | MALPVTALLLPLALLLHAARPELPTQGTFSNVSTNVSRIARLEEKVKTLKAQNSELAS TANMLREQVAQLKQKVMNAQGEIEAIVVPVCLAFLLTTLLGVLFCFNKRDLIKKHIWP NVPDDPSKSHIAQWSPHTPPRHNENSKDQMYSDGNFTDVSVVEIEANDKKPFPEDLKSL DLFKKEKINTEGHSSGIGGSSCMSSSRPSISSSDENESSQNTSSTVQFSTVVHSGYRH QQQYFKQNCSQHESSPDISHFERSKQVSSVNEEDFVRLKQQISDHISQSCGSGQMKMF QEVSAADAFGPGTEGQVERFETVGMEAATDEGMPKSYLPQTVRQGGYMPQ |
| 7 | QBEND 10-L-GP1304771-811 with | MALPVTALLLPLALLLHAARPELPTQGTFSNVSTNVSRIARLEEKVKTLKAQNSELAS TANMLREQVAQLKQKVMNAQGEIEAIVVPVCLAFLLTTLLGVLFCFNKRDLIKKHIWP NVPDDPSKSHIAQWSPHTPPRHNENSKDQMYSDGNFTDVSVVEIEANDKKPFPEDLKSL |

| | | informal sequence listing |
|---|---|---|
| SEQ ID NO | Name | Sequence |
| | leader sequence | DLFKKEKINTEGHSSGIGGSSCMSSSRPSISSSDENESSQNTSSTVQYSTVVHSGYRH QQQYFKQNCSQHESSPDISHFERSKQVSSVNEEDFVRLKQQISDHISQSCGSGQMKMF QEVSAADAFGPGTEGQVERFETVGMEAATDEGMPKSYLPQTVRQGGYMPQ |
| 8 | SPA-QBEND10-Cys-L-GP130 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQYSTVVH SGYRHQVPSVQVFSRSESTQPLLDSEERPEDLQLVDHVDGGDGILPRQQYFKQNCSQH ESSPDISHFERSKQVSSVNEEDFVRLKQQISDHISQSCGSGQMKMFQEVSAADAFGPG TEGQVERFETVGMEAATDEGMPKSYLPQTVRQGGYMPQ |
| 9 | SPA-L-gp130_ICD-hKRas-CAAX | MRIARLEEKVKTLKAQNSELASTANMLREQVAQLKQKVMNNKRDLIKKHIWPNVPDPS KSHIAQWSPHTPPRHNFNSKDQMYSDGNFTDVSVVEIEANDKKPFPEDLKSLDLFKKE KINTEGHSSGIGGSSCMSSSRPSISSSDENESSQNTSSTVQYSTVVHSGYRHQVPSVQ VFSRSESTQPLLDSEERPEDLQLVDHVDGGDGILPRQQYFKQNCSQHESSPDISHFER SKQVSSVNEEDFVRLKQQISDHISQSCGSGQMKMFQEVSAADAFGPGTEGQVERFETV GMEAATDEGMPKSYLPQTVRQGGYMPQMSKDGKKKKKKSKTKCVIM |
| 10 | SPA-QBEND10-Cys-L-GP130_ICD_trunc1 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNENSKDQMYSDGNFTDVSVVEIEANDKKPFPE TVQYSTVVHSGYRHQVPSVQVFSRSESTQPLLDSEERPEDLQLVDHVDGGDGILPRQQ YFKQNCSQHESSPDISHFERSKQVSSVNEEDFVRLKQQISDHISQSCGSGQMKMFQEV SAADAFGPGTEGQVERFETVGMEAATDEGMPKSYLPQTVRQGGYMPQ |
| 11 | SPA QBEND10-Cys-L-GP130Δ771-811(ICD_trunc2) with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQYSTVVH SGYRHQQQYFKQNCSQHESSPDISHFERSKQVSSVNEEDFVRLKQQISDHISQSCGSG QMKMFQEVSAADAFGPGTEGQVERFETVGMEAATDEGMPKSYLPQTVRQGGYMPQ |
| 12 | SPA-QBEND10-Cys-L-GP130_ICD_trunc3 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQYSTVVH SGYRHQVPSVQVFSRSESTQPLLDSEERPEDLQLVDHVDGGDGILPRQQYFKQPKSYL PQTVRQGGYMPQ |
| 13 | SPA QBEND10-Cys-L-GP130_ICD_trunc4 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNFNSKDQMYSDGNFTDVSVVEIEANDKKPFPE TVQYSTVVHSGYRHQQQYFKQNCSQHESSPDISHFERSKQVSSVNEEDFVRLKQQISD HISQSCGSGQMKMFQEVSAADAFGPGTEGQVERFETVGMEAATDEGMPKSYLPQTVRQ GGYMPQ |
| 14 | SPA-QBEND10-Cys-L-GP130_ICD_trunc5 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQYSTVVH SGYRHQQQYFKQPKSYLPQTVRQGGYMPQ |
| 15 | SPA QBEND10-Cys-L-GP130_ICD_trunc6 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNFNSKDQMYSDGNFTDVSVVEIEANDKKPFPE TVQYSTVVHSGYRHQVPSVQVFSRSESTQPLLDSEERPEDLQLVDHVDGGDGILPRQQ YFKQPKSYLPQTVRQGGYMPQ |
| 16 | SPA-QBEND10-Cys-L-GP130_ICD_trunc7 with leader sequence | MALPVTALLLPLALLLHAARPELPTQGTFSNVSTNVSELCGGRIARLEEKVKTLKAQN SELASTANMLREQVAQLKQKVMNAQGEIEAIVVPVCLAFLLTTLLGVLFCFNKRDLIK KHIWPNVPDPSKSHIAQWSPHTPPRHNFNSKDQMYSDGNFTDVSVVEIEANDKKPFPE TVQYSTVVHSGYRHQQQYFKQPKSYLPQTVRQGGYMPQ |
| 17 | SPA-QBEND10-L-GP130 with leader sequence | MALPVTALLLPLALLLHAARPELPTQGTFSNVSTNVSRIARLEEKVKTLKAQNSELAS TANMLREQVAQLKQKVMNAQGEIEAIVVPVCLAFLLTTLLGVLFCFNKRDLIKKHIWP NVPDPSKSHIAQWSPHTPPRHNFNSKDQMYSDGNFTDVSVVEIEANDKKPFPEDLKSL DLFKKEKINTEGHSSGIGGSSCMSSSRPSISSSDENESSQNTSSTVQYSTVVHSGYRH QVPSVQVFSRSESTQPLLDSEERPEDLQLVDHVDGGDGILPRQQYFKQNCSQHESSPD ISHFERSKQVSSVNEEDFVRLKQQISDHISQSCGSGQMKMFQEVSAADAFGPGTEGQV ERFETVGMEAATDEGMPKSYLPQTVRQGGYMPQ |

-continued

| | | |
|---|---|---| informal sequence listing

| SEQ ID NO | Name | Sequence |
|---|---|---|
| 18 | SPA-QBEND10-BCR-GP130 with leader sequence | MALPVTALLLPLALLLHAARPELPTQGTFSNVSTNVSMVDPVGFAEAWKAQFPDSEPP RMELRSVGDIEQELERCKASIRRLEQEVNQERFRMIYLQTLLAKEAIVVPVCLAFLLT TLLGVLFCFNKRDLIKKHIWPNVPDPSKSHIAQWSPHTPPRHNENSKDQMYSDGNFTD VSVVEIEANDKKPFPEDLKSLDLFKKEKINTEGHSSGIGGSSCMSSSRPSISSSDENE SSQNTSSTVQYSTVVHSGYRHQVPSVQVFSRSESTQPLLDSEERPEDLQLVDHVDGGD GILPRQQYFKQNCSQHESSPDISHFERSKQVSSVNEEDFVRLKQQISDHISQSCGSGQ MKMFQEVSAADAFGPGTEGQVERFETVGMEAATDEGMPKSYLPQTVRQGGYMPQ |
| 19 | SPA-QBEND10-cys-GP130 with leader sequence | MALPVTALLLPLALLLHAARPELPTQGTFSNVSTNVSELCGGAQGEIEAIVVPVCLAF LLTTLLGVLFCFNKRDLIKKHIWPNVPDPSKSHIAQWSPHTPPRHNFNSKDQMYSDGN FTDVSVVEIEANDKKPFPEDLKSLDLFKKEKINTEGHSSGIGGSSCMSSSRPSISSSD ENESSQNTSSTVQYSTVVHSGYRHQVPSVQVFSRSESTQPLLDSEERPEDLQLVDHVD GGDGILPRQQYFKQNCSQHESSPDISHFERSKQVSSVNEEDFVRLKQQISDHISQSCG SGQMKMFQEVSAADAFGPGTEGQVERFETVGMEAATDEGMPKSYLPQTVRQGGYMPQ |
| 20 | SPA-QBEND10-cys-GP130_TM_ICD with leader sequence | MALPVTALLLPLALLLHAARPELPTQGTFSNVSTNVSELCGGAIVVPVCLAFLLTTLL GVLFCFNKRDLIKKHIWPNVPDPSKSHIAQWSPHTPPRHNFNSKDQMYSDGNFTDVSV VEIEANDKKPFPEDLKSLDLFKKEKINTEGHSSGIGGSSCMSSSRPSISSSDENESSQ NTSSTVQYSTVVHSGYRHQVPSVQVFSRSESTQPLLDSEERPEDLQLVDHVDGGDGIL PRQQYFKQNCSQHESSPDISHFERSKQVSSVNEEDFVRLKQQISDHISQSCGSGQMKM FQEVSAADAFGPGTEGQVERFETVGMEAATDEGMPKSYLPQTVRQGGYMPQ |
| 21 | SPA-QBEND10-cys-GP130-L with leader sequence | MALPVTALLLPLALLLHAARPELPTQGTFSNVSTNVSELCGGAQGEIEAIVVPVCLAF LLTTLLGVLFCFNKRDLIKKHIWPNVPDPSKSHIAQWSPHTPPRHNFNSKDQMYSDGN FTDVSVVEIEANDKKPFPEDLKSLDLFKKEKINTEGHSSGIGGSSCMSSSRPSISSSD ENESSQNTSSTVQYSTVVHSGYRHQVPSVQVFSRSESTQPLLDSEERPEDLQLVDHVD GGDGILPRQQYFKQNCSQHESSPDISHFERSKQVSSVNEEDFVRLKQQISDHISQSCG SGQMKMFQEVSAADAFGPGTEGQVERFETVGMEAATDEGMPKSYLPQTVRQGGYMPQR IARLEEKVKTLKAQNSELASTANMLREQVAQLKQKVMN |
| 22 | SPA-QBEND10-cys-GP130_TM_ICD-L with leader sequence | MALPVTALLLPLALLLHAARPELPTQGTFSNVSTNVSELCGGAIVVPVCLAFLLTTLL GVLFCFNKRDLIKKHIWPNVPDPSKSHIAQWSPHTPPRHNFNSKDQMYSDGNFTDVSV VEIEANDKKPFPEDLKSLDLFKKEKINTEGHSSGIGGSSCMSSSRPSISSSDENESSQ NTSSTVQYSTVVHSGYRHQVPSVQVFSRSESTQPLLDSEERPEDLQLVDHVDGGDGIL PRQQYFKQNCSQHESSPDISHFERSKQVSSVNEEDFVRLKQQISDHISQSCGSGQMKM FQEVSAADAFGPGTEGQVERFETVGMEAATDEGMPKSYLPQTVRQGGYMPQRIARLEE KVKTLKAQNSELASTANMLREQVAQLKQKVMN |
| 23 | SPA-QBEND10-cys-GP130_TM_L-ICD with leader sequence | MALPVTALLLPLALLLHAARPELPTQGTFSNVSTNVSELCGGAQGEIEAIVVPVCLAF LLTTLLGVLFCFNKRDLIKKHRIARLEEKVKTLKAQNSELASTANMLREQVAQLKQKV MNIWPNVPDPSKSHIAQWSPHTPPRHNFNSKDQMYSDGNFTDVSVVEIEANDKKPFPE DLKSLDLFKKEKINTEGHSSGIGGSSCMSSSRPSISSSDENESSQNTSSTVQYSTVVH SGYRHQVPSVQVFSRSESTQPLLDSEERPEDLQLVDHVDGGDGILPRQQYFKQNCSQH ESSPDISHFERSKQVSSVNEEDFVRLKQQISDHISQSCGSGQMKMFQEVSAADAFGPG TEGQVERFETVGMEAATDEGMPKSYLPQTVRQGGYMPQ |
| 24 | SPA-QBEND10-GP130_TM_L-ICD with leader sequence | MALPVTALLLPLALLLHAARPELPTQGTFSNVSTNVSELCGGAIVVPVCLAFLLTTLL GVLFCFNKRDLIKKHRIARLEEKVKTLKAQNSELASTANMLREQVAQLKQKVMNIWPN VPDPSKSHIAQWSPHTPPRHNFNSKDQMYSDGNFTDVSVVEIEANDKKPFPEDLKSLD LFKKEKINTEGHSSGIGGSSCMSSSRPSISSSDENESSQNTSSTVQYSTVVHSGYRHQ VPSVQVFSRSESTQPLLDSEERPEDLQLVDHVDGGDGILPRQQYFKQNCSQHESSPDI SHFERSKQVSSVNEEDFVRLKQQISDHISQSCGSGQMKMFQEVSAADAFGPGTEGQVE RFETVGMEAATDEGMPKSYLPQTVRQGGYMPQ |
| 25 | SPA-QBEND10-FACD-CD8a_TMD_GP130_ICD with leader sequence | MALPVTALLLPLALLLHAARPELPTQGTFSNVSTNVSFACDIYIWAPLAGTCGVLLLS LVITLYCNKRDLIKKHIWPNVPDPSKSHIAQWSPHTPPRHNFNSKDQMYSDGNFTDVS VVEIEANDKKPFPEDLKSLDLFKKEKINTEGHSSGIGGSSCMSSSRPSISSSDENESS QNTSSTVQYSTVVHSGYRHQVPSVQVFSRSESTQPLLDSEERPEDLQLVDHVDGGDGI LPRQQYFKQNCSQHESSPDISHFERSKQVSSVNEEDFVRLKQQISDHISQSCGSGQMK MFQEVSAADAFGPGTEGQVERFETVGMEAATDEGMPKSYLPQTVRQGGYMPQ |
| 26 | SPA-QBEND10-CD8a_hinge-TMD_GP130_ICD with leader sequence | MALPVTALLLPLALLLHAARPELPTQGTFSNVSTNVSTTTPAPRPPTPAPTIASQPLS LRPEACRPAAGGAVHTRGLDFACDIYIWAPLAGTCGVLLLSLVITLYCNKRDLIKKHI WPNVPDPSKSHIAQWSPHTPPRHNFNSKDQMYSDGNFTDVSVVEIEANDKKPFPEDLK SLDLFKKEKINTEGHSSGIGGSSCMSSSRPSISSSDENESSQNTSSTVQYSTVVHSGY RHQVPSVQVFSRSESTQPLLDSEERPEDLQLVDHVDGGDGILPRQQYFKQNCSQHESS PDISHFERSKQVSSVNEEDFVRLKQQISDHISQSCGSGQMKMFQEVSAADAFGPGTEG QVERFETVGMEAATDEGMPKSYLPQTVRQGGYMPQ |
| 27 | SPA-QBEND10-cys-CD8a_TMD_GP130_ICD with leader | MALPVTALLLPLALLLHAARPELPTQGTFSNVSTNVSELCGGIYIWAPLAGTCGVLLL SLVITLYCNKRDLIKKHIWPNVPDPSKSHIAQWSPHTPPRHNFNSKDQMYSDGNFTDV SVVEIEANDKKPFPEDLKSLDLFKKEKINTEGHSSGIGGSSCMSSSRPSISSSDENES SQNTSSTVQYSTVVHSGYRHQVPSVQVFSRSESTQPLLDSEERPEDLQLVDHVDGGDG |

| | | informal sequence listing |
|---|---|---|

| SEQ ID NO | Name | Sequence |
|---|---|---|
| | sequence | ILPRQQYFKQNCSQHESSPDISHFERSKQVSSVNEEDFVRLKQQISDHISQSCGSGQM KMFQEVSAADAFGPGTEGQVERFETVGMEAATDEGMPKSYLPQTVRQGGYMPQ |
| 28 | SPA-QBEND10-cys-CD8a_TMD_GP130_ICD-L with leader sequence | MALPVTALLLPLALLLHAARPELPTQGTFSNVSTNVSELCGGIYIWAPLAGTCGVLLL SLVITLYCNKRDLIKKHIWPNVPDPSKSHIAQWSPHTPPRHNFNSKDQMYSDGNFTDV SVVEIEANDKKPFPEDLKSLDLFKKEKINTEGHSSGIGGSSCMSSSRPSISSSDENES SQNTSSTVQYSTVVHSGYRHQVPSVQVFSRSESTQPLLDSEERPEDLQLVDHVDGGDG ILPRQQYFKQNCSQHESSPDISHFERSKQVSSVNEEDFVRLKQQISDHISQSCGSGQM KMFQEVSAADAFGPGTEGQVERFETVGMEAATDEGMPKSYLPQTVRQGGYMPQRIARL EEKVKTLKAQNSELASTANMLREQVAQLKQKVMN |
| 29 | SPA-QBEND10-cys-L-CD8a_TMD_GP130_ICD with leader sequence | MALPVTALLLPLALLLHAARPELPTQGTFSNVSTNVSELCGGRIARLEEKVKTLKAQN SELASTANMLREQVAQLKQKVMNIYIWAPLAGTCGVLLLSLVITLYCNKRDLIKKHIW PNVPDPSKSHIAQWSPHTPPRHNFNSKDQMYSDGNFTDVSVVEIEANDKKPFPEDLKS LDLFKKEKINTEGHSSGIGGSSCMSSSRPSISSSDENESSQNTSSTVQYSTVVHSGYR HQVPSVQVFSRSESTQPLLDSEERPEDLQLVDHVDGGDGILPRQQYFKQNCSQHESSP DISHFERSKQVSSVNEEDFVRLKQQISDHISQSCGSGQMKMFQEVSAADAFGPGTEGQ VERFETVGMEAATDEGMPKSYLPQTVRQGGYMPQ |
| 30 | SPA-C7-gp130 with leader sequence | MLVRRGARAGPRMPRGWTALCLLSLLPSGFMSLDNNGTATPELPTQGTFSNVSTNVSY QETTTPSTLGSTSLHPVSQHGNEATTNITETTVKFTSTSVITSVYGNTNSSVQSQTSV ISTVFTTPANVSTPETTLKPSLSPGNVSDLSTTSTSLATSPTKPYTSSSPILSDIKAE IKCSGIREVKLTQGICLEQNKTSSCAEFKKDRGEGLARVLCGEEQADADAGAQVCSLL LAQSEVRPQCLLLVLANRTEISSKLQLMKKHQSDLKKLGILDFTEQDVASHQSYSQKT PILLTCPTISILSFFSVALLVILACVLWNKRDLIKKHIWPNVPDPSKSHIAQWSPHTP PRHNFNSKDQMYSDGNFTDVSVVEIEANDKKPFPEDLKSLDLFKKEKINTEGHSSGIG GSSCMSSSRPSISSSDENESSQNTSSTVQYSTVVHSGYRHQVPSVQVFSRSESTQPLL DSEERPEDLQLVDHVDGGDGILPRQQYFKQNCSQHESSPDISHFERSKQVSSVNEEDE VRLKQQISDHISQSCGSGQMKMFQEVSAADAFGPGTEGQVERFETVGMEAATDEGMPK SYLPQTVRQGGYMPQ |
| 31 | SPA-CD34-long-gp130 with leader sequence | MLVRRGARAGPRMPRGWTALCLLSLLPSGFMSLDNNGTATPELPTQGTFSNVSTNVSY QETTTPSTLGSTSLHPVSQHGNEATTNITETTVKFTSTSVITSVYGNTNSSVQSQTSV ISTVFTTPANVSTPETTLKPSLSPGNVSDLSTTSTSLATSPTKPYTSSSPILSDIKAE IKCSGIREVKLTQGICLEQNKTSSCAEFKKDRGEGLARVLCGEEQADADAGAQVCSLL LAQSEVRPQCLLLVLANRTEISSKLQLMKKHQSDLKKLGILDFTEQDVASHQSYSQKT AQGEIEAIVVPVCLAFLLTTLLGVLFCFNKRDLIKKHIWPNVPDPSKSHIAQWSPHTP PRHNFNSKDQMYSDGNFTDVSVVEIEANDKKPFPEDLKSLDLFKKEKINTEGHSSGIG GSSCMSSSRPSISSSDENESSQNTSSTVQYSTVVHSGYRHQVPSVQVFSRSESTQPLL DSEERPEDLQLVDHVDGGDGILPRQQYFKQNCSQHESSPDISHFERSKQVSSVNEEDF VRLKQQISDHISQSCGSGQMKMFQEVSAADAFGPGTEGQVERFETVGMEAATDEGMPK SYLPQTVRQGGYMPQ |
| 32 | SPA-CD34-gp130_ICD with leader sequence | MLVRRGARAGPRMPRGWTALCLLSLLPSGFMSLDNNGTATPELPTQGTFSNVSTNVSY QETTTPSTLGSTSLHPVSQHGNEATTNITETTVKFTSTSVITSVYGNTNSSVQSQTSV ISTVFTTPANVSTPETTLKPSLSPGNVSDLSTTSTSLATSPTKPYTSSSPILSDIKAE IKCSGIREVKLTQGICLEQNKTSSCAEFKKDRGEGLARVLCGEEQADADAGAQVCSLL LAQSEVRPQCLLLVLANRTEISSKLQLMKKHQSDLKKLGILDFTEQDVASHQSYSQKT AIVVPVCLAFLLTTLLGVLFCFNKRDLIKKHIWPNVPDPSKSHIAQWSPHTPPRHNFN SKDQMYSDGNFTDVSVVEIEANDKKPFPEDLKSLDLFKKEKINTEGHSSGIGGSSCMS SSRPSISSSDENESSQNTSSTVQYSTVVHSGYRHQVPSVQVFSRSESTQPLLDSEERP EDLQLVDHVDGGDGILPRQQYFKQNCSQHESSPDISHFERSKQVSSVNEEDFVRLKQQ ISDHISQSCGSGQMKMFQEVSAADAFGPGTEGQVERFETVGMEAATDEGMPKSYLPQT VRQGGYMPQ |
| 33 | SPA-QBEND10-VASP-GP130_ICD with leader sequence | MALPVTALLLPLALLLHAARPELPTQGTFSNVSTNVSPSSSDYSDLQRVKQELLEEVK KELQKVKEEIIEAFVQELRKRGSPAQGEIEAIVVPVCLAFLLTTLLGVLFCFNKRDLI KKHIWPNVPDPSKSHIAQWSPHTPPRHNENSKDQMYSDGNFTDVSVVEIEANDKKPFP EDLKSLDLFKKEKINTEGHSSGIGGSSCMSSSRPSISSSDENESSQNTSSTVQYSTVV HSGYRHQVPSVQVFSRSESTQPLLDSEERPEDLQLVDHVDGGDGILPRQQYFKQNCSQ HESSPDISHFERSKQVSSVNEEDFVRLKQQISDHISQSCGSGQMKMFQEVSAADAFGP GTEGQVERFETVGMEAATDEGMPKSYLPQTVRQGGYMPQ |
| 34 | SPA-QBEND10-GP130_ICD-VASP with leader sequence | MALPVTALLLPLALLLHAARPELPTQGTFSNVSTNVSAQGEIEAIVVPVCLAFLLTTL LGVLFCFNKRDLIKKHIWPNVPDPSKSHIAQWSPHTPPRHNFNSKDQMYSDGNFTDVS VVEIEANDKKPFPEDLKSLDLFKKEKINTEGHSSGIGGSSCMSSSRPSISSSDENESS QNTSSTVQYSTVVHSGYRHQVPSVQVFSRSESTQPLLDSEERPEDLQLVDHVDGGDGI LPRQQYFKQNCSQHESSPDISHFERSKQVSSVNEEDFVRLKQQISDHISQSCGSGQMK MFQEVSAADAFGPGTEGQVERFETVGMEAATDEGMPKSYLPQTVRQGGYMPQPSSSDY SDLQRVKQELLEEVKKELQKVKEEIIEAFVQELRKRGSP |
| 35 | SPA-QBEND10- | MALPVTALLLPLALLLHAARPELPTQGTFSNVSTNVSELCGGPSSSDYSDLQRVKQEL LEEVKKELQKVKEEIIEAFVQELRKRGSPAQGEIEAIVVPVCLAFLLTTLLGVLFCFN |

-continued

| informal sequence listing | | |
|---|---|---|

| SEQ ID NO | Name | Sequence |
|---|---|---|
| | cys-VASP-GP130_ICD with leader sequence | KRDLIKKHIWPNVPDPSKSHIAQWSPHTPPRHNFNSKDQMYSDGNFTDVSVVEIEAND KKPFPEDLKSLDLFKKEKINTEGHSSGIGGSSCMSSSRPSISSSDENESSQNTSSTVQ YSTVVHSGYRHQVPSVQVFSRSESTQPLLDSEERPEDLQLVDHVDGGDGILPRQQYFK QNCSQHESSPDISHFERSKQVSSVNEEDFVRLKQQISDHISQSCGSGQMKMFQEVSAA DAFGPGTEGQVERFETVGMEAATDEGMPKSYLPQTVRQGGYMPQ |
| 36 | SPA-QBEND10-cys-GP130_ICD-VASP with leader sequence | MALPVTALLLPLALLLLHAARPELPTQGTFSNVSTNVSELCGGAQGEIEAIVVPVCLAF LLTTLLGVLFCFNKRDLIKKHIWPNVPDPSKSHIAQWSPHTPPRHNFNSKDQMYSDGN FTDVSVVEIEANDKKPFPEDLKSLDLFKKEKINTEGHSSGIGGSSCMSSSRPSISSSD ENESSQNTSSTVQYSTVVHSGYRHQVPSVQVFSRSESTQPLLDSEERPEDLQLVDHVD GGDGILPRQQYFKQNCSQHESSPDISHFERSKQVSSVNEEDFVRLKQQISDHISQSCG SGQMKMFQEVSAADAFGPGTEGQVERFETVGMEAATDEGMPKSYLPQTVRQGGYMPQP SSSDYSDLQRVKQELLEEVKKELQKVKEEIIEAFVQELRKRGSP |
| 37 | SPA-CD34-TpoR-gp130 | MLVRRGARAGPRMPRGWTALCLLSLLPSGFMSLDNNGTATPELPTQGTFSNVSTNVSY QETTTPSTLGSTSLHPVSQHGNEATTNITETTVKFTSTSVITSVYGNTNSSVQSQTSV ISTVFTTPANVSTPETTLKPSLSPGNVSDLSTTSTSLATSPTKPYTSSSPILSDIKAE IKCSGIREVKLTQGICLEQNKTSSCAEFKKDRGEGLARVLCGEEQADADAGAQVCSLL LAQSEVRPQCLLLVLANRTEISSKLQLMKKHQSDLKKLGILDFTEQDVASHQSYSQKT ISLVTALLLVLGLNAVLGLLLLRKQFPAHYRRLRHAIWPNVPDPSKSHIAQWSPHTPP RHNFNSKDQMYSDGNFTDVSVVEIEANDKKPFPEDLKSLDLFKKEKINTEGHSSGIGG SSCMSSSRPSISSSDENESSQNTSSTVQYSTVVHSGYRHQVPSVQVFSRSESTQPLLD SEERPEDLQLVDHVDGGDGILPRQQYFKQNCSQHESSPDISHFERSKQVSSVNEEDFV RLKQQISDHISQSCGSGQMKMFQEVSAADAFGPGTEGQVERFETVGMEAATDEGMPKS YLPQTVRQGGYMPQ |
| 38 | SPA-TpoR-gp130_ICD with leader sequence | MALPVTALLLPLALLLLHAARPSDPTRVETATETAWISLVTALLLVLGLNAVLGLLLLR KQFPPAHYRRLRHAIWPNVPDPSKSHIAQWSPHTPPRHNFNSKDQMYSDGNFTDVSVVE IEANDKKPFPEDLKSLDLFKKEKINTEGHSSGIGGSSCMSSSRPSISSSDENESSQNT SSTVQYSTVVHSGYRHQVPSVQVFSRSESTQPLLDSEERPEDLQLVDHVDGGDGILPR QQYFKQNCSQHESSPDISHFERSKQVSSVNEEDFVRLKQQISDHISQSCGSGQMKMFQ EVSAADAFGPGTEGQVERFETVGMEAATDEGMPKSYLPQTVRQGGYMPQ |
| 39 | SPA-EpoR-gp130_ICD with leader sequence | MDHLGASLWPQVGSLCLLLAGAAWAPPPNLPDPKFESKAALLAARGPEELLCFTERLE DLVCFWEEAASAGVGPGNYSFSYQLEDEPWKLCRLHQAPTARGAVRFWCSLPTADTSS FVPLELRVTAASGAPRYHRVIHINEVVLLDAPVGLVACLADESGHVVLRWLPPPETPM TSHIRYEVDVSAGNGAGSVQRVEILEGRTECVLSNLRGRTRYTFAVRARMAEPSFGGF WSAWSEPVSLLTPSDLDPLILTLSLILVVILVLLTVLALLSNKRDLIKKHIWPNVPDP SKSHIAQWSPHTPPRHNFNSKDQMYSDGNFTDVSVVEIEANDKKPFPEDLKSLDLFKK EKINTEGHSSGIGGSSCMSSSRPSISSSDENESSQNTSSTVQYSTVVHSGYRHQVPSV QVFSRSESTQPLLDSEERPEDLQLVDHVDGGDGILPRQQYFKQNCSQHESSPDISHFE RSKQVSSVNEEDFVRLKQQISDHISQSCGSGQMKMFQEVSAADAFGPGTEGQVERFET VGMEAATDEGMPKSYLPQTVRQGGYMPQ |
| 40 | SPA-EpoR-gp130 with leader sequence | MDHLGASLWPQVGSLCLLLAGAAWAPPPNLPDPKFESKAALLAARGPEELLCFTERLE DLVCFWEEAASAGVGPGNYSFSYQLEDEPWKLCRLHQAPTARGAVRFWCSLPTADTSS FVPLELRVTAASGAPRYHRVIHINEVVLLDAPVGLVACLADESGHVVLRWLPPPETPM TSHIRYEVDVSAGNGAGSVQRVEILEGRTECVLSNLRGRTRYTFAVRARMAEPSFGGF WSAWSEPVSLLTPSDLDPAIVVPVCLAFLLTTLLGVLFCFNKRDLIKKHIWPNVPDPS KSHIAQWSPHTPPRHNFNSKDQMYSDGNFTDVSVVEIEANDKKPFPEDLKSLDLEKKE KINTEGHSSGIGGSSCMSSSRPSISSSDENESSQNTSSTVQYSTVVHSGYRHQVPSVQ VFSRSESTQPLLDSEERPEDLQLVDHVDGGDGILPRQQYFKQNCSQHESSPDISHFER SKQVSSVNEEDFVRLKQQISDHISQSCGSGQMKMFQEVSAADAFGPGTEGQVERFETV GMEAATDEGMPKSYLPQTVRQGGYMPQ |
| 41 | SPA-QBEND10-EpoR-gp130_ICD with leader sequence | MALPVTALLLPLALLLLHAARPELPTQGTFSNVSTNVSAPPPNLPDPKFESKAALLAAR GPEELLCFTERLEDLVCFWEEAASAGVGPGNYSFSYQLEDEPWKLCRLHQAPTARGAV RFWCSLPTADTSSFVPLELRVTAASGAPRYHRVIHINEVVLLDAPVGLVACLADESGH VVLRWLPPPETPMTSHIRYEVDVSAGNGAGSVQRVEILEGRTECVLSNLRGRTRYTFA VRARMAEPSFGGFWSAWSEPVSLLTPSDLDPLILTLSLILVVILVLLTVLALLSNKRD LIKKHIWPNVPDPSKSHIAQWSPHTPPRHNFNSKDQMYSDGNFTDVSVVEIEANDKKP FPEDLKSLDLFKKEKINTEGHSSGIGGSSCMSSSRPSISSSDENESSQNTSSTVQYST VVHSGYRHQVPSVQVFSRSESTQPLLDSEERPEDLQLVDHVDGGDGILPRQQYFKQNC SQHESSPDISHFERSKQVSSVNEEDFVRLKQQISDHISQSCGSGQMKMFQEVSAADAF GPGTEGQVERFETVGMEAATDEGMPKSYLPQTVRQGGYMPQ |
| 42 | SPA-QBEND10-EpoR-gp130 with leader sequence | MALPVTALLLPLALLLLHAARPELPTQGTFSNVSTNVSAPPPNLPDPKFESKAALLAAR GPEELLCFTERLEDLVCFWEEAASAGVGPGNYSFSYQLEDEPWKLCRLHQAPTARGAV RFWCSLPTADTSSFVPLELRVTAASGAPRYHRVIHINEVVLLDAPVGLVACLADESGH VVLRWLPPPETPMTSHIRYEVDVSAGNGAGSVQRVEILEGRTECVLSNLRGRTRYTFA VRARMAEPSFGGFWSAWSEPVSLLTPSDLDPAIVVPVCLAFLLTTLLGVLFCFNKRDL IKKHIWPNVPDPSKSHIAQWSPHTPPRHNFNSKDQMYSDGNFTDVSVVEIEANDKKPF PEDLKSLDLFKKEKINTEGHSSGIGGSSCMSSSRPSISSSDENESSQNTSSTVQYSTV |

-continued

| | | informal sequence listing |
|---|---|---|

| SEQ ID NO | Name | Sequence |
|---|---|---|
| | | VHSGYRHQVPSVQVFSRSESTQPLLDSEERPEDLQLVDHVDGGDGILPRQQYFKQNCS QHESSPDISHFERSKQVSSVNEEDFVRLKQQISDHISQSCGSGQMKMFQEVSAADAFG PGTEGQVERFETVGMEAATDEGMPKSYLPQTVRQGGYMPQ |
| 43 | SPA Myr(Src)-L- gp130 | MGSSKSKPKDPSQRRRRIARLEEKVKTLKAQNSELASTANMLREQVAQLKQKVMNNKR DLIKKHIWPNVPDPSKSHIAQWSPHTPPRHNENSKDQMYSDGNFTDVSVVEIEANDKK PFPEDLKSLDLFKKEKINTEGHSSGIGGSSCMSSSRPSISSSDENESSQNTSSTVQYS TVVHSGYRHQVPSVQVFSRSESTQPLLDSEERPEDLQLVDHVDGGDGILPRQQYFKQN CSQHESSPDISHFERSKQVSSVNEEDFVRLKQQISDHISQSCGSGQMKMFQEVSAADA FGPGTEGQVERFETVGMEAATDEGMPKSYLPQTVRQGGYMPQ |
| 44 | SPA- Myr(Src)- gp130-L | MGSSKSKPKDPSQRRRNKRDLIKKHIWPNVPDPSKSHIAQWSPHTPPRHNFNSKDQMY SDGNFTDVSVVEIEANDKKPFPEDLKSLDLFKKEKINTEGHSSGIGGSSCMSSSRPSI SSSDENESSQNTSSTVQYSTVVHSGYRHQVPSVQVFSRSESTQPLLDSEERPEDLQLV DHVDGGDGILPRQQYFKQNCSQHESSPDISHFERSKQVSSVNEEDFVRLKQQISDHIS QSCGSGQMKMFQEVSAADAFGPGTEGQVERFETVGMEAATDEGMPKSYLPQTVRQGGY MPQRIARLEEKVKTLKAQNSELASTANMLREQVAQLKQKVMN |
| 45 | SPA- Myr(Fyn)-L- gp130 | MGCVQCKDKEATKLTERIARLEEKVKTLKAQNSELASTANMLREQVAQLKQKVMNNKR DLIKKHIWPNVPDPSKSHIAQWSPHTPPRHNFNSKDQMYSDGNFTDVSVVEIEANDKK PFPEDLKSLDLFKKEKINTEGHSSGIGGSSCMSSSRPSISSSDENESSQNTSSTVQYS TVVHSGYRHQVPSVQVFSRSESTQPLLDSEERPEDLQLVDHVDGGDGILPRQQYFKQN CSQHESSPDISHFERSKQVSSVNEEDFVRLKQQISDHISQSCGSGQMKMFQEVSAADA FGPGTEGQVERFETVGMEAATDEGMPKSYLPQTVRQGGYMPQ |
| 46 | SPA- Myr(Fyn)- gp130-L | MGCVQCKDKEATKLTENKRDLIKKHIWPNVPDPSKSHIAQWSPHTPPRHNFNSKDQMY SDGNFTDVSVVEIEANDKKPFPEDLKSLDLFKKEKINTEGHSSGIGGSSCMSSSRPSI SSSDENESSQNTSSTVQYSTVVHSGYRHQVPSVQVFSRSESTQPLLDSEERPEDLQLV DHVDGGDGILPRQQYFKQNCSQHESSPDISHFERSKQVSSVNEEDFVRLKQQISDHIS QSCGSGQMKMFQEVSAADAFGPGTEGQVERFETVGMEAATDEGMPKSYLPQTVRQGGY MPQRIARLEEKVKTLKAQNSELASTANMLREQVAQLKQKVMN |
| 47 | SPA- Myr(Lck)- gp130-L | MGCGCSSHPEDDWMENNKRDLIKKHIWPNVPDPSKSHIAQWSPHTPPRHNFNSKDQMY SDGNFTDVSVVEIEANDKKPFPEDLKSLDLFKKEKINTEGHSSGIGGSSCMSSSRPSI SSSDENESSQNTSSTVQYSTVVHSGYRHQVPSVQVFSRSESTQPLLDSEERPEDLQLV DHVDGGDGILPRQQYFKQNCSQHESSPDISHFERSKQVSSVNEEDFVRLKQQISDHIS QSCGSGQMKMFQEVSAADAFGPGTEGQVERFETVGMEAATDEGMPKSYLPQTVRQGGY MPQRIARLEEKVKTLKAQNSELASTANMLREQVAQLKQKVMN |
| 48 | SPA- Myr(Lck)-L- gp130 | MGCGCSSHPEDDWMENRIARLEEKVKTLKAQNSELASTANMLREQVAQLKQKVMNNKR DLIKKHIWPNVPDPSKSHIAQWSPHTPPRHNFNSKDQMYSDGNFTDVSVVEIEANDKK PFPEDLKSLDLFKKEKINTEGHSSGIGGSSCMSSSRPSISSSDENESSQNTSSTVQYS TVVHSGYRHQVPSVQVFSRSESTQPLLDSEERPEDLQLVDHVDGGDGILPRQQYFKQN CSQHESSPDISHFERSKQVSSVNEEDFVRLKQQISDHISQSCGSGQMKMFQEVSAADA FGPGTEGQVERFETVGMEAATDEGMPKSYLPQTVRQGGYMPQ |
| 49 | SPA- Myr(Src)- VASP-gp130 ICD | MGSSKSKPKDPSQRRRPSSSDYSDLQRVKQELLEEVKKELQKVKEEIIEAFVQELRKR GSPGSNKRDLIKKHIWPNVPDPSKSHIAQWSPHTPPRHNFNSKDQMYSDGNFTDVSVV EIEANDKKPFPEDLKSLDLFKKEKINTEGHSSGIGGSSCMSSSRPSISSSDENESSQN TSSTVQYSTVVHSGYRHQVPSVQVFSRSESTQPLLDSEERPEDLQLVDHVDGGDGILP RQQYFKQNCSQHESSPDISHFERSKQVSSVNEEDFVRLKQQISDHISQSCGSGQMKMF QEVSAADAFGPGTEGQVERFETVGMEAATDEGMPKSYLPQTVRQGGYMPQ |
| 50 | SPA- Myr(Src)- gp130 ICD- VASP | MGSSKSKPKDPSQRRRNKRDLIKKHIWPNVPDPSKSHIAQWSPHTPPRHNFNSKDQMY SDGNFTDVSVVEIEANDKKPFPEDLKSLDLFKKEKINTEGHSSGIGGSSCMSSSRPSI SSSDENESSQNTSSTVQYSTVVHSGYRHQVPSVQVFSRSESTQPLLDSEERPEDLQLV DHVDGGDGILPRQQYFKQNCSQHESSPDISHFERSKQVSSVNEEDFVRLKQQISDHIS QSCGSGQMKMFQEVSAADAFGPGTEGQVERFETVGMEAATDEGMPKSYLPQTVRQGGY MPQGSPSSSDYSDLQRVKQELLEEVKKELQKVKEEIIEAFVQELRKRGSP |
| 51 | Myr(Src)-L- gp130 | MGSSKSKPKDPSQRRRRIARLEEKVKTLKAQNSELASTANMLREQVAQLKQKVMNNKR DLIKKHIWPNVPDPSKSHIAQWSPHTPPRHNFNSKDQMYSDGNFTDVSVVEIEANDKK PFPEDLKSLDLFKKEKINTEGHSSGIGGSSCMSSSRPSISSSDENESSQNTSSTVQYS TVVHSGYRHQVPSVQVFSRSESTQPLLDSEERPEDLQLVDHVDGGDGILPRQQYFKQN CSQHESSPDISHFERSKQVSSVNEEDFVRLKQQISDHISQSCGSGQMKMFQEVSAADA FGPGTEGQVERFETVGMEAATDEGMPKSYLPQTVRQGGYMPQ |
| 52 | Myr(Src)- gp130-L | MGSSKSKPKDPSQRRRNKRDLIKKHIWPNVPDPSKSHIAQWSPHTPPRHNFNSKDQMY SDGNFTDVSVVEIEANDKKPFPEDLKSLDLFKKEKINTEGHSSGIGGSSCMSSSRPSI SSSDENESSQNTSSTVQYSTVVHSGYRHQVPSVQVFSRSESTQPLLDSEERPEDLQLV DHVDGGDGILPRQQYFKQNCSQHESSPDISHFERSKQVSSVNEEDFVRLKQQISDHIS QSCGSGQMKMFQEVSAADAFGPGTEGQVERFETVGMEAATDEGMPKSYLPQTVRQGGY MPQRIARLEEKVKTLKAQNSELASTANMLREQVAQLKQKVMN |

-continued

| | | informal sequence listing |
|---|---|---|

| SEQ ID NO | Name | Sequence |
|---|---|---|
| 53 | Myr(Fyn)-gp130-L | MGCVQCKDKEATKLTENKRDLIKKHIWPNVPDPSKSHIAQWSPHTPPRHNFNSKDQMY<br>SDGNFTDVSVVEIEANDKKPFPEDLKSLDLFKKEKINTEGHSSGIGGSSCMSSSRPSI<br>SSSDENESSQNTSSTVQYSTVVHSGYRHQVPSVQVFSRSESTQPLLDSEERPEDLQLV<br>DHVDGGDGILPRQQYFKQNCSQHESSPDISHFERSKQVSSVNEEDFVRLKQQISDHIS<br>QSCGSGQMKMFQEVSAADAFGPGTEGQVERFETVGMEAATDEGMPKSYLPQTVRQGGY<br>MPQRIARLEEKVKTLKAQNSELASTANMLREQVAQLKQKVMN |
| 54 | Myr(Lck)-gp130-L | MGCGCSSHPEDDWMENNKRDLIKKHIWPNVPDPSKSHIAQWSPHTPPRHNFNSKDQMY<br>SDGNFTDVSVVEIEANDKKPFPEDLKSLDLFKKEKINTEGHSSGIGGSSCMSSSRPSI<br>SSSDENESSQNTSSTVQYSTVVHSGYRHQVPSVQVFSRSESTQPLLDSEERPEDLQLV<br>DHVDGGDGILPRQQYFKQNCSQHESSPDISHFERSKQVSSVNEEDFVRLKQQISDHIS<br>QSCGSGQMKMFQEVSAADAFGPGTEGQVERFETVGMEAATDEGMPKSYLPQTVRQGGY<br>MPQRIARLEEKVKTLKAQNSELASTANMLREQVAQLKQKVMN |
| 55 | Myr(Lck)-L-gp130 | MGCGCSSHPEDDWMENRIARLEEKVKTLKAQNSELASTANMLREQVAQLKQKVMNNKR<br>DLIKKHIWPNVPDPSKSHIAQWSPHTPPRHNFNSKDQMYSDGNFTDVSVVEIEANDKK<br>PFPEDLKSLDLFKKEKINTEGHSSGIGGSSCMSSSRPSISSSDENESSQNTSSTVQYS<br>TVVHSGYRHQVPSVQVFSRSESTQPLLDSEERPEDLQLVDHVDGGDGILPRQQYFKQN<br>CSQHESSPDISHFERSKQVSSVNEEDFVRLKQQISDHISQSCGSGQMKMFQEVSAADA<br>FGPGTEGQVERFETVGMEAATDEGMPKSYLPQTVRQGGYMPQ |
| 56 | Myr(Src)-VASP-gp130 ICD | MGSSKSKPKDPSQRRRPSSSDYSDLQRVKQELLEEVKKELQKVEEIIEAFVQELRKR<br>GSPGSNKRDLIKKHIWPNVPDPSKSHIAQWSPHTPPRHNFNSKDQMYSDGNFTDVSVV<br>EIEANDKKPFPEDLKSLDLFKKEKINTEGHSSGIGGSSCMSSSRPSISSSDENESSQN<br>TSSTVQYSTVVHSGYRHQVPSVQVFSRSESTQPLLDSEERPEDLQLVDHVDGGDGILP<br>RQQYFKQNCSQHESSPDISHFERSKQVSSVNEEDFVRLKQQISDHISQSCGSGQMKMF<br>QEVSAADAFGPGTEGQVERFETVGMEAATDEGMPKSYLPQTVRQGGYMPQ |
| 57 | Inducible (CAR-SPA) QBEND10-Cys-L-GP130 with leader sequence | MALPVTALLLPLALLLHAARPELPTQGTFSNVSTNVSELCGGRIARLEEKVKTLKAQN<br>SELASTANMLREQVAQLKQKVMNAQGEIEAIVVPVCLAFLLTTLLGVLFCFNKRDLIK<br>KHIWPNVPDPSKSHIAQWSPHTPPRHNFNSKDQMYSDGNFTDVSVVEIEANDKKPFPE<br>DLKSLDLFKKEKINTEGHSSGIGGSSCMSSSRPSISSSDENESSQNTSSTVQYSTVVH<br>SGYRHQVPSVQVFSRSESTQPLLDSEERPEDLQLVDHVDGGDGILPRQQYFKQNCSQH<br>ESSPDISHFERSKQVSSVNEEDFVRLKQQISDHISQSCGSGQMKMFQEVSAADAFGPG<br>TEGQVERFETVGMEAATDEGMPKSYLPQTVRQGGYMPQ |
| 58 | myr(Src)-JUN-gp130 | MGSSKSKPKDPSQRRRRIARLEEKVKTLKAQNSELASTANMLREQVAQLKQKVMNNKR<br>DLIKKHIWPNVPDPSKSHIAQWSPHTPPRHNFNSKDQMYSDGNFTDVSVVEIEANDKK<br>PFPEDLKSLDLFKKEKINTEGHSSGIGGSSCMSSSRPSISSSDENESSQNTSSTVQYS<br>TVVHSGYRHQVPSVQVFSRSESTQPLLDSEERPEDLQLVDHVDGGDGILPRQQYFKQN<br>CSQHESSPDISHFERSKQVSSVNEEDFVRLKQQISDHISQSCGSGQMKMFQEVSAADA<br>FGPGTEGQVERFETVGMEAATDEGMPKSYLPQTVRQGGYMPQ |
| 59 | Gp130 (IL6ST) UniProt P40189 | MLTLQTWLVQALFIFLTTESTGELLDPCGYISPESPVVQLHSNFTAVCVLKEKCMDYF<br>HVNANYIVWKTNHFTIPKEQYTIINRTASSVTFTDIASLNIQLTCNILTFGQLEQNVY<br>GITIISGLPPEKPKNLSCIVNEGKKMRCEWDGGRETHLETNFTLKSEWATHKFADCKA<br>KRDTPTSCTVDYSTVYFVNIEVWVEAENALGKVTSDHINFDPVYKVKPNPPHNLSVIN<br>SEELSSILKLTWTNPSIKSVIILKYNIQYRTKDASTWSQIPPEDTASTRSSFTVQDLK<br>PFTEYVFRIRCMKEDGKGYWSDWSEEASGITYEDRPSKAPSFWYKIDPSHTQGYRTVQ<br>LVWKTLPPFEANGKILDYEVTLTRWKSHLQNYTVNATKLTVNLTNDRYLATLTVRNLV<br>GKSDAAVLTIPACDFQATHPVMDLKAFPKDNMLWVEWTTPRESVKKYILEWCVLSDKA<br>PCITDWQQEDGTVHRTYLRGNLAESKCYLITVTPVYADGPGSPESIKAYLKQAPPSKG<br>PTVRTKKVGKNEAVLEWDQLPVDVQNGFIRNYTIFYRTIIGNETAVNVDSSHTEYTLS<br>SLTSDTLYMVRMAAYTDEGGKDGPEFTFTTPKFAQGEIEAIVVPVCLAFLLTTLLGVL<br>FCFNKRDLIKKHIWPNVPDPSKSHIAQWSPHTPPRHNFNSKDQMYSDGNFTDVSVVEI<br>EANDKKPFPEDLKSLDLFKKEKINTEGHSSGIGGSSCMSSSRPSISSSDENESSQNTS<br>STVQYSTVVHSGYRHQVPSVQVFSRSESTQPLLDSEERPEDLQLVDHVDGGDGILPRQ<br>QYFKQNCSQHESSPDISHFERSKQVSSVNEEDFVRLKQQISDHISQSCGSGQMKMFQE<br>VSAADAFGPGTEGQVERFETVGMEAATDEGMPKSYLPQTVRQGGYMPQ |
| 60 | Gp130 (IL6ST) intracellular signaling domain | NKRDLIKKHIWPNVPDPSKSHIAQWSPHTPPRHNFNSKDQMYSDGNFTDVSVVEIEAN<br>DKKPFPEDLKSLDLFKKEKINTEGHSSGIGGSSCMSSSRPSISSSDENESSQNTSSTV<br>QYSTVVHSGYRHQVPSVQVFSRSESTQPLLDSEERPEDLQLVDHVDGGDGILPRQQYF<br>KQNCSQHESSPDISHFERSKQVSSVNEEDFVRLKQQISDHISQSCGSGQMKMFQEVSA<br>ADAFGPGTEGQVERFETVGMEAATDEGMPKSYLPQTVRQGGYMPQ |
| 61 | Gp130 (IL6ST) transmembrane domain | AIVVPVCLAFLLTTLLGVLFCF |

| | | informal sequence listing |
|---|---|---|

| SEQ ID NO | Name | Sequence |
|---|---|---|
| 62 | L-gp130 | MALPVTALLLPLALLLHAARPDYKDDDDKELCGGRIARLEEKVKTLKAQNSELASTAN<br>MLREQVAQLKQKVMNAQGEIEAIVVPVCLAFLLTTLLGVLFCFNKRDLIKKHIWPNVP<br>DPSKSHIAQWSPHTPPRHNFNSKDQMYSDGNFTDVSVVEIEANDKKPFPEDLKSLDLF<br>KKEKINTEGHSSGIGGSSCMSSSRPSISSSDENESSQNTSSTVQYSTVVHSGYRHQVP<br>SVQVFSRSESTQPLLDSEERPEDLQLVDHVDGGDGILPRQQYFKQNCSQHESSPDISH<br>FERSKQVSSVNEEDFVRLKQQISDHISQSCGSGQMKMFQEVSAADAFGPGTEGQVERF<br>ETVGMEAATDEGMPKSYLPQTVRQGGYMPQ |
| 63 | QBEND10-<br>Cys-L-<br>GP130Y759F | ELPTQGTFSNVSTNVSELCGGRIARLEEKVKTLKAQNSELASTANMLREQVAQLKQKV<br>MNAQGEIEAIVVPVCLAFLLTTLLGVLFCFNKRDLIKKHIWPNVPDPSKSHIAQWSPH<br>TPPRHNFNSKDQMYSDGNFTDVSVVEIEANDKKPFPEDLKSLDLFKKEKINTEGHSSG<br>IGGSSCMSSSRPSISSSDENESSQNTSSTVQFSTVVHSGYRHQVPSVQVFSRSESTQP<br>LLDSEERPEDLQLVDHVDGGDGILPRQQYFKQNCSQHESSPDISHFERSKQVSSVNEE<br>DFVRLKQQISDHISQSCGSGQMKMFQEVSAADAFGPGTEGQVERFETVGMEAATDEGM<br>PKSYLPQTVRQGGYMPQ |
| 64 | QBEND10-<br>Cys-L-<br>GP130Y759F<br>4771-811 | ELPTQGTFSNVSTNVSELCGGRIARLEEKVKTLKAQNSELASTANMLREQVAQLKQKV<br>MNAQGEIEAIVVPVCLAFLLTTLLGVLFCFNKRDLIKKHIWPNVPDPSKSHIAQWSPH<br>TPPRHNfNSKDQMYSDGNFTDVSVVEIEANDKKPFPEDLKSLDLFKKEKINTEGHSSG<br>IGGSSCMSSSRPSISSSDENESSQNTSSTVQFSTVVHSGYRHQQQYFKQNCSQHESSP<br>DISHFERSKQVSSVNEEDFVRLKQQISDHISQSCGSGQMKMFQEVSAADAFGPGTEGQ<br>VERFETVGMEAATDEGMPKSYLPQTVRQGGYMPQ |
| 65 | QBEND10-<br>Cys-L-<br>GP1304771-<br>811 | ELPTQGTFSNVSTNVSELCGGRIARLEEKVKTLKAQNSELASTANMLREQVAQLKQKV<br>MNAQGEIEAIVVPVCLAFLLTTLLGVLFCFNKRDLIKKHIWPNVPDPSKSHIAQWSPH<br>TPPRHNFNSKDQMYSDGNFTDVSVVEIEANDKKPFPEDLKSLDLFKKEKINTEGHSSG<br>IGGSSCMSSSRPSISSSDENESSQNTSSTVQYSTVVHSGYRHQQQYFKQNCSQHESSP<br>DISHFERSKQVSSVNEEDFVRLKQQISDHISQSCGSGQMKMFQEVSAADAFGPGTEGQ<br>VERFETVGMEAATDEGMPKSYLPQTVRQGGYMPQ |
| 66 | QBEND10-L-<br>GP130 | ELPTQGTFSNVSTNVSRIARLEEKVKTLKAQNSELASTANMLREQVAQLKQKVMNAQG<br>EIEAIVVPVCLAFLLTTLLGVLFCFNKRDLIKKHIWPNVPDPSKSHIAQWSPHTPPRH<br>NFNSKDQMYSDGNFTDVSVVEIEANDKKPFPEDLKSLDLFKKEKINTEGHSSGIGGSS<br>CMSSSRPSISSSDENESSQNTSSTVQYSTVVHSGYRHQVPSVQVFSRSESTQPLLDSE<br>ERPEDLQLVDHVDGGDGILPRQQYFKQNCSQHESSPDISHFERSKQVSSVNEEDFVRL<br>KQQISDHISQSCGSGQMKMFQEVSAADAFGPGTEGQVERFETVGMEAATDEGMPKSYL<br>PQTVRQGGYMPQ |
| 67 | QBEND10-L-<br>GP130Y759F | ELPTQGTFSNVSTNVSRIARLEEKVKTLKAQNSELASTANMLREQVAQLKQKVMNAQG<br>EIEAIVVPVCLAFLLTTLLGVLFCFNKRDLIKKHIWPNVPDPSKSHIAQWSPHTPPRH<br>NFNSKDQMYSDGNFTDVSVVEIEANDKKPFPEDLKSLDLFKKEKINTEGHSSGIGGSS<br>CMSSSRPSISSSDENESSQNTSSTVQFSTVVHSGYRHQVPSVQVFSRSESTQPLLDSE<br>ERPEDLQLVDHVDGGDGILPRQQYFKQNCSQHESSPDISHFERSKQVSSVNEEDFVRL<br>KQQISDHISQSCGSGQMKMFQEVSAADAFGPGTEGQVERFETVGMEAATDEGMPKSYL<br>PQTVRQGGYMPQ |
| 68 | QBEND10-L-<br>GP130Y759F<br>4771-811 | ELPTQGTFSNVSTNVSRIARLEEKVKTLKAQNSELASTANMLREQVAQLKQKVMNAQG<br>EIEAIVVPVCLAFLLTTLLGVLFCFNKRDLIKKHIWPNVPDPSKSHIAQWSPHTPPRH<br>NFNSKDQMYSDGNFTDVSVVEIEANDKKPFPEDLKSLDLFKKEKINTEGHSSGIGGSS<br>CMSSSRPSISSSDENESSQNTSSTVQFSTVVHSGYRHQQQYFKQNCSQHESSPDISHF<br>ERSKQVSSVNEEDFVRLKQQISDHISQSCGSGQMKMFQEVSAADAFGPGTEGQVERFE<br>TVGMEAATDEGMPKSYLPQTVRQGGYMPQ |
| 69 | QBEND10-L-<br>GP1304771-<br>811 | ELPTQGTFSNVSTNVSRIARLEEKVKTLKAQNSELASTANMLREQVAQLKQKVMNAQG<br>EIEAIVVPVCLAFLLTTLLGVLFCFNKRDLIKKHIWPNVPDPSKSHIAQWSPHTPPRH<br>NFNSKDQMYSDGNFTDVSVVEIEANDKKPFPEDLKSLDLFKKEKINTEGHSSGIGGSS<br>CMSSSRPSISSSDENESSQNTSSTVQYSTVVHSGYRHQQQYFKQNCSQHESSPDISHF<br>ERSKQVSSVNEEDFVRLKQQISDHISQSCGSGQMKMFQEVSAADAFGPGTEGQVERFE<br>TVGMEAATDEGMPKSYLPQTVRQGGYMPQ |
| 70 | SPA-<br>QBEND10-<br>Cys-L-GP130 | ELPTQGTFSNVSTNVSELCGGRIARLEEKVKTLKAQNSELASTANMLREQVAQLKQKV<br>MNAQGEIEAIVVPVCLAFLLTTLLGVLFCFNKRDLIKKHIWPNVPDPSKSHIAQWSPH<br>TPPRHNFNSKDQMYSDGNFTDVSVVEIEANDKKPFPEDLKSLDLFKKEKINTEGHSSG<br>IGGSSCMSSSRPSISSSDENESSQNTSSTVQYSTVVHSGYRHQVPSVQVFSRSESTQP<br>LLDSEERPEDLQLVDHVDGGDGILPRQQYFKQNCSQHESSPDISHFERSKQVSSVNEE<br>DFVRLKQQISDHISQSCGSGQMKMFQEVSAADAFGPGTEGQVERFETVGMEAATDEGM<br>PKSYLPQTVRQGGYMPQ |
| 71 | SPA-<br>QBEND10-<br>Cys-L-<br>GP130_ICD_trunc1 | ELPTQGTFSNVSTNVSELCGGRIARLEEKVKTLKAQNSELASTANMLREQVAQLKQKV<br>MNAQGEIEAIVVPVCLAFLLTTLLGVLFCFNKRDLIKKHIWPNVPDPSKSHIAQWSPH<br>TPPRHNFNSKDQMYSDGNFTDVSVVEIEANDKKPFPETVQYSTVVHSGYRHQVPSVQV<br>FSRSESTQPLLDSEERPEDLQLVDHVDGGDGILPRQQYFKQNCSQHESSPDISHFERS |

| informal sequence listing | | |
| --- | --- | --- |

| SEQ ID NO | Name | Sequence |
| --- | --- | --- |
| | | KQVSSVNEEDFVRLKQQISDHISQSCGSGQKMFQEVSAADAFGPGTEGQVERFETVG MEAATDEGMPKSYLPQTVRQGGYMPQ |
| 72 | SPA- QBEND10- Cys-L- GP1304771- 811(ICD_trunc2) | ELPTQGTFSNVSTNVSELCGGRIARLEEKVKTLKAQNSELASTANMLREQVAQLKQKV MNAQGEIEAIVVPVCLAFLLTTLLGVLFCFNKRDLIKKHIWPNVPDPSKSHIAQWSPH TPPRHNFNSKDQMYSDGNFTDVSVVEIEANDKKPFPEDLKSLDLFKKEKINTEGHSSG IGGSSCMSSSRPSISSSDENESSQNTSSTVQYSTVVHSGYRHQQQYFKQNCSQHESSP DISHFERSKQVSSVNEEDFVRLKQQISDHISQSCGSGQKMKFQEVSAADAFGPGTEGQ VERFETVGMEAATDEGMPKSYLPQTVRQGGYMPQ |
| 73 | SPA- QBEND10- Cys-L- GP130_ICD_trunc3 | ELPTQGTFSNVSTNVSELCGGRIARLEEKVKTLKAQNSELASTANMLREQVAQLKQKV MNAQGEIEAIVVPVCLAFLLTTLLGVLFCFNKRDLIKKHIWPNVPDPSKSHIAQWSPH TPPRHNFNSKDQMYSDGNFTDVSVVEIEANDKKPFPEDLKSLDLFKKEKINTEGHSSG IGGSSCMSSSRPSISSSDENESSQNTSSTVQYSTVVHSGYRHQVPSVQVFSRSESTQP LLDSEERPEDLQLVDHVDGGDGILPRQQYFKQPKSYLPQTVRQGGYMPQ |
| 74 | SPA- QBEND10- Cys-L- GP130_ICD_trunc4 | ELPTQGTFSNVSTNVSELCGGRIARLEEKVKTLKAQNSELASTANMLREQVAQLKQKV MNAQGEIEAIVVPVCLAFLLTTLLGVLFCFNKRDLIKKHIWPNVPDPSKSHIAQWSPH TPPRHNFNSKDQMYSDGNFTDVSVVEIEANDKKPFPETVQYSTVVHSGYRHQQQYFKQ NCSQHESSPDISHFERSKQVSSVNEEDFVRLKQQISDHISQSCGSGQKMKFQEVSAAD AFGPGTEGQVERFETVGMEAATDEGMPKSYLPQTVRQGGYMPQ |
| 75 | SPA- QBEND10- Cys-L- GP130_ICD_trunc5 | ELPTQGTFSNVSTNVSELCGGRIARLEEKVKTLKAQNSELASTANMLREQVAQLKQKV MNAQGEIEAIVVPVCLAFLLTTLLGVLFCFNKRDLIKKHIWPNVPDPSKSHIAQWSPH TPPRHNFNSKDQMYSDGNFTDVSVVEIEANDKKPFPEDLKSLDLFKKEKINTEGHSSG IGGSSCMSSSRPSISSSDENESSQNTSSTVQYSTVVHSGYRHQQQYFKQPKSYLPQTV RQGGYMPQ |
| 76 | SPA- QBEND10- Cys-L- GP130_ICD_trunc6 | ELPTQGTFSNVSTNVSELCGGRIARLEEKVKTLKAQNSELASTANMLREQVAQLKQKV MNAQGEIEAIVVPVCLAFLLTTLLGVLFCFNKRDLIKKHIWPNVPDPSKSHIAQWSPH TPPRHNfNSKDQMYSDGNFTDVSVVEIEANDKKPFPETVQYSTVVHSGYRHQVPSVQV FSRSESTQPLLDSEERPEDLQLVDHVDGGDGILPRQQYFKQPKSYLPQTVRQGGYMPQ |
| 77 | SPA- QBEND10- Cys-L- GP130_ICD_trunc7 | ELPTQGTFSNVSTNVSELCGGRIARLEEKVKTLKAQNSELASTANMLREQVAQLKQKV MNAQGEIEAIVVPVCLAFLLTTLLGVLFCFNKRDLIKKHIWPNVPDPSKSHIAQWSPH TPPRHNfNSKDQMYSDGNFTDVSVVEIEANDKKPFPETVQYSTVVHSGYRHQQQYFKQ PKSYLPQTVRQGGYMPQ |
| 78 | SPA- QBEND10-L- GP130 | ELPTQGTFSNVSTNVSRIARLEEKVKTLKAQNSELASTANMLREQVAQLKQKVMNAQG EIEAIVVPVCLAFLLTTLLGVLFCFNKRDLIKKHIWPNVPDPSKSHIAQWSPHTPPRH NFNSKDQMYSDGNFTDVSVVEIEANDKKPFPEDLKSLDLFKKEKINTEGHSSGIGGSS CMSSSRPSISSSDENESSQNTSSTVQYSTVVHSGYRHQVPSVQVFSRSESTQPLLDSE ERPEDLQLVDHVDGGDGILPRQQYFKQNCSQHESSPDISHFERSKQVSSVNEEDFVRL KQQISDHISQSCGSGQKMKFQEVSAADAFGPGTEGQVERFETVGMEAATDEGMPKSYL PQTVRQGGYMPQ |
| 79 | SPA- QBEND10- BCR-GP130 | ELPTQGTFSNVSTNVSMVDPVGFAEAWKAQFPDSEPPRMELRSVGDIEQELERCKASI RRLEQEVNQERFRMIYLQTLLAKEAIVVPVCLAFLLTTLLGVLFCFNKRDLIKKHIWP NVPDPSKSHIAQWSPHTPPRHNFNSKDQMYSDGNFTDVSVVEIEANDKKPFPEDLKSL DLFKKEKINTEGHSSGIGGSSCMSSSRPSISSSDENESSQNTSSTVQYSTVVHSGYRH QVPSVQVFSRSESTQPLLDSEERPEDLQLVDHVDGGDGILPRQQYFKQNCSQHESSPD ISHFERSKQVSSVNEEDFVRLKQQISDHISQSCGSGQKMKFQEVSAADAFGPGTEGQV ERFETVGMEAATDEGMPKSYLPQTVRQGGYMPQ |
| 80 | SPA QBEND10- cys-GP130 | ELPTQGTFSNVSTNVSELCGGAQGEIEAIVVPVCLAFLLTTLLGVLFCFNKRDLIKKH IWPNVPDPSKSHIAQWSPHTPPRHNFNSKDQMYSDGNFTDVSVVEIEANDKKPFPEDL KSLDLFKKEKINTEGHSSGIGGSSCMSSSRPSISSSDENESSQNTSSTVQYSTVVHSG YRHQVPSVQVFSRSESTQPLLDSEERPEDLQLVDHVDGGDGILPRQQYFKQNCSQHES SPDISHFERSKQVSSVNEEDFVRLKQQISDHISQSCGSGQKMKFQEVSAADAFGPGTE GQVERFETVGMEAATDEGMPKSYLPQTVRQGGYMPQ |
| 81 | SPA- QBEND10- cys- GP130_TM_ICD | ELPTQGTFSNVSTNVSELCGGAIVVPVCLAFLLTTLLGVLFCFNKRDLIKKHIWPNVP DPSKSHIAQWSPHTPPRHNFNSKDQMYSDGNFTDVSVVEIEANDKKPFPEDLKSLDLF KKEKINTEGHSSGIGGSSCMSSSRPSISSSDENESSQNTSSTVQYSTVVHSGYRHQVP SVQVFSRSESTQPLLDSEERPEDLQLVDHVDGGDGILPRQQYFKQNCSQHESSPDISH FERSKQVSSVNEEDFVRLKQQISDHISQSCGSGQKMKFQEVSAADAFGPGTEGQVERF ETVGMEAATDEGMPKSYLPQTVRQGGYMPQ |
| 82 | SPA- QBEND10- cys-GP130-L | ELPTQGTFSNVSTNVSELCGGAQGEIEAIVVPVCLAFLLTTLLGVLFCFNKRDLIKKH IWPNVPDPSKSHIAQWSPHTPPRHNFNSKDQMYSDGNFTDVSVVEIEANDKKPFPEDL KSLDLFKKEKINTEGHSSGIGGSSCMSSSRPSISSSDENESSQNTSSTVQYSTVVHSG YRHQVPSVQVFSRSESTQPLLDSEERPEDLQLVDHVDGGDGILPRQQYFKQNCSQHES SPDISHFERSKQVSSVNEEDFVRLKQQISDHISQSCGSGQKMKFQEVSAADAFGPGTE |

-continued

| informal sequence listing | | |
|---|---|---|

| SEQ ID NO | Name | Sequence |
|---|---|---|
| | | GQVERFETVGMEAATDEGMPKSYLPQTVRQGGYMPQRIARLEEKVKTLKAQNSELAST ANMLREQVAQLKQKVMN |
| 83 | SPA- QBEND10- cys- GP130_TM_ICD-L | ELPTQGTFSNVSTNVSELCGGAIVVPVCLAFLLTTLLGVLFCFNKRDLIKKHIWPNVP DPSKSHIAQWSPHTPPRHNfNSKDQMYSDGNFTDVSVVEIEANDKKPFPEDLKSLDLF KKEKINTEGHSSGIGGSSCMSSSRPSISSSDENESSQNTSSTVQYSTVVHSGYRHQVP SVQVFSRSESTQPLLDSEERPEDLQLVDHVDGGDGILPRQQYFKQNCSQHESSPDISH FERSKQVSSVNEEDFVRLKQQISDHISQSCGSGQMKMFQEVSAADAFGPGTEGQVERF ETVGMEAATDEGMPKSYLPQTVRQGGYMPQRIARLEEKVKTLKAQNSELASTANMLRE QVAQLKQKVMN |
| 84 | SPA- QBEND10- cys- GP130_TM_L- ICD | ELPTQGTFSNVSTNVSELCGGAQGEIEAIVVPVCLAFLLTTLLGVLFCFNKRDLIKKH RIARLEEKVKTLKAQNSELASTANMLREQVAQLKQKVMNIWPNVPDPSKSHIAQWSPH TPPRHNFNSKDQMYSDGNFTDVSVVEIEANDKKPFPEDLKSLDLFKKEKINTEGHSSG IGGSSCMSSSRPSISSSDENESSQNTSSTVQYSTVVHSGYRHQVPSVQVFSRSESTQP LLDSEERPEDLQLVDHVDGGDGILPRQQYFKQNCSQHESSPDISHFERSKQVSSVNEE DFVRLKQQISDHISQSCGSGQMKMFQEVSAADAFGPGTEGQVERFETVGMEAATDEGM PKSYLPQTVRQGGYMPQ |
| 85 | SPA- QBEND10- GP130_TM_L- ICD | ELPTQGTFSNVSTNVSELCGGAIVVPVCLAFLLTTLLGVLFCFNKRDLIKKHRIARLE EKVKTLKAQNSELASTANMLREQVAQLKQKVMNIWPNVPDPSKSHIAQWSPHTPPRHN FNSKDQMYSDGNFTDVSVVEIEANDKKPFPEDLKSLDLFKKEKINTEGHSSGIGGSSC MSSSRPSISSSDENESSQNTSSTVQYSTVVHSGYRHQVPSVQVFSRSESTQPLLDSEE RPEDLQLVDHVDGGDGILPRQQYFKQNCSQHESSPDISHFERSKQVSSVNEEDFVRLK QQISDHISQSCGSGQMKMFQEVSAADAFGPGTEGQVERFETVGMEAATDEGMPKSYLP QTVRQGGYMPQ |
| 86 | SPA- QBEND10- FACD- CD8a_TMD_GP130_ICD | ELPTQGTFSNVSTNVSFACDIYIWAPLAGTCGVLLLSLVITLYCNKRDLIKKHHIWPNV PDPSKSHIAQWSPHTPPRHNFNSKDQMYSDGNFTDVSVVEIEANDKKPFPEDLKSLDL FKKEKINTEGHSSGIGGSSCMSSSRPSISSSDENESSQNTSSTVQYSTVVHSGYRHQV PSVQVFSRSESTQPLLDSEERPEDLQLVDHVDGGDGILPRQQYFKQNCSQHESSPDIS HFERSKQVSSVNEEDFVRLKQQISDHISQSCGSGQMKMFQEVSAADAFGPGTEGQVER FETVGMEAATDEGMPKSYLPQTVRQGGYMPQ |
| 87 | SPA- QBEND10- CD8a_hinge- TMD_GP130_ICD | ELPTQGTFSNVSTNVSTTTPAPRPPTPAPTIASQPLSLRPEACRPAAGGAVHTRGLDF ACDIYIWAPLAGTCGVLLLSLVITLYCNKRDLIKKHIWPNVPDPSKSHIAQWSPHTPP RHNFNSKDQMYSDGNFTDVSVVEIEANDKKPFPEDLKSLDLFKKEKINTEGHSSGIGG SSCMSSSRPSISSSDENESSQNTSSTVQYSTVVHSGYRHQVPSVQVFSRSESTQPLLD SEERPEDLQLVDHVDGGDGILPRQQYFKQNCSQHESSPDISHFERSKQVSSVNEEDFV RLKQQISDHISQSCGSGQMKMFQEVSAADAFGPGTEGQVERFETVGMEAATDEGMPKS YLPQTVRQGGYMPQ |
| 88 | SPA- QBEND10- cys- CD8a_TMD_GP130_ICD | ELPTQGTFSNVSTNVSELCGGIYIWAPLAGTCGVLLLSLVITLYCNKRDLIKKHIWPN VPDPSKSHIAQWSPHTPPRHNFNSKDQMYSDGNFTDVSVVEIEANDKKPFPEDLKSLD LFKKEKINTEGHSSGIGGSSCMSSSRPSISSSDENESSQNTSSTVQYSTVVHSGYRHQ VPSVQVFSRSESTQPLLDSEERPEDLQLVDHVDGGDGILPRQQYFKQNCSQHESSPDI SHFERSKQVSSVNEEDFVRLKQQISDHISQSCGSGQMKMFQEVSAADAFGPGTEGQVE RFETVGMEAATDEGMPKSYLPQTVRQGGYMPQ |
| 89 | SPA- QBEND10- cys- CD8a_TMD_GP130_ICD- L | ELPTQGTFSNVSTNVSELCGGIYIWAPLAGTCGVLLLSLVITLYCNKRDLIKKHIWPN VPDPSKSHIAQWSPHTPPRHNFNSKDQMYSDGNFTDVSVVEIEANDKKPFPEDLKSLD LFKKEKINTEGHSSGIGGSSCMSSSRPSISSSDENESSQNTSSTVQYSTVVHSGYRHQ VPSVQVFSRSESTQPLLDSEERPEDLQLVDHVDGGDGILPRQQYFKQNCSQHESSPDI SHFERSKQVSSVNEEDFVRLKQQISDHISQSCGSGQMKMFQEVSAADAFGPGTEGQVE RFETVGMEAATDEGMPKSYLPQTVRQGGYMPQRIARLEEKVKTLKAQNSELASTANML REQVAQLKQKVMN |
| 90 | SPA- QBEND10- cys-L- CD8a_TMD_GP130_ICD | ELPTQGTFSNVSTNVSELCGGRIARLEEKVKTLKAQNSELASTANMLREQVAQLKQKV MNIYIWAPLAGTCGVLLLSLVITLYCNKRDLIKKHIWPNVPDPSKSHIAQWSPHTPPR HNFNSKDQMYSDGNFTDVSVVEIEANDKKPFPEDLKSLDLFKKEKINTEGHSSGIGGS SCMSSSRPSISSSDENESSQNTSSTVQYSTVVHSGYRHQVPSVQVFSRSESTQPLLDS EERPEDLQLVDHVDGGDGILPRQQYFKQNCSQHESSPDISHFERSKQVSSVNEEDFVR LKQQISDHISQSCGSGQMKMFQEVSAADAFGPGTEGQVERFETVGMEAATDEGMPKSY LPQTVRQGGYMPQ |
| 91 | SPA-C7- gp130 | SLDNNGTATPELPTQGTFSNVSTNVSYQETTTPSTLGSTSLHPVSQHGNEATTNITET TVKFTSTSVITSVYGNTNSSVQSQTSVISTVFTTPANVSTPETTLKPSLSPGNVSDLS TTSTSLATSPTKPYTSSSPILSDIKAEIKCSGIREVKLTQGICLEQNKTSSCAEFKKD RGEGLARVLCGEEQADADAGAQVCSLLLAQSEVRPQCLLLVLANRTEISSKLQLMKKH QSDLKKLGILDFTEQDVASHQSYSQKTPILLTCPTISILSFFSVALLVILACVLWNKR DLIKKHIWPNVPDPSKSHIAQWSPHTPPRHNFNSKDQMYSDGNFTDVSVVEIEANDKK PFPEDLKSLDLFKKEKINTEGHSSGIGGSSCMSSSRPSISSSDENESSQNTSSTVQYS TVVHSGYRHQVPSVQVFSRSESTQPLLDSEERPEDLQLVDHVDGGDGILPRQQYFKQN |

| | informal sequence listing | |
|---|---|---|

SEQ
ID
NO   Name   Sequence

CSQHESSPDISHFERSKQVSSVNEEDFVRLKQQISDHISQSCGSGQMKMFQEVSAADA
FGPGTEGQVERFETVGMEAATDEGMPKSYLPQTVRQGGYMPQ

92   SPA-CD34-   SLDNNGTATPELPTQGTFSNVSTNVSYQETTTPSTLGSTSLHPVSQHGNEATTNITET
       long-gp130   TVKFTSTSVITSVYGNTNSSVQSQTSVISTVFTTPANVSTPETTLKPSLSPGNVSDLS
                TTSTSLATSPTKPYTSSSPILSDIKAEIKCSGIREVKLTQGICLEQNKTSSCAEFKKD
                RGEGLARVLCGEEQADADAGAQVCSLLLAQSEVRPQCLLLVLANRTEISSKLQLMKKH
                QSDLKKLGILDFTEQDVASHQSYSQKTAQGEIEAIVVPVCLAFLLTTLLGVLFCFNKR
                DLIKKHIWPNVPDPSKSHIAQWSPHTPPRHNFNSKDQMYSDGNFTDVSVVEIEANDKK
                PFPEDLKSLDLFKKEKINTEGHSSGIGGSSCMSSSRPSISSSDENESSQNTSSTVQYS
                TVVHSGYRHQVPSVQVFSRSESTQPLLDSEERPEDLQLVDHVDGGDGILPRQQYFKQN
                CSQHESSPDISHFERSKQVSSVNEEDFVRLKQQISDHISQSCGSGQMKMFQEVSAADA
                FGPGTEGQVERFETVGMEAATDEGMPKSYLPQTVRQGGYMPQ 93   SPA-CD34-   LDNNGTATPELPTQGTFSNVSTNVSYQETTTPSTLGSTSLHPVSQHGNEATTNITETT
       gp130_ICD   VKFTSTSVITSVYGNTNSSVQSQTSVISTVFTTPANVSTPETTLKPSLSPGNVSDLST
                TSTSLATSPTKPYTSSSPILSDIKAEIKCSGIREVKLTQGICLEQNKTSSCAEFKKDR
                GEGLARVLCGEEQADADAGAQVCSLLLAQSEVRPQCLLLVLANRTEISSKLQLMKKHQ
                SDLKKLGILDFTEQDVASHQSYSQKTAIVVPVCLAFLLTTLLGVLFCFNKRDLIKKHI
                WPNVPDPSKSHIAQWSPHTPPRHNFNSKDQMYSDGNFTDVSVVEIEANDKKPFPEDLK
                SLDLFKKEKINTEGHSSGIGGSSCMSSSRPSISSSDENESSQNTSSTVQYSTVVHSGY
                RHQVPSVQVFSRSESTQPLLDSEERPEDLQLVDHVDGGDGILPRQQYFKQNCSQHESS
                PDISHFERSKQVSSVNEEDFVRLKQQISDHISQSCGSGQMKMFQEVSAADAFGPGTEG
                QVERFETVGMEAATDEGMPKSYLPQTVRQGGYMPQ 94   SPA-   ELPTQGTFSNVSTNVSPSSSDYSDLQRVKQELLEEVKKELQKVKEEIIEAFVQELRKR
       QBEND10   GSPAQGEIEAIVVPVCLAFLLTTLLGVLFCFNKRDLIKKHIWPNVPDPSKSHIAQWSP
       VASP-   HTPPRHNFNSKDQMYSDGNFTDVSVVEIEANDKKPFPEDLKSLDLFKKEKINTEGHSS
       GP130_ICD   GIGGSSCMSSSRPSISSSDENESSQNTSSTVQYSTVVHSGYRHQVPSVQVFSRSESTQ
                PLLDSEERPEDLQLVDHVDGGDGILPRQQYFKQNCSQHESSPDISHFERSKQVSSVNE
                EDFVRLKQQISDHISQSCGSGQMKMFQEVSAADAFGPGTEGQVERFETVGMEAATDEG
                MPKSYLPQTVRQGGYMPQ 95   SPA-   ELPTQGTFSNVSTNVSAQGEIEAIVVPVCLAFLLTTLLGVLFCFNKRDLIKKHIWPNV
       QBEND10-   PDPSKSHIAQWSPHTPPRHNFNSKDQMYSDGNFTDVSVVEIEANDKKPFPEDLKSLDL
       GP130_ICD-   FKKEKINTEGHSSGIGGSSCMSSSRPSISSSDENESSQNTSSTVQYSTVVHSGYRHQV
       VASP   PSVQVFSRSESTQPLLDSEERPEDLQLVDHVDGGDGILPRQQYFKQNCSQHESSPDIS
                HFERSKQVSSVNEEDFVRLKQQISDHISQSCGSGQMKMFQEVSAADAFGPGTEGQVER
                FETVGMEAATDEGMPKSYLPQTVRQGGYMPQPSSSDYSDLQRVKQELLEEVKKELQKV
                KEEIIEAFVQELRKRGSP 96   SPA-   ELPTQGTFSNVSTNVSELCGGPSSSDYSDLQRVKQELLEEVKKELQKVKEEIIEAFVQ
       QBEND10-   ELRKRGSPAQGEIEAIVVPVCLAFLLTTLLGVLFCFNKRDLIKKHIWPNVPDPSKSHI
       cys-VASP-   AQWSPHTPPRHNFNSKDQMYSDGNFTDVSVVEIEANDKKPFPEDLKSLDLFKKEKINT
       GP130_ICD   EGHSSGIGGSSCMSSSRPSISSSDENESSQNTSSTVQYSTVVHSGYRHQVPSVQVFSR
                SESTQPLLDSEERPEDLQLVDHVDGGDGILPRQQYFKQNCSQHESSPDISHFERSKQV
                SSVNEEDFVRLKQQISDHISQSCGSGQMKMFQEVSAADAFGPGTEGQVERFETVGMEA
                ATDEGMPKSYLPQTVRQGGYMPQ 97   SPA-   ELPTQGTFSNVSTNVSELCGGAQGEIEAIVVPVCLAFLLTTLLGVLFCFNKRDLIKKH
       QBEND10-   IWPNVPDPSKSHIAQWSPHTPPRHNENSKDQMYSDGNFTDVSVVEIEANDKKPFPEDL
       cys-   KSLDLFKKEKINTEGHSSGIGGSSCMSSSRPSISSSDENESSQNTSSTVQYSTVVHSG
       GP130_ICD-   YRHQVPSVQVFSRSESTQPLLDSEERPEDLQLVDHVDGGDGILPRQQYFKQNCSQHES
       VASP   SPDISHFERSKQVSSVNEEDFVRLKQQISDHISQSCGSGQMKMFQEVSAADAFGPGTE
                GQVERFETVGMEAATDEGMPKSYLPQTVRQGGYMPQPSSSDYSDLQRVKQELLEEVKK
                ELQKVKEEIIEAFVQELRKRGSP 98   SPA-CD34-   SLDNNGTATPELPTQGTFSNVSTNVSYQETTTPSTLGSTSLHPVSQHGNEATTNITET
       TpoR-gp130   TVKFTSTSVITSVYGNTNSSVQSQTSVISTVFTTPANVSTPETTLKPSLSPGNVSDLS
                 TTSTSLATSPTKPYTSSSPILSDIKAEIKCSGIREVKLTQGICLEQNKTSSCAEFKKD
                RGEGLARVLCGEEQADADAGAQVCSLLLAQSEVRPQCLLLVLANRTEISSKLQLMKKH
                QSDLKKLGILDFTEQDVASHQSYSQKTISLVTALLLVLGLNAVLGLLLLRKQFPAHYR
                RLRHAIWPNVPDPSKSHIAQWSPHTPPRHNFNSKDQMYSDGNFTDVSVVEIEANDKKP
                FPEDLKSLDLFKKEKINTEGHSSGIGGSSCMSSSRPSISSSDENESSQNTSSTVQYST
                VVHSGYRHQVPSVQVFSRSESTQPLLDSEERPEDLQLVDHVDGGDGILPRQQYFKQNC
                SQHESSPDISHFERSKQVSSVNEEDFVRLKQQISDHISQSCGSGQMKMFQEVSAADAF
                GPGTEGQVERFETVGMEAATDEGMPKSYLPQTVRQGGYMPQ 99   SPA-TpoR-   SDPTRVETATETAWISLVTALLLVLGLNAVLGLLLLRKQFPAHYRRLRHAIWPNVPDP
       gp130_ICD   SKSHIAQWSPHTPPRHNFNSKDQMYSDGNFTDVSVVEIEANDKKPFPEDLKSLDLFKK
                EKINTEGHSSGIGGSSCMSSSRPSISSSDENESSQNTSSTVQYSTVVHSGYRHQVPSV -continued

| informal sequence listing | | |
|---|---|---|

| SEQ ID NO | Name | Sequence |
|---|---|---|
| | | QVFSRSESTQPLLDSEERPEDLQLVDHVDGGDGILPRQQYFKQNCSQHESSPDISHFE RSKQVSSVNEEDFVRLKQQISDHISQSCGSGQMKMFQEVSAADAFGPGTEGQVERFET VGMEAATDEGMPKSYLPQTVRQGGYMPQ |
| 100 | SPA-EpoR-gp130_ICD | APPPNLPDPKFESKAALLAARGPEELLCFTERLEDLVCFWEEAASAGVGPGNYSFSYQ LEDEPWKLCRLHQAPTARGAVRFWCSLPTADTSSFVPLELRVTAASGAPRYHRVIHIN EVVLLDAPVGLVACLADESGHVVLRWLPPPETPMTSHIRYEVDVSAGNGAGSVQRVEI LEGRTECVLSNLRGRTRYTFAVRARMAEPSFGGFWSAWSEPVSLLTPSDLDPLILTLS LILVVILVLLTVLALLSNKRDLIKKHIWPNVPDPSKSHIAQWSPHTPPRHNFNSKDQM YSDGNFTDVSVVEIEANDKKPFPEDLKSLDLFKKEKINTEGHSSGIGGSSCMSSSRPS ISSSDENESSQNTSSTVQYSTVVHSGYRHQVPSVQVFSRSESTQPLLDSEERPEDLQL VDHVDGGDGILPRQQYFKQNCSQHESSPDISHFERSKQVSSVNEEDFVRLKQQISDHI SQSCGSGQMKMFQEVSAADAFGPGTEGQVERFETVGMEAATDEGMPKSYLPQTVRQGG YMPQ |
| 101 | SPA-EpoR-gp130 | APPPNLPDPKFESKAALLAARGPEELLCFTERLEDLVCFWEEAASAGVGPGNYSFSYQ LEDEPWKLCRLHQAPTARGAVRFWCSLPTADTSSFVPLELRVTAASGAPRYHRVIHIN EVVLLDAPVGLVACLADESGHVVLRWLPPPETPMTSHIRYEVDVSAGNGAGSVQRVEI LEGRTECVLSNLRGRTRYTFAVRARMAEPSFGGFWSAWSEPVSLLTPSDLDPAIVVPV CLAFLLTTLLGVLFCFNKRDLIKKHIWPNVPDPSKSHIAQWSPHTPPRHNFNSKDQMY SDGNFTDVSVVEIEANDKKPFPEDLKSLDLFKKEKINTEGHSSGIGGSSCMSSSRPSI SSSDENESSQNTSSTVQYSTVVHSGYRHQVPSVQVFSRSESTQPLLDSEERPEDLQLV DHVDGGDGILPRQQYFKQNCSQHESSPDISHFERSKQVSSVNEEDFVRLKQQISDHIS QSCGSGQMKMFQEVSAADAFGPGTEGQVERFETVGMEAATDEGMPKSYLPQTVRQGGY MPQ |
| 102 | SPA-QBEND10-EpoR-gp130_ICD | ELPTQGTFSNVSTNVSAPPPNLPDPKFESKAALLAARGPEELLCFTERLEDLVCFWEE AASAGVGPGNYSFSYQLEDEPWKLCRLHQAPTARGAVRFWCSLPTADTSSFVPLELRV TAASGAPRYHRVIHINEVVLLDAPVGLVACLADESGHVVLRWLPPPETPMTSHIRYEV DVSAGNGAGSVQRVEILEGRTECVLSNLRGRTRYTFAVRARMAEPSFGGFWSAWSEPV SLLTPSDLDPLILTLSLILVVILVLLTVLALLSNKRDLIKKHIWPNVPDPSKSHIAQW SPHTPPRHNFNSKDQMYSDGNFTDVSVVEIEANDKKPFPEDLKSLDLFKKEKINTEGH SSGIGGSSCMSSSRPSISSSDENESSQNTSSTVQYSTVVHSGYRHQVPSVQVFSRSES TQPLLDSEERPEDLQLVDHVDGGDGILPRQQYFKQNCSQHESSPDISHFERSKQVSSV NEEDFVRLKQQISDHISQSCGSGQMKMFQEVSAADAFGPGTEGQVERFETVGMEAATD EGMPKSYLPQTVRQGGYMPQ |
| 103 | SPA-QBEND10-EpoR-gp130 | ELPTQGTFSNVSTNVSAPPPNLPDPKFESKAALLAARGPEELLCFTERLEDLVCFWEE AASAGVGPGNYSFSYQLEDEPWKLCRLHQAPTARGAVRFWCSLPTADTSSFVPLELRV TAASGAPRYHRVIHINEVVLLDAPVGLVACLADESGHVVLRWLPPPETPMTSHIRYEV DVSAGNGAGSVQRVEILEGRTECVLSNLRGRTRYTFAVRARMAEPSFGGFWSAWSEPV SLLTPSDLDPAIVVPVCLAFLLTTLLGVLFCFNKRDLIKKHIWPNVPDPSKSHIAQWS PHTPPRHNFNSKDQMYSDGNFTDVSVVEIEANDKKPFPEDLKSLDLFKKEKINTEGHS SGIGGSSCMSSSRPSISSSDENESSQNTSSTVQYSTVVHSGYRHQVPSVQVFSRSEST QPLLDSEERPEDLQLVDHVDGGDGILPRQQYFKQNCSQHESSPDISHFERSKQVSSVN EEDFVRLKQQISDHISQSCGSGQMKMFQEVSAADAFGPGTEGQVERFETVGMEAATDE GMPKSYLPQTVRQGGYMPQ |
| 104 | Inducible (CAR-SPA) QBEND10-Cys-L-GP130 | ELPTQGTFSNVSTNVSELCGGRIARLEEKVKTLKAQNSELASTANMLREQVAQLKQKV MNAQGEIEAIVVPVCLAFLLTTLLGVLFCFNKRDLIKKHIWPNVPDPSKSHIAQWSPH TPPRHNFNSKDQMYSDGNFTDVSVVEIEANDKKPFPEDLKSLDLFKKEKINTEGHSSG IGGSSCMSSSRPSISSSDENESSQNTSSTVQYSTVVHSGYRHQVPSVQVFSRSESTQP LLDSEERPEDLQLVDHVDGGDGILPRQQYFKQNCSQHESSPDISHFERSKQVSSVNEE DFVRLKQQISDHISQSCGSGQMKMFQEVSAADAFGPGTEGQVERFETVGMEAATDEGM PKSYLPQTVRQGGYMPQ |
| 105 | L-gp130 | DYKDDDDKELCGGRIARLEEKVKTLKAQNSELASTANMLREQVAQLKQKVMNAQGEIE AIVVPVCLAFLLTTLLGVLFCFNKRDLIKKHIWPNVPDPSKSHIAQWSPHTPPRHNEN SKDQMYSDGNFTDVSVVEIEANDKKPFPEDLKSLDLFKKEKINTEGHSSGIGGSSCMS SRPSISSSDENESSQNTSSTVQYSTVVHSGYRHQVPSVQVFSRSESTQPLLDSEERP EDLQLVDHVDGGDGILPRQQYFKQNCSQHESSPDISHFERSKQVSSVNEEDFVRLKQQ ISDHISQSCGSGQMKMFQEVSAADAFGPGTEGQVERFETVGMEAATDEGMPKSYLPQT VRQGGYMPQ |
| 238 | QBEND10 (CD34 epitope) | ELPTQGTFSNVSTNVS |
| 239 | BCR domain | MVDPVGFAEAWKAQFPDSEPPRMELRSVGDIEQELERCKASIRRLEQEVNQERERMIY LQTLLAKE |

--- informal sequence listing

| SEQ ID NO | Name | Sequence |
|---|---|---|
| 240 | VASP domain | PSSSDYSDLQRVKQELLEEVKKELQKVKEEIIEAFVQELRKRGSPAQGEIE |
| 241 | EpoR domain with cysteine mutation | APPPNLPDPKFESKAALLAARGPEELLCFTERLEDLVCFWEEAASAGVGPGNYSFSYQ<br>LEDEPWKLCRLHQAPTARGAVRFWCSLPTADTSSFVPLELRVTAASGAPRYHRVIHIN<br>EVVLLDAPVGLVACLADESGHVVLRWLPPPETPMTSHIRYEVDVSAGNGAGSVQRVEI<br>LEGRTECVLSNLRGRTRYTFAVRARMAEPSFGGFWSAWSEPVSLLTPSDLDP |
| 242 | CD34 ectodomain | SLDNNGTATPELPTQGTFSNVSTNVSYQETTTPSTLGSTSLHPVSQHGNEATTNITET<br>TVKFTSTSVITSVYGNTNSSVQSQTSVISTVFTTPANVSTPETTLKPSLSPGNVSDLS<br>TTSTSLATSPTKPYTSSSPILSDIKAEIKCSGIREVKLTQGICLEQNKTSSCAEFKKD<br>RGEGLARVLCGEEQADADAGAQVCSLLLAQSEVRPQCLLLVLANRTEISSKLQLMKKH<br>QSDLKKLGILDFTEQDVASHQSYSQKT |
| 243 | TpoR domain | ISLVTALLLVLGLNAVLGLLLL |

---

The invention claimed is:

1. A nucleic acid encoding a synthetic pathway activator (SPA) peptide comprising a chimeric polypeptide comprising:

a. an extracellular domain comprising a CD34 epitope or a CD34 ectodomain;

b. a lipid anchor or a transmembrane domain;

c. an intracellular signaling domain, wherein the intracellular signaling domain comprises a type I cytokine receptor superfamily box2 peptide motif comprising VSVVEIEANDKKP (SEQ ID NO: 107), and a tyrosine phosphorylation motif comprising YXPQ; and d. a multimerization region.

2. The nucleic acid of claim 1, wherein the intracellular signaling domain comprises a sequence having at least 80%, 85%, 90%, 95%, or 99% identity to the sequence as set forth in SEQ ID NO: 60, or comprises the sequence as set forth in SEQ ID NO: 60.

3. The nucleic acid of claim 1, wherein the extracellular domain comprises a CD34 epitope, the multimerization region comprises a multimerization region comprising an unpaired cysteine residue, the lipid anchor or transmembrane domain comprises a gp130 transmembrane domain, and the intracellular signaling domain comprises a gp130 intracellular signaling domain.

4. The nucleic acid of claim 1, wherein the SPA peptide comprises a sequence with at least 90% or 95% sequence identity to a sequence as set forth in SEQ ID NO: 81.

5. The nucleic acid of claim 1, wherein the SPA peptide comprises a sequence as set forth in SEQ ID NO: 81.

6. A synthetic pathway activator (SPA) peptide comprising a chimeric polypeptide comprising:

a. an extracellular domain comprising a CD34 epitope or a CD34 ectodomain;

b. a lipid anchor or a transmembrane domain;

c. an intracellular signaling domain, wherein the intracellular signaling domain comprises a type I cytokine receptor superfamily box2 peptide motif comprising VSVVEIEANDKKP (SEQ ID NO: 107), and a tyrosine phosphorylation motif comprising YXPQ; and d. a multimerization region.

7. The SPA peptide of claim 6, wherein the extracellular domain comprises a CD34 epitope, the multimerization region comprises a multimerization region comprising an unpaired cysteine residue, the lipid anchor or transmembrane domain comprises a gp130 transmembrane domain, and the intracellular signaling domain comprises a gp130 intracellular signaling domain.

8. The SPA peptide of claim 6, comprising a sequence with at least 90% or 95% sequence identity to a sequence as set forth in SEQ ID NO: 81.

9. The SPA peptide of claim 6, comprising a sequence as set forth in SEQ ID NO: 81.

10. A multimer comprising the SPA peptide of claim 6.

11. A multimer comprising the SPA peptide of claim 8.

12. A multimer comprising the SPA peptide of claim 9.

13. A vector comprising the nucleic acid of claim 1.

14. A vector comprising the nucleic acid of claim 4.

15. A vector comprising the nucleic acid of claim 5.

16. A system comprising:

a. optionally, a nucleic acid encoding a first chimeric polypeptide comprising a priming receptor;

b. a nucleic acid encoding a second chimeric polypeptide, optionally comprising a chimeric antigen receptor (CAR); and c. the nucleic acid of claim 1.

17. A cell or population of cells comprising the nucleic acid of claim 1.

18. A cell or population of cells comprising the nucleic acid of claim 4.

19. A cell or population of cells comprising the nucleic acid of claim 5.

20. A pharmaceutical composition comprising the cell or population of cells of 17, and a pharmaceutically acceptable excipient.

21. A pharmaceutical composition comprising the cell or population of cells of 18, and a pharmaceutically acceptable excipient.

22. A pharmaceutical composition comprising the cell or population of cells of 19, and a pharmaceutically acceptable excipient.

23. The nucleic acid of claim 1, wherein the CD34 epitope comprises a sequence as set forth in SEQ ID NO: 238.

24. The nucleic acid of claim 1, further comprising an inducible promoter or a constitutive promoter operably linked to the nucleic acid encoding the SPA, optionally wherein the inducible promoter is an HNF1α promoter and/or wherein the constitutive promoter is an EF1α promoter.

25. The SPA peptide of claim 6, wherein the intracellular signaling domain comprises a sequence having at least 80%, 85%, 90%, 95%, or 99% identity to a sequence as set forth in SEQ ID NO: 60, or comprises the sequence as set forth in SEQ ID NO: 60.

26. The SPA peptide of claim 6, wherein a. the CD34 epitope comprises a sequence as set forth in SEQ ID NO: 238; and/or b. the multimerization region comprises i. at least an unpaired cysteine residue, and/or ii. the multimerization region results in constitutive activity of the intracellular signaling domain.

27. The cell or population of cells of claim 17, wherein the cell is an immune cell, a human immune cell, a primary human immune cell, a natural killer (NK) cell, a T cell, a CD8+ T cell, a CD4+ T cell, a primary T cell, a primary human T cell or a T cell progenitor cell.

28. The nucleic acid of claim 1, wherein a. the multimerization region comprises at least an unpaired cysteine residue; and/or b. the multimerization region results in constitutive activity of the intracellular signaling domain.

29. The nucleic acid of claim 1, wherein the transmembrane domain comprises a sequence at least 90% or 95% identical to the sequence as set forth in SEQ ID NO: 61 or wherein the transmembrane domain comprises the sequence as set forth in SEQ ID NO: 61.

30. The SPA peptide of claim 6, wherein the transmembrane domain comprises a sequence at least 90% or 95% identical to the sequence as set forth in SEQ ID NO: 61 or wherein the transmembrane domain comprises the sequence as set forth in SEQ ID NO: 61.

* * * * *